(12) United States Patent
Peyman

(10) Patent No.: US 11,707,518 B2
(45) Date of Patent: Jul. 25, 2023

(54) METHOD OF TREATING, REDUCING, OR ALLEVIATING A MEDICAL CONDITION IN A PATIENT

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 17/699,055

(22) Filed: Mar. 18, 2022

(65) Prior Publication Data

US 2022/0202933 A1 Jun. 30, 2022

Related U.S. Application Data

(63) Continuation-in-part of application No. 17/180,784, filed on Feb. 20, 2021, and a continuation-in-part of (Continued)

(51) Int. Cl.
*A61K 39/215* (2006.01)
*A61K 31/155* (2006.01)
(Continued)

(52) U.S. Cl.
CPC .......... *A61K 39/215* (2013.01); *A61K 31/155* (2013.01); *A61K 31/422* (2013.01);
(Continued)

(58) Field of Classification Search
None
See application file for complete search history.

(56) References Cited

U.S. PATENT DOCUMENTS 3,760,807 A 9/1973 Neefe
4,563,779 A 1/1986 Kelman
(Continued)

FOREIGN PATENT DOCUMENTS

CA 2662943 A1 10/2009
EP 1616568 A2 1/2016
(Continued)

OTHER PUBLICATIONS

Agrawal et al. (Medicinal Chemistry Research. 2013; 22: 5504-5535).*

(Continued)

*Primary Examiner* — Shanon A. Foley
(74) *Attorney, Agent, or Firm* — The Law Office of Patrick F. O'Reilly III, LLC

(57) ABSTRACT

A therapeutic vaccination method includes growing and harvesting viruses, bacteria, fungi, parasites, or tumor cells on a cell culture or other appropriate medium; killing the viruses, bacteria, fungi, parasites, or tumor cells in the cell culture or other appropriate medium with a dose of methylene blue; separating the dead viruses, bacteria, fungi, parasites, or tumor cells from a remainder of the cell culture or other appropriate medium using a filter and/or centrifuge; adding antivirals, antibacterials, antifungals, antiparasitics, and/or anti-neoplastic medications at non-toxic therapeutic concentrations to the dead viruses, bacteria, fungi, parasites, or tumor cells so as to form a therapeutic vaccine; and administering the therapeutic vaccine to a patient in need thereof to simultaneously produces a therapeutic response and a humoral and cellular immune response in the body of the patient without resulting in deleterious side effects to the patient.

17 Claims, 3 Drawing Sheets

Related U.S. Application Data application No. 16/861,128, filed on Apr. 28, 2020, now Pat. No. 10,925,889.

(60) Provisional application No. 63/162,986, filed on Mar. 18, 2021, provisional application No. 63/177,916, filed on Apr. 21, 2021, provisional application No. 63/181,948, filed on Apr. 29, 2021, provisional application No. 63/209,331, filed on Jun. 10, 2021, provisional application No. 63/221,852, filed on Jul. 14, 2021, provisional application No. 63/239,927, filed on Sep. 1, 2021, provisional application No. 63/306,042, filed on Feb. 2, 2022, provisional application No. 63/039,959, filed on Jun. 16, 2020, provisional application No. 63/055,770, filed on Jul. 23, 2020, provisional application No. 63/077,677, filed on Sep. 13, 2020, provisional application No. 63/106,319, filed on Oct. 27, 2020, provisional application No. 63/131,761, filed on Dec. 29, 2020, provisional application No. 62/839,738, filed on Apr. 28, 2019, provisional application No. 63/016,258, filed on Apr. 27, 2020.

(51) Int. Cl.
| | | |
|---|---|---|
| *A61K 31/422* | (2006.01) | |
| *A61K 31/506* | (2006.01) | |
| *A61K 39/39* | (2006.01) | |
| *A61K 39/395* | (2006.01) | |
| *A61K 31/519* | (2006.01) | |
| *A61K 31/5377* | (2006.01) | |
| *A61K 45/06* | (2006.01) | |
| *A61K 35/13* | (2015.01) | |
| *A61K 35/66* | (2015.01) | |
| *A61K 35/74* | (2015.01) | |
| *A61K 35/76* | (2015.01) | |
| *A61K 36/06* | (2006.01) | |
| *A61K 39/00* | (2006.01) | |
| *C12N 1/00* | (2006.01) | |
| *C12N 1/02* | (2006.01) | |

(52) U.S. Cl.
CPC .......... *A61K 31/506* (2013.01); *A61K 31/519* (2013.01); *A61K 31/5377* (2013.01); *A61K 35/13* (2013.01); *A61K 35/66* (2013.01); *A61K 35/74* (2013.01); *A61K 35/76* (2013.01); *A61K 36/06* (2013.01); *A61K 39/00* (2013.01); *A61K 39/39* (2013.01); *A61K 39/3955* (2013.01); *A61K 45/06* (2013.01); *C12N 1/00* (2013.01); *C12N 1/02* (2013.01); *A61K 2039/543* (2013.01); *A61K 2039/55511* (2013.01); *C12N 2501/999* (2013.01)

(56) References Cited

U.S. PATENT DOCUMENTS

| | | |
|---|---|---|
| 4,665,913 A | 5/1987 | L'Esperance, Jr. |
| 4,718,418 A | 1/1988 | L'Esperance, Jr. |
| 4,793,344 A | 12/1988 | Cumming et al. |
| 4,799,931 A | 1/1989 | Lindstrom |
| 4,840,175 A | 6/1989 | Peyman |
| 4,842,599 A | 6/1989 | Bronstein |
| 4,903,695 A | 2/1990 | Warner et al. |
| 4,994,058 A | 2/1991 | Raven et al. |
| 5,171,318 A | 12/1992 | Gibson et al. |
| 5,336,261 A | 8/1994 | Barrett et al. |
| 5,552,452 A | 9/1996 | Khadem |
| 5,702,441 A | 12/1997 | Zhou |
| 5,964,748 A | 10/1999 | Peyman |
| 6,102,946 A | 8/2000 | Nigam |
| 6,110,166 A | 8/2000 | Juhasz |
| 6,180,687 B1 | 1/2001 | Hammer |
| 6,197,019 B1 | 3/2001 | Peyman |
| 6,537,545 B1 | 3/2003 | Karageozian et al. |
| 6,551,307 B2 | 4/2003 | Peyman |
| 7,001,374 B2 | 2/2006 | Peyman |
| 7,004,902 B2 | 2/2006 | Luce |
| 7,044,945 B2 | 5/2006 | Sand |
| 7,083,802 B2 | 8/2006 | Peyman |
| 7,598,288 B2 | 10/2009 | Hellberg et al. |
| 8,632,489 B1 | 1/2014 | Ahmed |
| 8,911,768 B2 | 12/2014 | Whitcup et al. |
| 8,986,738 B2 | 3/2015 | Meinert |
| 9,249,424 B2 | 2/2016 | Wolf et al. |
| 9,301,925 B2 | 4/2016 | Xu et al. |
| 9,370,446 B2 | 6/2016 | Peyman |
| 9,427,355 B1 | 8/2016 | Peyman |
| 9,486,357 B2 | 11/2016 | Peyman |
| 9,814,567 B2 | 11/2017 | Peyman |
| 9,861,521 B2 | 1/2018 | de Juan, Jr. et al. |
| 9,931,171 B1 | 4/2018 | Peyman |
| 10,925,889 B2 | 2/2021 | Peyman |
| 2001/0027314 A1 | 10/2001 | Peyman |
| 2002/0006394 A1 | 1/2002 | Redmond et al. |
| 2002/0071856 A1 | 6/2002 | Dillingham |
| 2002/0123744 A1 | 9/2002 | Reynard |
| 2003/0035843 A1 | 2/2003 | Livesey et al. |
| 2004/0029855 A1 | 2/2004 | Klaveness et al. |
| 2004/0049174 A1 | 3/2004 | Peyman |
| 2004/0234457 A1 | 11/2004 | Rennie |
| 2005/0070942 A1 | 3/2005 | Perez |
| 2005/0246018 A1 | 11/2005 | Grubbs |
| 2006/0110428 A1 | 5/2006 | deJuan et al. |
| 2006/0135477 A1 | 6/2006 | Haitjema |
| 2006/0166919 A1 | 7/2006 | Shepard et al. |
| 2007/0135754 A1 | 6/2007 | Akiyama et al. |
| 2007/0142908 A1 | 6/2007 | Xu |
| 2007/0255404 A1 | 11/2007 | Pinchuk |
| 2009/0171305 A1 | 7/2009 | El Hage |
| 2009/0177139 A1 | 7/2009 | Boyden et al. |
| 2009/0196903 A1 | 8/2009 | Kliman |
| 2009/0208577 A1 | 8/2009 | Xu et al. |
| 2009/0253661 A1 | 10/2009 | Peyman |
| 2009/0263899 A1 | 10/2009 | Steinfeld et al. |
| 2009/0287005 A1 | 11/2009 | Baker, Jr. et al. |
| 2010/0087920 A1 | 4/2010 | Marmo |
| 2010/0198348 A1 | 8/2010 | Hiles et al. |
| 2010/0210996 A1 | 8/2010 | Peyman |
| 2010/0215717 A1 | 8/2010 | Soker et al. |
| 2011/0076734 A1 | 3/2011 | Zhou et al. |
| 2011/0152219 A1 | 6/2011 | Stagni et al. |
| 2011/0166650 A1 | 7/2011 | Busin |
| 2011/0208300 A1 | 8/2011 | de Juan, Jr. et al. |
| 2011/0250688 A1 | 10/2011 | Hasan |
| 2012/0203161 A1 | 8/2012 | Herekar |
| 2012/0213841 A1 | 8/2012 | Peyman |
| 2012/0226139 A1 | 9/2012 | Peyman |
| 2012/0226351 A1 | 9/2012 | Peyman |
| 2012/0245683 A1 | 9/2012 | Christie et al. |
| 2013/0218167 A1 | 8/2013 | Coffey et al. |
| 2015/0134049 A1 | 5/2015 | Austen, Jr. et al. |
| 2015/0223930 A1 | 8/2015 | Shiuey |
| 2015/0342875 A1 | 12/2015 | Haffner |
| 2015/0366706 A1 | 12/2015 | Belkin et al. |
| 2016/0022495 A1 | 1/2016 | Feingold |
| 2016/0081852 A1 | 3/2016 | Peyman |
| 2016/0081920 A1 | 3/2016 | Csaky |
| 2016/0117443 A1 | 4/2016 | Van Ooijen et al. |
| 2016/0287700 A1 | 10/2016 | Griffin |
| 2016/0331868 A1 | 11/2016 | Grubbs et al. |
| 2016/0346389 A1 | 12/2016 | Friedman et al. |
| 2017/0007395 A1 | 1/2017 | Peyman |
| 2019/0054183 A1 | 2/2019 | Yang et al. |
| 2019/0083518 A1 | 3/2019 | Borody |

(56) References Cited

U.S. PATENT DOCUMENTS

| | | | |
|---|---|---|---|
| 2019/0142927 A1* | 5/2019 | Gregersen | A61K 39/12 424/186.1 |
| 2020/0222557 A1 | 7/2020 | Berlin | |

FOREIGN PATENT DOCUMENTS

| | | |
|---|---|---|
| WO | 89/04153 A1 | 5/1989 |
| WO | 92/16172 A1 | 10/1992 |
| WO | 01/58495 A2 | 8/2001 |
| WO | 2004/108064 A2 | 12/2004 |
| WO | 2008/055118 A2 | 5/2008 |

OTHER PUBLICATIONS

Xu et al. (European Journal of Medicinal Chemistry 164 (2019) 448e470).*
Clapperman et al. ("A field guide to optimizing peptoid synthesis." ACS Polymers Au (2022).*
Webster et al. (Frontiers in Cell and Developmental Biology 8 (2020): 365).*
Chuang et al. (Pharmaceuticals. May 2022; 15 (5), 621).*
Patidar et al. (International Journal of Medical Arts. Feb. 2022; 4 (2): 2129-2132).*
Wilder-Smith et al. (New England Journal of Medicine. Sep. 2021; 385 (10): 946-948).*
Sevinc et al. (Epidemiology and Infection. 2022; 150, e35: 1-6).*
Haas et al. (STAR protocols 2.4 (2021): 100869).*
Perez-Then et al. ("Immunogenicity of heterologous BNT162b2 booster in fully vaccinated individuals with CoronaVac against SARS-CoV-2 variants Delta and Omicron: the Dominican Republic Experience." Medrxiv. Jan. 1, 2021).*
Sanders, James M., et al. "Pharmacologic treatments for coronavirus disease 2019 (COVID-19): a review." JAMA (Apr. 13, 2020):1824-1836. doi:10.1001/jama.2020.6019 (Year: 2020).
Carnevale, Sergio, Paolo Beretta, and Patrizia Morbini. "Direct endothelial damage and vasculitis due to SARS-CoV-2 in small bowel submucosa of COVID-19 patient with diarrhea." Journal of Medical Virology. Jun. 3, 2020. https://doi.org/10.1002/jmv.26119 (Year: 2020).
Sarkar, K. "US FDA-approved ointment found to treat, kill viral infections including Covid-19." Hindustan Times (Aug. 22, 2020). (Year: 2020).
Moriguchi, Takeshi, et al. "A first case of meningitis/encephalitis associated with SARS-Coronavirus-2." International journal of infectious diseases 94 (Apr. 3, 2020): 55-58. https://doi.org/10.1016/j.ijid.2020.03.062 (Year: 2020).
First office action on the merits (Non-Final Rejection) in U.S. Appl. No. 17/180,784, dated Jun. 28, 2021.
Second office action on the merits (Final Rejection) in U.S. Appl. No. 17/180,784, dated Aug. 27, 2021.
Third office action on the merits (Non-Final Rejection) in U.S. Appl. No. 17/180,784, dated Jan. 12, 2022.
J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).
Wollensak et al., "Riboflavin/Ultraviolet-A—induced Collagen Crosslinking for the Treatment of Keratoconus", American Journal of Ophthalmology, vol. 135, pp. 620-627 (2003).
M. A. Bamashmus, M. F. Saleh, M. A. Awadalla, "Reasons For Not Performing Keratorefractive Surgery in Patients Seeking Refractive Surgery in a Hospital-Based Cohort in Yemen", Middle East Afr J Ophthalmol, Oct.-Dec. 2010; 17(4): pp. 349-353.
Goins et al., "Photodynamic biologic tissue glue to enhance corneal wound healing after radial keratotomy" (Nov. 1997), Journal of Cataract and Refractive Surgery, vol. 23, Issue 9, pp. 1331-1338. (Abstract only).
First office action on the merits (Non-Final Rejection) in U.S. Appl. No. 14/709,801, dated Jan. 11, 2016.
Second office action on the merits (Final Rejection) in U.S. Appl. No. 14/709,801, dated May 4, 2016.
Notice of Allowance in U.S. Appl. No. 14/709,801, dated Jul. 19, 2016.
First office action on the merits (Non-Final Rejection) in U.S. Appl. No. 15/230,445, dated Jul. 11, 2017.
Notice of Allowance in U.S. Appl. No. 15/230,445, dated Dec. 4, 2017.
First office action on the merits (Non-Final Rejection) in U.S. Appl. No. 15/816,140, dated Oct. 22, 2018.
Notice of Allowance in U.S. Appl. No. 15/816,140, dated Feb. 19, 2019.
PCT Form 210, International Search Report for PCT/US2019/030931, dated Jul. 17, 2019.
PCT Form 237, Written Opinion of the International Searching Authority for PCT/US2019/030931, dated Jul. 17, 2019.
Darwish et al. "Subbasal Nerve Fiber Regeneration after LASIK and LASEK Assessed by Noncontact Esthesiometry and in Vivo Confocal Microscopy: Prospective Study." Journal of Cataract & Refractive Surgery, vol. 33, No. 9, Sep. 2007, pp. 1515-1521, doi:https://doi.org/10.1016/j.jcrs.2007.05.023.
Townes-Anderson et al. "Fasudil, a Clinically Used ROCK Inhibitor, Stabilizes Rod Photoreceptor Synapses after Retinal Detachment." Translational Vision Science & Technology, vol. 6, No. 3, ser. 22, Jun. 22, 2017, doi:10.1167/tvst.6.3.22.
Abegunde et al. "Doxycycline plus Ivermectin versus Ivermectin Alone for Treatment of Patients with Onchocerciasis." The Cochrane Database of Systematic Reviews, U.S. National Library of Medicine, Jan. 15, 2016, www.ncbi.nlm.nih.gov/pmc/articles/PMC5029467/.
Hegde et al. "A Skin-Depth Analysis of Integrins: Role of the Integrin Network in Health and Disease." Cell Communication & Adhesion, vol. 20, No. 6, Nov. 2013, pp. 155-169, doi:https:1/doi.org/10.3109/15419061.2013.854334.
Todorich et al. "Simultaneous Dexamethasone Intravitreal Implant and Anti-VEGF Therapy for Neovascular Age-Related Macular Degeneration Resistant to Anti-VEGF Monotherapy." Journal of Vitreoretinal Diseases, vol. 1, No. 1, Jan. 26, 2017, pp. 65-74, doi:10.1177/2474126416683299.
Tao et al. "Treatment of Burn Scars in Fitzpatrick Phototype III Patients with a Combination of Pulsed Dye Laser and Non-Ablative Fractional Resurfacing 1550 Nm Erbium:Glass/1927 Nm Thulium Laser Devices." Scars, Burns & Healing, SAGE Publications, Feb. 23, 2018, www.ncbi.nlm.nih.gov/pmc/articles/PMC5965338/.
Stepp et al. "Wounding the Cornea to Learn How It Heals." Experimental Eye Research, U.S. National Library of Medicine, Apr. 2014, www.ncbi.nlm.nih.gov/pmc/articles/PMC4072315/.
Loewen. Ocular Surgery News. "How Many Medications Should Be Tried to Lower IOP before Moving on to SLT or Glaucoma Filtering Surgery?" Healio Ocular Surgery News, Healio, Oct. 25, 2010, www.healio.com/ophthalmology/glaucoma/news/print/ocular-surgery-news/%7Bd9857d89-570c-4b52-af40-26bfd5273ddc%7D/how-many-medications-should-be-tried-to-lower-iop-before-moving-on-to-slt-or-glaucoma-filtering-surgery.
Li et al. "Intranasal Delivery of FSD-C10, a Novel Rho Kinase Inhibitor, Exhibits Therapeutic Potential in Experimental Autoimmune Encephalomyelitis." Immunology, Blackwell Science Inc, Oct. 2014, www.ncbi.nlm.nih.gov/pmc/articles/PMC4172138/.
First office action on the merits (Non-Final Rejection) in U.S. Appl. No. 15/941,641, dated Sep. 27, 2018.
Notice of Allowance in U.S. Appl. No. 15/941,641, dated Mar. 21, 2019.
"KY02111", MedChemExpress Website, Web page <https://www.medchemexpress.com/KY02111.html?src=google-product&gclid=EAlaIQobChMI0OP38Ony5wIVFvbjBx3joQOGEAAYASAAEgJOkfD_BwE>, 3 pages, dated at least as early as Feb. 27, 2020, retrieved from MedChemExpress website on Feb. 27, 2020.
"WAY 316606", APExBIO Website, Web page <http://www.apexbt.com/way-316606.html?gclid=EAlaIQobChMIIsj51Ory5wIVxMDACh3qogldEAAYASAAEgISkfD_BwE>, 4 pages, dated at least as early as Feb. 27, 2020, retrieved from APExBIO website on Feb. 27, 2020.

(56) References Cited

OTHER PUBLICATIONS

"IWP-2", MedChemExpress Website, Web page <https://www.medchemexpress.com/IWP-2.html>, 3 pages, dated at least as early as Feb. 27, 2020, retrieved from MedChemExpress website on Feb. 27, 2020.

"LGK974", MedChemExpress Website, Web page <https://www.medchemexpress.com/LGK974.html?src=google-product&gclid-EAlalQobChMlylHI4_zy5wIV0YZbCh15nws7EAAYASAAEgKTTPD_BwE>, 3 pages, dated at least as early as Feb. 27, 2020, retrieved from MedChemExpress website on Feb. 27, 2020.

"C59", Abcam Website, Web page <https://www.abcam.com/c59-wnt-antagonist-wnt-signaling-pathway-inhibitor-ab142216.html>, 3 pages, dated at least as early as Feb. 27, 2020, retrieved from Abcam website on Feb. 27, 2020.

First office action on the merits (Non-Final Rejection) in U.S. Appl. No. 16/246,618, dated Nov. 27, 2019.

Second office action on the merits (Final Rejection) in U.S. Appl. No. 16/246,618, dated Mar. 5, 2020.

Third office action on the merits (Non-Final Rejection) in U.S. Appl. No. 16/246,618, dated Jul. 1, 2020.

Fourth office action on the merits (Final Rejection) in U.S. Appl. No. 16/246,618, dated Nov. 13, 2020.

Notice of Allowance in U.S. Appl. No. 16/246,618, dated Feb. 23, 2021.

First office action on the merits (Non-Final Rejection) in U.S. Appl. No. 16/861,128, dated Oct. 27, 2020.

Notice of Allowance in U.S. Appl. No. 16/861,128, dated Jan. 4, 2021.

Wang et al., Lancet 2020;295: 1569-78. (Year: 2020).

Laporte et al., Virology 2017,24:16-24. (Year: 2017).

Ma et al., Clinical Immunology 214 (2020) 108408 (available online Apr. 1, 2020). (Year: 2020).

Sedger, https://theconversation.com/in-the-fight-against-coronavirus-antivirals-are-as-important-as-a-vaccine-heres-where-the-science-is-up-to-133926 (last accessed Oct. 24, 2020). (Year: 2020).

Farkas, Internet Book of Critical Care (IBCC), https://emcrit.org/ibcc/covid19/ (last accessed Oct. 24, 2020). (Year: 2020).

Singh et al., Ther Adv Infectious Dis 2017, vol. 4(4) 105-131 (Year: 2017).

Xu, Jimin, et al. "Broad spectrum antiviral agent niclosamide and its therapeutic potential." ACS infectious diseases 6.5 (Mar. 3, 2020): 909-915. (Year: 2020).

Pulivendala, Gauthami, Swarna Bale, and Chandraiah Godugu. "Inhalation of sustained release microparticles for the targeted treatment of respiratory diseases." Drug delivery and translational research 10.2 (Dec. 23, 2019): 339-353. (Year: 2019).

Cagno, Valeria, et al. "Methylene Blue has a potent antiviral activity against SARS-CoV-2 in the absence of UV-activation in vitro " bioRxiv (Aug. 14, 2020). (Year: 2020).

Belen-Apak, F. B., and F. Sarialioglu. "The old but new: Can unfractioned heparin and low molecular weight heparins inhibit proteolytic activation and cellular internalization of SARS-CoV2 by inhibition of host cell proteases?." Medical hypotheses 142 (Apr. 20, 2020): 109743. (Year: 2020).

Diao, Bo, et al. "Human kidney is a target for novel severe acute respiratory syndrome coronavirus 2 (SARS-CoV-2) infection."—MedRxiv (Apr. 10, 2020). (Year: 2020).

Tandukar, Srijan, and Paul M. Palevsky. "Continuous renal replacement therapy: who, when, why, and how." Chest 155.3 (2019): 626-638. (Year: 2019).

Sarkar, Prasanta Kumar, and Chitrangada Das Mukhopadhyay. "Ayurvedic metal nanoparticles could be novel antiviral agents against SARS-CoV-2." International Nano Letters (Jan. 6, 2021): 1-7. (Year: 2021).

Baum, Alina, et al. "REGN-COV2 antibodies prevent and treat SARS-CoV-2 infection in rhesus macaques and hamsters." Science 370.6520 (2020): 1110-1115. (Year: 2020).

\* cited by examiner

METHOD OF TREATING, REDUCING, OR ALLEVIATING A MEDICAL CONDITION IN A PATIENT

CROSS-REFERENCE TO RELATED APPLICATIONS

This patent application claims priority to U.S. Provisional Patent Application No. 63/162,986, entitled "Treatment And Prevention Methods For Respiratory Infections", filed on Mar. 18, 2021; U.S. Provisional Patent Application No. 63/177,916, entitled "Treatment And Prevention Methods For Respiratory Infections", filed on Apr. 21, 2021; U.S. Provisional Patent Application No. 63/181,948, entitled "Treatment And Prevention Methods For Respiratory Infections", filed on Apr. 29, 2021; U.S. Provisional Patent Application No. 63/209,331, entitled "Treatment And Prevention Methods For Respiratory Infections", filed on Jun. 10, 2021; U.S. Provisional Patent Application No. 63/221,852, entitled "Treatment And Prevention Methods For Respiratory Infections", filed on Jul. 14, 2021; U.S. Provisional Patent Application No. 63/239,927, entitled "Treatment And Prevention Methods For Respiratory Infections", filed on Sep. 1, 2021; and U.S. Provisional Patent Application No. 63/306,042, entitled "Treatment And Prevention Methods For Respiratory Infections", filed on Feb. 2, 2022; and is a continuation-in-part of application Ser. No. 17/180,784, entitled "Method Of Treating, Reducing, Or Alleviating A Medical Condition In A Patient", filed Feb. 20, 2021, which claims priority to U.S. Provisional Patent Application No. 63/039,959, entitled "Treatment And Prevention Methods For Respiratory Infections", filed on Jun. 16, 2020; U.S. Provisional Patent Application No. 63/055,770, entitled "Treatment And Prevention Methods For Respiratory Infections", filed on Jul. 23, 2020; U.S. Provisional Patent Application No. 63/077,677, entitled "Treatment And Prevention Methods For Respiratory Infections", filed on Sep. 13, 2020; U.S. Provisional Patent Application No. 63/106,319, entitled "Treatment And Prevention Methods For Respiratory Infections", filed on Oct. 27, 2020; and U.S. Provisional Patent Application No. 63/131,761, entitled "Treatment And Prevention Methods For Respiratory Infections", filed on Dec. 29, 2020; and Ser. No. 17/180,784 is a continuation-in-part of application Ser. No. 16/861,128, entitled "Method Of Treating, Reducing, Or Alleviating A Medical Condition In A Patient", filed Apr. 28, 2020, now U.S. Pat. No. 10,925,889; which claims priority to U.S. Provisional Patent Application No. 62/839,738, entitled "Method Of Treating, Reducing, Or Alleviating A Medical Condition In A Patient", filed on Apr. 28, 2019; and to U.S. Provisional Patent Application No. 63/016,258, entitled "Treatment Methods For Respiratory Infections", filed on Apr. 27, 2020, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to treatment methods of treating, reducing, or alleviating a medical condition in a patient. More particularly, the invention relates to combination therapy for the treatment of various medical conditions, which include respiratory infections.

2. Background

Respiratory infections also involve inflammatory processes. Respiratory infections are mostly manifested as bacterial or viral infections affecting the nose, throat, epiglottis, trachea, and the lungs. Often these infections in the end stage can cause serious damage to the lungs as pneumonia and superinfection and serious consequences.

In an upper respiratory Infection (URI), the bacterial culprit is group A streptococcal bacteria producing sinusitis and or bronchitis. The common symptoms are redness of the throat and tonsils and moderately elevated temperature of about 38 degrees C. and enlarged cervical nodes. One of the symptoms of laryngotracheitis is roughness of the voice, etc. and positive culture of the organism.

The viral infection is caused often by influenza virus, Epstein Barr virus, Herpes virus, etc. and can be diagnosed by available rapid tests for antibody or polymerase chain reaction (PCR) viral proteins (e.g., enzyme assays for reverse transcriptase in retroviruses), or virus particles (e.g., by electron microscopy or Raman surface enhance spectroscopy, QuantiFERON-virus Gold test (QFV-G) and Surface-enhanced Raman scattering (SERS) for rapid detection of multiple viral antigens using magnetic capture of SERS-active nanoparticles as known in the art). In Surface Enhanced Raman Spectroscopy (SERS), antibody conjugated magnetic or paramagnetic and gold nanoparticles/virus complex is enhanced by an external magnetic field detected by SERS where the signal of the specific virus, e.g., COVID-19 or its mutations, gene, bacteria present in blood, dry blood, serum, or nasal, throat swab, etc. is enhanced by laser excitation and recognized using principal component analysis (PCA) and hierarchical cluster analysis (HCA) as known in the art at low picomolar concentration. In a hospitalized patient, a blood culture, sputum, nasal, skin, mouth conjunctival mucosa or urogenital mucosa, aqueous, vitreous, CSF, joint fluid, etc. might be taken to verify the extent of the localized or systemic involvement of the viruses or bacteria, etc. The use of a single strand of DNA/antibody or aptamer coated nanoparticles can be used to recognize the RNA expression of RNA viruses, etc. Management of these cases is done in general by oral and systemic antibiotics, penicillin, fluoroquinolones (e.g., levofloxacin, moxifloxacin etc.), tetracycline and its derivatives and antivirals, etc. Hospitalization might be required in advanced cases affecting the lung with the symptom of dyspnea. The viral infection of the upper respiratory tract is caused by a variety of viruses, among them, the most common are Rhinoviruses, Coxsackie viruses, Adenoviruses and Coronaviruses and Respiratory syncytial virus (RSV) and Epstein Barr Virus (EBV) causing a variety of disease manifestations, such as infectious mononucleosis, or Cytomegalovirus. Rhinoviruses cause a number of common cold infections in adults and are seasonal, appearing in fall and winter. These cause approximately 30-50% of colds in adults. The Adenovirus causes conjunctivitis and laryngitis. *H. influenzae* type b (Hib) often causes epiglottitis in children, whereas influenza, Human parainfluenza viruses (HPIVs) viruses and RSV cause laryngitis and some cause pelvic inflammatory diseases of various types. Most of the viral infections are initiated by close contact, travel, or in patients with immune suppression. In general vaccination can reduce a number of these infections. Some viruses are seen more often in male patients than females, or during menstrual cycles etc. and some with preference in children, yet others in the elderly. Some of the viruses produce epidemic diseases such as Middle East respiratory syndrome, pandemic H1N1, and H7N9, thus affecting a large number of the population and can be diagnosed by diagnosed by polymerase chain reaction (PCR) panels, etc. Therapy with antibiotics is ineffective in majorities of viral infections unless it is accompanied by a bacterial superinfection. However some viruses, such as influenza viruses and COVID-19 grow in the presence of the bacteria, therefore in these cases administration of some antibiotics such as tetracycline derivatives, a metalloproteinase inhibitor, as inhalation combined with antiviral work synergistically. The antiviral therapies are effective, such as administration of ribavirin in lung transplant patients with Motavizumab. However, they are not affordable for common viral infections, a second-generation anti-RSV antibody, or intravenous immunoglobin (RI-002).

Although influenza and parainfluenza viruses are often self-limited, unfortunately they can be associated with life threatening consequences in patients after lung transplantation or immunosuppressed patients, and may have a high mortality rate similar to RSV disease, and 20% of patients with SARS-CoV-2, COVID-19 or its mutations, have multiorgan failure due to cytokine storm.

Among viruses that cause epidemic or pandemic disease are severe acute respiratory syndrome coronavirus (SARS-CoV-2) and COVID-19 or its mutations, an RNA virus involving bird and mammals which was found initially in the Wuhan Seafood Wholesale market. By now, SARS-CoV-2, COVID-19 or its mutations, has affected every country in every continent. It is a highly contagious virus and survives 3-7 hours, and sometimes more hours on surfaces.

The SARS-CoV-2 and COVID-19 coronavirus affects the bronchoalveolar cell linings as seen with other Coronaviruses. The viruses utilize certain protease proteins of these cells membrane to enter in the cell cytoplasm and utilize the genetic machinery of the cell to multiply. The incubation time varies between 3-7 days or more, while the patient remains relatively asymptomatic. The transmission occurs by contact or aerosolized droplet sputum by sneezing or being close (less than 6 feet) from an infected person. Thus, one person can transmit the virus to many others. In addition, many patients who have recovered can still transmit the virus to others. At present, at least six or more different coronal viruses have been recognized. Among these are SARS-CoV coronavirus causing severe acute respiratory syndrome or MERS-CoV Middle Eastern respiratory syndrome and some that live in bats.

The mechanism of cell entry of the virus into the cell involves using the receptor binding domain (RBD) or the S protein of the virus to attach to the human receptor ACE2 of the alveoli cell where serine protease cleaves the S protein of the virus and causes the binding of the virus to the cell membrane and facilitates entry in the cell. Among the symptoms of coronavirus, a high fever of 100 Fahrenheit or more, is a common finding in addition to cough, shortness of breath, chills, headache, sore throat, muscle pain and gastrointestinal symptoms, loss of smell or taste, urticaria or discoloration of the foot or toes, etc., followed by laboratory finding of leukopenia, lymphocytopenia and thrombocytopenia, coagulopathy, increase in antiphospholipid antibodies, multiple infarcts, increased C-reactive protein greater than >10 mg/L, elevated lactate dehydrogenase (LDH), elevated creatinine, specifically in patients with cytokine storm, similarly increased IFNγ and increased pro-inflammatory ferritin, D-dimer. Cytokine storm induces damage to many organs, such as heart, kidney, etc. A cytokine storm is often associated with macrophage activation syndrome (MAS) and hemophagocytic lymphohistiocytosis (sHLH), increase in cytokines, such as tumor necrosis factor (TNF)-α, interferon (IFN)-γ, interleukin (IL)-1β, IL-2, IL-6, IL-7, IL-12, IL-18, and granulocyte colony-stimulating factor (GCSF). Interestingly, one finds also the anti-inflammatory stimuli, such as regulatory T cells, cytokines IL-10, transforming growth factor (TGF)-β. The latter can lead to pulmonary fibrosis when the patient has recovered, whereas the presence of IL-2, IL-6, IL-7, TNFα, IFNγ, and GCSF, indicates significant lung injury. Comorbidity conditions are old age, male sex, asthma, heart disease, diabetes, kidney disease, etc.

At present, there is no definite therapy for the SARS-CoV-2, COVID-19 or its coronavirus mutations. In general, the early stages are treated palliative. Since fever is a relatively an early symptom, aspirin and Tylenol are useful, but do not affect the replication of the virus. Protection against infection includes self-isolation quarantine, the use of a mask and gloves, and prevention of the virus spreads by sanitizing drops and handwashing. At present, patients with dyspnea, are treated with inhalation of oxygen through the nose or by ventilator, increasing the tissue oxygenation to a level of 92-96%. If a higher level is required, one has recommended the use of nonrebreather mask, with a flow rate up to 6-10 L while providing 100% $FiO_2$ (fraction of inspired oxygen (FiO20).

Inflammatory disease of the brain is called encephalitis. It is caused by viral or bacterial invasion of the brain through the circulation, but most independently through the nasal mucosa and lamina cribrosa, a thin layer of bone that separates the brain and cerebrospinal fluid from the nasal cavity, directly through the olfactory nerve that begins one side inside from the nasal cavity with its receptors between the nasal epithelial cells, and ends with the olfactory bulb located inside the skull under the brain and another nerve "the trigeminal nerve" that transmits sensation of touch or pain from the facial skin, or mouth, throat, and nasal mucosa to trigeminal ganglion cells located at the brain.

The olfactory neurons are close to the nasal cavity and have access to the subarachnoid space in the brain, therefore virus can migrate from the nasal cavity to the olfactory bulb and migrate to brain, thalamus, cerebrum, and cerebellum.

All viruses show a tropism for the olfactory epithelium, bovine herpesvirus 5 and equine herpesvirus 9 spread from the nasal mucosa to the central nervous system (CNS) via the olfactory nerves, herpesvirus 6 has been found in the nasal mucosa in healthy controls, multiple sclerosis patients, and patients with a loss of smell.

The bony structure of skull protects the brain which is surrounded by meninges, consisting of dura mater, arachnoid and pita matter. The cerebrospinal fluid is produced in the brain ventricle existing through the venous system of the meninges and through the lamina cribrosa, etc. and the lymphatic system of the nose.

The thigh junction of the endothelial cells and pericytes, astrocytes and epithelial cells of the arachnoid mainly prevent passage of the blood and its components including the potentially invasive pathogens in the brain substance.

The brain is composed of many ganglion cells, microglia, astrocytes, dendritic cells, oligodendrocytes, etc. of which the neuronal cells and glial cells build the majority of cells. The cerebrospinal fluid (CSF) contains many migrating mononuclear cells, such as monocytes, and dendritic cells, T cells, B cells, macrophages, the T-cell exit the subarachnoid space access the lymphatic system that drains in the nasal mucosal lymphatic system.

The viral and microbial pathogens can gain access to the brain passing through the damaged endothelial cells of the brain or spinal cord vessels through the circulation or alternatively through the olfactory or trigeminal nerves directly bypassing all barriers of the brain.

The neurotrophic viruses often invade the nasal mucosa where they proliferate then gain preferentially access to the olfactory nerve and the brain and its vasculature inducing vasculitis and encephalitis, followed by the release of cytokines and enzymes such as metalloproteinases, etc. enhances the degradation of the blood brain barrier (BBB), with poring blood plasma, fibrinogen that is converted into fibrin in the brain, increased intraocular pressure, headache, changes in mental cognition, and difficulty of interaction and death of the neuronal cells.

Viruses constitute the majority of the pathogens involved in cases of encephalitis. The infection produces a combined inflammation of the brain substance and its vasculature (Vasculitis). Other viruses beside herpes virus that cause encephalitis are, influenza viruses, Epstein-Barr viruses, measles virus, enteroviruses, varicella-zoster virus and arboviruses, Japanese encephalitis virus, West Nile virus, and Murray Valley encephalitis virus.

In some cases, the encephalitis (brain inflammation) is caused by viruses which gain access to the brain through the circulation. However, more commonly, the nasal cavity and its mucosa are affected initially, and the viruses multiply there, before spreading to the vascular endothelial cells or brain through the lamina cribrosa, a thin plate of bone between the nasal cavity and brain.

The pathogens induce vasculitis, breakdown of the blood brain barrier leading to further invasion of the bacteria or viruses affecting the ganglion cell function, stimulating glial cell and immune cells, proliferation and migration in the affected area.

Viral encephalitis occurs after nasal invasion by the viruses, such as common cold, influenza viruses, coronaviruses, SARS-CoV-2, COVID-19 or their mutations, influenza viruses, herpes simplex, varicella zoster, shingles, but also measles, rubella and mumps, or Epstein-Barr virus (EBV), Ebola virus, enteroviruses, cytomegalovirus, other viruses such as Zika chikungunya, and arboviruses that are transmitted via mosquitos' bites and subsequently affect the CNS, etc. or via circulation. Herpes simplex type 1 virus can become as deadly as some other viruses, such as Ebola if not treated rapidly. Sever inflammatory process specifically in bacterial infection produces brain abscess.

Conjunctivitis is one of the most common infectious diseases of the eye affecting the conjunctiva, cornea or the lid, kwon as keratoconjunctivitis, or blepharoconjuctivitis. The acute inflammation is initiated by invading bacterial or viral organism such as streptococcal or staphylococcal bacteria, etc. Bacterial conjunctivitis is associated with trichiasis, chronic blepharitis or dry eye. The most commonly viral pathogens are adenoviruses causing pinkeye or adenoviral epidemic keratoconjunctivitis (EKC) or herpes simplex virus (HSV) viruses. Other viral infection causing conjunctivitis are varicella-zoster virus (VZV), picornavirus (enterovirus 70, Coxsackie A24), Poxvirus (molluscum contagiosum, vaccinia), and human immunodeficiency virus (HIV) or rarely, influenza virus, SARS-CoV-2, COVID-19 or their mutations, Epstein-Barr virus, paramyxovirus (measles, mumps, Newcastle), or rubella, Most of viral conjunctivitis, are contagious and can be transmitted to others and to majorities of body's organs.

The COVID-19 virus or its mutations can induce numerous inflammatory disorders in the including conjunctivitis scleritis, or nodular conjunctivitis and scleritis, uveitis and retinitis, and/or optic nerve vasculitis.

The infection can be caused by the virus invasion directly, or the inflammation is caused by the presence of the cytokine released causing hyperemia of the conjunctiva. The diagnosis is done by detection of the virus using PCR from the conjunctival fluid, saliva anterior chamber fluid or vitreous samples or from the nasal fluid which is drained in the nose through the nasolacrimal duct or to the throat and lung, etc.

The patients with conjunctivitis have typically some pain, itching, watery or thick discharge associated with redness of the conjunctiva, photophobia, keratitis and lid swelling.

Conjunctivitis can also be caused as an allergic response to an external antigen in children or adults known as vernal conjunctivitis often seen in warm season appearing as dot-like swelling involving the pre-corneal or limbal conjunctiva.

Giant papillary conjunctivitis is seen in people who do not tolerate wearing contact lens. The symptoms involve the upper conjunctiva, usually under the upper lid. It is associated with increased mucus production and itching resembling venereal disease.

BRIEF SUMMARY OF EMBODIMENTS OF THE INVENTION

Accordingly, the present invention is directed to a method of treating, reducing, or alleviating a medical condition in a patient that substantially obviates one or more problems resulting from the limitations and deficiencies of the related art.

In accordance with one or more embodiments of the present invention, there is provided a method of treating, reducing, or alleviating a medical condition in a patient. The method includes administering to a patient in need thereof a biocompatible drug comprising one or more antiviral medications together with one or more cell pathway inhibitors dissolved in a non-toxic semifluorinated alkane or other liquids, the patient having one or more respiratory tract inflammatory diseases, the one or more cell pathway inhibitors blocking an inflammatory response of inflamed tissue without inhibiting an immune response of the patient, and the semifluorinated alkane evaporating quickly upon administration to the patient so as to leave the biocompatible drug at a desired treatment location. The administration of the biocompatible drug to the patient treats the one or more respiratory tract inflammatory diseases, reduces the symptoms associated with the one or more respiratory tract inflammatory diseases, and/or alleviates the one or more respiratory tract inflammatory diseases.

In a further embodiment of the present invention, the one or more respiratory tract inflammatory diseases are selected from the group consisting of influenza, parainfluenza, severe acute respiratory syndrome, a coronavirus, an Epstein-bar virus, a herpes virus, an infection, and combinations thereof.

In yet a further embodiment, the one or more respiratory tract inflammatory diseases comprise a coronavirus, the coronavirus selected from the group consisting of COVID-2, COVID-19, and combinations thereof.

In still a further embodiment, the biocompatible drug further comprises nanoparticles or microparticles used as a carrier of the biocompatible drug; and the biocompatible drug with the semifluorinated alkane and the nanoparticles or microparticles is administered by inhalation to the patient to treat one or more respiratory tract inflammatory diseases.

In yet a further embodiment, wherein the nanoparticle or microparticle carriers comprise slow release polymeric nanoparticles or microparticles; and the semifluorinated alkane is used to transport the biocompatible drug with the slow release polymeric nanoparticles or microparticles.

In still a further embodiment, the slow release polymeric nanoparticles or microparticles are conjugated with a viral specific antibody while carrying at least two antiviral medications for intranasal inhalation to specifically target one or more viruses, the viral specific antibody being obtained from plasma/serum of patients who have recovered from a viral infection or the viral specific antibody being produced in a tissue culture using dead viruses cultured with T-cell lymphocytes or natural killers that produce the viral specific antibody in addition to producing exosomes or extracellular vesicles (ECV) that are both able to be harvested.

In yet a further embodiment, the one or more antiviral medications are selected from the group consisting of medications preventing the virus entry in the cell, such as protease inhibitors, or prevention of virus multiplication, such as transcription factor inhibitors, nucleoside reverse transcriptase inhibitor (NRTI) or polymerase inhibitor, etc. These one or more antiviral medications include, for example, amantadine, Lopinavir, linebacker and equivir, Arbidol, a nanoviricide, remdesivir, oseltamivir, ribavirin, and combinations thereof.

In still a further embodiment, the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

In yet a further embodiment, the biocompatible drug further comprises one or more protease inhibitors in combination with the one or more antiviral medications and the one or more cell pathway inhibitors.

In still a further embodiment, the method further comprises the step of, after treatment with the biocompatible drug, removing cytokines, enzymes, dead cells, from the circulation of the patient by plasmapheresis so as to prevent a cytokine storm.

In yet a further embodiment, the biocompatible drug is administered to the patient by inhalation, orally, intravenously, or combinations thereof.

In still a further embodiment, the biocompatible drug is administered through the nasal mucosa to reach branches of the trigeminal nerve or olfactory nerve for delivery of the biocompatible drug to the brain, brain vasculature, and the cerebrospinal fluid where the semifluorinated alkane rapidly evaporates at body temperature in the tissue leaving the biocompatible drug at the desired treatment location.

In yet a further embodiment, the method further comprises administering a stabilized hypochlorous acid, hypobromous acid (HOBr), bromamine, or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] or Benzalkonium chloride and slow release polymeric nanoparticles carrying at least two of the antiviral medications together with one or more cell pathway inhibitors and heparin or low molecular weight heparin, or with poly phenols, such as catechin, found in fruit and vegetables, in a semifluorinated alkane or a suitable medium, the administration being in the nose as inhalation, in spray or nebulized form to treat viral encephalitis or lung inflammation to kill one or more viruses and prevent the side effects of inflammation or as prophylaxis of viral infection in the respiratory tract, encephalitis, vasculitis, dementia.

In still a further embodiment, the method further comprises administering tocilizumab in combination with at least one antiviral medication to treat a viral infection of the lung, viral brain encephalitis, and/or brain vasculitis; and administering at least one cell pathway inhibitor, Wnt inhibitor, GSK inhibitor, or integrin inhibitor with or without complement pathway inhibitors such as C3 inhibitors—AMY-101 (NCT04395456) and APL-9 (NCT04402060); C5 inhibitors—eculizumab (NCT04346797 and NCT04355494), C1 esterase inhibitors, which block the classical complement pathway, through nose inhalation by spraying, aerosolization, or nebulization to reach both brain and lung tissue, and to reduce the inflammatory process and eliminate the side effects of the infection.

In yet a further embodiment, the method further comprises administering interferon or pegylated interferon and another antiviral medication in combination with the one or more cell pathway inhibitors, where the interferon or pegylated interferon acts as an antiviral in the upper and lower respiratory tract, thereby blocking the replication of the RNA and DNA of the viruses at an early stage of viral infection.

In still a further embodiment, the method further comprises administering a TMPRSS2 inhibitor and an ACE-2 inhibitor in combination with the one or more cell pathway inhibitors, where the TMPRSS2 inhibitor inhibits entry of the virus into the cell.

In accordance with one or more other embodiments of the present invention, there is provided a method of preventing a medical condition in a patient. The method includes administering prophylactically a treatment compound or substance to prevent the occurrence of a viral infection, the treatment compound or substance being selected from the group consisting of one or more antiviral medications, one or more cell pathway inhibitors, a type of mouthwash, hydrogen peroxide, povidone-iodine, ethanol, chlorhexidine, cetylpyridinium chloride, an IL-1 inhibitor, an IL-6 inhibitor, an IL-8 inhibitor, and combinations thereof. The treatment compound or substance is administered topically, intranasally, or as a mouthwash.

In a further embodiment of the present invention, the viral infection is COVID-19, and the treatment compound or substance disrupts the COVID-19 lipid envelope.

In yet a further embodiment, the method further comprises administering a stabilized hypochlorous solution, or in chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], or Benzalkonium chloride in a semifluorinated alkane or liquid with slow release chitosan encapsulated nanoparticles in a saline solution or in oral form to pass through the stomach to release a medication in the intestine to locally prevent the intestinal side effect of the viral infection.

In still a further embodiment, the method further comprises administering prophylactically one or two antiviral medications as a nasal spray, in aerosolized or nebulized form, or spray together with zinc in a saline solution orally in aliginate or chitosan encapsulated beads or nasally in polycaprolactone in a saline solution to damage the invading viruses before entering the nasal mucosa.

In yet a further embodiment, the method further comprises administering tamoxifen in combination with at least one antiviral medication to treat a viral infection of the lung, viral brain encephalitis, and/or brain vasculitis; and administering at least one cell pathway inhibitor, Wnt inhibitor, GSK inhibitor, and/or integrin inhibitor through the nose inhalation by spraying, aerosolization, or nebulization to reach both brain and lung tissue, and to reduce the inflammatory process and eliminate the side effects of the infection.

In accordance with yet one or more other embodiments of the present invention, there is provided a method of preventing a medical condition in a patient. The method includes administering to a patient, experiencing a medical condition, one or more antiviral medications together with one or more additional medications selected from the group consisting of one or more Wnt inhibitors, one or more Rock inhibitors, one or more GSK inhibitors, one or more integrin inhibitors, one or more IL-6 inhibitors, one or more TGF beta inhibitors, one or more macrolides, low molecular weight heparin, or with catechin in a semifluorinated alkane or a suitable medium and combinations thereof. The one or more antiviral medications and the one or more additional medications are administered orally, intranasally, intravenously, subcutaneously, topically, intraperitoneally, and/or by inhalation in a simultaneous, sequential, or separate manner.

In a further embodiment of the present invention, the medical condition is selected from the group consisting of a lung viral infection, a brain viral infection, an intestinal viral infection, vasculitis, COVID-2, COVID-19, Alzheimer's disease, dementia, neuralgia, kidney disease, cardiac disease, encephalitis, and combinations thereof.

In yet a further embodiment, the medical condition is in a form of an end stage medical condition selected from the group consisting of an end stage lung infection, an end stage brain infection, encephalitis, and combinations thereof; and wherein the one or more antiviral medications comprise a plurality of different antiviral medications to treat the end stage lung infection, the end stage brain infection, and/or encephalitis.

In still a further embodiment, the one or more additional medications administered to the patient comprise low molecular weight heparin to enhance nerve repair and prevent blood coagulation so as to combat an overactive immune response.

In yet a further embodiment, the one or more antiviral medications and/or the one or more additional medications are administered in a physiological solution or semifluorinated alkane or a physiological liquid using polymeric slow release nanoparticles or microparticles, micelles, liposomes, and/or dendrimers and lipid nanoparticles (LNP) as a drug carrier, the polymeric slow release nanoparticles or microparticles comprising at least one of polylactic acid, polyglycolic acid, polycaprolactone, porous silicon, chitosan, and a polyethylene glycol-polylactic acid (PEG-PLA) block copolymer.

In still a further embodiment, the slow release polymeric nanoparticles or microparticles, micelles, liposomes, and/or dendrimers are conjugated with a viral specific antibody so as to form antibody-coated slow release polymeric nanoparticles or microparticles, antibody-coated micelles, antibody-coated liposomes, and/or antibody-coated dendrimers or antibody coated LNP.

In yet a further embodiment, the one or more antiviral medications are selected from the group consisting of amantadine, Lopinavir, linebacker and equivir, Arbidol, a nanoviricide, remdesivir, oseltamivir, ribavirin, and combinations thereof.

In still a further embodiment, the one or more additional medications administered in a physiological solution or semifluorinated alkane or a physiological liquid or any other suitable medium to the patient comprise one or more Rock inhibitors in a form of botulinum toxin at a picogram concentration level.

In one embodiment, the semifluorinated alkane and medications are administered preferably by nasal inhalation mouth inhalation, inhaler, as a spray, nanoparticles or microparticles, in a solution, or powder, or subcutaneous, or intramuscular, or intravenously, combined as a cocktail or sequentially, orally etc.

In yet a further embodiment, the method further comprises administering viral-like particles to induce humoral and cellular immune response and interferon production for therapy and/or for vaccination of the patient.

In one embodiment, the method comprises administering 1-2 or more vaccines such as, dead organisms, or their proteins or mRNA such as Moderna vaccine and Pfizer vaccine, or AstraZeneca vaccine and with viral like particles (VLP) or one or more adjuvants conjugated with the viral antigen at a lower concentration of vaccine than normally is given and if needed an adjuvant in a semifluorinated alkane or in a solution with or without a pathway inhibitor or complement C1-C3-C5 inhibitor either nasally by inhalation or intramuscularly or intravenously separately or sequentially, or combined as a cocktail to reduce the side effects of the vaccines and increase the efficacy of the vaccination or to be repeated multiple times in an intervals of 3, 6, 9, or 12 months, etc. as needed, while the intranasal or inhalation simplifies for the people storing the vaccine at a low temperature using a home refrigerator for self-administration in different intervals as prescribed by a doctor.

In one embodiment, a vaccine is prepared from viruses or bacteria, fungi, etc. in a semifluorinated alkane and a saline, etc. solution containing riboflavin, methylene blue or another photosensitizer, with an adjuvant or viral like particles (VLP), etc., with or without anti-inflammatory cell pathway inhibitors or another anti-inflammatory compound or antiviral or antibiotic, antifungal where the organism is killed with or without radiation exposure, such as x-ray or cobalt radiation etc. or preferably UV radiation such as UVA, UVB, or UVC wavelength or another wavelength of a LED, diode or laser, etc., applied to the entire pathogen in the container, Petri dish for a period of one second to 5 minutes or more and stored in a refrigerator with or without Benzalkonium chloride (BAC) or other compounds damaging DNA or RNA at a low temperature and can be used for repeated vaccination as needed by nasal or intramuscular, or oral administration, or as adjuvant to another vaccine prepared by other means or used after initial use of another vaccine for the same organism, eliminating the need for the use of formalin, thimerosal, formaldehyde, glutaraldehyde, or heating at high temperature, etc. which are toxic and produce excessive and lasting inflammation at the site of the administration or because of unpleasant smell cannot be used for nasal spray or inhalation. In one embodiment, (1) (3-propiolactone (BPL) can also be used after culturing (viruses, bacteria, fungi, parasites or tumor cells) to damage DNA and RNA of the organism, however, increasing its concentration of BPL more than 1:2000 V/V (the concentration of 1 in 2000 w/v can be expressed as 0.05% w/v or 0.5 mg/mL) damages the antigenicity of the protein, (2) therefore a combination of 3-propiolactone (BPL) at a low concentration with methylene blue at concentrations of <2 micogram/ml, (3) plus one or two antivirals (in viral infection), or antibiotics, (in bacterial infection) or antiparasitics (e.g. in Malaria) or antifungals (e.g. in *Candida* infection) or antineoplastics (in any cancer) potentiate damage to RNA and DNA reducing the damage to the protein, proteoglycans, etc. antigenicity of the vaccine samples, (4) while killing the viruses, bacteria, parasites, fungi and tumor cells in the culture media for use as vaccine, (5) then the dead viruses, bacteria, parasites, fungi or tumor cells are ultimately filtered washed in a physiological solution and other components, such as remaining methylene blue and 3-propiolactone (BPL) are removed, and (6) the remaining proteins, saccharides, or glycoproteins of the organism are used with non-toxic doses of antiviral, antibacterial, anti-fungal, antiparasitic, and/or antineoplastic medication as a therapeutic vaccine.

In one embodiment, a vaccine cocktail is prepared from viruses or bacteria, fungi, etc. in a semifluorinated alkane and a saline etc. solution containing riboflavin or methylene blue (<1 microgram/ml) or another photosensitizer, with an adjuvant with or without viral like particles (VLP), etc., with or without pathway inhibitors or another anti-inflammatory compound or antivirals or antibiotics, antifungals where the organism is killed with radiation exposure such as x-ray or cobalt radiation, etc. or preferably UV radiation, such as UVA, UVB or UVC wavelength or another wavelength of an LED, diode or laser, etc., applied to the entire pathogen in the container, Petri dish for a period of one second to 5 minutes or more and the solution, etc. is collected, filtered, and stored in a refrigerator with or without Benzalkonium chloride (BAk) less than 0.01% at a low temperature and can be used for repeated self-vaccination/administration as needed by nasal or intramuscular administration, or as adjuvant to another vaccine prepared by other means, such as mRNA vaccines or oral polymerase inhibitor, AT-527.etc. or used after initial use of another vaccine for the same organism, but self-administered preferably by inhalation or orally, weekly for 1-2 months or more intranasally as a spray or nebulization to eliminate all potential pathogens, such as viruses that might remain in the nasal cavity, throat, pharynx, trachea, or in the alveoli and potentially reactivate and induce an epidemic or pandemic infection.

In one embodiment, the vaccines are distributed as a single dosage to be stored in refrigerator and administrated intranasally, orally, or subcutaneously by people for 1 to 3 months, up to 5 months or longer, etc. as needed.

In one embodiment, the vaccines are distributed in older patients as a single dosage with spermidine and vitamin D to enhance their immune response, to be stored in refrigerator and administrated intranasally, orally, or subcutaneously by people for 1 to 3 months, up to 5 months or longer, etc. as needed.

In another embodiment, one or more anti-inflammatory agents, such as NSAIDs, combined with one or more vaccines along one or more cell inflammatory pathway inhibitors are administered to reduce a severe immune response to vaccines in patients with allergic history.

In one embodiment, vaccine is administered in a semifluorinated alkane combined with pathway inhibitors as a spray simultaneously or sequentially, with or without antibody-coated nanoparticles, etc., the combination therapy can include a vaccine such as dead viruses or mRNA or antibodies against viral proteins such as spike proteins, etc., the vaccination also include medications such as low molecular weight heparin, Ebselen, catechin, mycophenolic acid or inflammatory cell pathway inhibitors or complement inhibitors that modify the severe immune response such as bone ache, fever, malaise, headache, etc. or side effect after a second challenge with repeated vaccinations, or observed immediately after administration of the vaccine combination preferably through the nose by inhalation though it can be given intramuscularly or subcutaneously by an injector, etc. as known in the art.

In still a further embodiment, the method further comprises administering one or more serum antibodies conjugated with the viral-like particles to induce an enhanced cellular immune response and interferon production in the patient.

In yet a further embodiment, during treatment or after treatment with the one or more antiviral medications and/or the one or more additional medications, the method further comprises the step of removing cytokines, enzymes, and/or dead cells from the circulation of the patient by kidney dialysis, blood dialysis, and/or plasmapheresis so as to suppress a cytokine storm.

In still a further embodiment, a vaccine is prepared from viruses placed in methylene blue solution, a derivative of phenothiazine, is prepared at a concentration of 0.25-1 mg/liter in semifluorinated alkanes or in a fluid for nasal inhalation, oral, topical or intravenous administration alone to act as an antioxidant, or with one or two antivirals such as Ebselen or remdesivir, valacyclovir, etc. and one or more Wnt inhibitors or anti-integrins, etc. or LMWH to treat viral respiratory tract infections and/or CNS viral involvement prophylactically or therapeutically.

In yet a further embodiment, when a patient has a severe viral kidney or liver disease, or viral respiratory disease, or viral brain encephalitis, an intravenous administration or oral or inhalation or topical application of methylene Blue, which acts as antioxidant and converts methemoglobin to hemoglobin and acts as an antiviral at a concentration of 0.25-1 mg/liter or less than 1 nM concentration, with one or two antivirals, such as Ebselen or remdesivir, Favipiravir, doxycycline, nitazoxanide, valacyclovir for inhalation or oral administration, etc. with one or more Wnt inhibitors or an anti-integrin, Rock inhibitor or GSK inhibitor, etc. and LMWH in a semifluorinated alkane or in a fluid containing bile salt to kill the viruses including influenza, COVID-19 and reduce severe inflammatory processes followed with dialysis, hemodialysis, serum electrophoresis to remove unwanted toxins and creatinine, etc. and simultaneously act to prevent blood clothing after methylene blue administration.

In still a further embodiment, a vaccine is prepared from viruses or bacteria, fungi, etc. in a semifluorinated alkane and a saline, such as a bile salt, etc. solution containing riboflavin or methylene Blue or another photosensitizer, or combined with β-propiolactone (BPL) with an adjuvant or viral-like particles (VLP), etc., with or without pathway inhibitors or another anti-inflammatory compound or antiviral, such as remdesivir, Favipiravir, valacyclovir, administered by inhalation or orally, and with or without an antibiotic, such as tetracycline derivatives and/or an antifungal where the organism is killed with or without radiation exposure to UV radiation, such as UVA, UVB, or UVC wavelengths or another wavelength (670 nm) produced by an LED, diode or laser, etc., applied to the pathogens in a container, Petri dish to damage the viral DNA and/or viral RNA and parts of the capsular protein, etc. for a period of one second to 5 minutes or more and then the remaining dead components of the virus is stored in a refrigerator with or without Benzalkonium chloride (BAC) at a low temperature to be used for repeated vaccination as needed, e.g., by nasal self-administration or intramuscular administration, or orally or as an adjuvant to another vaccine, such as mRNA vaccines, etc. or after initial administration of another vaccine of the same organism, to stimulate an immune response to the pathogen, thereby eliminating the need for the standard use of formalin, thimerosal, formaldehyde, glutaraldehyde, etc. for the production of vaccines, but are toxic and produce excessive and lasting inflammation at the site of the administration.

In yet a further embodiment, the vaccine is prepared from viruses or bacteria, fungi, etc. in a semifluorinated alkane and a saline, etc. solution containing, riboflavin or methylene Blue alone in combination at a <5 microMolar or 0.25%-1% concentration in sodium phosphate buffer of pH 7.4 at 50 mM concentration or another photosensitizer, or β-propiolactone (BPL), at low concentrations to prevent excessive aggregation of the viral particles and addition of antivirals, killed viruses are separated, washed, and the remaining is combined with a physiological solution or a semifluorinated alkane with an adjuvant with or without pathway inhibitors or another anti-inflammatory compound such as Baricitinib or antivirals any desired antivirals affecting the attachment of the virus to the cell receptor, or preventing entrance in the cells, or protease inhibitor or polymerase inhibitors, etc. or antivirals including valacyclovir, etc. or an antibiotic, antifungal where the organism is killed for vaccine production with or without UV radiation, such as UVA, UVB or UVC wavelengths, or another wavelength (670 nm) of a LED, diode, or laser, etc., applied to the entire pathogen in a container, for a period of one second to 5 minutes or more to damage viral capsid, etc. and the remaining dead viruses are stored in a refrigerator with or without Benzalkonium chloride (BAC) at a low temperature and used for repeated vaccination as needed by nasal inhalation, oral, or intramuscular administration, or as adjuvant to another vaccine prepared by other means after the initial use of another vaccine for the same organism, or another organism, thereby eliminating the need for the standard use of formalin, thimerosal, formaldehyde, glutaraldehyde, etc. which are toxic and produce excessive and lasting inflammation at the site of the administration.

In still a further embodiment, methylene Blue at a 1 mg/L concentration administered intravenously with LMWH or heparin mimetics or complement inhibitors or pathway inhibitors and at least one or more antivirals, such as remdesivir and valacyclovir with or without polyclonal antibodies cocktails and/or anti-inflammatory agents such as Baricitinib, etc. to kill the viral pathogens with or without simultaneous light/laser radiation of the blood inflow tubing, for a period or 4, 8, 16, or 30 minutes followed by dialysis, hemodialysis, serum electrophoresis to remove dead viruses and unwanted toxins and methylene Blue from the blood that is re-infused to the patient.

In yet a further embodiment, one administers a vaccine as a cocktail, etc. to boost the immune response of a person to specific viral, bacterial or fungal pathogens by administering a low dose of a vaccine that is presently used for vaccination, the amount of this booster vaccine can be from 5%-99% of the original volume and its contents, or preferably 10% or 20% or 40% or 60% volume, etc. with or without pathway inhibitors such as Rock, Wnt, GSK or integrin inhibitors, or complement C1, C3, C5 inhibitors, etc. along with or without antivirals, antibiotics or antifungals or with or without an-anti-inflammatory agent, such as a IL-7 inhibitor, DMF or Baricitinib, etc. or an immune enhancer such as spermidine, etc. injected intramuscularly, subcutaneously, or orally or intravenously or preferably by nasal inhalation or by an inhaler etc. so the patients can either self-administer the vaccine in different doses at described intervals either before the regular standard vaccination, during the sickness, shortly thereafter, or beyond the original vaccination or sickness to either recognize an allergic response to the vaccine and/or to boost gradually the immune response of the patient who is old or too young or is an immunosuppressed patient, where the vaccine can be prepared the standard way of killing the bacteria, or render them defenseless, or using a specific protein part of the virus, or using mRNA, etc. of the virus.

In still a further embodiment, the method further comprises the step of: delivery of oxygen to the patient by extracorporeal membrane oxygenation when the blood oxygenation level of the patient is low.

In accordance with still one or more embodiments of the present invention, there is provided a method of treating, reducing, or alleviating a medical condition in a patient. The method includes administering to a patient in need thereof a biocompatible drug comprising one or more antiviral medications together with one or more cell pathway inhibitors, the patient having at least one of a respiratory tract inflammatory disease, a central nervous system inflammatory disease, and vasculitis, the one or more antiviral medications preventing an attachment of viruses to cell walls, blocking a penetration of the viruses into cells, and/or inhibiting virus replication by damaging nucleic acids of the viruses, and the one or more cell pathway inhibitors blocking an inflammatory response of inflamed tissue without inhibiting an immune response of the patient. The administration of the biocompatible drug to the patient treats the at least one of the respiratory tract inflammatory disease, the central nervous system inflammatory disease, and the vasculitis, reduces the symptoms associated with the at least one of the respiratory tract inflammatory disease, the central nervous system inflammatory disease, and the vasculitis, and/or alleviates the at least one of the respiratory tract inflammatory disease, the central nervous system inflammatory disease, and the vasculitis.

In a further embodiment of the present invention, the patient has a respiratory tract inflammatory disease, and the respiratory tract inflammatory disease is selected from the group consisting of influenza, parainfluenza, severe acute respiratory syndrome, a coronavirus disease, an Epstein-bar virus disease, a herpes virus disease, a bacterial infection, and combinations thereof.

In yet a further embodiment, the patient has a respiratory tract inflammatory disease, and the respiratory tract inflammatory disease comprises a coronavirus, the coronavirus being selected from the group consisting of COVID-19, mutations of COVID-19, mutations of the SARS CoV-2 virus, and combinations thereof.

In still a further embodiment, the biocompatible drug further comprises a semifluorinated alkane and polymeric slow release nanoparticles or microparticles used as a carrier of the biocompatible drug; and the biocompatible drug with the semifluorinated alkane and the polymeric slow release nanoparticles or microparticles is administered by inhalation or as a topical ointment to the patient to treat the at least one of the respiratory tract inflammatory disease, the central nervous system inflammatory disease, and the vasculitis, the semifluorinated alkane evaporating quickly upon administration to the patient so as to leave the polymeric slow release nanoparticles or microparticles with the biocompatible drug at a desired treatment location.

In yet a further embodiment, the polymeric slow release nanoparticles, lipid nanoparticles (LNP), or microparticles are conjugated with a viral specific antibody while carrying at least two antiviral medications for intranasal inhalation or topically as an ointment to specifically target one or more viruses, the viral specific antibody being obtained from plasma/serum of patients who have recovered from a viral infection or the viral specific antibody being produced in a tissue culture using dead viruses cultured with T-cell lymphocytes or natural killers that produce the viral specific antibody in addition to producing exosomes or extracellular vesicles (ECV) that are both able to be harvested.

In still a further embodiment, the biocompatible drug is administered through the nasal mucosa to reach branches of the trigeminal nerve or olfactory nerve for delivery of the biocompatible drug to the brain, brain vasculature, and the cerebrospinal fluid where the semifluorinated alkane rapidly evaporates at body temperature in the tissue leaving the polymeric slow release nanoparticles or microparticles with the biocompatible drug at the desired treatment location.

In yet a further embodiment, the one or more antiviral medications are selected from the group consisting of amantadine, Lopinavir, linebacker and equivir, Arbidol, a nanoviricide, remdesivir a polymerase inhibitor, Favipiravir, Ebselen, oseltamivir, oseltamivir, indinavir, molnupiravir a polymerase inhibitor, MK-4482/EIDD-2801, ribavirin, Oya1, Glidesivir, Xofluza, interferon, umifenovir, tamivir, baloxavir, and combinations thereof; and the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, TGF beta inhibitors, and combinations thereof.

In still a further embodiment, the biocompatible drug further comprises one or more protease inhibitors in combination with the one or more antiviral medications and the one or more cell pathway inhibitors.

In yet a further embodiment, the at least one of the respiratory tract inflammatory disease, the central nervous system inflammatory disease, and the vasculitis comprises at least one of a viral infection of the lung, a viral brain encephalitis, and a brain vasculitis; and the method further comprises administering tocilizumab or tamoxifen in combination with the one or more antiviral medications and the one or more cell pathway inhibitors to treat the viral infection of the lung, the viral brain encephalitis, and/or the brain vasculitis; and administering the one or more cell pathway inhibitors through nose inhalation by spraying, aerosolization, or nebulization to reach both brain and lung tissue, and to reduce the inflammatory process and eliminate the side effects of the viral infection of the lung, the viral brain encephalitis, and/or the brain vasculitis.

In still a further embodiment, the method further comprises administering interferon or pegylated interferon in combination with the one or more antiviral medications and the one or more cell pathway inhibitors to the patient, where the interferon or pegylated interferon acts as an antiviral in the upper and lower respiratory tract, thereby blocking the replication of the RNA and DNA of the viruses at an early stage of viral infection.

In yet a further embodiment, the method further comprises administering a TMPRSS2 inhibitor, an ACE-2 inhibitor, and/or a neuropilin inhibitor in combination with the one or more cell pathway inhibitors to the patient where the TMPRSS2 inhibitor, the ACE-2 inhibitor, and/or the neuropilin inhibitor inhibits entry of the virus into the cell.

In still a further embodiment, the method further comprises administering a low molecular weight heparin or synthetic heparin mimetics in combination with a macrolide to the patient to enhance nerve repair and prevent blood coagulation so as to combat an overactive immune response.

In yet a further embodiment, the macrolide comprises cyclosporine A.

In still a further embodiment, the method further comprises administering a polyphenol and/or a derivative of a polyphenol that binds to heparan sulfate, thereby preventing viral attachment to cell receptors. In this further embodiment, the polyphenol and/or the derivatives of the polyphenol are selected from the group consisting of Epigallocatechin gallate (EGCG), green tea, and catechin.

In yet a further embodiment, the method further comprises administering a polyclonal antibody cocktail so as to effectively treat multiple proteins of a mutated virus.

In still a further embodiment, the method further comprises administering intravenously or by inhalation methylene blue, which acts as an antioxidant and converts methemoglobin to hemoglobin and acts as an antiviral at a concentration of 0.25-2 mg/L to 5 µg/ml or 4 mg/kg or less than 80 mg/L or 80 µM concentration, or 1 µg/ml for topical applications together with one or more antiviral medications, and the one or more cell pathway inhibitors; and further administering low molecular weight heparin to the patient to prevent blood coagulation; and performing dialysis, hemodialysis, or serum electrophoresis to remove unwanted toxins and creatinine and simultaneously acting to prevent blood clotting after administration of the methylene blue and the low molecular weight heparin. However, the only side effects of methylene blue observed has been in patients with a glucose 6 phosphate dehydrogenase (G-6-PD) deficiency.

In yet a further embodiment, the methylene blue together with the one or more antiviral medications and the one or more cell pathway inhibitors are administered using ultra small pluralities of gold nanoparticles to enhance viral damage.

In still a further embodiment, the method further comprises administering methylene blue, which acts as antioxidant and converts methemoglobin to hemoglobin and acts as an antiviral at a concentration of 0.25-2 mg/liter or less than 1 nM concentration, together with the one or more antiviral medications and the one or more cell pathway inhibitors; administering low molecular weight heparin to the patient to prevent blood coagulation; and performing dialysis, hemodialysis, or serum electrophoresis to remove unwanted toxins and creatinine and simultaneously acting to prevent blood clotting after administration of the methylene blue and the low molecular weight heparin.

In yet a further embodiment, the methylene blue together with the one or more antiviral medications and the one or more cell pathway inhibitors are administered using ultra small pluralities of gold nanoparticles to enhance viral damage, and initiate an immune response to the virus In still a further embodiment, the method further comprises administering dimethyl fumarate orally, by injection, or by inhalation to prevent pyroptosis of cells resulting from an excessive immune response.

In yet a further embodiment, the method further comprises administering mycophenolic acid or metalloproteinase inhibitors to blocking an excessive immune response of inflamed tissue.

In still a further embodiment, the method further comprises administering an anti-vascular endothelial growth factor medication in combination with the one or more antiviral medications, wherein the anti-vascular endothelial growth factor medication blocks the release of the vascular endothelial growth factor from affected capillary endothelial cells or inflamed alveoli cells and prevents exhaustion of a cellular immune response.

In yet a further embodiment, the method further comprises administering prophylactically the one or more antiviral medications and methylene blue as a nasal spray, in aerosolized or nebulized form, or as a vapor, together with zinc in a saline solution orally in aliginate, chitosan encapsulated beads, or polycaprolactone, or nasally in a saline solution, to damage the invading viruses before entering the nasal mucosa along with an antibiotic or antiviral ointment applied to the nasal passages to kill the viruses in the nose and respiratory tract.

In still a further embodiment, the method further comprises administering prophylactically the one or more antiviral medications and methylene blue as a nasal spray, in aerosolized or nebulized form, or as a vapor, together with zinc in a saline solution orally in alginate, chitosan encapsulated beads, or polycaprolactone, or nasally in a saline solution, to damage the invading viruses before entering the nasal mucosa along with an antibiotic or antiviral ointment applied to the nasal passages to kill the viruses in the nose and respiratory tract.

In accordance with yet one or more embodiments of the present invention, there is provided a therapeutic vaccination method for a medical condition in a patient, the method comprising: (i) growing viruses, bacteria, fungi, parasites, or tumor cells on a cell culture or other appropriate medium; (ii) harvesting the viruses, bacteria, fungi, parasites, or tumor cells from the cell culture or other appropriate medium; (iii) killing the viruses, bacteria, fungi, parasites, or tumor cells in the cell culture or other appropriate medium with a dose of methylene blue that is greater than 2.0 micrograms per milliliter so as to damage the RNA and/or the DNA of the viruses, bacteria, fungi, parasites, or tumor cells, wherein the viruses, bacteria, fungi, parasites, or tumor cells remain in contact with the methylene blue for a period of time that is sufficient for the methylene blue to penetrate the viruses, bacteria, fungi, parasites, or tumor cells and attach to RNA or DNA of the viruses, bacteria, fungi, parasites, or tumor cells and prevent multiplication of the viruses, bacteria, fungi, parasites, or tumor cells; (iv) separating the dead viruses, bacteria, fungi, parasites, or tumor cells from a remainder of the cell culture or other appropriate medium using a filter and/or centrifuge; (v) depending on the type of organism, adding antivirals, antibacterials, antifungals, antiparasitics, and/or anti-neoplastic medications at non-toxic therapeutic concentrations to the dead viruses, bacteria, fungi, parasites, or tumor cells so as to form a therapeutic vaccine; and (vi) administering the therapeutic vaccine to a patient in need thereof. In these one or more embodiments, the therapeutic vaccine simultaneously produces a therapeutic response and a humoral and cellular immune response to viruses, bacteria, fungi, parasites, or tumor cells in the body of the patient without resulting in deleterious side effects to the patient.

In a further embodiment of the present invention, the method further comprises the step of: (vii) adding one or more adjuvants and one or more cell pathway inhibitors to the dead viruses, bacteria, fungi, parasites, or tumor cells to prevent an excessive immune response of the patient.

In yet a further embodiment, the method further comprises the steps of:
(vii) administering metformin with GSK inhibitors to protect the kidneys of the patient; and
(viii) performing kidney dialysis or electrophoresis to remove excess toxins from the body of the patient.

In still a further embodiment, the method further comprises the step of: (vii) repeatedly administering the therapeutic vaccine to the patient as needed until the viruses, bacteria, fungi, parasites, or tumor cells are eliminated and verified by polymerase chain reaction and/or imaging.

In yet a further embodiment, the step of killing the viruses, bacteria, fungi, parasites, or tumor cells in the cell culture or other appropriate medium further comprises conjugating the methylene blue with gold nanoparticles so as to enhance a penetration of the methylene blue into the viruses, bacteria, fungi, parasites, or tumor cells and attach to the RNA or DNA of the viruses, bacteria, fungi, parasites, or tumor cells and prevent multiplication of the viruses, bacteria, fungi, parasites, or tumor cells.

In still a further embodiment, the step of killing the viruses, bacteria, fungi, parasites, or tumor cells in the cell culture or other appropriate medium further comprises adding a peptide nucleic acid (PNA), one or more anti-neoplastic medications, and/or one or more antivirals to the cell culture or other appropriate medium so as to enhance the effect of the methylene blue on the RNA and/or the DNA of the viruses, bacteria, fungi, parasites, or tumor cells.

In yet a further embodiment, the step of administering the therapeutic vaccine to the patient further comprises administering the therapeutic vaccine together with antigens, gold nanoparticles, and a low non-toxic dose of at least two additional medications, the at least two additional medications comprising two or more antivirals, two or more antibacterials, two or more antifungals, two or more antiparasitics, and/or two or more anti-neoplastic medications.

In still a further embodiment, the method further comprises the step of:
(vii) administering one or more immune stimulators, spermidine, anti-depressant agents, and/or diamidobenzimidazole (diABZI-4) to trigger the stimulator of interferon genes (STING), thereby enhancing the immune response of the patient.

In yet a further embodiment, the method further comprises the step of:
(vii) administering Ceapin-A7 and KIRA8 to eliminate damaged cells, bacteria, viruses, fungi, parasites, or tumor cells in the patient.

In still a further embodiment, the step of administering the therapeutic vaccine to the patient further comprises administering the therapeutic vaccine together with an mRNA vaccine or a modified mRNA vaccine and a low non-toxic dose of at least one additional medication, the at least one additional medication comprising one or more antivirals, one or more antibacterials, one or more antifungals, one or more antiparasitics, and/or one or more anti-neoplastic medications.

In yet a further embodiment, the method further comprises the step of:
(vii) administering one or more inflammatory cell pathway inhibitors, one or more steroidal anti-inflammatory agents, one or more non-steroidal anti-inflammatory drugs (NSAIDs), mycophenolate mofetil or other macrolides, methotrexate, an anti-TGF, at least two types of antibody-coated nanoparticles, and/or one or more anticoagulants so as to create a therapeutic vaccine that can be administered during infection to kill the viruses, bacteria, fungi, parasites, or tumor cells in the patient, and to induce a humoral and cellular immune response in the patient.

In still a further embodiment, the method further comprises the step of:
(vii) administering one or more inflammatory cell pathway inhibitors to the patient together with the antivirals, antibacterials, antifungals, antiparasitics, and/or anti-neoplastic medications so that the therapeutic vaccine is able to be used prophylactically or for treatment of the patient as needed, thereby increasing an immune response of the patient to the organism while simultaneously treating the organism.

In yet a further embodiment, the step of killing the viruses, bacteria, fungi, parasites, or tumor cells in the cell culture or other appropriate medium further comprises killing the viruses, bacteria, fungi, parasites, or tumor cells with a high dose of at least two medications that damage the RNA and/or DNA of the viruses, bacteria, fungi, parasites, or tumor cells; and the method further comprises the steps of: (vii) filtering the dead viruses, bacteria, fungi, parasites, or tumor cells from the remainder of the cell culture or other appropriate medium; (viii) extracting the antigens from the damaged viruses, bacteria, fungi, parasites, or tumor cells; and (ix) adding one or more additional medications to the extracted antigens at a low non-toxic dose to the patient, but at a dose that is still toxic to the organisms.

In still a further embodiment, the method further comprises the steps of: (vii) adding a poly (ADP-ribose) polymerase (PARP) inhibitor to the therapeutic vaccine that blocks the RNA and/or DNA repair of the viruses, bacteria, fungi, parasites, or tumor cells; (viii) adding one or more inflammatory pathway inhibitors to the therapeutic vaccine; and (ix) adding one or more immune stimulators to the therapeutic vaccine so as to enhance the immune response of the patient.

In yet a further embodiment, the step of administering the therapeutic vaccine further comprises repeatedly administering the therapeutic vaccine as needed to the patient at a low dose or a gradually increasing dose until a sufficient neutralizing antibody response is achieved in the serum of the patient.

In still a further embodiment, the therapeutic vaccine is used for therapy-resistant bacteria, fungi, parasites, or tumors.

In yet a further embodiment, a tumor of the patient has become resistant to checkpoint inhibitors and has created a milieu in which the newly grown tumor cells are resistant to standard immune therapy; the method further comprising the steps of: (vii) administering a combination of two different therapeutic vaccines, a first one of the two different therapeutic vaccines directed toward existing tumor cells and a second one of the two different therapeutic vaccines directed toward another antigen from bacteria, viruses, or fungi to re-stimulate the cellular and humoral immune response of the body of the patient against the therapy-resistant tumor cells; (viii) administering one or two anti-neoplastic medications in combination with the first one or the second one of the two different therapeutic vaccines; and (ix) simultaneously administering one or more cell pathway inhibitors, immune stimulators, and/or anti-VEGFs to the patient as a cocktail.

In still a further embodiment, the method further comprises the step of: (vii) administering monoamine oxidase inhibitors, melatonin and spermidine to the patient so as to prevent exhaustion of the cellular immune response of the patient.

In yet a further embodiment, the cell culture on which the viruses, bacteria, fungi, parasites, or tumor cells are grown and harvested comprises yeast culture media that permits the organisms to not only grow, but also mutate rapidly such that the therapeutic vaccine has a predictive value for mutation of the viruses, bacteria, fungi, parasites, or tumor cells even before the mutation occurs in the patient; the therapeutic vaccine contains antigenic material from the mutated and un-mutated organism such that the therapeutic vaccine induces a humoral and cellular immune response against the past, present, and future mutations of the organism so as to kill the organism; and the therapeutic vaccine is administered simultaneously with an anti-organism medication to effectively prevent viral, bacterial, fungal, parasitic, and tumor cell mutation in the patient.

In still a further embodiment, the method further comprises the step of:
(vii) administering light or electrical pulses to the viruses, bacteria, fungi, parasites, or tumor cells grown in the yeast culture media so as to encourage the mutation of the viruses, bacteria, fungi, parasites, or tumor cells to be harvested and killed for vaccination.

In yet a further embodiment, the method further comprises the step of:
(vii) administering a poly (ADP-ribose) polymerase (PARP) inhibitor with the therapeutic vaccine so as to block the RNA and/or DNA repair of the viruses, bacteria, fungi, parasites, or tumor cells.

In still a further embodiment, the method further comprises the step of:
(vii) administering the therapeutic vaccine to the patient as topical drops, an ointment, spray for inhalation, in an inhaler, nasally by spraying powder, intravenously, by intramuscular injection, systemically, orally as a capsule, or locally inside a tumor.

In yet a further embodiment, the method further comprises the step of:
(vii) administering the therapeutic vaccine to the patient using a conical nasal drug delivery implant, the therapeutic vaccine being delivered to one or more nasal passageways of a patient.

In still a further embodiment, the conical nasal drug delivery implant is formed from a semi-flexible polymeric material by 3D printing the conical nasal drug delivery implant.

In yet a further embodiment, the conical nasal drug delivery implant is attached to a pair of glasses, an outer nose cover, an elastic headband configured to be worn on the head of the patient, or is held in place by elastic components on the conical nasal drug delivery implant itself.

In still a further embodiment, the step of killing the viruses, bacteria, fungi, parasites, or tumor cells in the cell culture or other appropriate medium further comprises adding at least one of beta-propiolactone (BPL), NSP13 inhibitors, bananin, and chromone-4c to the cell culture or other appropriate medium so as to enhance the effect of the methylene blue on the RNA and/or the DNA of the viruses, bacteria, fungi, parasites, or tumor cells; and wherein the method further comprises the step of: (vii) washing and filtering the therapeutic vaccine to eliminate all unbound methylene blue, beta-propiolactone, NSP13 inhibitors, bananin, and/or chromone-4c prior to adding the antivirals, the antibacterials, the antifungals, the antiparasitics, and/or the anti-neoplastic medications.

In yet a further embodiment, the therapeutic vaccine is formed from a plurality of different virus types and/or mixed with other related vaccines for other virus types in order to treat both a coronavirus and another latent virus of the patient.

In still a further embodiment, the therapeutic vaccine is mixed with another vaccine made for bacteria, fungi, parasites, or tumor cells so that both vaccines collectively stimulate cellular and humoral response of the body of the patient.

In yet a further embodiment, the method further comprises the step of: (vii) adding synthetically produced peptoids to the tissue culture or other appropriate medium, the synthetically produced peptoids penetrating the envelope of the viruses, bacteria, fungi, parasites, or tumor cells, and attaching to RNA and DNA of the viruses, bacteria, fungi, parasites, or tumor cells so as to prevent the RNA and DNA from being activated.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE DRAWINGS

The invention will now be described, by way of example, with reference to the accompanying drawings, in which.

Throughout the figures, the same elements are always denoted using the same reference characters so that, as a general rule, they will only be described once.

DETAILED DESCRIPTION OF EMBODIMENTS OF THE INVENTION

Figure 1:
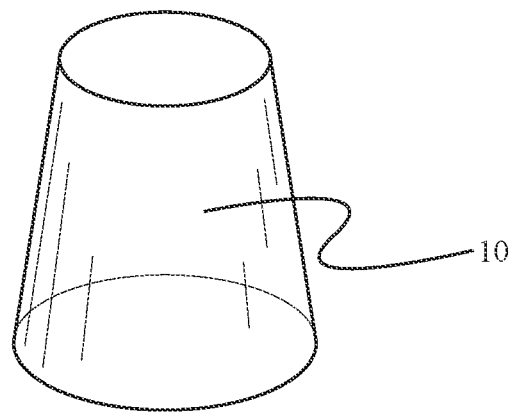
FIG. 1 illustrates a single nasal drug delivery implant, according to one embodiment of the invention, where the implant is conical in shape and formed from a semi-flexible polymeric material.

In accordance with one or more embodiments, there is provided a method of treating, reducing, or alleviating a medical condition in a patient. The method includes administering to a patient in need thereof a biocompatible drug comprising one or more antiviral medications together with one or more cell pathway inhibitors dissolved in a non-toxic semifluorinated alkane or other liquids, the patient having one or more respiratory tract inflammatory diseases, the one or more cell pathway inhibitors blocking an inflammatory response of inflamed tissue without inhibiting an immune response of the patient, and the semifluorinated alkane evaporating quickly upon administration to the patient so as to leave the biocompatible drug at a desired treatment location. The administration of the biocompatible drug to the patient treats the one or more respiratory tract inflammatory diseases, reduces the symptoms associated with the one or more respiratory tract inflammatory diseases, and/or alleviates the one or more respiratory tract inflammatory diseases.

In a further embodiment, the one or more respiratory tract inflammatory diseases are selected from the group consisting of influenza, parainfluenza, severe acute respiratory syndrome, a coronavirus, an Epstein-bar virus, a herpes virus, an infection, and combinations thereof.

In yet a further embodiment, the one or more respiratory tract inflammatory diseases comprise a coronavirus, the coronavirus selected from the group consisting of COVID-2, COVID-19, or their mutations, and combinations thereof.

In still a further embodiment, the biocompatible drug further comprises nanoparticles or microparticles used as a carrier of the biocompatible drug; and the biocompatible drug with the semifluorinated alkane and the nanoparticles or microparticles is administered by inhalation to the patient to treat one or more respiratory tract inflammatory diseases.

In yet a further embodiment, wherein the nanoparticle or microparticle carriers comprise slow release polymeric nanoparticles or microparticles; and the semifluorinated alkane is used to transport the biocompatible drug with the slow release polymeric nanoparticles or microparticles.

In still a further embodiment, the slow release polymeric nanoparticles or microparticles are conjugated with a viral specific antibody/antigen; glycoprotein, polysaccharides, etc. while carrying at least two antiviral medications for intranasal inhalation to specifically target one or more viruses, the viral specific antibody being obtained from plasma/serum of patients who have recovered from a viral infection or the viral specific antibody being produced in a tissue culture using dead viruses cultured with T-cell lymphocytes or natural killers that produce the viral specific antibody in addition to producing exosomes or extracellular vesicles (ECV) that are both able to be harvested.

In yet a further embodiment, the one or more antiviral medications are selected from the group consisting of amantadine, Lopinavir, linebacker and equivir, Arbidol, a nanoviricide, remdesivir, oseltamivir, ribavirin, and combinations thereof In still a further embodiment, the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

In yet a further embodiment, the biocompatible drug further comprises one or more protease inhibitors in combination with the one or more antiviral medications and the one or more cell pathway inhibitors.

In still a further embodiment, the method further comprises the step of, after treatment with the biocompatible drug, removing cytokines, enzymes, dead cells, from the circulation of the patient by plasmapheresis so as to prevent a cytokine storm.

In yet a further embodiment, the biocompatible drug is administered to the patient by inhalation, orally, intravenously, or combinations thereof.

In still a further embodiment, the biocompatible drug is administered through the nasal mucosa to reach branches of the trigeminal nerve or olfactory nerve for delivery of the biocompatible drug to the brain, brain vasculature, and the cerebrospinal fluid where the semifluorinated alkane rapidly evaporates at body temperature in the tissue leaving the biocompatible drug at the desired treatment location.

In yet a further embodiment, the method further comprises administering a stabilized hypochlorous acid, hypobromous acid (HOBr), bromamine, or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] or Benzalkonium chloride and slow release polymeric nanoparticles, or LNP carrying at least two of the antiviral medications together with one or more cell pathway inhibitors and heparin or low molecular weight heparin, or with poly phenols, such as catechin, found in fruit and vegetables, in a semifluorinated alkane or a suitable medium, the administration being in the nose as inhalation, in spray or nebulized form to treat viral encephalitis or lung inflammation to kill one or more viruses and prevent the side effects of inflammation or as prophylaxis of viral infection in the respiratory tract, encephalitis, vasculitis, dementia.

In still a further embodiment, the method further comprises administering tocilizumab in combination with at least one antiviral medication to treat a viral infection of the lung, viral brain encephalitis, and/or brain vasculitis; and administering at least one cell pathway inhibitor, Wnt inhibitor, GSK inhibitor, or integrin inhibitor with or without complement pathway inhibitors such as C3 inhibitors—AMY-101 (NCT04395456) and APL-9 (NCT04402060); C5 inhibitors—eculizumab (NCT04346797 and NCT04355494), C1 esterase inhibitors, which block the classical complement pathway, through nose inhalation by spraying, aerosolization, or nebulization to reach both brain and lung tissue, and to reduce the inflammatory process and eliminate the side effects of the infection.

In yet a further embodiment, the method further comprises administering interferon or pegylated interferon and another antiviral medication in combination with the one or more cell pathway inhibitors, where the interferon or pegylated interferon acts as an antiviral in the upper and lower respiratory tract, thereby blocking the replication of the RNA and DNA of the viruses at an early stage of viral infection.

In still a further embodiment, the method further comprises administering a TMPRSS2 inhibitor and an ACE-2 inhibitor in combination with the one or more cell pathway inhibitors, where the TMPRSS2 inhibitor inhibits entry of the virus into the cell.

In accordance with one or more other embodiments of the present invention, there is provided a method of preventing a medical condition in a patient. The method includes administering prophylactically a treatment compound or substance to prevent the occurrence of a viral infection, the treatment compound or substance being selected from the group consisting of one or more antiviral medications, one or more cell pathway inhibitors, a type of mouthwash, hydrogen peroxide, povidone-iodine, ethanol, chlorhexidine, cetylpyridinium chloride, an IL-1 inhibitor, an IL-6 inhibitor, an IL-8 inhibitor, and combinations thereof. The treatment compound or substance is administered topically, intranasally, or as a mouthwash.

In a further embodiment of the present invention, the viral infection is SARS-CoV-2, COVID-19, or a mutation thereof, and the treatment compound or substance disrupts the SARS-CoV-2, COVID-19 or their mutations' lipid envelope.

In yet a further embodiment, the method further comprises administering a stabilized hypochlorous solution, or in chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], or Benzalkonium chloride in a semifluorinated alkane or liquid with slow release chitosan encapsulated nanoparticles in a saline solution or in oral form to pass through the stomach to release a medication in the intestine to locally prevent the intestinal side effect of the viral infection.

In still a further embodiment, the method further comprises administering prophylactically one or two antiviral medications as a nasal spray, in aerosolized or nebulized form, or spray together with zinc in a saline solution orally in aliginate or chitosan encapsulated beads or nasally in polycaprolactone in a saline solution to damage the invading viruses before entering the nasal mucosa.

In yet a further embodiment, the method further comprises administering tamoxifen in combination with at least one antiviral medication to treat a viral infection of the lung, viral brain encephalitis, and/or brain vasculitis; and administering at least one cell pathway inhibitor, Wnt inhibitor, GSK inhibitor, and/or integrin inhibitor through the nose inhalation by spraying, aerosolization, or nebulization to reach both brain and lung tissue, and to reduce the inflammatory process and eliminate the side effects of the infection.

In accordance with yet one or more other embodiments of the present invention, there is provided a method of preventing a medical condition in a patient. The method includes administering to a patient, experiencing a medical condition, one or more antiviral medications together with one or more additional medications selected from the group consisting of one or more Wnt inhibitors, one or more Rock inhibitors, one or more GSK inhibitors, one or more integrin inhibitors, one or more IL-6 inhibitors, one or more TGF beta inhibitors, one or more macrolides, low molecular weight heparin, or with catechin in a semifluorinated alkane or a suitable medium and combinations thereof. The one or more antiviral medications and the one or more additional medications are administered orally, intranasally, intravenously, subcutaneously, topically, intraperitoneally, and/or by inhalation in a simultaneous, sequential, or separate manner.

In a further embodiment of the present invention, the medical condition is selected from the group consisting of a lung viral infection, a brain viral infection, an intestinal viral infection, vasculitis, COVID-2, COVID-19, or their mutations, Alzheimer's disease, dementia, neuralgia, kidney disease, cardiac disease, encephalitis, and combinations thereof.

In yet a further embodiment, the medical condition is in a form of an end stage medical condition selected from the group consisting of an end stage lung infection, an end stage brain infection, encephalitis, and combinations thereof; and wherein the one or more antiviral medications comprise a plurality of different antiviral medications to treat the end stage lung infection, the end stage brain infection, and/or encephalitis.

In still a further embodiment, the one or more additional medications administered to the patient comprise low molecular weight heparin to enhance nerve repair and prevent blood coagulation so as to combat an overactive immune response.

In yet a further embodiment, the one or more antiviral medications and/or the one or more additional medications are administered in a physiological solution or semifluorinated alkane or a physiological liquid using polymeric slow release nanoparticles or microparticles, micelles, liposomes, and/or dendrimers as a drug carrier, the polymeric slow release nanoparticles or microparticles comprising at least one of polylactic acid, polyglycolic acid, polycaprolactone, porous silicon, chitosan, and a polyethylene glycol-polylactic acid (PEG-PLA) block copolymer.

In still a further embodiment, the slow release polymeric nanoparticles or microparticles, micelles, liposomes, lipid nanoparticles (LNP), and/or dendrimers are conjugated with a viral specific antibody so as to form antibody-coated slow release polymeric nanoparticles, LNP, or microparticles, antibody-coated micelles, antibody-coated liposomes, and/or antibody-coated dendrimers.

In yet a further embodiment, the one or more antiviral medications are selected from the group consisting of amantadine, Lopinavir, linebacker and equivir, Arbidol, a nanoviricide, remdesivir, oseltamivir, ribavirin, ritonavir and combinations thereof.

In still a further embodiment, the one or more additional medications administered in a physiological solution or semifluorinated alkane or a physiological liquid or any other suitable medium to the patient comprise one or more Rock inhibitors in a form of botulinum toxin at a picogram concentration level.

In one embodiment, the semifluorinated alkane and medications are administered preferably by nasal inhalation mouth inhalation, inhaler, as a spray, nanoparticles or microparticles, in a solution, or powder, or subcutaneous, or intramuscular, or intravenously, combined as a cocktail or sequentially, orally etc.

In one embodiment to produce a vaccine, various methodologies can be employed, such as a weakened virus is administered to the patient to produce lasting antibodies, such as the use of polio vaccine developed initially by Sabin and improved by Salk by using killed or inactivated viruses.

In another embodiment, one can use a subunit of the virus, such as one of a protein of the virus, such as in the hepatitis B vaccination made by Novavax and similar vaccines used in Russia, where the genetic material of one virus is inserted in another virus, such as Baculovirus, to build the spike protein by infecting other cells that grow and build the spike protein which is purified and used for vaccination of the people.

In one embodiment, the gene is implanted to a harmless virus, such as the chimpanzee adenovirus producing flu-like symptoms, such as in Sars-COVID-2, or engineered spike-protein. When the human adenovirus is used to carry a part of the gene that makes the spike-protein, it potentially has the side effect of inflammation against the adenoprotein if the patient has been previously exposed to adenovirus.

In one embodiment, one can inject the genetic code with human RNA or DNA if needed by electroporation which is not very effective, but using messenger RNA or mRNA to carry the code letters that make a part of the virus (S-Protein) can be administered to instruct the cell to make, e.g., the S-protein of the virus where the cell produces it and initiates an immune response to the virus in the body. In order to bring mRNA inside the cells they are encapsulated in lipid nanoparticles (LNP), which penetrate the body's cell membrane, into its cytoplasm not in the nucleus and use the cells machinery to build the appropriate antigenic protein. This technology permits the immune cells to recognize the antigen and attack the viruses or other organism.

In yet a further embodiment, despite the technological advances there are some shortcomings that one does not know how long the mRNA vaccines provides an immune response to the patients, therefore there is still a need for alternative technologies or improving the standard technologies, by further administering viral-like particles to induce humoral and cellular immune response and interferon production for therapy and/or for vaccination of the patient.

In one embodiment, the method comprises administering one to two or more vaccines such as, dead organisms, or their proteins or mRNA such as Moderna vaccine and Pfizer vaccine, or AstraZeneca vaccine and with viral like particles (VLP) conjugated with the viral antigen with nanoparticles at a lower concentration of vaccine than normally is given and if needed an adjuvant in a semifluorinated alkane or in a solution with or without a pathway inhibitor or complement C1-C3-C5 inhibitor either nasally by inhalation or intramuscularly, or orally or intravenously separately or sequentially, or combined as a cocktail to reduce the side effects of the vaccines and increase the efficacy of the vaccination or to be repeated multiple times in an intervals of 3, 6, 9, or 12 months, etc. as needed, while the intranasal or inhalation or ointment or oral as pills simplifies for the people storing the vaccine at a low temperature using a home refrigerator for self-administration in different intervals as prescribed by a doctor.

In one embodiment, a vaccine is prepared from viruses or bacteria, fungi, etc. in a semifluorinated alkane and a saline, etc. solution containing riboflavin or preferably another dye, such as methylene blue, with another adjuvant or viral like particles (VLP) conjugated with or without an antibody, or toll-like receptor 4, etc. with or without pathway inhibitors or another anti-inflammatory compound or antiviral or antibiotic, antifungal is administered where the organism is killed preferably without radiation or with radiation exposure, such as x-ray or cobalt radiation etc. with or without or UV radiation such as UVA, UVB, or UVC wavelength or another wavelength of a LED, diode or laser, etc., applied to the entire pathogen in the container, Petri dish for a period of one second to 5 minutes or more and stored in a refrigerator with or without Benzalkonium chloride (BAC) at a low temperature and can be used with nanoparticles/and antivirals for repeated vaccination as needed by nasal or oral, or intramuscular administration, or as adjuvant to another vaccine prepared by other means or used after initial use of another vaccine for the same organism, eliminating the need for the use of formalin, thimerosal, formaldehyde, glutaraldehyde, etc. which are toxic and produce excessive and lasting inflammation at the site of the administration or because of unpleasant smell cannot be used for nasal spray or inhalation.

In one embodiment, a vaccine cocktail is prepared from viruses or bacteria, fungi, etc. in a semifluorinated alkane and a saline etc. solution containing methylene blue, with an adjuvant with or without viral like particles (VLP), etc., with or without pathway inhibitors or another anti-inflammatory compound or antivirals or antibiotics, antifungals where the organism is killed with methylene blue and an antiviral applied to the entire pathogen in the container, Petri dish for a period of one second to 5 minutes or more and the solution, etc. is collected, filtered, and stored in a refrigerator with or without Benzalkonium chloride (BAk) less than 0.01% or less at a low temperature and can be used for repeated self-vaccination/administration as needed by nasal spray, inhalation, or oral pills or gummies or intraperitoneal or intramuscular administration, or as adjuvant to another vaccine prepared by other means, such as mRNA vaccines or monoclonal or polyclonal antibody coated nanoparticles, or LNP etc. or used after initial use of another vaccine for the same organism, but self-administered preferably by inhalation or orally, weekly for 1-2 months or more intranasally as a spray or nebulization to eliminate all potential pathogens, such as viruses that might remain in the nasal cavity, throat, pharynx, trachea, or in the alveoli and potentially reactivate and induce an epidemic or pandemic infection.

In one embodiment, the vaccines are distributed as a single dosage to be stored in refrigerator and administrated intranasally, orally, or subcutaneously by people for 1 to 3 months, up to 5 months or longer, etc. as needed.

In one embodiment, the vaccines are distributed in older patients as a single dosage with spermidine to enhance their immune response, to be stored in refrigerator and administrated intranasally, orally, or subcutaneously by people for 1 to 3 months, up to 5 months or longer, etc. as needed.

In another embodiment, one or more anti-inflammatory agents, such as NSAIDs, combined with one or more vaccines along one or more pathway inhibitors are administered to reduce a severe immune response to vaccines in patients with allergic history.

In one embodiment, vaccine is administered in a semifluorinated alkane combined with pathway inhibitors as a spray simultaneously or sequentially, with or without antibody-coated nanoparticles, etc., the combination therapy can include a vaccine such as dead viruses or mRNA or antibodies against viral proteins such as spike proteins, etc., the vaccination also include medications such as low molecular weight heparin, Ebselen, catechin, mycophenolic acid or pathway inhibitors or complement inhibitors that modify the severe immune response such as bone ache, fever, malaise, headache, etc. or side effect after a second challenge with repeated vaccinations, or observed immediately after administration of the vaccine combination preferably through the nose by inhalation though it can be given intramuscularly or subcutaneously by an injector nasally, by spray, or orally by pills and/or gummies, etc. as known in the art.

In still a further embodiment, the method further comprises administering one or more serum antibodies conjugated with the viral-like particles to induce an enhanced cellular immune response and interferon production in the patient.

In yet a further embodiment, during treatment or after treatment with the one or more antiviral medications and/or the one or more additional medications, the method further comprises the step of removing cytokines, enzymes, and/or dead cells from the circulation of the patient by kidney dialysis, blood dialysis, and/or plasmapheresis so as to suppress a cytokine storm.

In still a further embodiment, a methylene Blue solution, a derivative of phenothiazine, is prepared at a concentration of 0.25-4 mg/liter in semifluorinated alkanes or in a fluid for nasal inhalation, oral, topical or intravenous administration alone to act as an antioxidant, or with one or two antivirals, such as Ebselen or remdesivir, valacyclovir, etc. and one or more Wnt inhibitors or anti-integrins, etc. and/or LMWH to treat viral respiratory tract infections and/or CNS viral involvement prophylactically or therapeutically.

In yet a further embodiment, when a patient has a severe viral kidney or liver disease, or viral respiratory disease, or viral brain encephalitis, an intravenous administration or oral or inhalation or topical application of methylene blue, which acts as antioxidant and converts methemoglobin to hemoglobin and acts as an antiviral at a concentration of 0.25-4 mg/L or less than 4 muM concentration, with one or two antivirals, such as Ebselen or remdesivir, Favipiravir, doxycycline, llopinavir, valacyclovir for inhalation or oral administration, etc. with one or more Wnt inhibitors or an anti-integrin, Rock inhibitor or GSK inhibitor, etc. and LMWH in a semifluorinated alkane or in a fluid containing bile salt to kill the viruses including influenza, SARS-CoV-2, COVID-19, or their mutations and reduce severe inflammatory processes followed with dialysis, hemodialysis, serum electrophoresis to remove unwanted toxins and creatinine, etc. and simultaneously act to prevent blood clothing after methylene blue administration.

In still a further embodiment, a therapeutic vaccine is prepared from viruses or bacteria, fungi, etc. or an adjuvant or a synthetic adjuvant, such as toll-like receptor 4 agonist in a semifluorinated alkane and a saline, such as a bile salt, etc. solution containing methylene blue with or without antibody coated viral-like particles (VLP), etc., with or without pathway inhibitors or another anti-inflammatory compound or antiviral, such as remdesivir, Favipiravir, lopinavir, valacyclovir, etc. administered by inhalation or orally, and with or without an antibiotic, such as tetracycline derivatives and/or an antifungal, where the organism is killed preferably by medication without radiation where the viruses' RNA or DNA are damaged with methylene blue/medication while the S-antigen remains undamaged to induce a strong immune response to the virus applied to the pathogens in a cell culture container to damage the viral DNA and/or viral RNA and parts of the capsular protein, etc. for a period of one hours or a day or more, and then the remaining dead components of the virus is stored in a refrigerator with or without Benzalkonium chloride (BAC) at a low temperature to be used for repeated vaccination as needed, e.g., by nasal self-administration or oral as pills or in liposomes etc. or intramuscular administration, or as an adjuvant to another vaccine, such as mRNA vaccines, etc. or after initial administration of another vaccine of the same organism, to stimulate an immune response to the pathogen, thereby eliminating the need for the standard use of formalin, thimerosal, formaldehyde, glutaraldehyde, etc. for the production of vaccines, but are toxic and produce excessive and lasting inflammation at the site of the administration.

In one embodiment, the RNA or DNA of the viruses are damaged with methylene blue and or while the S-antigen or other viral proteins, etc. remain undamaged, and are administered along with antivirals or benzalkonium chloride or another adjuvant, such as toll like receptor 4 or VLP, etc. to induce a strong immune response to the virus in the body kept with the pathogens that have grown in a container or cell culture to damage the viral DNA and/or viral RNA and parts of the capsular protein, of the virus etc. for a period of few hours or more depending on the concentration of methylene blue, and then the remaining dead components of the dead virus can be stored in a refrigerator with or without Benzalkonium chloride (BAC) at a low temperature to be used for repeated vaccination with pathway inhibitor, such as Wnt, Rock, or GSK inhibitors or GSK beta inhibitors or another adjuvant such as toll-like receptor agonists, etc. as needed, e.g., by nasal self-administration, or ointment or orally as encapsulated with vax or as gummy, etc. or intramuscular or subcutaneous, intraperitoneal, etc. administration, or used as an adjuvant to another vaccine by nasal or oral self-administration, such as mRNA vaccines, etc. or after initial administration of another vaccine of the same organism, to stimulate an immune response to the pathogen, by measuring the neutralizing antibodies in the blood, thereby eliminating the need for the standard use of formalin, thimerosal, formaldehyde, glutaraldehyde, etc. for the production of vaccines, that are toxic and produce excessive and lasting inflammation at the site of the administration.

In one embodiment, antivirals can be combined with methylene blue, a phenothiazine dye, a cationic compound to enhance damage to the viruses, bacteria's anionic RNA or DNA, and simultaneously acting as an in vivo vaccine and therapeutically as anti-oxidant and anti-depressant when given in combination with of one of the pathway inhibitors, such as GSK inhibitors or GSK beta inhibitors and/or Wnt inhibitors, such as Ivermectin or Niclosamide, in a solution or as polymeric slow release nanoparticles or in semifluorinated alkanes to be administered systemically, or preferentially by inhalation, one or multiple times daily at below the toxic dose of methylene blue at 1-2 mg/L to reach both the lung and the brain preventing or treating viral inflammatory disease of the lung or the brain, etc. and preventing subsequent chronic Alzheimer's or Parkinson diseases and nerve damage and preventing or treating the tangled tau neurofibriles and preventing Tau protein's toxicity by activating plasma membrane calcium ATPase, thus preventing endoplasmic reticulum (ER) stress response and unfolding the protein.

In one embodiment, methylene blue, a tricyclic phenothiazine compound approved by the FDA for treatment of methemoglobinemia can block the viral interaction at concentrations of 3 µM-5 µM and more including SAR-CoV-2 and COVID-19 or their mutations or other flaviviruses, etc. with the body's mucosa or respiratory cells or nerves, etc.

In one embodiment, methylene blue-photomediated viral RNA-protein crosslinkage in presence of oxygen can be used for numerous therapy. However, methylene blue or in combination with one or more antivirals can be used as therapy or vaccination either with or without VLP to enhance vaccination effect in any viral disease.

In one embodiment, methylene blue at a concentration of <4 µg/ml with or without light activation can inactivate most viruses, such as West Nile Virus, a flavivirus, ebola or Marburg viruses, etc., coronavirus, alphavirus, myxovirus, filovirus, norovirus and flavivirus family members henipaviruses, bunyaviruses, arenaviruses, and other zoonotic RNA viruses.

In one embodiment, the combined use of methylene blue and an antiviral, such as Favipiravir inhibit the RDRP enzyme (RNA dependent RNA) to transcribe and permits incorporation of Favipiravir in the RNA of the virus, thus the combination of methylene blue and an antiviral without light or other combinations can be used to damage viral RNA while preserving the viral antigenic virus membrane, thus the preparation is therapeutic and simultaneously immune stimulating, such as a therapeutic vaccine, for the humoral or cellular response to specific virus's antigenic membranes, such as S-protein, etc. as used in vaccination, etc.

In one embodiment, methylene blue in combination with Remdesivir inhibits an enzyme that is important for replication of the RNA while preserving the antigenicity of the viral protein or S-protein or their mutations that can be used for both therapy and vaccination if administered orally, such as pills, vax, or gummy etc. or intramuscularly, spraying nasally, by inhalation, by an inhaler, as an ointment, as a powder, or inside a body cavity, etc.

In one embodiment, Lopinavir inhibits the protease needed for replication of the virus. Thus, any combination of Lopinavir and methylene blue at <5 µM or more concentrations damages the RNA of the virus, while preserving the antigenecity of the cell membrane without the use of light for vaccination. Many flaviviruses, including the Dengue virus (DENY), Zika virus (ZIKV), West Nile virus, Yellow Fever virus, and Japanese encephalitis virus are significant human pathogens, can be treated.

In one embodiment methylene blue, an FDA-approved drug, is a broad-spectrum and potent antiviral against Zika virus and Dengue virus both in vitro and in vivo; methylene blue alone or in combination with one or more antivirals can considerably inhibit viral protease activity, inhibit viral growth, protect the brain organoids from ZIKV, methylene blue works on the entry and post-entry in cell processes, inhibiting virus replication alone or in combination with another antiviral or pathway inhibitors or in combination with LMWH preventing blood doting, etc.

In yet a further embodiment, the vaccine production uses a simple easy to produce methodology to be used anywhere, but specially in developing countries, for any known or unknown viruses or bacteria or fungi where the incubation of the methylene blue with viruses or bacteria, or fungi, etc., where after the organism has grown on a cell culture media, etc. with or without a semifluorinated alkane or in cell culture media, a physiological saline solution, etc., one adds a solution containing methylene blue alone at a <5 micro-Molar or 0.25%4% or more concentration in sodium phosphate buffer of pH 7.4 or at 50 mM concentration or preferably more, for less than 2 days, in absence of light, etc. with or without another adjuvant, such as toll like receptor 4, with or without an antiviral, or with or without pathway inhibitors or another anti-inflammatory compound, such as Baricitinib or antivirals including remdesivir, favipiravir, Lopanovir, valacyclovir, or Aplidin, etc. or an antibiotic, such as tetracycline derivatives, where the RNA or DNA of the organism is damaged without damaging the viral or bacterial membrane containing the S-protein (antigen), etc. for vaccine production using the remaining dead viruses or proteins without crosslinking the viral or bacterial proteins, storing them in a refrigerator with or without Benzalkonium chloride (BAC) 0.004 to 0.01%, at a low temperature and used for repeated vaccination as needed by nasal inhalation, inhaler, spray, ointment, or orally as a pill or gummy, etc. for self vaccination in different intervals, at a low volume that can be subsequently increased until neutralizing antibodies are discovered in the body or as adjuvant to another vaccine prepared by other means, such as mRNA vaccines for nasal inhalation, ointment or orally or after the initial use of another vaccine from the same organism, while eliminating the side effects of vaccines and the amount needed, thereby eliminating the need for the standard use of formalin, thimerosal, formaldehyde, glutaraldehyde, etc., which are toxic and produce excessive and lasting inflammation at the site of the administration, while reducing the cost of vaccination for a large population.

In still a further embodiment, methylene Blue at a <1 mg/L concentration is administered intravenously, topically, nasally, orally, intramuscularly, intravenously, or intraperitoneally, with LMWH or heparin mimetics or complement inhibitors or pathway inhibitors and at least one or more antivirals, such as Remdesivir, Favipiravir, monoclonal antibody-conjugated nanoparticles, and Acyclovir, valacyclovir, Lopinavir, linebacker and equivir, Arbidol, a nanoviricide, oseltamivir, ribavirin, and combinations thereof with or without monoclonal or polyclonal antibody cocktails and/or anti-inflammatory agents, such as Baricitinib, or TGFbeta inhibitors, etc. to kill the viral pathogens with or without simultaneous light/laser radiation of the blood inflow tubing, for a period or 4, 8, 16, or 30 minutes or more followed by dialysis, hemodialysis, serum electrophoresis to remove dead viruses and unwanted toxins and methylene blue from the blood that is re-infused to the patient, and to prevent lung fibrosis or myocardial damage or intestinal damage or brain damage in the patients.

In still a further embodiment, methylene Blue solution, a derivative of phenothiazine, is prepared at a concentration of 0.25-2 mg/liter in semifluorinated alkanes or in a fluid for nasal inhalation, oral, topical or intravenous administration alone to act as an antioxidant, or with one or two antivirals such as Ebselen or remdesivir, valacyclovir, etc. and one or more Wnt inhibitors or anti-integrins, etc. or LMWH to treat viral respiratory tract infections and/or CNS viral involvement prophylactically or therapeutically.

In yet a further embodiment, when a patient has a severe viral kidney or liver disease, or viral respiratory disease, or viral brain encephalitis, an intravenous administration or oral or inhalation or topical application of methylene Blue, which acts as antioxidant and converts methemoglobin to hemoglobin and acts as an antiviral at a concentration of 0.25-2 mg/liter or less than 1 nM concentration, with one or two antivirals, such as Ebselen or remdesivir, Favipiravir, nitazoxanide, doxycycline, valacyclovir for inhalation or oral administration, etc. with one or more Wnt inhibitors or an anti-integrin, Rock inhibitor or GSK inhibitor, etc. and LMWH in a semifluorinated alkane or in a fluid containing bile salt to kill the viruses including influenza, SARS-CoV-2, COVID-19, or their mutations and reduce severe inflammatory processes followed with dialysis, hemodialysis, serum electrophoresis to remove unwanted toxins and creatinine, etc. and simultaneously act to prevent blood clothing after methylene Blue administration.

In still a further embodiment, a vaccine is prepared from viruses or bacteria, fungi, etc. or an adjuvant or a synthetic adjuvant such as toll-like receptor 4 agonist in a semifluorinated alkane and a saline, such as a bile salt, etc. solution containing riboflavin or methylene Blue or another photosensitizer, with or without viral-like particles (VLP), etc., with or without pathway inhibitors or another anti-inflammatory compound or antiviral, such as remdesivir, Favipiravir, valacyclovir, administered by inhalation or orally, and with or without an antibiotic, such as tetracycline derivatives and/or an antifungal where the organism is killed with radiation exposure to UV radiation such as UVA, UVB, or UVC wavelengths or another wavelength (670 nm) produced by an LED, diode or laser, etc., or the viruses' RNA or DNA are damaged with methylene blue while the s antigen remains undamaged to induce a strong immune response to the virus applied to the pathogens in a container, Petri dish to damage the viral DNA and/or viral RNA and parts of the capsular protein, etc. for a period of one second to 5 minutes or more and then the remaining dead components of the virus is stored in a refrigerator with or without Benzalkonium chloride (BAC) at a low temperature to be used for repeated vaccination as needed, e.g., by nasal self-administration or intramuscular administration, or as an adjuvant to another vaccine, such as mRNA vaccines, etc. or after initial administration of another vaccine of the same organism, to stimulate an immune response to the pathogen, thereby eliminating the need for the standard use of formalin, thimerosal, formaldehyde, glutaraldehyde, etc. for the production of vaccines, but are toxic and produce excessive and lasting inflammation at the site of the administration.

In one embodiment, the RNA or DNA of the viruses are damaged with methylene blue while the S-antigen remains undamaged, and are administered along with antivirals or benzalkonium chloride or another adjuvant to induce a strong immune response to the virus in the body kept with the pathogens that has grown in a container, cell culture to damage the viral DNA and/or viral RNA and parts of the capsular protein, of the virus etc. for a period of few hours or more and then the remaining dead components of the dead virus can be irradiated once more with a light of 670 nm wavelength for a few more minutes, stored in a refrigerator with or without Benzalkonium chloride (BAC) at a low temperature to be used for repeated vaccination with pathway inhibitors such as Wnt, Rock, or GSK inhibitors or GSK beta inhibitors or another adjuvant such as toll-like receptor agonists etc. as needed, e.g., by nasal self-administration or intramuscular or subcutaneous, etc. administration, or as an adjuvant to another vaccine, such as mRNA vaccines, etc. or after initial administration of another vaccine of the same organism, to stimulate an immune response to the pathogen, thereby eliminating the need for the standard use of formalin, thimerosal, formaldehyde, glutaraldehyde, etc. for the production of vaccines, that are toxic and produce excessive and lasting inflammation at the site of the administration.

In one embodiment, antivirals can be combined with Methylene blue, a phenothiazine dye, a cationic compound to enhance damage to the viruses, bacteria's anionic RNA or DNA, and simultaneously acting as anti-oxidant and anti-depressant when given in combination with of one of the pathway inhibitors, such as GSK inhibitors or GSK beta inhibitors and/or Wnt inhibitors, such as Ivermectin or Niclosamide, in a solution or as polymeric slow release nanoparticles or in semifluorinated alkanes to be administered systemically, or preferentially by inhalation, one or multiple times daily at below the toxic dose of methylene blue at 1-2 mg/L to reach both the lung and the brain preventing or treating viral inflammatory disease of the lung or the brain, etc. and preventing subsequent chronic Alzheimer's or Parkinson diseases and nerve damage and preventing or treating the tangled tau neurofibriles and preventing Tau protein's toxicity by activating plasma membrane calcium ATPase, thus preventing endoplasmic reticulum (ER) stress response and unfolding the protein (UPR).

In yet a further embodiment, the vaccine production uses a simple easy to produce methodology to be used anywhere, but specially in developing countries, for any known or unknown viruses or bacteria where the incubation of the methylene blue with viruses or bacteria, or fungi, etc., after the organism has grown on a cell culture media, etc. with or without a semifluorinated alkane or in culture media, a physiological saline solution, etc., one adds a solution containing methylene Blue alone at a <5 microMolar or 0.25%-1% or more concentration in sodium phosphate buffer of pH 7.4 at 50 microM concentration or preferably more, for less than 2 hours to days, etc. with or without another adjuvant, with or without pathway inhibitors or another anti-inflammatory compound, such as Baricitinib or antivirals including valacyclovir, etc. or an antibiotic if available, where the RNA or DNA of the organism is damaged without damaging the viral or bacterial membrane containing the S-protein (antigen), etc. for vaccine production using the remaining dead viruses or proteins without crosslinking the viral or bacterial proteins, stored in a refrigerator with or without Benzalkonium chloride (BAC) at a low temperature and used for repeated vaccination as needed by nasal inhalation, at a low volume that can be subsequently be increased until neutralizing antibodies are discovered in the body or oral, or intramuscular administration, or as adjuvant to another vaccine prepared by other means, such as mRNA vaccines for nasal inhalation or after the initial use of another vaccine from the same organism, thereby eliminating the need for the standard use of formalin, thimerosal, formaldehyde, glutaraldehyde, etc. which are toxic and produce excessive and lasting inflammation at the site of the administration.

In still a further embodiment, methylene Blue at a 1 mg/L concentration is administered intravenously with LMWH or heparin mimetics or complement inhibitors or pathway inhibitors and at least one or more antivirals, such as remdesivir and valacyclovir, and with or without polyclonal antibodies cocktails and/or anti-inflammatory agents such as Baricitinib, etc. to kill the viral pathogens with or without simultaneous light/laser radiation of the blood inflow tubing, for a period or 4, 8, 16, or 30 minutes followed by dialysis, hemodialysis, serum electrophoresis to remove dead viruses and unwanted toxins and methylene Blue from the blood that is re-infused to the patient.

In yet a further embodiment, one administers a vaccine as a cocktail, etc. to boost the immune response of a person to specific viral, bacterial or fungal pathogens by administering a low dose of a vaccine that is presently used for vaccination, the amount of this booster vaccine can be from 5%-99% of the original volume and its contents, or preferably 10% or 20% or 40% or 60% volume, etc. with or without pathway inhibitors such as Rock, Wnt, GSK or integrin inhibitors, or complement C1, C3, C5 inhibitors, etc. along with or without antivirals, antibiotics or antifungals or with or without an-anti-inflammatory agent, such as a IL-7 inhibitor, DMF or Baricitinib, etc. or an immune enhancer such as spermidine, etc. for inhalation or injected intramuscularly, subcutaneously, or orally or intravenously or preferably by nasal inhalation, as drops or spray, or by an inhaler etc. so the patients can either self-administer the vaccine in different doses at described intervals either before the regular standard vaccination, during the sickness, shortly thereafter, or beyond the original vaccination or sickness to either recognize an allergic response to the vaccine and/or to boost gradually the immune response of the patient who is old or has cancer or is an immunosuppressed patient, where the vaccine can be prepared the standard way of killing the bacteria, or render them defenseless, or using a specific protein part of the virus, or using mRNA, etc. of the virus.

In still a further embodiment, the method further comprises the step of: delivery of oxygen to the patient by extracorporeal membrane oxygenation when the blood oxygenation level of the patient is low.

In another further embodiment, the treatment does not apply any means that provides 100% oxygen to the patient, since 100% oxygen is toxic to the tissue and increases the inflammatory response that is not desirable in patients with COVID-19.

In one embodiment, the amount of oxygen for inhalation is 20-30% or 30-40% or 40-50% or 50-80% best with standard C-Pap used for sleep apnea coupled with an oxygen tube supplying a certain amount of oxygen or with glutathione peroxidase to the air through the nose or mask.

In one embodiment, the treatment is divided into two or three stages, depending on the severity of the lung inflammation, at least one or two antivirals, one to two Rock inhibitors or one to two Wnt inhibitors, one or two GSK inhibitors, or one or two integrin inhibitors, at least one or two protease inhibitors alone or at least one or two IL-1 or IL inhibitors or one to two known antivirals, such as amantadine, nucleoside analogues, such as AZT, aciclovir, ganciclovir, and vidarabine in combinations are used as inhalation where the medication is dissolved in semifluorinated alkanes or combined as polymeric release nanoparticles or one to two known antivirals such as amantadine, nucleoside analogues, such as AZT, aciclovir, ganciclovir, and vidarabine, or again depending on the severity of the disease, e.g., in end-stage disease, one can administer these combination of medications, orally, intravenously, semifluorinated alkanes with alkyl chains are harmless in the examined range from $C_6$ to $C_{10}$ but preferably $C_6$, in addition to inhalation with simultaneous administration of macrolide immune-suppressants, such as cyclosporine A, mycophenolic acid and with heparin or low molecular weight heparin (Lovenox) with or without catechin in a semifluorinated alkane or a suitable medium, such as low carbon perfluorocarbon liquid C4-C6, to block viral receptors, heparan sulfate and Sialic acid, and to enhance nerve repair and prevent blood coagulation, etc. to prevent overactive immune response and blood clot formation and to prevent vascular infarct, a side effect of the COVID-19 infection. Furthermore plasmapheresis, kidney dialysis can be done to remove cytokines with or without extra-corporal oxygenation if blood oxygenation remains low with the ventilator, or along with Glutathione peroxidase, catalase, etc.

In the above-described treatment with two or three stages, the antiviral agents prevent either the attachment of viruses to the cell wall or block their cell penetration or inhibit the virus replication by damaging the nucleic acid (DNA or RNA) of the virus, etc. The anti-inflammatory compounds affect the cell pathway of cell inflammation in response to various agents affecting the cells in a tissue or in an organ. Among the most important anti-inflammatory compounds are Wnt inhibitors that prevent early stage inflammation, Rock inhibitors that prevent rock proteins activation, which blocks TGF beta that stimulates scar formation after the inflammation is controlled. Similarly, integrin inhibitors contribute to healing of the inflamed tissue preventing it from becoming overactive producing over active scarring, and GSK-3 are active in intracellular signaling pathways, involved in cellular proliferation, migration, and apoptosis. Inhibition of GSK-3 contributes to the healing process. GSK-3 inhibitors increase the CD8(+) OT-I CTL function and the clearance of viral infections. Interleukins (ILs) are a group of cytokines produced by cells and participate in a number of inflammatory processes. There are a number of interleukins from IL-1 to IL-17, inhibition of these cytokines significantly reduces an inflammatory response in the tissue produced after a number of diseases, such as bacterial and viral infections, etc. Azidothymidine (AZT) or Zidovudine (ZDV) is an antiretroviral used to prevent and treat HIV/AIDS infection along with Acyclovir, ganciclovir and Vidarabine are active against a broad spectrum of viral infection in patients with AIDS or acquired immunodeficiency syndrome, etc. Semifluorinated alkanes are non-toxic and do not cause irritation, and can carry oxygen used previously as a blood substitute. However, no one has used this characteristic to deliver simultaneously oxygen in the lung simultaneously with other medications by loading them also with oxygen prior to its administration as aerosolized nanodrops or microdrops in the spray system. Semifluorinated alkanes dissolve numerous hydrophilic or hydrophobic compounds. Their temperature transition from liquid to vapor is low, so they can evaporate easily. They can be formed as a liquid compound or can be aerosolized for inhalation through the nose or mouth along with various medications. Their applications are best for surfaces of the skin or mucosa or aerosolized for inhalation to reach the alveoli of the lung, etc. They may not be approved yet for intravenous application. For the latter application, one can use a physiologic solution with a pH of 7-7.5 and osmolality of about 300 mosmol having 0.9% or more saline, to administer the medications intravenously or as spray for inhalation. The anti-inflammatory agents described above, including the anti-virals can be taken orally, such as Zidovudine and Acyclovir, ganciclovir and Vidarabine, etc. However, a formulation of these and others antivirals can be given intravenously or intramuscularly in solution or can be dissolved in semifluorinated alkanes for inhalation.

In one embodiment, a method of drug delivery is described for treatment of respiratory tract inflammatory diseases or encephalitis caused by various viruses, such as influenza, parainfluenza, SAR or coronaviruses, COVID-2 or COVID-19, or their mutations, etc., EBV, Herpes virus, etc., or a bacterial infection, etc., where the anti-viral medications are administered along with cell pathway inhibitors to block an inflammatory response of the tissue which does not inhibit an immune response, such as a Rock inhibitor, Wnt inhibitor, GSK inhibitor, integrin inhibitors, with or without complement pathway inhibitors such as C3 inhibitors—AMY-101 (NCT04395456) and APL-9 (NCT04402060); C5 inhibitors—eculizumab (NCT04346797 and NCT04355494), eculizumab, Ultomiris, and C1 esterase inhibitors, which block the classical complement pathway or in combination, dissolved in a non-toxic or non-irritative semifluorinated alkanes liquid, or other liquids, which are amphiphilic liquids dissolving both hydrophilic and hydrophobic drugs, or as polymeric slow release nanoparticles carrying the medication applied as a spray or evaporative solution or in a evaporative aerosolized drops during the inhalation passing through the nose or mouth or olfactory or trigeminal nerves, etc. to the brain or the lung alveoli, while on the way the nano- or micro-droplets attach to the nerve receptors, fibers of olfactory nerve reaching the olfactory bulb and the brain or attach to the mucosa, epithelia or endothelial cells of the nose pharynx, larynx, epiglottis, trachea, bronchi and lung alveoli. The semifluorinated alkanes rapidly evaporates at body temperature leaving the medication(s) or slow release nanoparticle on the surface of the tissue in the brain or the lung, thus releasing the medication over a time period of one day to one week to 3 weeks or months depending on the composite of the polymer.

In one embodiment, the semifluorinated alkanes or perfluorocarbon liquid which are non-toxic fluidics, and serve as solvents alone or in combination with other solvents, such as polyethylene glycol (PEG) or ethanol, etc., dissolve hydrophobic and hydrophilic medications with ease and thereby enhancing the penetration of the medication in the tissue therefore are best suitable for inhalation, spray or nebulization delivery of medications both to the lung and brain through the respiratory pathway or through the olfactory and trigeminal nerves to the brain.

In one embodiment, the semifluorinated alkanes or perfluorocarbon liquid with low carbon chains evaporate faster in one day to a week, and higher carbon chain forms evaporate in a few weeks to months.

In one embodiment, the low density semifluorinated alkane or perfluorocarbon liquid or another solution are used by mixing them with viral or bacterial or fungi antigens or modified mRNA, for vaccination, or combined with antibodies or other medications, etc. to be administered by injection intramuscular or inside a body cavity or preferably to be applied locally or topically or as an ointment or as a spray or nebulized as micro-droplets or nano-droplets or the vaccination is combined with therapeutic medications such as pathway inhibitors, Rock, Wnt, GSK, or integrin inhibitors or complement inhibitors C1, C3, C5 inhibitors alone or as slow release polymeric nanoparticles for nasal spray or inhaler where the nanodroplets or microdroplets after inhalation locate themselves over the mucosal surfaces of the nose, pharynx, and deliver medication to the mucosal cells or to the blood, etc. and the nanoparticles continue releasing the medications for weeks, or months depending on their compositions to prevent excessive inflammatory or anaphylactic response to the vaccination.

In one embodiment, a low density semifluorinated alkane or perfluorocarbon liquids or another solution are used by mixing them with combinations with various slow release PEGylated polymeric slow release polymeric nanoparticles or microparticles, such as lactic acid, glycolic acid, or in combination or polycaprolactone, porous silicon, anhydride, micelles, liposomes, solid lipids, etc. conjugated with antibodies or other medications, such as antivirals, antibacterials, antifungals, or anti-parasites, etc. to be administered by injection intravenously or inside a body cavity as an emulsion or to be applied locally or topically or injectable emulsion or ointment or as spray or nebulized as microdroplets or nano-droplets for therapeutic medication for nasal inhalation as a spray or inhaler where the nano-drops or micro-drops after inhalation locate themselves over the mucosal surfaces of the nose, pharynx, larynx, bronchi, and alveoli to be positioned between the fluid on the surface of the mucosal cells and the air and prevent dryness of the alveoli mucosa and deliver medication to the cells or to the blood, etc. and the nanoparticles continue releasing the medications for weeks, months or years depending on the compositions.

In one embodiment, oxygenated or non-oxygenated semifluorinated alkanes or perfluorocarbon liquid with carbon chain of 3-10 C with antibody-coated viral-like particles and/or viral-like particles are conjugated with viral antigens administered nasally as a spray or inhalation or repeated in another time interval from one month to one year, etc. as needed to create an immune response to the viral antigen or viral protein or proteins or to the combination of VLP and antigens enhancing the immune response and, since the spray or the inhaler can be stored in the refrigerator, the patient can be instructed to perform repeated self-vaccination as prescribed by the doctor depending on the presence or absence of the neutralizing antibody in the blood of the patient.

In another embodiment, oxygenated or non-oxygenated low density semifluorinated alkanes or a perfluorocarbon liquid with antibody-coated viral-like particles in combination with complement inhibitors administered nasally as a spray or inhalation and repeated in another time of one month to one year as needed to create an immune response to the viral antigens or viral proteins while complement inhibitors reduce the allergic response to the antigens or VLPs, the spray or the inhaler can be stored in the refrigerator, and the patient can be instructed to perform repeated self-vaccination as prescribed by the doctor depending on the presence or absence of neutralizing antibody in the blood of the patient.

In one embodiment, the antibody-coated PEGylated polymeric slow release nanoparticles with desired medications are mixed with a low density oxygenated or non-oxygenated semifluorinated alkanes (SFA) having 4-8 carbons and 100% oxygen in the container that is capable of delivering a puff of oxygen and nebulized SFA or perfluorocarbon liquids at a low carbon chain of 4-8 carbons that evaporate within one week to a month or longer depending on the carbon chain.

In one embodiment, the oxygenated semifluorinated alkanes (SFA) carries PEGylated nanoparticles that carry the needed gene(s) along with CRISPR with a cationic compound and thiol where the gene delivery is done through the nasal delivery or with an inhaler to the lung to modify genetic defect of the alveolar cells, etc. such as pulmonary fibrosis, the nanoparticles are conjugated with thiol or cell penetrating peptides to enhance their penetration in the cells.

In one embodiment, the oxygenated or non-oxygenated semifluorinated alkanes/nanoparticle emulsions evaporate and leave the slow release polymeric nanoparticles on the cell surface to release the medication for a long time to the lung, or brain, or in the circulation.

In one embodiment, the oxygenated or non-oxygenated semifluorinated alkanes or perfluorocarbon liquids are administered by spraying, nebulization or an inhaler along with medications where the droplets of SFA or PFCL pass through the nasal pathways to the lung alveoli where they can pick up oxygen from the air or blood and release them when the blood oxygen concentration drops below 94%.

In another embodiment, the semifluorinated alkane with an emulsion of polymeric release nanoparticles and genes penetrate or are picked up through the cell membrane where the medication is released or they may picked up by the endothelial cells and enter the circulation to continue being active and release the medication elsewhere in the body such as lung, heart, and brain, etc.

In one embodiment, a low density semifluorinated emulsion with antibody-coated particles carrying the medication are picked up by the neuronal cells in the mucosal cells of the nose and elsewhere, and travel to the brain through the olfactory nerve and bulb or through the trigeminal nerves brought to the brain and are released to treat viral bacterial, or fungal encephalitis.

In one embodiment, the semifluorinated emulsion with antibody-coated slow release polymeric nanoparticles carrying the medication such as antivirals, antibiotics, or antifungals alone or in combination with pathway inhibitors or complement inhibitors where the nanoparticles are picked up by the neuronal cells, in the mucosal lining of the nose and elsewhere and travel to the brain through the olfactory nerve and bulb or through the trigeminal nerves brought to the brain and are released to treat viral bacterial, or fungal encephalitis, or chronic inflammatory diseases, such as Alzheimer's disease or Parkinson's disease.

In one embodiment, the inhaled semifluorinated alkanes with nano-droplets and/or micro-droplets work as lubricants in the respiratory tract after their inhalation by nasal spray or nebulization or through an inhaler reducing the dryness of the respiratory pathways.

In one embodiment, the oxygenated semifluorinated alkanes and polymeric slow release nanoparticles can enhance medication penetration in the tissue such as antiviral, protease inhibitors, or polymerase inhibitors or transcriptase inhibitors (NRTIs) and since they are not nutrients will prevent bacterial growth on them and the oxygen damages the bacteria and viruses enhancing the effect of antivirals and antibiotics or antifungal medication on these organisms.

In one embodiment, a method of drug delivery is described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication is administered in a physiological solution or semifluorinated alkane or a physiological liquid or a suitable medium along with cell pathway inhibitors to block an inflammatory response of the tissue which does not inhibit immune response, such as Rock inhibitors such as Fasudil hydrochloride, or ROCK2, Fasudil1-(5-Isoquinolinesulfonyl)-2 Methylpiperazine Calcium Channel Blockers, or as SAR407899, or Inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor Y-27632 dihydrochloride, Botox or botulinum toxin in conjunction with at least two antivirals, such as Glidesivir, Favipiravir, Remdesivir, nanoviricides, GS-6207 (Lenacapavir/Gilead) in picomolar concentration, or GS-CA1, Oya1, umifenovir, tamivir ribavirin dissolved in a liquid semifluorinated alkanes, or other liquids, or as polymeric slow release nanoparticles applied as drops or spray or evaporative solution or in a evaporative aerosolized nano- to micro-drops that travels through the nasal mucosa to reach the lung alveoli, while on the way, attaches to the mucosa, epithelia or endothelial cells or nose pharynx, larynx, epiglottis, trachea, bronchi and lung alveoli. The semifluorinated alkanes rapidly evaporate at body temperature leaving the medication(s) or slow release nanoparticles of polylactic, polyglycolic acid or combination thereof, or combination of polycaprolactone, anhydrides, porous silicone, micelles, and/or liposomes on the surface of the tissue or slow release nanoparticles on the surface of the tissue, releasing the medication over a time period of one day to one week to 3 weeks or months depending on the composite of the polymer.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medications are administered in a physiological solution or semifluorinated alkane or a physiological liquid or a suitable medium with a cell pathway inhibitor to block an inflammatory response of the tissue which does not inhibit an immune response, such as in a physiologic pH adjusted to 7-7.5 pH and osmolarity of 280-300 mOsm or slow release polymeric nanoparticles from the Wnt compound, such as FH535, IWP-2, PNU-74654, IWR-lendo, IWR-exo, Demethoxycurcumin, CCTO36477, KY02111, WAY-316606, SFRP, IWP, LGK974, C59, Ant1.4Br/Ant 1.4Cl, Ivermectin, Niclosamide, apicularen and bafilomycin, XAV939, XAV939, G007-LK and G244-LM, NSC668036, SB-216763, gemtuzumab, etc., small molecule Wnt inhibitor PKF118-310, the Wnt/β-catenin pathway inhibitor dissolved in a liquid semifluorinated alkane, or other liquids, or as polymeric slow release nanoparticles applied as a spray or evaporative solution or in evaporative aerosolized drops that travel through the nasal mucosa to reach the lung alveoli while on the way attaches to the mucosal, epithelial, or endothelial cells of nose pharynx, larynx, epiglottis, trachea, bronchi and lung alveoli. The semifluorinated alkane rapidly evaporates at body temperature, thereby leaving the medication(s) or slow release nanoparticles on the surface of the tissue, releasing the medication over a time period of one day to one week to 3 weeks or months depending on the composite of the polymer.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication is administered in a physiological solution or semifluorinated alkane or a physiological liquid or a suitable medium with a cell pathway inhibitor to block an inflammatory response of the tissue which does not inhibit an immune response like steroids, the cell pathway inhibitor being, for example, a GSK 269962 inhibitor or GSK inhibitors, such as synthetic small-molecule ATP-competitive inhibitors, and substrate-competitive inhibitors, non-ATP-competitive inhibitors, where FRAT/GBP competes with Axin inhibiting GSK-3 activity or anti-integrins such as Risuteganib, vedolizumab, anti-integrins, such as abciximab, Eptifibatide, Tirofiban, αIIbβ3 antagonists, Natalizumab, 3 mg to ±52 µg/mL, MLN-00002, Firategrast, IVL745, antagonists of αvβ3 and/or αvβ5 integrins, Vitaxin, Abegrin, CNTO95, Cilengitide. MLD-based disintegrins, L000845704, SB273005, Volociximab, JSM6427 or dissolved in a liquid semifluorinated alkanes or other liquids with other medications or as polymeric slow release nanoparticles applied as a spray or evaporative solution or in evaporative aerosolized drops that travels through the nasal mucosa to reach the lung alveoli while on the way attaching to the mucosal, epithelial or endothelial cells or nose pharynx, larynx, epiglottis, trachea, bronchi and lung alveoli where the semifluorinated alkane/medication(s) rapidly evaporates leaving the medication(s) or slow release nanoparticles on the surface of these organs after inhaling one time to 10 times as needed, thereby releasing the medication over a time from one day to 2 weeks or more. However, the dose applied through this methodology is <30 times in concentration compared to systemic medication given intravenously, etc. and it is more effective locally, to combat the viruses and their complications.

In one embodiment, a method of drug delivery described for treatment of respiratory tract inflammatory diseases caused by various viruses, such as influenza, parainfluenza, SAR or coronaviruses, COVID-2 or COVID-19 or their mutations, etc., EBV, Herpes virus, etc., or bacterial infections, etc. where the anti-viral medications are administered in a physiological solution or semifluorinated alkane or a physiological liquid or a suitable medium with IL-1 and/or IL-6 inhibitors, such as Kevzara (sarilumab) or nitric oxide (NO) donor (NONOate), interleukin antagonists, or in combination with Rock inhibitors, etc. to block inflammatory response IL-6 of the tissue which does not inhibit immune response (as steroids do), dissolved in liquid semifluorinated alkanes or other liquids with other medications or as polymeric slow release nanoparticles applied as a spray or an evaporative solution or in evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where dissolved medication in the semifluorinated alkanes rapidly evaporates from the lung leaving the medication(s) and/or slow release nanoparticles on the surface of these organs after inhaling, one time to 10 times or more as needed releasing the medication over a time period from one day to 2 weeks or more.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication is administered in a physiological solution or semifluorinated alkane or a physiological liquid or a suitable medium with a protease inhibitor, such as Ebselen, an inhibitor to target SARS-CoV-2, COVID-19, or their mutations, Mpro or Ganovo to block the entry of the virus in the cell dissolved in a liquid semifluorinated alkane or other liquids which does not cause irritation, with other medications, or as polymeric slow release nanoparticles applied as a spray or evaporative solution or in a evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where the semifluorinated alkane rapidly evaporates leaving the medication(s) or slow release nanoparticles on the surface of these organs after inhaling one time to 10 times as needed, thereby releasing the medication over a time from one day to 2 weeks to months or years.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus etc., or bacterial infections, etc. where the anti-viral medication such as Lopinavir, or linebacker and equivir, or HIV protease inhibitor darunavir, is administered in a physiological solution or semifluorinated alkane or a physiological liquid or a suitable medium with a protease inhibitor such as Ganovo or INO-4800 to block the entry of the virus into the cell and APNO1 an angiotensin converting enzyme 2 to block the virus adhesion to the cells, or in combination with a Rock inhibitor, Wnt inhibitor, GSK inhibitor, or integrin inhibitor or IL-1 or IL-6 inhibitor Kevzara or nitric oxide (NO) donor (NONOate) or interleukin antagonists, such as anakinra, dissolved in a liquid semifluorinated alkane or other liquids with other medications as a nanoparticle compound or as polymeric slow release nanoparticles applied as spray or evaporative solution or in evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where the semifluorinated alkane rapidly evaporates because of high body temperature, leaving the medication(s) or slow release nanoparticles on the surface of these organs after inhaling one time to 10 times or more as needed, releasing the medication over a time from one day to 2 weeks to months or years in the chronic disease of the lung.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial or fungal infections, etc. where the anti-viral medication such as Lopinavir, or linebacker and equivir, Arbidol, NanoViricide and/or an HIV protease inhibitor darunavir, is administered in a physiological solution or semifluorinated alkane or a physiological liquid or a suitable medium with a protease inhibitor such as Ganovo or INO-4800 to block the entry of the virus to the cell and APNO1 an angiotensin converting enzyme 2 to block the virus adhesion to the cells, or in combination with PolyTop mAb therapy or cocktail of antibody therapy by Regeneron Velochimmune or Vir's antibody platform or VAAST platform human monoclonal antibody or TZLS-501 an IL 6 inhibitor or Kevzara or Actems Tocilizumab with Rock inhibitors, Wnt inhibitors, GSK inhibitors or integrin inhibitors or anti-bacteria or antifungal or IL-1 inhibitors dissolved in a liquid semifluorinated alkane or other liquids and other medications and polymeric slow release nanoparticles are applied as a spray or evaporative solution or in evaporative aerosolized drops that travel through the nasal mucosa or mouth to reach the lung alveoli while on the way attaching to the mucosal, epithelial or endothelial cells or nose pharynx, larynx, epiglottis, trachea, bronchi and lung alveoli where the semifluorinated alkane/medication(s) rapidly evaporates leaving the medication(s) or slow release nanoparticles on the surface of these organs after inhaling one time to 10 times or more as needed releasing the medication over a time from one day to 2 weeks, months, or years.

In one embodiment, after inhalation or systemic treatment of viral inflammation with antivirals, a severe inflammatory response is treated with Rock, Wnt, GSK, or integrin inhibitors alone or in conjunction with other therapeutic immunosuppressant agents dissolved in the semifluorinated alkanes or other liquids with other medications, such as a macrolide, cyclosporine A, mycophenolic acid, ascomycin Immunomycin, FR-900520, FK520, is an ethyl analogue of tacrolimus (FK506) for inhalation, can reduce the overt inflammatory response of the disease process; while MPA inhibits inosine monophosphate dehydrogenase. Mycophenolate mofetil alone, or in combination with a protease inhibitor, and reverse transcriptase inhibitor abacavir, and polymerase inhibitor, remdesivir, prevents most viral replications by depletion of Guanine, depletion of guanosine in substrate guanine triphosphate (GTP), while simultaneously preventing endoplasmic stress induced by viral infections in the neuronal cells, thereby preventing neurofibrillary and misfolding of proteins such as amyloid, however, in a later stage of the disease, steroids can be used even though steroids have their unwanted side effects and also can be replaced with NSAIDs that are more desirable, however, inhalation, or by an inhaler would be preferable to systemic therapy, except in desperate end stage cases where systemic steroids, such as prednisone, dexamethasone, fluoroquinolone, etc. might be useful in combination with antivirals and antibacterials, such as Tetracycline derivative medications, a metalloproteinase inhibitor, demeclocycline, doxycycline, Adoxa, Vibramycin, Minocycline, Minocin, etc. to treat inflammatory viral lung or brain infections through the nasal inhalation, etc.

In one embodiment, in an immunosuppressed individual after organ transplantation, for viral infection prophylaxis or therapeutically in addition to inhalation therapy, systemic administration of natural killer cells or modified killer T-cells systemically along with Wnt, Rock, GSK inhibitors and integrin inhibitors, antibiotics such as, Tetracycline derivative medications a metalloproteinase inhibitor, include Demeclocycline, Doxycycline, Adoxa, Vibramycin, Minocycline, Minocin, antifungals, both as inhalation dissolved in semifluorinated alkanes or other liquids, or systemically can be given to combat an inflammation or any superinfection with bacteria and fungi which require additional antibacterial and/or antifungal medications can be administered in a physiological solution or semifluorinated alkane or a physiological liquid or a suitable medium both systemically, inside a body cavity, or by inhalation dissolved in semifluorinated alkanes or other liquids as needed.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication such as Lopinavir, favipiravir or linebacker and equivir, unifenovir and a vaccine, such as lipid-encapsulated mRNA 1273, COVID-19 S-Timer, or SARS-COVID-2, viral-like particles (VLP) or an adjuvant or viral Lily vaccine etc. with antibody-coated nanoparticles administered simultaneously or sequentially with a Rock inhibitor, Wnt inhibitor, GSK inhibitor, or integrin inhibitor in a solution or dissolved in a liquid semifluorinated alkane or other liquids with other medications or as polymeric slow release nanoparticles applied as a spray or evaporative solution or in evaporative aerosolized drops that travel through the nasal mucosa to reach the lung alveoli while on the way attaching to the mucosal, epithelial, or endothelial cells or nose, pharynx, larynx, epiglottis, trachea, bronchi and lung alveoli where the semifluorinated alkane rapidly evaporates leaving the medication(s) or slow release nanoparticles on the surface of these organs after one or more times of inhalation as needed.

In one embodiment, a vaccine prepared as described with methylene blue is administered prophylactically or therapeutically alone or with one or more antivirals in a physiological solution or semifluorinated alkane or a physiological liquid with or without LMWH in a suitable medium administered by inhalation, or intranasally, by ointment, orally as pills to a patient every 2-4 months or at a lower quantity to prevent re-infection by a coronavirus that causes COVID-19 or its mutations, etc.

In one embodiment, the described medications can be supported by frequent inhalation and oral administration of Glutathione peroxidase, catalase, flavonoid, containing polyphenyls, epigallocatechin gallate catechins (EGCG) having antioxidants compounds found in black tea, coffee, oolong, white tea, Pu-reh, Chamomile tea, the vegetable, such as fruits or coco, Mpro enzyme inhibitors and antioxidant, antimicrobial, antidiabetic, antiallergic, anticancer, hypocholesterolemic, statins and immunomodulatory mangiferin, genistein, estradiol, berberine and baicalein, sulforaphane, vitamin D and high doses of vitamin C, vitamin E, D, or quercetin, curcumin, resveratrol, Alpha-lipoic acid, tocopherols and tocotrienols, carotenoids, glutathione tocopherols, carotenoids, and other plant based Wnt inhibitors, ivermectin, niclosamide, etc. reducing excessive glutamate that can cause neuronal death, and Alzheimer's disease.

In one embodiment, a patient is treated with a combination of remdesivir, a Wnt inhibitor (e.g., Ivermectin), and a protease inhibitor, such as ritonavir or Ganovo, dissolved in a semifluorinated alkane or other liquids used for inhalation 4 times along with supportive therapy for 3 weeks to produce a gradual recovery.

In one embodiment, in early coronavirus infection, it is treated with a combination of an antiviral medication such as Remdesivir, oseltamivir ribavirin at non-toxic concentrations or Rock inhibitor or Wnt inhibitor, or GSK inhibitor or integrin inhibitor at non-toxic concentrations in a liquid of semifluorinated alkanes or other liquids which does not cause irritation, sprayed in the nose or through the mouth or nebulized for deep breathing through the mouth 1-10 times or more as needed.

In one embodiment, a patient who tests positive for an influenza virus test is treated with a combination of fasudil, a Rock inhibitor and oseltamivir (Tamiflu) in a semifluorinated alkane for inhalation 4 times daily dissolved in semifluorinated alkane or other liquids and oral Tylenol, and baby aspirin 2-3 times daily as needed, and his symptoms improve gradually within 3 days while he is on therapy, and he is followed for 5 weeks until the symptoms completely subside and he is able to return to work.

In one embodiment, in early coronavirus infection without history of hypertension or known cardiac disease, QTC prolongation or failure, stent or infarct, it is treated with a combination of an antiviral medication such as Remdesivir, tamivir, ribavirin at non-toxic concentrations and/or Rock inhibitor or Wnt inhibitor, or GSK inhibitor or integrin inhibitor, TGF beta inhibitors or in combinations, at non-toxic low concentration of Hydroxychloroquine/chloroquine and amodiaquine which has shown some efficacy against viruses such as HIV, Zika virus, even SARS-CoV, by oral administration high doses of 400 mg to 600 mg with the side effect of heart and kidney disease, but low concentrations of 6 mg or less were used in a liquid semifluorinated alkane which does not cause irritation, sprayed in the nose, or through the mouth, or nebulized for inhalation, deep breathing through the mouth 1-4 times or more as needed to block intracellular penetration of the virus. Of note is that previously high oral doses of 600 mg Hydroxychloroquine/chloroquine and amodiaquine had been given orally and not by inhalation at 1/100 of the oral dose. The oral daily administration can have serious systemic complications.

In one embodiment, antivirals alone or combined with protease inhibitors, such as Ganovo, or with convalescent plasma, antibody against COVID-19, Baricitinib, etc. can be administered when dissolved in semifluorinated alkanes or other liquids which does not cause irritation, sprayed in the nose or through the mouth or nebulized for inhalation, with C-Puff for deep breathing through the mouth 1-4 times daily or as slow release polymeric nanoparticles once for prophylactic viral upper respiratory tract prior to the start of the infection or in situations that one suspects that he or she might come or have come in contact with a person carrying viral diseases wherein the antiviral can be chosen depending on the expectation of specific viruses and the treatment can continue for a period of time until the danger passes, e.g., in traveling by plane to certain areas with reported cases.

In one embodiment, a person prophylactically self-administers a daily application of combination therapy with oseltamivir (Tamiflu) and Baricitinib, and a GSK inhibitor, intra-nasally followed with deep breathing 3-4 times daily in a semifluorinated alkane for 3 days until he returns from a trip. The person is then examined for signs of COVID-19 disease. The person feels that the medication is well tolerated and no side effects are produced, his repeat examination shows he is normal with no fever, cough, or running nose, etc.

In one embodiment, a method of drug delivery described for treatment of respiratory tract inflammatory diseases caused by various viruses, bacteria, etc. or chronic smoking or exposure to toxic aerosolized nanoparticles and air pollution or asthma and allergens and pathogens, where the inflammation or its consequences are treated with an inflammatory cell pathway inhibitor to block the inflammatory response of the tissue while it does not inhibit an immune response, such as a Rock inhibitor, Wnt inhibitor, GSK inhibitor, or integrin inhibitors IL-1 and IL-6 inhibitors dissolved in liquid semifluorinated alkanes or other liquids as the drug, or in polymeric slow release nanoparticles applied locally as a spray or evaporative solution or in evaporative aerosolized drops that travels through the nasal cavity or mouth to reach the lung alveoli and while on the way attaching to the mucosa, epithelial or endothelial cells of the mouth, nose throat, pharynx, larynx, epiglottis, trachea, bronchi and lung alveoli where the semifluorinated alkanes which is non-toxic or causes irritation to the tissue, rapidly evaporates leaving the medication(s) or slow release nanoparticles, such as polymeric lactic, glycolic acid, or in combination, or porous silicon or polycaprolactone, etc. on the surface of these tissues, releasing the medications over a time of daily inhalation, daily for one week to 3 weeks, then the release of the medication from the nanoparticles continues for months or years to inhibit chronic inflammatory lung diseases.

In one embodiment, the disease process affects many other organs and creates an inflammatory response that can damage these organs, such as in bacterial or viral infections or immune or autoimmune response, chronic inflammation of the prostate, gastro-intestinal tract, joints, one applies a similar strategy for treatment combining anti-bacterial and antiviral with Rock inhibitors, Wnt inhibitors, GSK inhibitors, and integrin inhibitors, IL-6 inhibitors, Baricitinib interleukin antagonists (anakinra), in a known non-toxic dose administered locally, systematically, or orally either with semifluorinated alkane or the standard way in a physiological solution, or in the form of polymeric functionalized nanoparticles for slow release of the medication.

In one embodiment, the patient having a cytokine storm as a result of a viral infection and body's cellular immune/humoral response receiving the inventive therapy, undergoes plasmapheresis to remove, e.g., such cytokines, enzymes, dead cells, etc. from the circulation. Plasmapheresis is a known method to remove unwanted toxic components from blood plasma. Because the patient's plasma is treated extracorporeal, then reinfused, in contrast to reinfusing only cellular components of the patient's blood, plasmapheresis also beneficially detoxifies the patient's plasma without compromising blood volume and with minimal or no fluid loss. This technique avoids the serious complications and side effects of simply returning the cellular components of the blood to the patient. Additionally, all precautions are observed to avoid hypotension and loss of calcium ions in the process of citrate anticoagulation that this procedure requires. The patient can be treated initially with presently available anticoagulants such as heparin, or low molecular weight heparin, polyphenols, such as catechins, coumadin, etc., which can be immediately neutralized post-procedure. Neutralization uses standard techniques known in the art, such as calcium, etc. Hemofiltration treatment is performed with activated carbon, treatment on non-ionic exchange resins, etc. for removing free toxins and also toxin bound with plasma proteins, etc. as in renal dialysis methods. The process may be instituted or repeated as needed. The addition of Rock inhibitors or Wnt inhibitors, GSK inhibitors, integrin inhibitors, IL-1 inhibitors, or IL-6 inhibitors along with other therapeutic agents, such as disulfiram, anakinra, or macrolide immune suppressants such as cyclosporine, Tacrolimus, mycophenolic acid, Ascomycin, Immunomycin, FR-900520, FK520, is an ethyl analogue of tacrolimus (FK506) which can be administered in a physiological solution or semifluorinated alkane or a physiological liquid or a suitable medium, systemically or for inhalation dissolved in semifluorinated alkanes or a suitable medium can reduce the overt inflammatory response seen in immune therapy or an autoimmune disease. In some cases with kidney involvement or its protection, kidney dialysis, hemodialysis and or serum electrophoresis is done to remove unwanted toxins and creatinine, etc.

The viral and microbial pathogens can gain access to the brain passing through the damaged endothelial cells of the brain or spinal cord vessels through the circulation or alternatively through the olfactory or trigeminal nerves directly bypassing all barriers of the brain. In one embodiment, a similar route through the nasal mucosa can be utilized to deliver medications such as antivirals or antibiotics such as rifampin and Rock inhibitors to fight the pathogens or provide medications needed to enhance brain nerve survival such as in Alzheimer's disease or Parkinson's disease, etc.

In one embodiment, the viruses are transmitted to brain via circulation using transcellular penetration of the brain capillaries with infected leukocytes.

In one embodiment, the virus gains access to the tissue by using the ACE2 cell receptors of the nasal epithelial cells with the assistance of TMPRSS2 and Purine protein that are found in the mucosa lining of the nose where they reside and multiply before moving toward the respiratory airways and the lung or use the existing channels that lead to the brain through the olfactory nerve or trigeminal nerves. In one embodiment, one can block these enzymes using Rock inhibitors or other protease inhibitors at microgram to milligram concentrations of Rock inhibitors, Wnt inhibitors, GSK inhibitors, or integrin inhibitors, or low concentrations of hydroxychloroquine and amodiaquine at 1-6 milligrams in solubilized or aerosolized formulation for inhalation, etc. or blocks the viruses by at least two antivirals such as Tamiflu, Baricitinib, Glidesivir, Tonofovir Disproxil fumarate, lamivudine, efavirenz, Delutegravir and maraviroc, or Velpatasvir, JFD00244, etc. a SIRT2 inhibitor affecting nsp16 protein, or in combinations, Favipiravir, nitazoxanide, Xofluza, Remdesivir, nanoviricides, Oya1, umifenovir, tamivir ribavirin dissolved in liquid semifluorinated alkanes or other physiological liquids in combination or sequentially.

In one embodiment, one or at least two antivirals are used with Rock inhibitors, Wnt inhibitors, GSK inhibitors, or integrin inhibitors as polymeric slow release nanoparticles applied as drops or spray or an evaporative solution or dissolved in liquid semifluorinated alkanes or other physiological liquids, in an evaporative aerosolized nano- to micro-drops that travels through the nasal mucosa to reach the branches of trigeminal nerve or olfactory nerve to the brain, brain vasculature, and cerebrospinal fluid where the semifluorinated alkanes rapidly evaporate at body temperature in the tissue leaving the medication(s) or slow release nanoparticles of polylactic, polyglycolic acid, polycaprolactone, porous silicon, micelles or liposomes combination thereof, or the medications move in the respiratory tract, through the nose, throat, and bronchi to the lung alveoli, and release slowly the medications from the nanoparticles over a time period of one day or one week to 3 weeks or months depending on the composition of the nanoparticles.

In one embodiment, the slow release polymeric pluralities of nanoparticles are conjugated with a viral specific antibody while carrying at least one or two antivirals to specifically target the viruses.

In one embodiment, the viral antibody can be obtained from plasma/serum of the patients who have recovered from the infection or the antibody can be produced in the tissue culture against the dead viruses which is cultured with T-cell lymphocytes or natural killers that produce the antibody in addition to producing exosomes or extracellular vesicles (ECV) that can both be harvested to be conjugated with the slow release polymeric nanoparticles or alone to be used for intranasal administration to travel to the brain and lung and kill viruses and the ECV contribute to recovery of the brain and its vasculature by their anti-inflammatory effect.

In one embodiment, the viral antibody coated polymeric nanoparticles are conjugated with antivirals and pluralities of antibodies coated nanoparticles combined with cellular pathway inhibitors or IL-1 and/or IL-6 inhibitors, such as kevzara or nitric oxide (NO) donor (NONOate), interleukin antagonists or rituximab, tocilizumab, etc. administered intra-nasally by inhalation and the same delivery system of semifluorinated alkane or a physiological saline solution with slow release polymeric nanoparticles to seek the viruses, release the medication and block their entry to the endothelial cells, brain, etc. or kill the viruses while releasing the medications and protecting the nose, lung, or brain tissue from further invasion of viruses and reducing the inflammation of the brain and the nerves involved that cause neuralgia and pain.

In one embodiment, pluralities of viral or a fragment of the viral S protein antibody(s) coated polymeric nanoparticles are conjugated with CPP, or ACPP and one or two antivirals with semifluorinated alkanes or a solution is administered intra-nasally, intravenously intramuscularly, topically to enhance cell penetration of the nanoparticle inside the cells to damage the viruses outside the cells and those which have penetrated the cells In one embodiment, pluralities of ACE-2 or neuropilin receptors antibody(s) coated polymeric nanoparticles or LNP are conjugated with CPP, or ACPP, or heparin or catechins or linoleic acid and one or two antivirals to block the viruses to enter the cells via ACE-receptors or neuropilin receptors inside the cells by nasal or topical, or systemic administration.

In one embodiment, after inhalation of antivirals, and cellular pathway inhibitors or IL-1 and/or IL 6 inhibitors, such as kevzara of rituximab, tocilizumab, etc. are absorbed through the lung capillaries in the blood and travel to the heart and brain via circulation first, before they are diluted as is the case with intravenous administration, since in brain vasculitis, the blood brain barrier (BBB) is broken, the medication and nanoparticles or LNP gain access rapidly to the inflamed areas of the brain where the medication is released over a long time protecting the brain substance and preventing fibrin induced beta amyloid oligomers production and microglial proliferation that encourages a chronic inflammation leading to Alzheimer disease, dementia or neuralgia, etc.

In one embodiment, the intranasal administration and inhalation reduces the side effects or systemic administration of medications, such as cellular pathway inhibitors or IL-1 and/or IL 6 inhibitors such as kevzara of rituximab, tocilizumab, or antivirals, etc. because the medication reaches directly to the source of inflammation and it is applied at a significantly lower dose than the systemic administration of these medications.

In one embodiment, the medications can be simultaneously administered in a physiological solution or semifluorinated alkane or a physiological liquid or a suitable medium orally, intravenously and nasally as spray, ointment with or without methylene blue with or without tetracycline or doxycycline with heparin as a prophylactic with LMWH to prevent entry of the virus inside the cell by blocking the Furin endoprotease or metalloproteinase inhibitors or heparin mimetics with metalloproteinase inhibitors, such as doxycycline, etc., as needed for therapy and/or as prophylaxis of the viral infection when traveling, or flying by airplane, etc.

In one embodiment, Hypochlorous acid (HOCL) is produced by myeloid cells such as neutrophils, immune cells, eosinophils, mononuclear phagocytes, and B lymphocytes. The non-myeloid cells such as fibrocytes, etc. can also generate Hypochlorous acid (HOC1) in the presence of a solution of sodium chloride (NaCl) in the tissue.

In one embodiment, the stabilized Hypochlorous acid is in general prepared in a physiological saline solution of 0.9%-1.5%, preferably 1%, with Hypochlorous acid at 0.01%, 0.03%, and 0.1% w/v at pH of 3.0-5.0 and the concentration of 0.1 to 2.8 µg/ml. In the cell, the primary enzyme responsible for production of the Hypochlorous acid in presence of NaCl is myeloperoxidase found in phagosomes. In one embodiment, hypochlorous acid is conjugated with taurine that is an antioxidant reducing to toxicity of Hypochlorous acid when it is used in combination of other medications to treat respiratory disease or medication is intended to reach brain through the nasal administration.

In one embodiment, stabilized Hypochlorous acid or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] and slow release polymeric nanoparticles carrying at least two antivirals and Rock inhibitors or GSK inhibitors or Wnt inhibitors and IL-6 inhibitors, interleukin antagonists, etc. are administered in a physiological solution of or Benzalkonium chloride or semifluorinated alkane or a physiological liquid or a suitable solution in the nose as inhalation in spray or nebulized form in viral encephalitis or lung inflammation in SARS-CoV-2, COVID-19, or their mutations to kill the viruses and prevent the side effects of inflammation in the brain and lung.

In one embodiment, stabilized Hypochlorous acid or chloramines, the stable N-chloro derivatives and slow release polymeric nanoparticles carrying at least two antivirals and Rock inhibitors or GSK inhibitors and IL-6 inhibitors, etc. are administered in a physiological solution or semifluorinated alkane or a physiological liquid along with heparin or low molecular weight heparin, or heparin mimetics or synthetic heparin, such as PG500 and PG545, or polyphenols such as catechins or Ebselen and/or glutathione peroxidase, and superoxide dismutase (SOD)—metabolize oxidative toxic intermediates requiring zinc, selenium, manganese iron, copper, and for ideal catalytic activity applied in the nose as inhalation, in spray or nebulized form to treat viral encephalitis or lung inflammation in SARS-CoV-2, COVID-19, or their mutations to kill the viruses, etc., such as coronaviruses and prevent the side effects of inflammation or as prophylaxis of viral infection in the respiratory tract, encephalitis, vasculitis, dementia, and neuralgia, etc.

In one embodiment, one can administer prophylactically, one or two antivirals as nasal spray, aerosolized or nebulized form, or oral zinc lozenges, or zinc orally at about 15 mg/day, vitamin D<than 4000 IU/day, atrovastatin or other statins oral 10-50 mg/day more and/or gargle with salt and lukewarm water at a salt concentration of >0.9% to 1.5% or more Na Cl or spray it as aerosolized or nebulized for nasal inhalation, etc. to damage the invading viruses before entering the nasal mucosa, etc.

In one embodiment, increasing the salt concentration enhances the action of the myeloperoxidase to create Hypochlorous acid or chloramines, the stable N-chloro derivatives to fight viruses.

In one embodiment, one can administer prophylactically, antiviral nasal spray, aerosolized or nebulized form of zinc or oral zinc lozenges, or zinc at about 15 mg, vitamin D<than 4000 IU/day and/or with salt and lukewarm water or as spray it as aerosolized or nebulized for nasal inhalation, or hydrogen peroxide at <3% concentration mouthwash or gargle in a short time.

In one embodiment, the mouthwash Listerine in low concentrations or diluted form can be applied to the nose, mouth, or throat mucosa to eliminate viruses.

In one embodiment, povidone iodine toxicity to the eye was tested after injection in the eye 0.1 mL of 50, 100, 200, or 400 micrograms (microg) of PVP-I in 1 eye without toxic effect; higher concentrations of 100 milligrams to 1000 milligrams or more has been used routinely to sterilize the skin prior to surgery.

In one embodiment, povidone iodine at 400 micrograms to 10 milligrams or more can be used as inhalation/day, inhalation through both nostrils for 1-14 days or using Q-tipped applicator with a mixture of 1-20% ethanol and 0.1-1% or more povidone iodide or other iodine preparations, such as cadexomer, Inadine, tincture of iodine iodophor, lugol iodine, etc. can be administered with or without Ebselen and/or glutathione peroxidase, and superoxide dismutase (SOD)—metabolize oxidative toxic intermediates requiring zinc, selenium, manganese iron, copper, and for ideal catalytic activity applied in the nose in a physiological solution or semifluorinated alkane or a physiological liquid or another medium to eliminate viruses and bacteria in the nose respiratory tract.

In one embodiment, Povidone iodine 0.1% is combined with zinc <15 mg in a solution or ointment, etc. applied to the skin of the upper lip, nasal skin, and nose mucosa entrance to damage the invading viruses/bacteria before entering the nasal mucosal cells, etc. reducing the chance of the infection during traveling by plane, etc.

In one embodiment, squalene nanoparticles combined with riboflavin applied to the nose and exposed to a low level of UV radiation of 3 mW/cm2 for one minute damage the viral particles in the nose without crosslinking the nasal proteins.

In one embodiment, the hypochlorous acid (HOCL) is stabilized at PH 5 and less can be applied as drops or spray or nebulized form locally or by inhalation to the nose and its surrounding tissue to eliminate viruses.

In one embodiment, the stabilized hypochlorous solution is acid at a pH 3 to pH 9 and the concentration of 0.01% to about 0.05% or in a semifluorinated alkane or liquid as a slow release nanoparticles of lactic acid, polyglycolic acid, polycaprolactone, or as micelles or in liposomes for nasal or inhalation as spray or aerosolized form.

In one embodiment, the purpose of the invention is to block the viruses, such as SARS-CoV-2, COVID-19, or their mutations, influenza, herpes, zoster, Zika, Epstein-bar, HIV etc. at different levels of entry in the cell or block the mechanisms involved in its replication and release of the virus including the virucidal activity by preventing attachment or of the viruses' glycoprotein with the glycosylated host protein on the cell membrane surface or inside the cell preventing its capsid formation by inhibiting viral reverse transcriptase, preventing the DNA or RNA transport to the nucleus, or the viral integrase and viral integration in the chromosome, or preventing viral protease to breakdown the cell protein to build viral capsid, or by inducing an innate immune response, such as stimulation of complement C1, C3, C5, toll-like receptors and NK cells and cytotoxic T cells. Other approaches are the use of venom peptides affecting the viral replication cycle, inhibiting viral attachment glycoprotein to the cells, such as ChTx and Scyllatoxin-based mimetics or cecropin A, Magainin or by preventing attachment of virus glycoprotein to CXCR4 and CCR5 co-receptors or disintegration of viral capsid or interfering with the reverse transcription using melittin peptides or preventing the viral assembly of the viral capsid using peptide hecate and interfering in the assembly of the viral capsid and in the organization of the polymerase complex or using peptides derived from Wasp venom to affect Zika virus, chikungunya, dengue, and HIV virus.

In one embodiment, the stabilized hypochlorous or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] solution is acid at a pH 3 to pH 9 and the concentration of 0.01% to about 0.05% or with mimetic heparin with or without Benzalkonium chloride in or with catechin combined with LMWH in a semifluorinated alkane or a suitable medium to block viral receptors, heparan sulfate and Sialic acid, present in the mucosa cells, endothelial cells or neuronal cells, or olfactory bulb and the thiol bound of the viruses, etc., as a slow release nanoparticles of lactic acid, polyglycolic acid, polycaprolactone, or as micelles or in liposomes and chitosan and encapsulated in a non-dissolvable compound given orally to pass through the stomach and is released by enzymatic action in the intestinal tract to release the medication and get absorbed in the intestine to kill the viruses such as SARS-CoV-2, COVID-19, or their mutations locally preventing the intestinal side effect of viral infection.

In one embodiment, certain compounds can be used prophylactically as mouthwash or hand cleansing, nasal spray, such as hydrogen peroxide, povidone-iodine, ethanol, chlorhexidine, cetylpyridinium chloride, to disrupt the SARS-CoV-2 lipid envelope, COVID-19 lipid envelope, or their mutations, etc.

In one embodiment, for prophylaxis such as traveling by airplane, one can combine two or more antivirals with zinc, or povidone iodine, etc. or in a semifluorinated alkane or in a physiologic fluid in the form of slow release polymeric pluralities of nanoparticles, micelles liposomes, polyglycolic acid, or lactic acid, etc. administered through the nose or orally to last one week or more and release medication after administration in the form of spraying or nebulization by an intranasal route and inhalation to prevent viral attachment to the surface of the nose, throat, mucosa or lung alveoli or kill the incoming viruses or prevent their multiplication before reaching the brain and prevent their migration to the brain via the olfactory nerve.

In one embodiment, certain compounds can be used prophylactically as mouthwash or hand cleansing, such as hydrogen peroxide, povidone-iodine, ethanol, chlorhexidine, cetylpyridinium chloride, Hypochlorous acid, or chloramines, the stable N-chloro derivatives, or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] alone or in combination to disrupt the SARS-CoV-2, COVID-19, or their mutations lipid envelope.

In one embodiment, the damage to the capillary endothelial cells causes accumulation of platelets and other blood cells causing vascular occlusion, pain, stroke, paralysis, etc.; therefore, in one embodiment, any treatment to combat viral or bacterial central nervous system (CNS) vasculitis or vasculitis in an autoimmune response, such as lupus or in immunotherapy of cancer, etc. should be treated also with oral or systemic anticoagulants, such as aspirin in low molecular weight heparin, and/or in severe conditions, anticoagulants, such as Coumadin, or heparin, low molecular weight heparin (Lovenox), without or with catechin in a semifluorinated alkane or a suitable medium as slow release nanoparticles of lactic acid, polyglycolic acid, polycaprolactone, or as micelles or in liposomes and chitosan with or without Benzalkonium chloride or to block viral receptors, heparan sulfate and Sialic acid, in the mucosa, endothelial cells or neuronal cells, or olfactory bulb, etc., as slow release nanoparticles of lactic acid (LA), polyglycolic acid (PGLA), polycaprolactone, or as micelles, or in liposomes and chitosan to prevent cellular damage by virus and to enhance nerve repair and prevent blood coagulation or TPA to dissolve the blood clot, etc. followed by plasmapheresis, and/or kidney dialysis to remove excessive cytokines.

In one embodiment, the cytokines can be measured by using either the saliva, expectorations, tear, urine, or nasal secretion, cerebrospinal fluid or aqueous fluid of the eye, or blood circulation, etc., the concentrations of cytokines, such as IL-1 and/or IL-6, IL-8 are higher in the inflammatory diseases, etc., and the increase or decrease of their concentrations are indicative of the progression of viral infection or its prognosis.

In the brain and spinal cord, microglial cells act as immune cells, such as macrophages and respond to any pathogen encountered.

In one embodiment, several viruses can affect the upper respiratory system and brain simultaneously, such as influenza viruses or SARS-CoV-2, COVID-19 viruses, or their mutations, and herpes simplex, mumps, or measles, EBV etc.

In one embodiment, the patient with early cases of viral CNS vasculitis can be treated with one or two or more anti-virals or IL-6 inhibitors, interleukin antagonists via inhalation using aerosolized or nebulized medication, in semifluorinated alkane, as polymeric slow release nanoparticles to cover the nasal passages to the brain from the olfactory epithelium to olfactory bulb, and subsequently to the posterior gyms rectus and the cerebrospinal fluid and simultaneously lower respiratory tract infection is treated as described here, while the presence of the virus and cytokines, such as IL-6, before and after therapy can be verified through the nasal secretion or cerebrospinal fluid (CSF), blood, etc. as prognostic indication of the disease process.

In one embodiment, the persistence of headache is a sign of brain vasculitis and increase in the intracranial pressure associated damage to pericytes of small brain capillaries leading to leakage of the blood enriched fibrinogen and accumulation and activation of microglial cells leading to loss of myelin and white matter and buildup of tau and amyloid oligomers, fibrils, and plaque and Alzheimer's disease or Parkinson's disease, dementia; in one embodiment, the nasal application or inhalation of one or more antivirals and anti-inflammatory agents, such as Rock inhibitors, Wnt inhibitors, GSK inhibitors, and integrin inhibitors with or without complement pathway inhibitors, such as C3 inhibitors—AMY-101 (NCT04395456) and APL-9 (NCT04402060); C5 inhibitors—eculizumab (NCT04346797 and NCT04355494), C1 esterase inhibitors, which block the classical complement pathway with anti-IL6 medication, such as Kevzara, tocilizumab, rituximab, etc., or antiviral, baloxavir marboxil, and antibiotics such as tetracycline derivatives a metalloproteinase inhibitor and/or low molecular weight heparin (Levonox) with or without catechin and LMWH in a semifluorinated alkane or a suitable medium to block viral receptors, heparan sulfate, and Sialic acid, as a slow release nanoparticles of lactic acid, polyglycolic acid, polycaprolactone, or as micelles, or in liposomes and chitosan or tissue plasminogen activator (tpa) in the form of nasal spray or aerosolized medication or nebulized medication to reduce the inflammatory process and low molecular weight heparin assists in clearing the fibrinogen and oligodendrocyte loss preventing future side effects of viral encephalitis, such as dementia, Alzheimer's disease, neuralgia, etc.

In one embodiment, viral infection of the lung and brain vasculitis, produce anoxia and ischemia through HIF-1 factor that induces angiogenesis. TiPARP is activated in the cell nucleus that eliminates the HIF-1alpha and TiPARP. Tamoxifen works similarly for the breast tumor and degrades HIF-1 and prevent ischemia and anoxia. In one embodiment, Tamoxifen is combined with an antiviral in a viral infection of the lung and viral brain encephalitis and brain vasculitis and cell pathway inhibitors, Wnt inhibitor, GSK inhibitors, and integrin inhibitors administered in a physiological solution or semifluorinated alkane or a physiological liquid or a suitable medium combined or sequentially through the nose inhalation by spraying, aerosolization, or nebulization to reach both brain and the lung tissue, reduce the inflammatory process and eliminate the side effects of the infection.

In one embodiment, in respiratory viral infection of the upper or lower respiratory system or brain is associated with significant fibrin formation, the treatment is given as nasal application or inhalation of one or more antivirals and anti-inflammatory agents, such as Rock inhibitors, Wnt inhibitors, GSK inhibitors, and integrin inhibitors with anti-IL6 medication, such as Kevzara, or nitric oxide (NO) donor (NONOate), tocilizumab, etc., or tPA tissue plasminogen activator in nanogram to microgram concentrations in the form of nasal spray or aerosolized medication or nebulized medication to reduce the inflammatory process and tPA assists in clearing the fibrinogen/fibrin preventing future side effects of viral encephalitis, or enhancing the clearing the lung from the fibrinous exudates initiated by the viral inflammatory disease. In one embodiment, Mucinex given orally will work synergistically to cleanse the lung alveoli, or a mucomyst is delivered by inhalation which contains acetylcysteine, n-acethylsystein, or its derivatives, which have an anti-inflammatory and antithrombotic effect when combined with antivirals and call pathway inhibitors for therapeutic vaccines, etc.

In one embodiment, the TPA can be administered in a physiological solution or semifluorinated alkane or a physiological liquid or a suitable medium intravenously either to dissolve the blood clot in the vessels or prevent coronary stent clot formation.

In one embodiment, the brain vasculitis and viral infection produces headache as a sign of cranial vasculitis and increased intracranial pressure, in addition to other symptoms of fever, shiver, and neck stiffness, or nerve palsy, etc., release of viral cytokines and cellular and humoral immune response enhance the inflammatory process in the brain. In one embodiment, one treats the viral brain and upper respiratory infection by simultaneous administration of antiviral agents, with one or more anti-inflammatory cell pathway inhibitors to block the excessive inflammatory response of the brain tissue and its vasculature while maintaining a normal immune response, with one or more Rock inhibitors antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor Y-27632 dihydrochloride, Botox or botulinum toxin, ROCK2 inhibitor, KD025, Netarsudil, Fasudil, and its derivatives, and/or Wnt inhibitors, GSK inhibitors, integrin inhibitors, or IL-1 and/or IL-6, IL-8 inhibitors dissolved in liquid semifluorinated alkanes or other liquids as the drug, or in a polymeric slow release nanoparticles administered locally as a spray or evaporative solution or in evaporative aerosolized drops or nebulization that travels through the nasal cavity where the semifluorinated alkanes which is non-toxic or causes irritation to the tissue, rapidly evaporates leaving the medication(s) or slow release nanoparticles, such as polymeric lactic, glycolic acid, or in combination, or porous silicon or polycaprolactone, liposomes, micelles, etc. on the surface of these tissues, or travel to the brain through the olfactory or trigeminal nerves releasing the medications over time to the brain, or simultaneously to the mouth to reach the lung alveoli, and while on the way attaching to the mucosa, epithelial or endothelial cells of the trachea, bronchi and lung alveoli and its vasculature and simultaneous absorption of the medication through the nasal capillaries, and lung capillaries provide the delivery of the medication through the circulation to the heart, and brain to their inflamed vasculature by daily inhalation, for one week to three weeks, or the release of the medication from the nanoparticles continues for months or years to inhibit chronic inflammatory processes in the brain that is associated with silent dementia and Alzheimer's disease, Neuralgia, or Parkinson's disease depending on the location of the inflammation.

In one embodiment, the antiviral delivery and pathway inhibitors are conjugated with antibody coated nanoparticles made of pluralities of dimethyl fumarate (DMF), squalene, lanosterol or squalamine or their derivatives that per se are antibiotic/anti-inflammatory compounds, tetracycline and doxycycline, a metalloproteinase inhibitor, to reduce the excessive inflammatory immune response, combined with semifluorinated alkanes or a physiological solution as aerosolized drops or spray for intranasal administration to the lung, brain, and heart.

In one embodiment, the antiviral delivery and pathway inhibitors are conjugated with antibody coated nanoparticles made of pluralities of heparin or synthetic heparin mimetics or synthetic heparin, such as PG500 and polyphenols, such as catechins or hyaluronic acid or their derivatives that per se are anti-inflammatory compounds to reduce the excessive fibrin release or breakdown the fibrinogen and inflammatory immune response, combined with semifluorinated alkanes or a physiological solution as aerosolized drops or spray for intranasal administration to prevent blood clotting, closure of vasculature or coronary stent, etc.

In one embodiment, the nasal approach to the delivery of antivirals, pathway inhibitors or IL-6 inhibitors, etc. using a semifluorinated alkane compound or in physiologic fluid combined with slow release polymeric nanoparticles or antibody-coated nanoparticles can be considered as a systemic application of the drug delivery in viral diseases involving the lung, heart, and brain or their generalized vascular involvement (vasculitis) of the intestinal tract, brain or increased coagulopathy, a single disease complex that is best treated through judicious intranasal route or inhalation, since the major organs (e.g., heart, lung, intestine, and brain) are reached very fast and the lung absorption provide the circulation route to reach the rest of body's vasculature to be treated immediately and also long term with slow release polymeric nanoparticles.

In one embodiment, the administration of the inflammatory pathway inhibitors, such as a Rock inhibitor, Wnt inhibitor, GSK inhibitor, such as synthetic small-molecule ATP-competitive inhibitors, and substrate-competitive inhibitors, non-ATP-competitive inhibitors, where FRAT/

GBP competes with Axin inhibiting GSK-3 activity or integrin inhibitors or IL-1 and/or IL-6 inhibitors via nasal administration and inhalation using a semifluorinated alkane compound or in physiologic fluid with polymeric slow release nanoparticles, block the severe inflammatory response of the brain tissue caused by the invasion of the pathogens, which stimulate glial cells proliferation and migration producing oligomers of amyloid that coalesce building fibrils, tau and amyloid plaques, and the medication over time prevents the consequences of the brain vasculitis and encephalopathy in viral diseases of the brain.

In one embodiment, the viral encephalitis, if not treated in time, causes slow simmering or sui generous inflammatory process that may not become recognized, in time, to be treated leading to glial response, production of oligomers of beta amyloid and to self-sustained progressive Alzheimer's disease years or decades later.

In one embodiment, one or two antivirals, such as Tamiflu, Baricitinib, Glidesivir, Favipiravir, Xofluza Remdesivir, nanoviricides, Lenacapavir/Gilead in picomolar concentrations or GS-CA1, Oya1, interferon, umifenovir, tamivir ribavirin, baloxavir can be used orally, systemically or with or without IL-6 inhibitors, etc. Intranasal and orally as prophylaxis of the viral infection in the winter season or when traveling, or flying etc.

In one embodiment, at least one antiviral is combined with one pathway inhibitor, such as Wnt inhibitor FH535, IWP-2, PNU-74654, IWR-lendo, IWR-exo, Demethoxycurcumin, CCTO36477, KY02111, WAY-316606, SFRP, IWP, LGK974, C59, Ant1.4Br/Ant 1.4Cl, Ivermectin, Niclosamide, apicularen and bafilomycin, XAV939, XAV939, G007-LK and G244-LM, NSC668036, SB-216763, gemtuzumab, etc., small molecule Wnt inhibitor PKF118-310, Niclosamide with both antiviral and anti-inflammatory effect, Fasudil, Netarsudil, the Wnt/β-catenin pathway inhibitor or Rock inhibitors with an IL-6 inhibitor or Kevzara, or nitric oxide (NO) donor (NONOate), or Actems are used in combination with interferon which is normally produced by natural killer cells in the body to excite cellular immune response in the body where interferons or pegylated interferon act as antivirals in the upper and lower respiratory tract blocking the replication of the RNA and DNA of the viruses at an early stage of viral infection.

The interferons are released in the body as cytokines to excite protective immune such as natural killers, macrophages, major Histocompatibility complex, etc. The interferons act as an antiviral preventing the virus growth in the cells. Interferon or pegylated interferon attaches to the cell receptors of the nasal or throat of the airway system and brain vasculatures, etc. and prevents DNA or RNA of the virus from replicating, the medication is administered in a physiological solution or semifluorinated alkane or a physiological liquid or a suitable medium as a spray of aerosolized liquid or nebulized liquid with or without semifluorinated alkanes preferably at an early stage in the disease process and not if a cytokine storm is eminent.

In one embodiment, antivirals and pathway inhibitors, such as Wnt inhibitors, such as Ivermectin, Niclosamide, etc. can be given orally specially in children or when intestinal involvement is predicted or intranasal inhalation as slow release polymeric nanoparticles or LNP or gold nanoparticles at a significantly lower concentration than systemic administration for both viral infection of the lung and brain vasculitis, etc.

In one embodiment, interferon enhances cellular response while cell pathway inhibitors such as Rock, Wnt, GSK, or integrin inhibitors such as such as abegrin, cilengitide, abciximab, tirofiban, natalizumab, eptifibatide, or risuteganib in a low concentration of 1 microgram to 10 micrograms as a solution and IL-6 inhibitor or Kevzara, and/or nitric oxide (NO) donor (NONOate) or Actems to inhibitors, retuaximab, tocilizumab, control the inflammatory process preventing a cytokine response.

In one embodiment, viruses may affect upper or lower respiratory system followed by a bacterial infection with pathogens such as *Streptococcus pneumonia, Haemophilus influenza, Staphylococcus aureus,* or *E. Coli,* etc. However, the bacterial encephalitis, or meningitis is caused more commonly through the circulation. In these cases, a combination use of an antibacterial and one or two antivirals and one pathway inhibitor with or without complement pathway inhibitors, such as C3 inhibitors—AMY-101 (NCT04395456) and APL-9 (NCT04402060); C5 inhibitors—eculizumab (NCT04346797 and NCT04355494); C1 esterase inhibitors, which block the classical complement pathway can be administered in a physiological solution or semifluorinated alkane or a physiological liquid or a suitable medium by inhalation and systemic administration of a non-toxic dose of the antibacterial, antibiotics, or refabutin, etc. medications.

In one embodiment, the TMPRSS2 inhibitor Camostat inhibits entry of the virus in the cells and one or two antivirals nasal combined with Rock inhibitors or GSK inhibitors, or integrin inhibitors, such as abegrin cilengitide, abciximab, tirofiban, natalizumab, eptifibatide, or risuteganib in a low concentration of 1 microgram to 10 micrograms as a solution with or without semifluorinated alkanes or as polymeric nanoparticles can be administered in a physiological solution or semifluorinated alkane or a physiological liquid, simultaneously or sequentially by inhalation for prophylactic as well and treatment of viral infection affecting the brain and its vasculature or the lung.

In one embodiment of viral encephalitis, one can combine intranasal admiration of two antivirals such as lopinavir and ritonavir or Baricitinib, Glidesivir, Favipiravir, Xofluza, Remdesivir, nitazoxanide, nanoviricides, Oya1, interferon, or pegylated interferon, umifenovir, tamivir, lopinavir, etc. with protease inhibitors such as NSAIDS, or cox-2 inhibitors celecoxib, propanoic acid derivatives, etc. that block the main protease of the virus (M-Pro) essential for virus replication or MicroRNAs or atovaquone with its antiviral effect against RNA viruses, or antisense molecule fomivirsen, antiherpes drugs inhibit viral replication with a Rock inhibitor, or Wnt inhibitor, GSK inhibitor, integrin inhibitor or an IL-6 inhibitor such as kevzara, rituximab, Melatonin, etc. in a semifluorinated alkane or a physiologic solution as polymeric slow release delivery as nasal spray of aerosolized, or nebulized drops to treat or use it as prophylaxis in susceptible patients or those who are exposed, such as health care workers etc., or first responders.

In one embodiment, in end stage viral encephalitis or lung infection, one can combine antivirals with Wnt inhibitors, or integrin inhibitors or Rock inhibitors with IL-6 inhibitors, a macrolide such as tacrolimus, mycophenolic acid, or cyclosporine administered in a physiological solution or semifluorinated alkane or a physiological liquid or a suitable medium intranasal with intravenous administration or orally to suppress cytokine storm with simultaneous kidney dialysis and blood dialysis or plasma electrophoresis.

In one embodiment, antivirals are administered in combination with MPA, an antiviral and TNF inhibitor, and LMWH, catechins, and a Wnt inhibitor, such as niclosamide or ivermectin, or melatonin in polymeric slow release nanoparticles with or without semifluorinated alkanes as a nasal spray or by inhaler to prevent or treat viral encephalitis or prevent the side effect of the viral infection of the brain or after traumatic brain injuries, such as Alzheimer's disease or Parkinson's disease, by eliminating the infection and reducing the endoplasmic reticulum stress in the neuronal cells.

In one embodiment, one administer intranasal antivirals along with medications that block the ACE-2 receptor to which viral particles attach as the compound hydroxyquinoline at low concentration of micro to milligrams, Rock inhibitors where rock inhibition reduces the blood pressure, and while reducing the angiotensin II and increases Ang (1-9) plasma levels and inhibiting the NOX4-Derived ROS-Mediated RhoA/Rho Kinase Pathway, or follicle stimulating hormone or finistride to inhibit testosterone production, along with IL-6 inhibitors or tocilizumab dissolved in a semifluorinated alkane or in a physiologic solution as polymeric slow release antibody coated polymeric nanoparticles as aerosolized delivery system, etc.

In one embodiment, the two viruses such as SARS-CoV-2, COVID-19, or their mutations and a herpes virus is involved simultaneously or sequentially one can add two antivirals with ganciclovir or acyclovir or valacyclovir, Cidofovir, Vidarabine, Penciclovir, Foscarnet Fomivirsen Famciclovir or Oseltamivir phosphate, Rimantadine, Amantadine, Zanamivir, Telbivudine, Lamivudine, Entecavir, Emtricitabine, Adefovir and heparin mimics containing glucosamine saccharides/acrylamide to bind to 13-Secretase (BACE-1) involved in Alzheimer's disease (AD) administered with or without polyphenols, such as catechins, with or without fluvoxamine, selective serotonin reuptake inhibitors (SSRIs), or tetracycline derivatives, a metalloproteinase inhibitor, or doxycycline, etc., as an antibacterial such as rifampin with Rock inhibitors or other anti-inflammatory compounds in a physiological solution or semifluorinated alkane or a physiological liquid or a suitable medium intranasally as slow release polymeric nanoparticles with or without semifluorinated alkanes with a Rock inhibitor and IL-6 inhibitor, or nitric oxide (NO), donor (NONOate) as antiviral and anti-cytokines such as or nitric oxide (NO) donor (NONOate), interleukin antagonists or DMF by inhalation, systemic, oral, topical locally to halt spread of the virus to the brain or its reactivation or to prevent continuation of inflammation as nasal inhalation, etc. in the brain leading to Alzheimer's disease, dementia, and neuralgia, etc.

In one embodiment, two or more antivirals that can be used with the described therapeutic vaccine as a cocktail, in the semifluorinated alkane as a cocktail of antivirals and with pathway inhibitors or complement inhibitors, such as: Fosfonet Sodium; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime, zinc, heparin, anionic polymers. Ganciclovir; Ganciclovir Sodium; Idoxuridine; Kethoxal; Lamivudine; Lobucavir; Memotine Hydrochloride; Methisazone, Adefovir; Alovudine; Alvircept Sudotox; Amantadine Hydrochloride; Aranotin; Arildone; Atevirdine Mesylate; Avridine, Acyclovir; Acyclovir Sodium; Desciclovir; Didanosine; Disoxaril; Edoxudine; Enviradene; Acemannan; Nevirapine; Penciclovir; Pirodavir; Ribavirin; Rimantadine Hydrochloride; Saquinavir Mesylate; Somantadine Hydrochloride; Sorivudine; Statolon; Stavudine; Enviroxime; Famciclovir; Famotine Hydrochloride; Fiacitabine; Fialuridine; Fosarilate; Foscarnet Sodium, Cidofovir; Cipamfylline; Cytarabine Hydrochloride; Delavirdine Mesylate, zanamivir, amantadine, and Palivizumab. Other examples of anti-viral agents include, but are not limited to Acemannan; Nevirapine; Penciclovir; Pirodavir; Ribavirin; Rimantadine Hydrochloride; Saquinavir Mesylate; Somantadine Hydrochloride; Sorivudine; Statolon; Stavudine, etc.

In one embodiment, with a viral infection, the antiviral can be given with an anti-inflammatory compound such as naltrexone, or disulfiram, combined with cox-2 inhibitors or Rock or Wnt or GSK inhibitors or anti-integrin intranasal with a semifluorinated or liquid solution with slow release nanoparticles or polylactic, polyglycolic, polycaprolactone, or porous silicon, micelles, or liposomes, etc. with or without IL-6 inhibitors.

In one embodiment of viral infection, the virus induces a storm cytokine response causing generalized vasculitis and thrombus formation, on treating this condition in addition to the antivirals such as the inhibitor Sofosbuvir, a polymerase inhibitor and ribavirin, umifenovir, tamivir, lopinavir etc., pathway inhibitors, such as Rock inhibitors, with inhibition of cytokine IL-6 with an inhibitor such as Kevzara or nitric oxide (NO), donor (NONOate), or rituximab intranasal administration with semifluorinated or liquid solution with slow release nanoparticles or polylactic, polyglycolic, polycaprolactone, or porous silicon, micelles, or liposomes, etc.

In one embodiment, the medications can be simultaneously administered in a physiological solution or semifluorinated alkane or a physiological liquid or medium orally, intravenously, and nasally as needed for therapy and/or as prophylaxis of the viral infection or when traveling, or flying by airplane, etc.

In one embodiment, one can administer prophylactically, antivirals nasal spray, aerosolized or nebulized form of zinc or oral zinc lozenges, or zinc at about 15 mg, vitamin D<than 4000 IU/day and/or with salt and lukewarm water or spray it as aerosolized or nebulized for nasal inhalation, or hydrogen peroxide at <3% concentration in combination with Listerine mouthwash at low concentration or gargle in a short time.

In one embodiment, the mouthwash Listerine in low concentration or diluted form can be applied to the nose, mouth or throat mucosa with salt water to eliminate viruses.

In one embodiment, povidone iodine toxicity to the eye was tested after injection in the eye 0.1 mL of 50, 100, 200, or 400 micrograms (microg) of PVP-I in one eye without toxic effect; higher concentrations of 100 milligram to 1000 milligram or more has been used routinely to sterilize the skin prior to surgery.

In one embodiment, povidone iodine at 400 micrograms to 10 milligrams or more can be used as inhalation/day through both nostrils for 1-14 days or using Q-tipped applicator with a mixture of 1-20% ethanol and 0.1-1% or more povidone iodide or other iodine preparations such as cadexomer, Inadine, tincture of iodine iodophor, lugol, iodine, with or without LMWH, etc. can be administered in a physiological solution or semifluorinated alkane or a physiological liquid or salt water to eliminate viruses and bacteria in the nose or respiratory tract.

In one embodiment, Povidone iodine 0.1% in salt water is combined with zinc <15 mg in a solution or ointment, etc. applied to the skin of the upper lip, nasal skin, and nose mucosa entrance to damage the invading viruses/bacteria before entering the nasal mucosal cells, etc. reducing the chance of the infection during traveling by plane, etc.

In one embodiment, nanoparticles of squalene nanoparticles combine with riboflavin in salt water 0.9% NaCl applied to the nose and exposure to a low level of UV radiation of 3 mW/cm2 for one minute damage the viral particles in the nose without crosslinking the nasal proteins.

In one embodiment, hypochlorous acid (HOCL) is stabilized at PH 5 and leas in salt water >0.9% NaCl can be applied as drops or spray or nebulized form locally or by inhalation to the nose and its surrounding tissue to eliminate viruses.

In one embodiment, certain compounds can be used prophylactically as mouthwash or hand cleansing, nasal spray, such as hydrogen peroxide, povidone-iodine, ethanol, chlorhexidine, cetylpyridinium chloride to disrupt the COVID-19 lipid envelope.

In one embodiment, for prophylaxis such as traveling by airplane or visiting a patient, or in the office, one can combine two or more antivirals with zinc, or povidone iodine, or another antiseptics, etc. or in semifluorinated alkane or in a physiologic fluid in form of slow release polymeric pluralities of nanoparticles, micelles, liposomes, polyglycolic acid, or lactic acid, etc. administered in form of spraying or nebulization by intranasal route and inhalation to last one week or more and release medication to prevent viral attachment to the surface of the nose, throat, mucosa, or lung alveoli, etc. or kill the incoming viruses or preventing their multiplication before reaching the brain and prevent their migration to the brain via olfactory nerve.

In one embodiment, the stabilized hypochlorous acid or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] solution has a pH 3 to pH 9 and a concentration of 0.02% to about 0.05% or in a semifluorinated alkane or liquid such as 1% or more NaCl solution as a slow release nanoparticles of lactic acid, polyglycolic acid, polycaprolactone or as micelles or in liposomes for nasal administration or inhalation as a spray or aerosolized form with or without antivirals.

In one embodiment, the stabilized hypochlorous acid or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] at a concentration of 0.025% in 1% sodium chloride with electrolyzed water is obtained from Ecolox-Tech, Envirolite®, etc. without phosphates, or Phosphate Buffered Saline (PBS) and sodium Hypochloride, phosphate with or without a Rock inhibitor, at 1-20 microgram/ml or more, Wnt inhibitor at pico-nanogram/ml concentrations or more, GSK 50 microgram/ml inhibitor or statins at <100 microgram/ml concentration or integrin inhibitors at 25-200 microgram/ml or more concentration with one or more antivirals or bronchodilators.

In one embodiment, 60 milligrams of iron oxide administered in a physiological solution or semifluorinated alkane or a physiological liquid once every two days enhances the production of hemoglobin.

In one embodiment, the nose can be disinfected with intra-nasal Miramistin solution, an old non-toxic disinfectant that kills the bacteria and viruses without affecting the normal cells.

In one embodiment, one or more convalescent plasma's antibodies are used to coat or conjugate with slow release polymeric nanoparticles which seek and attach to the viruses; where the nanoparticles are made from lactic, polyglycolic acid, polycaprolactone, anhydrides, porous silicon, micelles, liposomes, etc. carrying medications, such as antivirals or pluralities of nanoparticles are used carrying two or more antivirals in a physiological solution or administered in a physiological solution or semifluorinated alkane or a physiological liquid or a suitable medium intra-nasally as spray or drops or nebulization for inhalation to treat the early stage viral infection and reduce both viral infection side effects of the infection in the brain or the lung.

In one embodiment, pluralities of one or more antibody-coated slow release polymeric nanoparticles, such as polylactic acid, polyglycolic acid, porous silicon, micelles, liposomes, polyanhydrides, polyesters, polycaprolactone with cell penetrating peptides carry antivirals, such as nelfinavir, or Remdesivir, etc. along with bronchodilators such as, emetine, hydroxychloroquine and amodiaquine or its derivatives, salbutamol, obatoclax, albuterol, with or without Rock inhibitors, Wnt inhibitors, GSK inhibitors or integrin inhibitors, intra-nasally or through the mouth as inhalation, to enhance relaxation of the bronchi that bring air in the lung alveoli by relaxing the smooth muscles of the vessels of the lung and brain.

In one embodiment, a combination of antivirals and salbutamol, and IL-6 inhibitors, Rock inhibitors, Wnt inhibitors, GSK inhibitors, or integrin inhibitors, or nitric oxide (NO), donor (NONOate) with or without DMF to inhibit inflammatory processes of the brain or lung vessels leading to leakage of fibrinogen stimulating production of oligomeric beta-amyloid in the brain or fibrin in the lung and can slow down or inhibit formation of Alzheimer's plaques, tau and tangled fibrils or dementia, etc. or reduce oxygen absorption by the lung capillaries and hemoglobin.

In one embodiment, the combination of antivirals with or without tetracycline derivatives, a metalloproteinase inhibitor which antibacterial and an anti-inflammatory and/or nitric oxide (NO), donor (NONOate), with antibody-coated polymeric slow release nanoparticles, such as polylactic acid, polyglycolic acid, porous silicon, micelles, liposomes, polyanhydrides, polyesters, polycaprolactone and antivirals with pathway inhibitors to reduce the inflammation and with cell penetrating peptides or activatable cell penetrating peptides (ACPPs) or cyclodextrin or low-molecular-weight (2-5 kDa) polyethylene glycol, or low molecular weight heparin, synthetic heparin mimetics heparin mimics containing glucosamine saccharides/acrylamide to bind to 13-Secretase (BACE-1) involved in Alzheimer's disease (AD), or synthetic heparin, such as PG500, etc. or Epigallocatechin gallate (EGCG), a green tea catechin, that binds to heparan sulfate or in combination with low molecular weight heparin or heparin mimetics to bind to heparan sulfate and sialic acid preventing the viral attachment to viral cell receptors, such as Neuroplin-1 and ACE-2 receptors of the mucosa, endothelial cells or neuronal cells, or olfactory bulb, etc. as slow release nanoparticles of lactic acid, polyglycolic acid, polycaprolactone, or as micelles or in liposomes and chitosan administered in semifluorinated alkane or a suitable medium through inhalation or vapor, nasal spray or nebulization to reach the brain directly and lung endothelial cells and cells of alveoli directly to inhibit the intracellular viral replication, in the brain, and lung and kill them with minimal amount of antiviral medication compared to the systemic administration of the antiviral that requires production of a large amount of medication with its associated expenses and complications.

In one embodiment of a method of treating, reducing, or alleviating a medical condition in a patient, the method comprising administering to a patient in need thereof a biocompatible drug comprising one or more antiviral medications together with one or more green tee, oolong, cinnamon, or orange with or without linoleic acid in the warm to boiling water or a nebulizer creating vapor containing the active ingredient of the cocktail for simultaneous inhalation of the vapor's components to inhibit attachment of viruses to ACE-2 receptors or neuropilins's receptors in the nasal pathway to the lung to through the olfactory nerve and trigeminal nerve to brain thereby preventing the viral attachment to enter the nasal or respiratory pathway to the alveoli cells and olfactory nerve or sensory trigeminal nerves, to gain access to the brain cell producing viral encephalitis, or lung infection, where the cocktail can be consumed orally after it is cooled down to be absorbed through the gut preventing damage to the intestine, liver, kidney and the brain through the blood circulation.

In one embodiment of a method of treating, reducing, or alleviating a medical condition in a patient, the method comprises administering to a patient in need thereof a biocompatible drug cocktail comprising one or more antiviral medications together with or without one or more green tee, oolong, Cinnamon, or orange with or without linoleic acid polyphenyls, epigallocatechin gallate catechins (EGCG) having antioxidants compounds cocktail also and catechins etc. found in black tea, or coffee, oolong, white tea, Pu-reh, Chamomile tea, the vegetable, such as fruits or coco, alone or in combinations as a cocktail, or in addition to it one or more antioxidants, antimicrobial, statins and immunomodulatory mangiferin, genistein, estradiol, berberine and baicalein, sulforaphane, with or without vitamin D and high doses of vitamin C, vitamin E, D, or with or without quercetin, curcumin, resveratrol, Alpha-lipoic acid, tocopherols and tocotrienols, carotenoids, glutathione tocopherols, carotenoids alone or with or without linoleic acid mixed in the warm to boiling water or a nebulizer to create a vapor containing the active ingredients for nasal inhalation of the components of the cocktail which are inhibiting attachment of viruses to ACE-2 receptors or neuropilins's receptors etc. thereby preventing the viral attachment or entering the nasal or respiratory pathway to the alveoli cells and olfactory nerve or sensory trigeminal nerves, to gain access to the brain cell producing viral encephalitis, where the cocktail can also be consumed orally after it is cooled down.

In one embodiment, phosphorylation of endoplasmic reticulum resident kinase (PERK) and increased eIF-2a phosphorylation is a marker of endoplasmic reticulum (ER) stress response. The intranasal application of inhibitors of phosphorylation with medications, such as Baricitinib, a Janus kinases inhibitor as anti-TNF and/or cycloheximide at low concentrations of nanogram/ml to 1-4 microgram/ml, with methylene blue at a concentration of 1 µg/ml for inhalation multiple times a day as needed, or naproxen prevents/treats not only the viral growth and infection/inflammation in the lung and brain (encephalitis/Alzheimer disease) but also prevent ER stress induced protein misfolding, such as beta amyloid tangles or plaques, chronic inflammation and neuropathy.

In one embodiment, inhibitors of phosphorylation of endoplasmic reticulum resident kinase (PERK) a marker of endoplasmic reticulum (ER) stress response, and prevention of hyperphosphorylation of eIF-2a, such as with a short lasting cycloheximide in DMSO in nanogram/ml to 1-microgram/ml concentration or Baricitinib, a Janus kinases inhibitor as anti-TNF, or naproxen that interacts with the viral nucleocapsid and anti-inflammatory and an antiviral, such as remdesivir or favipiravir or nitazoxanide, in semi-fluorinated alkanes is administered in combination with nitric oxide (NO), donor (NONOate), pathway inhibitors and LMWH with antivirals as a topical application or nebulization, spray in the nose to prevent or treat viral replication and protein misfolding in the brain diseases caused by viral encephalitis including influenza viruses, coronaviruses, e.g., SARS-CoV-2, COVID-19, or their mutations herpes viruses, herpes zoster, Epstein Barr virus, cytomegalovirus and subsequent Alzheimer's disease formation, etc., the medications are used sequentially or combined or at different time of the day preferentially as a nasal inhalation, etc.

In one embodiment, other viruses that can be treated with the described therapeutic vaccine are certain RNA viruses that are antigens in vertebrate animals which include, but are not limited to, the following: members of the family Retroviridae, the genus Orbivirus Colorado Tick Fever virus), the genus Rotavirus (human rotavirus); the family Picomaviridae, including the genus Enterovirus, poliovirus, Coxsackie virus A and B, enteric cytopathic human orphan (ECHO) viruses, hepatitis A virus, Porcine enteroviruses, the genus Cardiovirus (Encephalomyocarditis virus) the genus Rhinovirus (Human rhinoviruses the genus Apthovirus; the family Calciviridae, Feline picornavirus and Norwalk virus; the family Togaviridae, including the genus Alphavirus, Ross river virus, Venezuelan equine encephalitis virus, Western equine encephalitis virus, the genus Flavirius, yellow fever virus; Dengue virus, Japanese encephalitis virus, St. Louis encephalitis virus, Murray Valley encephalitis virus, West Nile virus, Central European tick borne virus, Far Eastern tick borne virus, Omsk hemorrhagic fever virus), the genus Rubivirus (Rubella virus), the genus Pestivirus (Mucosal disease virus, the family Bunyaviridae, including the genus Bunyvirus (Bunyamwera and related viruses, California encephalitis group viruses), the genus Phlebovirus, Sandfly fever Sicilian virus, Rift Valley fever virus, the genus Nairovirus, hemorrhagic fever virus, and the genus Uukuvirus\the family Orthomyxoviridae, including the genus influenza virus (influenza virus type A, many human subtypes; Swine influenza virus, and Avian and Equine Influenza viruses; influenza type B many human subtypes, and influenza type C, the family paramyxoviridae, including the genus Paramyxovirus, Parainfluenza virus type I, Parainfluenza viruses types 2 to 5, Newcastle Disease Virus, Mumps virus, the genus Morbillivirus, Measles virus, subacute sclerosing panencephalitis virus, distemper virus, Rinderpest virus, the genus Pneumovirus respiratory syncytial virus (RSV), Bovine respiratory syncytial virus, forest virus, Sindbis virus, Chikungunya virus, O'Nyong-Nyong virus, Ross river virus, Venezuelan equine encephalitis virus, Western equine encephalitis virus, the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, related viruses, California encephalitis group viruses, the genus Phlebovirus Sandfly fever Sicilian virus, Rift Valley fever, virus, the genus Nairovirus, Crimean-Congo hemorrhagic fever virus, Nairobi sheep disease virus), and the genus Uukuvirus (Uukuniemi and related viruses); the family Orthomyxoviridae, including the genus Influenza virus, Influenza virus type A, many human subtypes; Swine influenza virus, and Avian and Equine Influenza viruses; influenza type B and influenza type C the family paramyxoviridae, including the genus Paramyxovirus, Parainfluenza virus type I, Sendai virus, Hemadsorption virus, Parainfluenza viruses types 2 to 5, Newcastle Disease Virus, Mumps virus, the genus Morbillivirus, Measles virus, subacute sclerosing panencephalitis virus, distemper virus, Rinderpest virus, the genus Pneumovirus, respiratory syncytial virus (RSV), Bovine respiratory syncytial virus and Pneumonia virus of mic); the family Rhabdoviridae, including the genus Vesiculovirus (VSV), Chandipura virus, Flanders-Hart Park virus), the genus Lyssavirus (Rabies virus) (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), the infectious bronchitis virus (IBV) in chickens, picornavirus, and/or hepeviridae virus infection, betacoronaviruses gama, sarbecoviruses (SARS-like viruses including SARS-CoV-2) and merbecoviruses, Mouse Hepatitis virus, Human enteric coronavirus, and Feline infectious peritonitis (Feline coronavirus). In addition, other viruses that can be treated with the described therapeutic vaccine are certain DNA viruses that are antigens in vertebrate animals which include, but are not limited to: the family Poxviridae, including the genus Orthopoxvirus (Variola major, *Variola minor*, Monkey pox Vaccinia, Cowpox, the family Herpesviridae, including the alpha-Herpesviruses, Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus, the Beta-herpesviruses Human cytomegalovirus and cytomegaloviruses of swine, monkeys and rodents; the gamma-herpes viruses, Epstein-Barr virus (EBV), Marek's disease virus, Herpes saimiri, Herpesvirus ateles, the family Adenoviridae, including the genus Mastadenovirus, Human subgroups A, B, C, D, E and ungrouped; simian adenoviruses, infectious canine hepatitis, (Avian adenoviruses); and non-cultivatable adenoviruses; the family Papoviridae, including the genus Papillomavirus, Human papilloma viruses, human immunodeficiency virus (HIV), bovine papilloma viruses, bovine coronavirus, various pathogenic papilloma viruses of other species), the genus Polyomavirus); the family Parvoviridae including the genus Adeno-associated viruses, the genus Parvovirus, bovine parvovirus, canine parvovirus, Aleutian mink disease virus, DNA viruses may include viruses that do not fit into the above families such as Creutzfeldt-Jacob disease viruses and chronic infectious neuropathic agents, animals include porcine Feline Coronavirus: two forms, Feline enteric coronavirus, feline infectious peritonitis (FIP), canine coronavirus (CCoV), and Mouse hepatitis virus (MHV).

In one embodiment, one can administer antivirals with pathway inhibitors in combination with TNF alpha inhibitors, such as baricitinib, and Raf inhibitors, such as sorafenib, regorafenib, dabrafenib, with or without anti-VGEFs, aerosolized or in slow release polymeric nanoparticles with or without semifluorinated alkanes by nasal application, inhalation, etc. at low concentrations to inhibit inflammatory processes and excessive activation of glial cell stimulation in viral encephalitis or traumatic brain injuries while protecting the existing neuronal cells and preventing side effects, such as Alzheimer's disease or Parkinson's disease, etc.

In one embodiment, the combination of antivirals and salbutamol with antibody-coated nanoparticles, such as polylactic acid, polyglycolic acid, porous silicon, micelles, liposomes, polyanhydrides, polyesters, polycaprolactone with cell penetrating peptides or activatable cell penetrating peptides (ACPPs) or cyclodextrin or low molecular weight heparin, synthetic heparin mimetics, or synthetic heparin, such as PG500 and semifluorinated alkane or catechins alone or combined with low molecular weight heparin or heparin mimetics that bind to heparan sulfate or to sialic acid which are the component of ACE-2 and neuropilin-1 receptors of the mucosa, endothelial cells or neuronal cells, or olfactory bulb, etc. as slow release nanoparticles of lactic acid, polyglycolic acid, polycaprolactone, or as micelles or in liposomes and chitosan that the site where the influenza, SARS-CoV-2, COVID-19, or their mutations and other viruses enter the cells, etc. in a hyaluronic acid solution at <1% concentration or LMWH are administered in a physiological solution or semifluorinated alkane or a physiological liquid through inhalation, or by an inhaler or through the nose to reach the brain directly and lung endothelial cells and remain there for a period of time before the semifluorinated alkane evaporates, leaving the antibody-coated polymeric slow release nanoparticles in place to penetrate the alveoli cells or brain vessels cells directly to inhibit the intracellular viral particles, and kill them with a minimal amount of antiviral medication compared to the systemic administration while the nanoparticles can deliver the medication for a long period of time, reducing the need for a production or availability of medication in a pandemic viral infection, while salbutamol and low molecular weight heparin or synthetic heparin mimetics and polyphenols, such as catechins and/or Probenecid inhibits Panex-1 and prevent formation of fibrin and beta-amyloid that encourages tau plaque and neurofibrillary formation as a precursor of dementia or Alzheimer's disease occurring after inflammatory processes of the brain.

In another embodiment, where the disease has progressed, the combination of inhalation and intravenous administration of antibody-coated polymeric slow release nanoparticles/antivirals with cell penetrating peptides or activatable cell penetrating peptides (ACPPs) or cyclodextrin, or polyethylene glycol, or low molecular weight heparin, micelles, etc. is given simultaneously intravenously or orally that enhances also the cellular immune response of the body directly in the gut, lung, or brain directly which clears the dead viruses or dead cells, etc. that can produce toxins and multi-system inflammatory disease in adults or children after viral infection.

In one embodiment, the combination of antivirals and salbutamol, adrenaline, Albuterol bronchodilator, hyaluronic acid, with antibody-coated polymeric slow release nanoparticles, such as polylactic acid, polyglycolic acid, porous silicon, PEG-PLA, micelles, liposomes, polyanhydrides, polyesters, polycaprolactone with cell penetrating peptides or activatable cell penetrating peptides (ACPPs) or cyclodextrin or epigallocatechin gallate (EGCG), that bind to heparan sulfate or to sialic acid preventing the viral attachment to its cell receptors or pegylated heparin or synthetic heparin mimetics, or synthetic heparin, such as PG500, or catechins alone or combined with low molecular weight heparin, or low molecular weight heparin (LMWH), or heparin mimetics that bind to heparan sulfate or to sialic acid which are the component of ACE-2 and neuropilin-1 receptors of the mucosa, endothelial cells or neuronal cells, or olfactory bulb etc. as a slow release nanoparticles of lactic acid, polyglycolic acid, polycaprolactone, or as micelles or in liposomes and chitosan that the site where the influenza, SARS-CoV-2, COVID-19, or their mutations and other viruses enter the cells, etc. in nanoparticles, micelles, or liposomes are administered with protease (PLpro or Mpro, etc.) blocking agents, such as Ebselen, Ebseleno, or Ebselenum, and or glutathione peroxidase, GPx and superoxide dismutase (SOD)—metabolize oxidative toxic intermediates requiring zinc, selenium, manganese iron, copper, and for ideal catalytic activity applied in the nose etc., which also is an antiviral, antibacterial, anti-inflammatory, anti-prostaglandin, and neuroprotective effect, administered in a physiological solution or semifluorinated alkane or a physiological liquid or as vapor by inhalation through the nose, or through the mouth by an inhaler to reach the brain directly in lung, brain blood vessel endothelial cells, and remain in the nose, alveoli, brain endothelial cells, and to inhibit the replication of intracellular viruses, and kill them with minimal amount of antiviral medications compared to the systemic administration of the medications while improving breathing through the relaxation of bronchi smooth vessels and in the brain enhancing neuronal regeneration and prevention of amyloid plaque formation.

In one embodiment, the combination of antivirals with antibody-coated polymeric slow release nanoparticles, such as polylactic acid, polyglycolic acid, porous silicon, micelles, liposomes, polyanhydrides, polyesters, polycaprolactone with cell penetrating peptides or activatable cell penetrating peptides (ACPPs) or pegylated low-molecular-weight heparin or synthetic heparin mimetics or synthetic heparin, such as PG500, or epigallocatechin gallate (EGCG), that binds to sialic acid, combined low molecular weight heparin (LMWH) or heparin mimetics that bind to heparan sulfate or to sialic acid preventing the viral attachment to its cell receptors in slow release nanoparticles of lactic acid, polyglycolic acid, polycaprolactone, or as micelles or in liposomes and chitosan or cyclodextrin are administered with naturally or synthetically produced compounds to inhibit protease (PLpro or Mpro), such as Ebselen, and/or glutathione peroxidase and superoxide dismutase (SOD)—metabolize oxidative toxic intermediates requiring zinc, selenium, manganese iron, copper, and for ideal catalytic activity applied in the nose, blocking proteases, which also has an antiviral, antibacterial, anti-inflammatory, anti-prostaglandin, and neuroprotective effect, or preventing the SARS-CoV-2, COVID-19, or their mutations spikes attachment to the cells, by administration in a semifluorinated alkane or a suitable medium through inhalation or through the mouth by an inhaler to reach the brain directly through the nose, lung, brain blood vessel endothelial cells and to remain in the nose, alveoli, brain endothelial cells for a longer period of time to inhibit the cell entry through the ACE-2 or preventing replication of intracellular viruses, and kill them with minimal amount of antiviral medications compared to the systemic administration for a long period of time for the patient to recover.

In one embodiment, one can examine and assess the degree of vascular and brain involvement or damage after viral brain involvement using an electroencephalogram prior and after administration of the antiviral and Rock inhibitors, etc. medications through the nose or orally or intravenously, with the administration of polymeric slow release nanoparticles carrying antivirals with or without Rock inhibitors, Wnt inhibitors, GSK inhibitors, or integrin inhibitors, etc. or salbutamol which indicates the functional recovery of the affected brain cells or treating seizure, sleep difficulty, etc.

In one embodiment, the combination of antivirals with antibody-coated polymeric slow release nanoparticles, such as polylactic acid, polyglycolic acid, porous silicon, PEG-PLA, micelles, liposomes, polyanhydrides, polyesters, polycaprolactone with cell penetrating peptides or activatable cell penetrating peptides (ACPPs) or cyclodextrin or pegylated nanoparticles or PEG-PLA or PGG-PGLA or PEG-Heparin, or synthetic heparin mimetics, or synthetic heparin, such as PG500, nanoparticles with polyphenols, such as catechins alone that bind to sialic acid or combined with low molecular weight heparin that bind to both heparan sulfate and to sialic acid which are the component of ACE-2 and neuropilin-1 receptors of the mucosa, endothelial cells or neuronal cells, or olfactory bulb, etc. that the site where the influenza, COVID-19 and other viruses enter the cells, etc. as slow release antibody-coated nanoparticles of lactic acid, polyglycolic acid, polycaprolactone, or as micelles or in liposomes and chitosan, etc. are administered in a physiological solution or semifluorinated alkane or a physiological liquid by spray or inhalation or through the nose, mouth by an inhaler in combination with bronchodilators, such as xanthine bronchodilators terbutaline, non-selective beta.-stimulants, isoprenaline, adrenaline, Sudafed, beta.sub.2-agonist fenoterol, formoterol, pirbuterol, reproterol, salbutamol, indacaterol, aminophylline and choline theophyllinate and anti-allergic agents, such as ketotifen, cromoglycate, and anti-inflammatory agents, such as Dexamethasone, fluticasone, betamethasone, budesonide, flunisolide, beclomethasone, dipropionate, ciclesonide, triamcinolone acetonide, etc., anticholinergic agents, ipratropium bromide, oxitropium bromide and tiotropiumetc, alone or in combinations as needed to treat viral brain infection, encephalitis or lung viral infections, such as influenza viruses or SARS-CoV-2, COVID-19, or their mutations, etc.

In one embodiment, with encephalitis viral infection, the vasculitis causes severe migraines, which are treated with the combination of antivirals with antibody-coated nanoparticles such as polylactic acid, polyglycolic acid, porous silicon, PEG-PLA, micelles, liposomes, polyanhydrides, polyesters, polycaprolactone with cell penetrating peptides or activatable cell penetrating peptides (ACPPs) or pegylated nanoparticles or PEG-PLA or PGG-PGLA or PEG-Heparin or synthetic heparin mimetics or synthetic heparin, such as PG500, or catechins alone or combined with low molecular weight heparin that bind to heparan sulfate or to sialic acid which are the component of ACE-2 and neuropilin-1 receptors of the mucosa, endothelial cells or neuronal cells, or olfactory bulb, etc. the site where the influenza, SARS-CoV-2, COVID-19, or their mutations and other viruses enter the cells, etc. as slow release antibody-coated nanoparticles of lactic acid, polyglycolic acid, polycaprolactone, LNP or gold nanoparticles or as micelles or in liposomes and chitosan or nanoparticles or cyclodextrin administered in a physiological solution or semifluorinated alkane or a physiological liquid by spray or inhalation or through the mouth by an inhaler, in combination with bronchodilators, such as isoprenaline, adrenaline, Sudafed, salbutamol, albuterol, indacaterol, glycopyrrolate, formoterol, aminophylline or in combinations and choline theophylline and anti-inflammatory agents, such as Dexamethasone, fluticasone, betamethasone, Rock inhibitors, Wnt inhibitors, GSK inhibitors, or integrin inhibitors or in combinations, anticholinergic agents, ipratropium bromide, oxitropium bromide and tiotropiumetc, alone or in combinations with anti-migraine medications, such as almotriptan, rizatriptan, triptan through inhalation, or orally or NSAIDs, such as propionic acid derived non-steroidal agents.

In one embodiment, the combination of antivirals such as Remdesivir, zanamivir, ribavirin, flumist, ruprintrivir and pleconaril, Favipiravir, etc. and protease inhibitors, such as Ganovo, with antibody-coated polymeric nanoparticles, such as polylactic acid, polyglycolic acid, porous silicon, PEG-PLA, micelles, liposomes, polyanhydrides, polyesters, polycaprolactone conjugated with or without cell penetrating peptides or activatable cell penetrating peptides (ACPPs) or cyclodextrin, or low-molecular-weight (2-5 kDa) polyethylene glycol or PEG-modified NPs densely coated by low MW PEG or Pluronic F-127 modified NPs, as PEG-polyacrylic acid, or papain or pegylated nanoparticles or PEG-PLA or PGG-PGLA or PEG-Heparin or synthetic heparin mimetics or synthetic heparin, such as PG500, or catechins alone or combined with low molecular weight heparin that bind to heparan sulfate or to sialic acid which are the component of ACE-2 and neuropilin-1 receptors of the mucosa, endothelial cells or neuronal cells, or olfactory bulb, etc. that the site where the influenza, COVID-19 and other viruses enter the cells, etc., as nanoparticles, PEG-LA, polysorbates are administered in a physiological solution or semifluorinated alkane or a physiological liquid as drops or spray, orally or intravenously in combination with anti-allergic agents, such as ketotifen, cromoglycate, and anti-inflammatory agents, such as Dexamethasone, fluticasone, budesonide, flunisolide, ciclesonide, beclomethasone, dipropionate, triamcinolone acetonide, fluorocinolone, betamethasone, etc., anticholinergic agents, ipratropium bromide, oxitropium bromide and tiotropiumetc, melatonin, alone or GABA inhibitors such as KDS2010, low molecular weight heparin (Lovenox) to simultaneously act as an antiviral (e.g., SARS-CoV-2 and COVID-19) or their mutations or antibacterial and to enhance nerve repair and prevent blood coagulation, NSAIDS in combinations with polyphenols, such as catechins as needed to treat intestinal viral infections (e.g., COVID-19) as inhalation therapy or through the mouth by an inhaler, with or without semifluorinated alkanes.

In one embodiment, end stage viral brain and lung infection antivirals are administered in a physiological solution or semifluorinated alkane or a physiological liquid or a suitable medium by inhalation or intravenously or orally in combination with anticoagulants, aspirin, Coumadin, non-coagulative low molecular weight heparin, or synthetic heparin mimetics or synthetic heparin, such as PG500, etc., and immunomodulators, Rock inhibitors, Wnt inhibitors, integrin inhibitors, cyclosporine, macrolide, mycophenolic acid, ascomycin, tacrolimus, etc. with GABA inhibitors, such as KDS2010, or melatonin that regulates the sleep-wake cycle or low molecular weight heparin (Lovenox) and polyphenols, such as catechins that bind to heparan sulfate or to sialic acid which are the component of ACE-2 and neuropilin-1 receptors of the mucosa, endothelial cells or neuronal cells, or olfactory bulb cells, etc. the site where the influenza, SARS-CoV-2, COVID-19, or their mutations and other viruses enter the cells, etc. as a polymeric slow release nanoparticles of lactic acid, polyglycolic acid, polycaprolactone, or as micelles or in liposomes and chitosan to enhance nerve repair and prevent blood coagulation in antibody-coated polymeric slow release nanoparticles to combat an overactive immune response.

In one embodiment, when the viral infection is associated with a cytokine storm or multi-organ disease, blood electrophoresis, kidney dialysis, and/or dielectrophoresis are needed to remove excessive cytokine and killed cells and viruses, etc.

In the cells, TRIM proteins are generated by the interferon. A number of TRIMs are needed to block viral infections. Trim2 binds to the antibody conjugated non-enveloped virions in the infected cells and directs the virions to the proteasomes where the virions are degraded.

In one embodiment, since there are no antivirals for newly genetically modified viruses, the body's immune response including cellular response with killer cells is the only way to overcome a viral infection; the immune stimulation is beneficial at the early diseases process but excessive response damages the vital organs of the patient the so called multi-organ disease.

In one embodiment, to stimulate the immune response, one can use viral-like particles along with serum antibody(s) obtained from convalescent person or an animal to conjugate with viral-like particles (VLP) that naturally produce a strong cellular immune response and interferon against any invading organism in this case the viral antigen that VLPs are conjugated with the viral antigen, e.g., COVID-19 or their mutations, spike protein or multiple antigens, etc. to initiate humoral and cellular response against the recently propagated epidemic viral infection. In one embodiment, this methodology using methylene blue can be used to produce a vaccine in antibody-coated polymeric slow release nanoparticles to produce or enhance the immune system to fight the viral (e.g., COVID-19) infection in general or SARS-CoV-2, COVID-19, or their mutations or other specific viruses, by inhalation or nasal drops or spray or aerosolized drops.

In one embodiment, using the antibody(s) coated VLPs used with the methylene blue vaccine production technology produces a strong cellular immune response by stimulating interferon production against any invading organism in this case the viral antigen, VLPs are conjugated with the viral antigen e.g., SARS-CoV-2, COVID-19, or their mutations spike protein or RNA or multiple antigens, etc. to initiate humoral and cellular response against the recently propagated epidemic viral infection and natural killer cells that are culture grown with SARS-CoV-2, COVID-19, or their mutations, antigen(s) or protein(s) are administered in a physiological solution or semifluorinated alkane or a physiological liquid with or without antivirals simultaneously with or without Rock inhibitors, or Wnt inhibitors as ivermectin, niclosamide or integrin inhibitors, simultaneously or sequentially by inhalation, subcutaneously, intraperitoneally, intramuscularly or intravenously to initiate a cellular and humoral immune response against the SARS-CoV-2, COVID-19 virus, or their mutations, or in immunosuppressed patient, where the natural killer cells attack the viruses to eliminate the infected cells and viruses.

In one embodiment, antibody-coated VLP that induces interferon production conjugated with spike protein of the virus is prepared with the known technology in the art for vaccination in antibody and CPP or Mucus penetrating agents coated polymeric slow release nanoparticles, with or without antivirals, and administered in a physiological solution or semifluorinated alkane or a physiological liquid intra-nasally, subcutaneously, or orally or systemically at low concentrations which can be repeated initially monthly, every three months, or six months or yearly by measuring the antibody or neutralizing antibody in a person.

In one embodiment, antibody-coated VLP that induces interferon production conjugated with fragments of RNA of the virus is prepared or after irradiation with UV light to crosslink it to lose its activity, but maintaining its antigenicity for vaccination in antibody (s), ACPP or MPP-coated polymeric slow release polymeric nanoparticles with or without antivirals simultaneously or sequentially and administered in a physiological solution or semifluorinated alkane or a physiological liquid intra-nasally, subcutaneously, or orally or systemically at low concentrations which can be repeated initially monthly, every three months, or six months or yearly by measuring the antibody or neutralizing antibody present in a person.

In one embodiment, using the spike protein or crosslinked DNA or RNA fragments of a number of viruses can be used with an antibody, CPP or MPP-coated VLP that enhance interferon production and to induce a humoral and cellular response against any viruses or other pathogens administered, in a physiological solution or semifluorinated alkane or a physiological liquid initially at very low but gradually increasing concentrations to render immune response against any organism.

In one embodiment, vaccination is performed with multiple viral antibodies, and CPP coated VLPs that induces interferon production conjugated with slow release polymeric nanoparticles with or without antivirals simultaneously or sequentially and administered in a physiological solution or semifluorinated alkane or a physiological liquid, etc. intra-nasally, subcutaneously, or orally or systemically at low concentrations which can be repeated initially monthly, every three months, or six months or yearly by measuring the antibody or neutralizing antibody present in a person.

In one embodiment, the VLPs can be coated with one or more viral (COVID-19) antibodies and another adjuvant, such as acrylic-acid-based adjuvant (ADJ) in antibody-coated polymeric slow release nanoparticles with or without antivirals, or catechins or Lovenox such as Remdesivir, favipiravir, etc. used in vaccine with and or an adjuvant production to create an incremental increase in immune response to the viruses, bacteria, etc. intramuscularly, by inhalation, intranasally without inducing a cytokine storm.

In one embodiment, the VLP or an adjuvant/antigen/antibody/Rock inhibitors, etc. vaccination is done with or without an antibody and ACPP-coated polymeric slow release of viral antibody, or antiviral-coated pluralities of nanoparticles alone or in an oxygenated semifluorinated alkane with adjuvants, such as Analgesic adjuvants, calcium phosphate hydroxide, saponin-based adjuvants (SBAs) aluminum phosphate, alum, aluminum hydroxide, paraffin oil, *Mycobacterium bovis*, squalene detergents, antivirals, catechins and/or Lovenox, antibiotics, such as tetracycline, a metalloproteinase inhibitor which are antibacterial and anti-inflammatory or doxycycline, Egg proteins, yeast proteins, Acidity regulators, or modified sugar molecules against viruses, such as Tamiflu, etc. in a semifluorinated alkane or a liquid for inhalation or intramuscularly, etc.

In one embodiment, the VLP/antigen/antibody/Rock inhibitors, etc. vaccination is done with or without antibody and ACPP, or MPP-coated polymeric slow release nanoparticles having dexamethasone or Rock inhibitors, Wnt inhibitors, integrin inhibitors, or GSK inhibitors with adjuvants such as Analgesic adjuvants, calcium phosphate hydroxide, aluminum phosphate, alum, aluminum hydroxide, paraffin oil, *Mycobacterium bovis*, squalene detergents, antiviral, antibiotics, Saponin-based adjuvants (SBAs), antivirals with Tetracycline derivative medications, a metalloproteinase inhibitor which is antibacterial and anti-inflammatory include demeclocycline, doxycycline, Minocycline, Minocin, etc. to treat inflammatory viral lung or brain infection through the nasal inhalation, etc., Egg proteins, yeast proteins, acidity regulators, or modified sugar molecules against viruses, such as Tamiflu, green tee extracts etc. or other antivirals, such as baloxavir marboxil, combined with nanoparticles or polymeric slow release antibody-coated pluralities of nanoparticles coated with a virus, SARS-CoV-2, COVID-19, or their mutations or influenza or other viruses in combination with LMWH/catechins, LMWH, heparin mimetics or viral-like or antibody coated viral like nanoparticles and an adjuvant such as acrylic-acid-based adjuvant (ADJ) to induce an immunity against the specific virus or treat specific viruses, etc. or vaccination for inhalation, or subcutaneous, intraperitoneal, or intramuscular or intravenous injection monthly, every three months, or six months or yearly by measuring the antibody or neutralizing antibody present in a person.

In one embodiment of viral lung or brain involvement the antibody, CPP or low-molecular-weight (2-5 kDa) polyethylene glycol or poloxamer, Lovenox-coated, VLP that induces interferon production is combined with or without polyphenols such as catechins with LMWH that block ACE-2 and neuropilin-1 receptors for the virus cell entry, and one of Rock inhibitors, Wnt inhibitors, GSK and/or integrin inhibitors, or with therapeutic medications, such an antiviral in a semifluorinated alkane or suitable medium administered by inhalation, with such as salbutamol, fenoterol, adrenalin, dobutamine, in antibody-coated polymeric slow release nanoparticles to reduce the side effect of vaccination and enhance recovery regardless of its application, intranasal, intramuscular, inhalation, or through the mouth by an inhaler, or intraperitoneal or intravenously.

In one embodiment, antivirals combined with antibody (monoclonal or polyclonal antibodies) coated or aptamer or mRNA or in combinations conjugated pluralities of nanoparticles or polymeric slow release nanoparticles coated against a virus, SARS-CoV-2, COVID-19, or their mutations or influenza or other viruses in combination with LMWH, heparin mimetics/catechins, or a metalloproteinase inhibitor tetracycline derivatives which antibacterial and anti-inflammatory and antibody-coated viral-like nanoparticles or an adjuvant as a vaccine to induce interferon and an immune response to the antigens and a pathway inhibitor, with or without additional adjuvants to induce an immunity against the specific virus/bacteria, etc. or treat specific viruses while blocking excessive type 2 immune response.

In one embodiment, an adjuvant can be used or added to a vaccine to enhance the immune response including amorphous aluminum hydroxyphosphate sulfate (AAHS), aluminum hydroxide, aluminum phosphate, potassium aluminum sulfate (Alum), Oil in water emulsion made of squalene, Monophosphoryl lipid A (MPL), QS-21, extracted from the Chilean soapbark tree in liposomes, Cytosine phosphoguanine (CpG) a synthetic DNA mimicking viral bacteria genetic material, Glucopyranosyl Lipid Adjuvant-Stable Emulsion (GLA-SE), synthetic Toll-like receptor (TLR)4 agonist, adjuvant Fluzone®. The GLA-SE adjuvant Fluzone vaccine, or saponins, etc.

In one embodiment, one can start with VLP antigen/antibodies vaccination through the inhalation or variation of vaccines repeatedly combined with pathway inhibitors.

In one embodiment, one can start with one mRNA vaccine and move to second application of the same or another vaccine, one such as VLP antigen/antibodies or synthetic toll-like receptor agonist in a semifluorinated alkane or perfluorocarbon liquid through the inhalation or variation of vaccines repeatedly combined with pathway inhibitors in slow release polymeric nanoparticles.

In one embodiment to prevent vasculitis, one can administer two or more antivirals, combined with cell inflammatory pathway inhibitors, with LMWH, or heparin mimetic, linoleic acid etc. complement inhibitors, anti-inflammatory compounds, by inhalation, orally, systemically, intravenously, subcutaneously, intramuscularly, etc.

In one embodiment of viral encephalitis, one prevents Alzheimer's and Parkinson's disease and other viral-related CNS infections with an antiviral in combination with cell inflammatory pathway inhibitors and with LMWH, or a heparin mimetic, complement inhibitors and specific medications such as Bariticinib, Kezara, and with LMWH, or heparin mimetics, complement inhibitors, etc. and GSK inhibitors by inhalation, orally, systemically, intravenously, subcutaneously, intramuscularly, etc.

In one embodiment, the endoplasmic reticulum stress of the neuronal cell in viral diseases and also traumatic brain injuries, etc. is treated by adding anti-inflammatory medications, such as such as Bariticinib, Kezara, to pathway inhibitors and combining ACE-2 inhibitors, neuropilin receptor blockage, catechins and linoleic acid, etc.

In one embodiment, as described with the use of methylene blue, for self-vaccination with a single dose unit or vaccine for nasal inhalation with one or multiple vaccines produced for numerous viruses that is obtained or ordered for home delivery from the pharmacists by doctor's prescription by inhalation, orally, systemically, intravenously, subcutaneously, intramuscularly, etc.

In one embodiment, two healthy laboratory animals with a body temperature of 37° C. are vaccinated, one by nasal inhalation/jet injector, and the other one by intramuscular injection of a vaccine made of treated (damaged) COVID-19 viruses grown in the cell culture media, with a solution of methylene blue at a concentration of 30 µg/ml in the dark environment for about two days. The samples of these treated viruses are placed in a cell culture and do not show any sign of growth. EM microscopy of the samples show these viruses have damaged RNA genetic material with some breaks in the single stranded RNA. The animals tolerate the vaccination well without showing much of a malaise, their temperature rises less than one degree C. by the second day. Both animals develop neutralizing antibodies in their blood after two to three weeks. The animals are challenged one month after vaccination through nasal inhalation of the COVID-19. Except for a mild rise in the body temperature and an increase in neutralizing antibodies in their blood, which last for few months that followed, the animals do not show any other signs of infection.

In another embodiment, two healthy laboratory animals with a body temperature of 37° C. are inoculated with 105 COVID-19 plaque forming units of the virus through the nose. The animals' temperatures are monitored regularly for any sign of increase. As soon as the animals' temperature rise one degree C. above the normal temperature to 38 degrees C., and the animals appear reluctant to play, a nose swab is taken from the animals and evaluated by PCR which becomes positive and the viruses are also grown on cell culture simultaneously. One animal immediately receives an intravenous dose of 3 mg/Kg of a solution of methylene blue in a normal physiological solution intravenously daily after a short intramuscular anesthesia, if the temperature remains high and is allowed to recover with monitoring his temperature for another day. A nasal swab is done daily for verification of the virus. The other animal having an increased body temperature and positive nasal swab, etc. is treated both by nasal inhalation with a methylene blue solution having 5 µg/ml methylene blue, by a jet injector/nebulizer two times daily and intravenous injection of the methylene blue at <3 mg/Kg dose. By three days, their body temperatures are dropped to 37.3 degree C., and gradually normalize though the animal with combination therapy with nasal inhalation is less affected.

In one embodiment, the vaccine is produced by a combination of VLP, dead bacteria, or viruses and methylene blue, in combination with pathway inhibitors, etc. for self-administration by nasal inhalation or subcutaneously or intramuscularly as needed and single dose vaccines use or add this vaccine to other existing mRNA vaccines.

In one embodiment, pluralities of viral or a fragment of the viral S protein antibody(s) coated polymeric nanoparticles are conjugated with CPP, or ACPP and one or two antivirals to enhance cell penetration of the nanoparticle inside the cells to damage the viruses which have penetrated the cells by nasal or topical, or systemic administration.

In one embodiment, pluralities of ACE-2 or neuropilin receptors antibody(s) coated polymeric nanoparticles are conjugated with CPP, or ACPP, or heparin or catechins or linoleic acid and one or two antivirals to block the viruses to enter the cells via ACE-receptors or neuropilin receptors inside the cells by nasal or topical, or systemic administration.

In one embodiment, antivirals can be combined with or without methylene blue, a phenothiazine dye, a cationic compound to enhance damage to the viruses, bacteria anionic RNA or DNA, and simultaneously acting as antioxidant and anti-depressant when given in combination with one of the pathway inhibitors, such as GSK inhibitors or GSK beta inhibitors and/or antivirals in a solution or as polymeric slow release nanoparticles or in semifluorinated alkanes to be administered by systemic or preferentially by inhalation one or multiple times daily below the toxic dose of 1-2 mg/L to reach both the lung and the brain preventing or treating viral inflammatory disease of the lung or the brain, and preventing subsequent Alzheimer's or Parkinson's diseases and nerve damage and preventing or treating the tangled tau neurofibriles and preventing Tau protein's toxicity by activating plasma membrane calcium ATPase, thus preventing endoplasmic reticulum (ER) stress response and unfolding the protein.

In one embodiment of vaccine preparation, to avoid the use of formaldehyde or glutaraldehyde, which are toxic and crosslink the viral and bacterial membranes which are harvested from the viruses or bacterial for their proteins for vaccine production and or auto vaccination to be used as prophylaxis or treatment of the viral or bacterial diseases such as SAR-Cov-2 or COVID-19, MCV, EBV, papilloma virus, Zoster or Hopes viruses, coronavirus, Zika, EBV, Zoster, etc. and their mutations, these organisms are grown in cell culture and harvested by centrifuge and filtration, then exposed to concentrations of methylene blue with or without cell penetrating peptides (CPP) or cyclodextrin or in combination with cysteine, etc., to enhance membrane penetration at concentration of above 1 mg/L to 50 mg/L or more with an antiviral at low concentrations for a period of about <30 minutes to 24 hours or more depending on the concentration of methylene blue alone or the antiviral without external light radiation to damage RNA or DNA of the virus, e.g., flaviviruses including the Dengue virus (DENY), Ebola Zaire, West Nile virus, Zika virus (ZIKV), Japanese encephalitis virus, Yellow Fever virus, influenza viruses, coronaviruses, herpes viruses, EBV, hepatitis A, B, and C viruses, or papilloma virus, while protecting the viral protein membranes and S-proteins of the viruses for vaccination; since methylene blue passes easily through viral or bacterial membrane because of its cationic charge to attach to RNA and DNA with its anionic charge and oxidizes the Guanine in presence of oxygen, thereby damaging the RNA or DNA and creating single-strand breaks (ssb) in the RNA of the viruses or bacteria. The presence of antivirals and antibacterials enhances the process, while leaving the viral capsid membrane or bacterial membrane intact to be used later alone or with other synthetic adjuvants such as Toll-like receptor 4, Saponin-based adjuvants (SBAs), etc. for vaccination alone, preferably in combination with LMWH or heparin mimetic to prevent simultaneous blood clotting induced by methylene blue. While methylene blue acts therapeutic by activating PI3-Akt and inhibiting GSK3β reducing edema of the brain produced by breakdown of blood brain barrier at the site or the endothelial cells and reduce inflammatory cytokines production, such as tumor necrosis factor (TNF)-α, (IL-6), interleukin (IL)-1β, and reduces the neutrophil cell infiltration in the brain and reduces microglial cell activation in encephalitis, while methylene blue and/or catechins or lineolic acid, and LMWH, etc. inhibit the entrance of the virus inside a cell through the ACE-2 receptor inhibition after inhalation, nasally, spray, ointment or orally as a solution, liposomes, pills, or gummy, polycaprolactone, intravenous, etc. administration with or without pathway inhibitors to reduce inflammatory response to the toxins at different sites in the brain and lung or intestinal tract or in brain infarct or in ischemic reperfusion syndrome or as in traumatic brain injuries, etc. preventing subsequent Alzheimer's or Parkinson's diseases.

In one embodiment, administration of this vaccine with or without antivirals, or LMWH or pathway inhibitors, nasally by spray or nebulization one can apply a light source of 670 nm for a short period of time through a fiber optic, the nasal cavity or oral cavity, throat, or through pharynx to kill the viruses directly.

In one embodiment, one administers stabilized hypochlorous acid, the stable N-chloro derivative, or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], glutathione peroxidase, and slow release polymeric nanoparticles that carry at least two of the antiviral medications together with one or more cell pathway inhibitors and heparin or low molecular weight heparin, synthetic heparin mimetics, or in combination with polyphenols and its derivatives that bind to heparan sulfate, linoleic acid, catechins and/or to sialic acid, thereby preventing the viral attachment to its cell receptors in the respiratory system or intestinal tract or brain as slow release nanoparticles or antibody-coated nanoparticles of lactic acid, polyglycolic acid, polycaprolactone, or as micelles, or in liposomes and chitosan; or as antibody-coated antiviral nanoparticles, such as gold or silver or zinc nanoparticles of 1-100 nm, preferably 1-10 nm in diameter, which act as antivirals and can penetrate the virus with or without methylene blue to damage the RNA or DNA of the virus and kill them with or without LMWH for vaccine production or therapeutic.

In one embodiment, this preparation is used for administration in the nose as inhalation, in spray, or by an inhaler, or nebulized form or orally to treat viral encephalitis or lung inflammation or orally for intestinal tract involvement for treatment of the virus to kill one or more viruses that remain in the nose/pharynx/throat or in the intestine after vaccination, or after having recovered from a virus infection, and prevent their reactivation, or further virus transmission to the healthy people, or it can be used as prophylaxis.

In one embodiment, antibody-coated slow release polymeric nanoparticles that carry at least two of the antiviral medications together with one or more cell pathway inhibitors and heparin or low molecular weight heparin, synthetic heparin mimetics, or in combination with polyphenols and its derivatives that bind to heparan sulfate, linoleic acid, catechins and/or to sialic acid, thereby preventing the viral attachment to its cell receptors as a slow release nanoparticles or antibody coated nanoparticles of lactic acid, polyglycolic acid, polycaprolactone, or as micelles, or in liposomes and chitosan; or as antibody-coated antiviral nanoparticles, such as gold or silver or zinc nanoparticles of 1-100 nm, preferably 1-10 nm in diameter, which act as antivirals and can penetrate the virus with or without methylene blue to damage the RNA or DNA of the virus, and kill them or after they are heated with light radiation in the nose, etc. after inhalation.

In another embodiment, the method further comprises the steps of administering a stabilized hypochlorous acid, the stable N-chloro derivative, or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], with antiviral medications together with pathway inhibitors and low molecular weight heparin or linoleic acid, and catechins conjugated with antibody-coated gold or silver or zinc nanoparticle of 1-100 nm preferably 1-10 nm in diameter which act as antivirals and can penetrate the virus conjugated with or without methylene blue for administration in the nose as inhalation, in spray or nebulized form, or orally to treat viral encephalitis or lung inflammation to kill one or more viruses that remain in the nose/pharynx/throat or in pills or gummy for oral delivery, after vaccination or after having recovered from a virus infection to eliminate remaining of resistant viruses by the above combinations to prevent reactivation or further virus transmission to healthy people or as prophylaxis.

In one embodiment of vaccine production, the viruses are grown by incubating them in the cell culture, after the viruses invade the cells, using the cell machinery they grow to the degree that they can exit or burst the cell wall, at this stage the viruses are separated from the cells by filtration by passing them through the pores of less than 200 micron by centrifugation. The intact viruses with their intact membranes and capsid containing the genetic component of the virus are incubated with a solution of methylene blue or combined with cell penetrating peptides or cyclodextrin, etc. at a desired concentration of 1 microgram/ml to 50 micrograms or more; the methylene blue with its positive charge and partially lipophilic action penetrates the outer membrane of the virus entering the virus with or without an antiviral, passing through the viral capsid and tightly attaches to the negatively charged RNA or DNA of the virus that in presence of the oxygen damages the Guanine of the RNA of DNA, which occurs rapidly at this stage or simultaneously one adds metallic nanoparticles of gold or silver, or zinc with the size of preferably <10 nm to one nanometer in diameter which has an antiviral effect with or without CPP or ACPP, which because of their size they penetrate the virus and attach to the DNA or RNA of the virus then entire viral culture is passed through a beam of laser radiation at a wavelength that is absorbed by the metallic nanoparticles attached to RNA or DNA of the virus, while it does not damage the outer membrane proteins or S-antigen, etc. of the virus by creating only locally an increased temperature at the site of the nanoparticles damaging the RNA or DNA to which the positively charged nanoparticles are attached, this process might take less than few seconds to a few minutes or more depending on the laser power and the spot size of the laser. At this stage, the DNA or RNA of the viruses are severely damaged while the viruses' membranes and their S-proteins and capsid proteins remain intact with their antigenic properties that can be harvested and utilized as a vaccine to be administered by inhalation, self-administration, injection intramuscularly, orally, in solution, ointment, in pills, in gummy, etc., alone or in combination with other antivirals and cell pathway inhibitors, such as Rock, GSK, integrin, and Wnt inhibitors, such as ivermectin or niclosamide, or LMWH, etc.

In one embodiment, the viral protein can also be combined with a synthetic adjuvants such as toll like receptor 4 or non-synthetic adjuvants, etc., to enhance the immune response of the patient or animals to the vaccine which can be used as nasal inhalation at repeated intervals as needed to induce sufficient immune response that can be checked for presence of neutralizing antibodies in the patient or the vaccine can be added to other vaccines such as mRNA vaccine, etc. to boost their effect or if the virus has mutated, and administered when needed as self-administration by inhalation through the nose, mouth and to vaccinate a large number of the population fast or the vaccine can be also injected initially as ordered by the physician, where the method simplifies the production and application of the vaccine application in a large population everywhere, specifically in developing countries, etc. the components can be premade to be used for any potential virus, etc. or the vaccine can be stored by freezing it in a regular refrigerator.

In one embodiment, the vaccines can be prepared from circulating tumor cells or tumor tissue from the cancerous circulating tumor cells or obtained by biopsy from any part of the body to be grown in the tissue culture and treated the same way with methylene blue, etc. or other appropriate dye and antibody-conjugated gold, silver or zinc nanoparticles of smaller than 10 microns, magnetic, paramagnetic or non-magnetic, nanoparticles and can be killed in vitro with or without radiation for vaccine production with or without pathway inhibitors and antitumor medication, etc. with or without external laser, or other source of energy if needed such as alternating magnetic field, the vaccine can be administered with or without LMWH to the patient locally or intra-arterially or intravenously, by inhalation, etc.

In one embodiment, in patients with viral infections, etc., such as COVID-19, there is an increased inflammatory process in the blood with release of cytokines causing a cytokine storm, etc. in these conditions anti-inflammatory compounds or inflammatory pathway inhibitors, such as Rock inhibitors, Wnt inhibitors, integrin inhibitors, and GSK inhibitor in antibody and CPP or PEG-coated polymeric slow release nanoparticles along with antiviral with or without DMF can be therapeutic or prophylactic if used by inhalation, orally, subcutaneously or intravenously or injected locally.

In one embodiment, anti-inflammatory compounds or inflammatory pathway inhibitors such as Rock inhibitors, Wnt inhibitors, integrin inhibitors, and GSK inhibitors along with antivirals can be combined with IL-1, IL-2, IL-6, and/or IL-17 inhibitors in antibody-coated and CPP or PEG conjugated polymeric slow release nanoparticles with LMWH/catechins as therapeutic or prophylactic if used by inhalation, orally, subcutaneously, intravenously, injected locally, or topically.

In one embodiment, anti-inflammatory compounds or inflammatory pathway inhibitors such as Rock inhibitors, Wnt inhibitors, integrin inhibitors and GSK inhibitors along with antivirals and/or GABA inhibitors such as KDS2010, low molecular weight heparin (Lovenox) to simultaneously act as antiviral (e.g., COVID-19) and other RNA viruses or anti-bacterial and/or synthetic heparin mimetics/catechins to block virus entry in the cells and probenecid Panex-1 inhibitor to enhance nerve repair and prevent blood coagulation and has an antiviral effect, with or without CPP-conjugated with pluralities of polymeric slow release antibody-coated pluralities of nanoparticles can be combined with IL-1 IL-2, IL-6, IL-17 inhibitors or a metalloproteinase inhibitor which are antibacterial, antiviral, and anti-inflammatory as therapeutic or prophylactic with extended release of the medication, if used by inhalation, orally, subcutaneously, or intravenously or injected locally or intraperitoneally.

In one embodiment, anti-inflammatory compounds or inflammatory pathway inhibitors, such as Rock inhibitors, Wnt inhibitors, integrin inhibitors and GSK inhibitors along TGF beta inhibitors, such as botulinum toxin at pictogram concentrations, with antiviral and/or protease inhibitors, such as indinavir, ritonavir, nelfinavir, darunavir, amprenavir, favipiravir, fosamprenavir, lopinavir, atazanavir, saquinavir, tipranavir, nitazoxanide, Apilimod or vacuolin-1 in polymeric slow release antibody-conjugated polymeric nanoparticles/CPP conjugated can be combined with IL-6, Kevzara, or Baricitinib, IL-17 inhibitors, antiviral mycophenolic acid as therapeutic or prophylactic with extended release of the medication if used by inhalation, or by an inhaler, orally, topically, subcutaneously, intravenously, or injected locally.

In one embodiment, anti-inflammatory compounds or inflammatory pathway inhibitors such as Rock inhibitors, Wnt inhibitors, integrin inhibitors and GSK inhibitors along with antiviral and/or protease inhibitors, such as Ganovo, in ACPP conjugated polymeric slow release antibody-conjugated nanoparticles can be combined with IL-6 Kevzara, IL-17 inhibitors, antivirals, mycophenolic acid, as therapeutic or prophylactic with extended release of the medication if used by inhalation, or by an inhaler, orally, subcutaneously or intravenously or injected locally.

In one embodiment, anti-inflammatory compounds or inflammatory pathway inhibitors, such as Rock inhibitors, Wnt inhibitors, integrin inhibitors, and GSK inhibitors along with an antiviral, such as, favipiravir, ritonavir, Remdesivir, Burton tyrosine kinase inhibitor (BTK) ibrutinib, zanubritinib, acalabrutinib, or JAK-STAT, or JAK1/JAK2 inhibitor ruxolitinib, baricitinib, Pacritinib or inhibition of oxidative stress with Thalidomide and lenalidomide, PI3K/AKT/mTOR pathway inhibitors, Duvelisib, inhibitors of phosphorylation of endoplasmic reticulum resident kinase (PERK), Rapamycin, with or without complement pathway inhibitors, such as C3 inhibitors—AMY-101 (NCT04395456) and APL-9 (NCT04402060); C5 inhibitors—eculizumab (NCT04346797 and NCT04355494); C1 esterase inhibitors, which block the classical complement pathway and antiandrogen bicalutamide or anti-VEGFs avastin, dexamethasone, or tetracycline derivatives, metalloproteinase inhibitors which are antibacterial, antiviral, and anti-inflammatory or nitric oxide (NO) or donor (NONOate) in antibody-coated polymeric slow release pluralities of nanoparticles as a nasal spray or inhalation therapy in viral lung infection or viral encephalitis as anti-inflammatory agents to release the medication slowly without affecting other organs and treat or prevent an autoimmune response in various organs, such as type 1 diabetes, autoimmune encephalitis that becomes chronic leading to Alzheimer's disease and dementia, Bechet disease, temporal arteritis, Crohn's disease, unknown causes of uveitis and many chronic diseases.

In one embodiment, generalized damage to the brain, lung, retina blood vessels, and/or endothelial cells that caused blood clot formation and/or leakage of the capillaries is seen in fluorescein retinal angiography, etc. or large veins and arteries are reported. In one embodiment, anti-inflammatory compounds or inflammatory pathway inhibitors such as Rock inhibitors, Wnt inhibitors, integrin inhibitors, and GSK inhibitor along with an antiviral, such as ritonavir, Remdesivir, favipiravir, nitazoxanide, etc. are combined with antibody-coated polymeric slow release pluralities of nanoparticles are conjugated with dipyridamole, to treat endothelial cell damage or simultaneously or sequentially with GABA inhibitors such as KDS2010, probenecid a panx-1 inhibitor, low molecular weight heparin (Lovenox)/polyphenols, such as catechins, epicatechin (EC), epigallocatechin (EGC), epicatechin gallate (ECG), and epigallocatechin gallate (EGCG), to simultaneously prevent viral cell entry, act as an antiviral (e.g., COVID-19) and other viruses or anti-bacterial if present, such as a metalloproteinase inhibitor which is an antibacterial and an anti-inflammatory in a semifluorinated alkane or other medium, and to enhance nerve repair and prevent blood coagulation as a nasal spray or inhalation, or by an inhaler, or intravenous applications along with anti-blood coagulants, such as aspirin, Coumadin, low molecular weight heparin (Lovenox), or synthetic heparin mimetics, or synthetic heparin, such as PG500, non-anticoagulant low molecular weight pegylated heparin or non-anticoagulant low molecular weight heparin and to enhance nerve repair and prevent blood coagulation, etc.

In one embodiment, Protease inhibitors, such as Ulinastatin, leupeptin epsilon-aminocaproic acid, Aprotinin Camostat mesilate, etc., indinavir, fosamprenavir, Artemisinin, ritonavir, nelfinavir, amprenavir, lopinavir, saquinavir atazanavir, tipranavir, and darunavir, etc., block the viral attachment and entry in the cell, such as combined with a viral polymerase inhibitor, such as Remdesivir, favipiravir, Ribavirin (RIB), nitazoxanide, etc. with or without α(1)-antitrypsin (AA T), Stachyflin, acetylstachyflin, Thiobenzamide, and an anti-inflammatory agent, such as dexamethasone and/or pathway inhibitor, such as Rock inhibitor (e.g., Fasudil) and/or Wnt inhibitors (e.g., Niclosamide) with both an antiviral and anti-inflammatory effect, ivermectin, etc., GSK inhibitor, or integrin inhibitor conjugated with antibody-coated polymeric slow release nanoparticles with a physiological solution or semifluorinated alkane or low molecular weight heparin (Lovenox), or synthetic heparin mimetics, non-anticoagulant low molecular weight, pegylated heparin, or non-anticoagulant low molecular weight heparin administered as a spray, aerosolized through the nose, mouth or injected subcutaneously, intravenously in a non-toxic dose, as topical ointment for intranasal application, or as a dry powder or liquid formulations to be used for inhalation as aerosolized preparation.

In one embodiment, one or more antivirals are used with pluralities of heparin or anti-coagulative or low molecular weight heparin to simultaneously act as antiviral, e.g., SARS-CoV-2, COVID-19, or their mutations or other RNA or DNA viruses and anti-bacterials, such as tetracycline derivatives, a metalloproteinase inhibitor which are antibacterial and anti-inflammatory or synthetic heparin mimetics or unfractionated heparins or synthetic heparin, such as PG500, conjugated with antibody-coated slow release polymeric pluralities of nanoparticles with or without and anti-VEGF (e.g., Avastin or Eylea) and are administered in a physiological solution or semifluorinated alkane or a physiological liquid as an aerosolized formulation for inhalation, or by an inhaler, subcutaneously, intramuscularly, or intravenously to treat early stage SARS-CoV-2, COVID virus, or other influenza viruses, or injected subcutaneously for treatment of Zika and or dengue viruses, Epstein Barr virus, viral encephalitis, etc., and reduce inflammatory processes in the body, eliminate the viruses in brain, in encephalitis or multi-organ disease after coronavirus infection, etc.

In one embodiment, a polymerase inhibitor, such as favipiravir (Faviflu), moroxydine, Azaindole VX-787, an inhibitor of PB2 and one or more protease inhibitors, such as Stachyflin, Doxycycline, acetylstachyflin, Thiobenzamide or darunavir, saquinavir, ritonavir, nelfinavir, Artemisinin, fosamprenavir, lopinavir, Faviflu, amprenavir, atazanavir, tipranavir, and one or more anti-inflammatory agents, such as dexamethasone and/or pathway inhibitor, such as a Rock inhibitor (Fasudil) and/or Wnt inhibitor (Niclosamide), ivermectin, etc., GSK inhibitor, or integrin inhibitor conjugated with antibody-coated polymeric slow release nanoparticles with a physiological solution or semifluorinated alkane administered in a physiological solution or semifluorinated alkane or a physiological liquid as a spray, aerosolized through the nose, mouth, or injected subcutaneously, intravenously in a non-toxic dose, or as topical ointment for intranasal application.

In one embodiment, a nuclear pathway inhibitor such as Leptomycin B is combined with an antiviral (including SARS-CoV-2 and COVID-19) or their mutations, such as Remdesivir, favipiravir and dexamethasone or Kevzara, or a pathway inhibitor such as a Wnt inhibitor such as Niclosamide with both an antiviral and anti-inflammatory effect, or synthetic heparin mimetics, or synthetic heparin, such as PG500, and GABA inhibitors such as KDS2010, low molecular weight heparin (Lovenox) or other non-anticoagulant low molecular weight heparin/catechins to simultaneously act as antiviral (e.g., against Covid-19), etc. and tetracycline derivatives, a metalloproteinase inhibitor which are antibacterial, antiviral, and anti-inflammatory or antibacterial by inhibiting the proteases and/or mycophenolic acid, an immunomodulator, with potent antiviral activity to enhance nerve repair and prevent blood coagulation, etc. conjugated with multiple antibody-coated slow release nanoparticles with a physiological solution or semifluorinated alkane or a physiological liquid administered as a spray, aerosolized through the nose, mouth or injected subcutaneously, intravenously, or orally in a non-toxic dose.

In one embodiment, a viral RNA and protein synthesis inhibitor such as Nucleozin or Cycloheximide or Naproxen and a polymerase inhibitor such as moroxydine are combined with an antiviral, such as remdesivir, Faviflu, Baricitinib, a Janus kinases inhibitor as anti-TNF and dexamethasone or a pathway inhibitor such as Wnt inhibitor such as niclosamide, etc. conjugated with multiple antibody-coated slow release slow release nanoparticles with a physiological solution or semifluorinated alkane administered as spray, aerosolized through the nose, mouth, or injected subcutaneously, intravenously in a non-toxic dose or as dry powder or liquid formulations to be used for inhalation as aerosolized preparation or ointment.

In one embodiment, a compound such as an influenza virus inhibitor such as sialidase is combined with a viral inhibitor such as Remdesivir, Favipiravir, Ribavirin (RIB), histone deacetylases (HDACs), such as Sodium Phenylbutyrate (PB) and Valproic Acid (VPA), etc. with or without α(1)-antitrypsin (AA T), Stachyflin, acetylstachyflin, Thiobenzamide, and an anti-inflammatory agent such as dexamethasone and/or a pathway inhibitor, such as a Rock inhibitor (Fasudil) and/or Wnt inhibitor (Niclosamide), ivermectin, etc., GSK inhibitor, or integrin inhibitor conjugated with antibody-coated polymeric slow release nanoparticles with a physiological solution or semifluorinated alkane, or low molecular weight heparin (Lovenox), or synthetic heparin mimetics, non-anticoagulant low molecular weight pegylated heparin, or non-anticoagulant low molecular weight heparin/catechins administered as a spray, aerosolized through the nose, mouth, orally or injected subcutaneously, intravenously in a non-toxic dose for lung, brain or multiorgan diseases after coronavirus infection or other viral infections or Multisystem Inflammatory Syndrome in Children (MIS-C).

In one embodiment, a compound such as an influenza virus inhibitor, such as indinavir, fosamprenavir, Artemisinin, ritonavir, nelfinavir, amprenavir, lopinavir, saquinavir atazanavir, tipranavir, and darunavir, etc., block the viral attachment and entry in the cell, such as combined with a viral inhibitor such as Remdesivir, favipiravir, Ribavirin, GS-20 67, GS-CA1, polyphenol and its derivatives such as catechins and an anti-inflammatory agent, such as dexamethasone and/or a pathway inhibitor, such as a Rock inhibitor (Fasudil), etc. and/or Wnt inhibitor (Niclosamide), ivermectin, etc., GSK inhibitor, or integrin inhibitors conjugated with antibody-coated polymeric slow release pluralities of nanoparticles with a physiological solution or semifluorinated alkane, with or without spironolactone against prions EBV, or other viruses by nasal application, reduces pulmonary edema at a lower dose than systemic administration and reduces the transmembrane serine protease 2 (TMPRSS2) action and as an antioxidant or low molecular weight heparin (Lovenox), or synthetic heparin mimetics, non-anticoagulant low molecular weight pegylated heparin, or non-anticoagulant low molecular weight heparin administered as a spray, aerosolized through the nose, mouth, orally or injected subcutaneously, intramuscularly, intravenously, by inhalation and/or combined with a known anti-inflammatory agent that can prevent pyroptosis of cells, such as dimethyl fumarate (DMF), administered orally, by injection or by inhalation in a slow release polymeric pluralities of nanoparticle format for a short period or time of 1-2 weeks as needed in a non-toxic dose of 100-1000 mg as needed for lung, brain, or multi-organ diseases after coronavirus infection, such as SARS-CoV-2, COVID-19, or their mutations or other severe viral infections or with mycophenolic acid, an immunomodulator, with potent antiviral activity in Multisystem Inflammatory Syndrome in Children (MIS-C), DMF or Fumaric acid esters (FAEs) inhibit the activity of the transcription factor NF-κB and proinflammatory cytokines by T cells by its immunomodulatory mechanisms.

In another embodiment, in a systemic multisystem disease, where there is a genetic flaw in alpha-interferon, one administers synthetic interferons made by recombinant DNA technology with anti-inflammatory agents, such as doxycycline, a metalloproteinase inhibitor, which has an antibacterial and anti-inflammatory effect along with LMWH, polyphenol and its derivatives, such as catechins, NSAIDS or dexamethasone, with or without an anti-VEGF (e.g., Avastin or Eylea), one or more pathway inhibitors, such as Wnt, Rock, GSK, integrin inhibitors with TGF-alpha inhibitors with or without an anti-VEGF (e.g., Avastin or Eylea), with one or more antiviral agents, such as indinavir, molnupiravir, or MK-4482/EIDD-2801, and mycophenolic acid, an immunomodulator, with potent antiviral activity in a semifluorinated alkane of other suitable medium for inhalation, intramuscular, or intravenously.

In one embodiment of virals or COVID-19 disease or in multisystem disease, one administers LMWH, polyphenol and its derivatives, such as catechins, NSAIDS, doxycycline, one or more pathway inhibitors, such as Wnt, Rock, GSK, integrin inhibitors with TGF-alpha inhibitors, in addition to Pegaptanib sodium, with or without an anti-VEGF (e.g., Avastin or Eylea), a nucleotide polyethylene glycol RNA aptamer that inhibits angiogenesis that binds to $VEGF_{165}$, or another anti-VEGF with one or more antiviral agents or with ebselen and or glutathioneperoxidase and superoxide dismutase (SOD)—requiring additional zinc, or manganese, or heparin for ideal catalytic activity applied to the nasal passages, in a semifluorinated alkane or other suitable medium for inhalation, intramuscular, intravenously or inside a body cavity injection.

In one embodiment, one or more antivirals, such as Remdesivir, Ribavirin (RIB), histone deacetylases (HDACs), such as Sodium Phenylbutyrate (PB) and Valproic Acid (VPA) as an antiviral and protection of the liver and kidney, etc. are combined with NS1 inhibitors combined with MEK1 and MEK2, NFKB inhibitors, such as Bortezomib and glycosylation inhibitors, such as L-fructose and L-xylulose and one or more Rock inhibitors or Wnt inhibitors are combined with GSK inhibitors or integrin inhibitors conjugated with antibody-coated polymeric slow release nanoparticles with a physiological solution or semifluorinated alkane administered as a spray, aerosolized through the nose, mouth, at a non-toxic dose or as a dry powder or liquid formulations to be used for inhalation as aerosolized preparation.

In one embodiment, one or more antivirals, such as Remdesivir, Favipiravir, Ribavirin (RIB), oseltamivir, cyclosporine, etc. and an anti-oxidants or immunomodulators, such as calcitrol, Rolipram, a selective phosphodiesterase-4 (PDE-4) inhibitor to reduce bronchospasm, anti TNF alpha inhibitor Baricitinib, a Janus kinase inhibitor, interleukin antagonists, low molecular weight heparin, or synthetic heparin mimetics, an antiviral used in HIV infection, such as GS-6207, a long acting HIV capsid inhibitor, IL-6, Kevzara, PDE5 inhibitors sildenafil and tadalafil, enhance the level and action of cGMP, relax the smooth muscles of the lung or brain etc. improve tissue oxygenation and remove toxic proteins such as beta amyloid etc., IL10 inhibitors such as Canakinumab (Ilaris), GABA inhibitors such as KDS2010, low molecular weight heparin (Lovenox) to enhance nerve repair and prevent blood coagulation, NSAIDs ibuprofen, Dexamethasone, and one or more Rock inhibitors or Wnt inhibitors are combined with a GSK inhibitor or integrin inhibitor conjugated with antibody-coated polymeric slow release nanoparticles, where the antibody prevents the virus from entering the cells is administered with a physiological solution or semifluorinated alkane administered at a non-toxic dose in a physiological solution or semifluorinated alkane or a physiological liquid as a spray, aerosolized through the nose, mouth, intravenously or intramuscular or subcutaneously as needed in lung, brain or multi-organ diseases after coronavirus infection or other viral infections.

In one embodiment, the inflammatory viral diseases of the lung, brain, and other organs are treated as described in this application in addition with high oral doses of antioxidants such as ascorbic acid, Octyl gallate (octyl 3,4,5-trihydroxybenzoate), gallate (propyl 3,4,5-trihydroxybenzoate), Calcium 1-ascorbate Propyl 6-O-Palmitoyl-l-ascorbic acid (ascorbyl palmitate, natural or tocopherols, Synthetic α-tocopherol Synthetic γ-tocopherol Synthetic 6-tocopherol, tetracycline and/or mycophenolic acid, an immunomodulator, has potent antiviral activity or Baricitinib, etc. or an anti-inflammatory agent such as dimethyl fumarate (DMF), used orally or with or without and anti-VEGF by inhalation at low concentrations, inhibit pore formation and pyroptosis with its indiscriminate cellular destruction in the lung, brain, or multi-organ diseases after coronavirus infection or viral or SARS-CoV-2, COVID-19 infections, etc. or severe inflammation of the lung or brain or intestinal tract inflammation, the so-called Multisystem Inflammatory Syndrome in Children (MIS-C) diseases, etc.

In one embodiment, a compound such as an influenza virus inhibitor such as sialidase is combined with a viral inhibitor such as Remdesivir, Favipiravir, Thiobenzamide, and an anti-inflammatory agent such as dexamethasone and/or a pathway inhibitor, such as Rock inhibitor (Fasudil) and/or Wnt inhibitor (Niclosamide), ivermectin, etc., GSK inhibitor, or integrin inhibitor conjugated with antibody-coated polymeric slow release nanoparticles, or conjugated with antibody-coated liposomes filled with low molecular weight heparin (Lovenox) or synthetic heparin mimetics or synthetic heparin, such as PG500, or non-anticoagulant low molecular weight pegylated heparin filled liposomes or PEG-PLA, micelles or non-anticoagulant low molecular weight heparins administered in a physiological solution or semifluorinated alkane or a physiological liquid as a spray, aerosolized through the nose, mouth, orally or injected subcutaneously, intravenously in a non-toxic dose or dry powder and liquid formulations is used for inhalation as a aerosolized preparation.

In one embodiment, one or two antivirals such as Remdesivir, Favipiravir, Ribavirin (RIB), oseltamivir, cyclosporine, and/or Niclosamide are combined with another antiviral heparin or low molecule weight heparin such as Lovenox or synthetic heparin mimetics which acts in blocking virus attachment and entrance to the cells or endothelial cells used with a Rock inhibitor (Fasudil) and/or Wnt inhibitor (Niclosamide), ivermectin, etc., GSK inhibitor, or integrin inhibitor conjugated with antibody-coated polymeric slow release nanoparticles, or conjugated with antibody-coated liposomes filled with low molecular weight heparin (Lovenox) or synthetic heparin mimetics or non-anticoagulant low molecular weight pegylated heparin-filled liposomes or micelles or non-anticoagulant low molecular weight heparins <600KD or other heparins, such as recombinant heparin, high molecular weight heparin, low molecular weight heparin, unfractionated heparin, heparin fragments, heparin analogue, low-molecular-weight heparin-taurocholate 7 (LHT7) and sulfonated polysaccharides containing heparin activity, heparan sulfate. In one embodiment, heparin, sulfated heparin, or synthetic heparin, such as PG500, can be combined with catechins or cyclodextrin or conjugated with chitosan and poly(lactide-co-glycolide) complexes with or without other antivirals, such as faviflu, remdesivir, etc., to be used as nasal spray or combined with 0-pamitoyol to treat various viral infections, such as herpes simplex viruses of types 1 and 2), and the respiratory syncytial virus (SRV), influenza viruses, SARS-CoV-2, COVID-19, or their mutations human papilloma virus 16 (HVP-16), etc. administered in a physiological solution or semifluorinated alkane or a solvent such as polyethylene glycol or ethanol or a physiological liquid as a spray, aerosolized through the nose, mouth, orally, or injected subcutaneously, intravenously in a non-toxic dose, or as a dry powder and liquid formulations used for inhalation as a aerosolized preparation to inhibit viral invasion in the cell or its proliferation.

In one embodiment, giant papillary conjunctivitis (GPC) is treated with artificial tears while avoiding the use of a contact lens or administration of topical with an NSAID, such as Ketorolac 0.4%, etc. combined with low molecular weight heparin, e.g., enoxaparin or heparin mimetics.

In one embodiment, the viral infection, such as SARS-CoV-2, COVID-19, or their mutations etc. is treated with a topical application of low molecular weight heparin, such as lovenox, etc. with cyclosporine A as an anti-inflammatory and antiviral agent and anti-fungal at 0.0000001%-5% concentration with or without antivirals such as Faviflu, Remdesivir, Favipiravir, etc. with or without Wnt inhibitors, such as ivermectin or niclosamide which work synergistically with heparin or heparin mimetics or heparin nanoparticles and Ebselen and/or glutathione peroxidase, and superoxide dismutase (SOD)—metabolize oxidative toxic intermediates requiring zinc, selenium, manganese iron, copper, and for ideal catalytic activity and LMWH to treat viral conjunctivitis and/or scleritis, vasculitis, retinitis, loss of the smell, cerebral vasculitis, or lung infection caused by SARS-CoV-2, COVID-19, or their mutations virus, etc.

In one embodiment, the viral infection, such as SARS-CoV-2, COVID-19, or their mutations, etc. is treated with a topical, intranasal, inhalation, etc. application of low molecular weight heparin or heparin nanoparticles, such as Lovenox, etc., with cyclosporine A or Tacrolimus, or a mycophenolic acid, an immunomodulator, has potent antiviral activity and an anti-inflammatory and antiviral agents at 0,0000001%-5% concentration with or without other anti-inflammatory agents, such as colchicine or in combination with Panx1 inhibitor probenecid in viral vasculitis to protect neurons from damage in the brain or after refractive corneal surgery.

In one embodiment, low molecular weight heparin, synthetic heparin mimetics, or synthetic heparin, such as PG500, work synergistically with cyclosporine A, antiviral and antifungal, synergistically to treat topically blepharitis, and dry eye with or without Wnt inhibitors at a non-toxic concentration.

In one embodiment, low molecular weight heparin or heparin nanoparticles or antibody conjugated nanoparticles and/or microparticles of heparin mimetics, or synthetic heparin, such as PG500, PG 545, work synergistically with catechins or with cyclosporine A, and anti-fungal and/or mycophenolic acid an immunomodulator, with potent antiviral activity and an anti-inflammatory and antiviral agent where the antibody prevents the virus from entering the cells with or without a solution of stabilized hypochlorous acid at pH 6-8 or another medium in bacterial and viral infections of the lid and conjunctiva, etc.

In one embodiment, a topical application of low molecular weight heparin, such as Lovenox, or synthetic heparins, such as PG500, PG 545, etc. with cyclosporine A antiviral and anti-fungal at 0.0000001%-5% concentration with or without antivirals such as Faviflu, remdesivir, etc. with or without Wnt inhibitors such as ivermectin or niclosamide work synergistically to treat conjunctivitis and or scleritis caused by COVID-19 virus.

In one embodiment, one or two antivirals, such as Remdesivir, Favipiravir, Ribavirin (RIB), oseltamivir, histone deacetylases (HDACs), such as Sodium Phenylbutyrate (PB) and Valproic Acid (VPA), cyclosporine, mycophenolic acid as an anti-inflammatory and antiviral anti-fungal agent, and/or Niclosamide are combined with another antiviral heparin or heparin mimetics, such as PG500, or PG 545, or heparin nanoparticles or low molecule weight heparin, such as Lovenox, which acts in blocking numerous viruses attachment and entrance to the cells or endothelial cells used with a Rock inhibitor (Fasudil), TGF beta inhibitors, and/or Wnt inhibitor (Niclosamide), ivermectin, etc., GSK inhibitor, or integrin inhibitor conjugated with antibody-coated polymeric slow release nanoparticles, such as polylactic, polyglycolic or a combination or polycaprolactone, polyanhydride, etc., or conjugated with antibody-coated liposomes filled with low molecular weight heparin (LMWH), such as (Lovenox) or non-anticoagulant low molecular weight pegylated heparin-filled liposomes or micelles, heparin nanoparticles where antibody prevents the virus from entering the cells or non-anticoagulant low molecular weight heparins <6000KD, other heparins for use such as recombinant heparin, high molecular weight heparin, low molecular weight heparin, unfractionated heparin, heparin fragments, heparin analogue, low-molecular-weight heparin-taurocholate 7 (LHT7) and sulfonated polysaccharides containing heparin activity, heparan sulfate. or heparin mimetics/catechins administered in a physiological solution or semifluorinated alkane or a physiological liquid as a spray, aerosolized through the nose, mouth, orally, or injected subcutaneously, intravenously in a non-toxic dose, or as a dry powder and liquid formulations is used for topical application, on the conjunctiva, intranasal inhalation as a aerosolized preparation to inhibit viral invasion in the cell or its proliferation in conjunctivitis, nasal, throat, pharynx, lung, or through the nasal sensory nerves to brain and brain vessel to prevent or treat vasculitis.

In one embodiment, LMWH or heparin nanoparticles or synthetic heparin or heparin mimetics, such as PG500, or PG 545, at 0.01 mg/ml to 30 mg/ml is used in combination with or without catechins and/or doxycycline with pH adjusted to 7.5 and a concentration of 0.1% to 2% is in blepharoconjunctivitis caused by bacterial infection, or antivirals in blepharoconjunctivitis as topical drops or spray.

In one embodiment, LMWH or heparin nanoparticles at 0.01 mg/ml to 30 mg/ml concentration is used topically in combination with one or two antivirals in blepharoconjunctivitis, such as in viral conjunctivitis, such as SARS-CoV-2, COVID-19, etc.

In one embodiment, LMWH or heparin nanoparticles or synthetic heparin, such as PG500, PG 545, etc. at 0.01 mg/ml to 30 mg/ml concentration and/or as a combination with or without catechins and doxycycline or with doxycycline with pH adjusted to 7.5 and concentration of 0.1% to 2% and/or triamcinolone at 400 microgram/0.1 ml are used topically in scleritis caused by a viral infection or in an autoimmune response to a pathogen.

In one embodiment, LMWH or pegylated heparin or heparin mimetics, such as PG500, PG 545 etc., nanoparticles is used topically in combination with a solution of sodium hypochlorite at concentrations 0.01-10%, stabilized to a pH of 5-10 preferably 7.5 to treat bacterial or viral conjunctivitis or viral keratoconjunctivitis, such as SARS-CoV-2, COVID-19 or their mutations, HSV1-2, VZV or intranasally for upper or lower respiratory viral infection or viral encephalitis as prophylaxis or therapeutic.

In one embodiment, LMWH or heparin mimetic, such as PG500, PG 545, etc. is used topically for inhalation, intranasally, etc. in combination with hypochlorous acid or sodium hypochlorite or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] or their nanoparticles sequentially in viral upper respiratory infection, such as SARS-CoV-2, COVID-19, or their mutations, influenza, HSV 1-2 or Epstein Bar virus or VZV, etc. infection or viral encephalitis, vasculitis with or without probenecid or histone deacetylases (HDACs), such as Sodium Phenylbutyrate (PB) and Valproic Acid (VPA).

In one embodiment, LMWH or pegylated heparin antibody-coated pluralities of nanoparticles or heparin mimetics, such as PG500, PG 545, etc., is used topically or for inhalation, intranasally, etc. in combination with anti-virals, such as Baricitinib, Glidesivir, Favipiravir, Xofluza Remdesivir, nanoviricides, Oya1, interferon, umifenovir, tamivir ribavirin, baloxavir in viral upper respiratory infection, such as SARS-CoV-2, COVID-19, or their mutations, influenza, HSV 1-2 or Epstein Bar virus or VZV, etc. infection or viral encephalitis or vasculitis.

In one embodiment, heparin, or sulfated heparin, or heparin mimetics with or without polyphenols with and without TGF beta inhibitors can be combined with cyclodextrin or conjugated with chitosan and poly(lactide-co-glycolide) complexes with or without other antivirals, such as faviflu, remdesivir, Baricitinib, Glidesivir, Favipiravir, Xofluza Remdesivir, nanoviricides, Oya1, interferon, Artemisinin, umifenovir, tamivir. ribavirin, baloxavir, etc., to be used as nasal spray or combined with 0-pamitoyol to treat various viral infections to the eye, nose, or respiratory tract, such as herpes simplex viruses of types 1 and 2), and the respiratory syncytial virus (SRV), influenza viruses, SARS-CoV-2, COVID-19, or their mutations, human papilloma virus 16 (HVP16), etc.

In one embodiment, when internal eye structures are involved in SARS-CoV-2, COVID-19, or their mutations or other viruses, one administers non-toxic concentrations of Baricitinib, Glidesivir, Favipiravir, remdesivir, Artemisinin, etc. topically or injected inside in uveitis, retinitis and vasculitis with or without low molecular weight heparin.

In one embodiment, the GPC is treated with administering slow release polymeric nanoparticles carrying one or more cell pathway inhibitors, such as the Rock inhibitor Fasudil, wmt.IL6 or TGF-beta inhibitor such as Kavzara, Ivermectin or antiviral PLpro or Mpro inhibitors, such as Ebselen, Ebseleno, or Ebselen, and/or glutathione peroxidase and superoxide dismutase (SOD)—metabolize oxidative toxic intermediates requiring zinc, selenium, manganese iron, copper, and for ideal catalytic activity applied in the nose, conjunctiva and/or with NSAIDs or low molecular weight heparin or pegylated heparin antibody-coated pluralities of nanoparticles, such as Lovenox, Fragmin, dalteparin or non-anti-thrombotic heparin, or heparin mimetic such as PG500, PG 545, etc., unfractionated heparin, an antibiotic, such as tetracycline derivatives doxycycline, etc. or antiviral combinations.

In one embodiment, an intranasal application of low molecular weight heparin or heparin is administered with pluralities of nanoparticles and vasoconstricting agent, and Wnt inhibitors or mast cell stabilizer control itching and Astemizole an antihistaminic agent, at 0.1-0.5 microgram/ml for as inhalation or spray running nose and allergic response, in lid, conjunctiva, nose and throat, etc.

In one embodiment, a topical application of low molecular weight heparin, such as Lovenox or synthetic heparin, such as PG500, PG 545, etc., with cyclosporine or mycophenolic acid or Baricitinib as an anti-inflammatory and antiviral agent at a 0.0000001%-5% concentration or with Ebselen or doxycycline which also has an antiviral, antibacterial, anti-inflammatory, anti-prostaglandin, and neuroprotective effect, with or without antivirals, such as Faviflu, remdesivir, etc. and, vidarabine ointment, and trifluridine solution (Viroptic) or idoxuridine solution and ointment, work synergistic to treat conjunctivitis caused by bacteria and viruses or COVID-19 virus or its mutations and dry eye.

In one embodiment, a topical application in the conjunctiva or nasal of low molecular weight heparin, such as Lovenox, or heparin antibody-coated pluralities of nanoparticles, etc. with probenecid or probenecid nanoparticles and/or with Ebselen and/or glutathione peroxidase and superoxide dismutase (SOD)—metabolize oxidative toxic intermediates requiring zinc, selenium, manganese iron, copper, and for ideal catalytic activity applied with mycophenolic acid/Doxycycline which acts as an antiviral, antibacterial, anti-inflammatory, anti-prostaglandin and neuroprotective as solution or ointment, work synergistically to treat ocular inflammation caused by bacteria and viruses or SARS-CoV-2, COVID-19 virus, or their mutations, and dry eye or after corneal refractive surgery.

In one embodiment, a topical application of low molecular weight heparin or antibody-coated heparin nanoparticles, or LMWH as Lovenox, etc., with administration of topical with an NASID, such as Ketorolac 0.4% in dry eye and blepharoconjunctivitis.

In one embodiment, a topical application of low molecular weight heparin or with or without antivirals or pegylated heparin antibody-coated pluralities of nanoparticles, such as Lovenox from 0.1 mg to 10 mg, etc. with mycophenolic acid, etc. at 0.0000001%-5% concentration work synergistically to treat dry eye, allergic blepharoconjunctivitis or Giant papillary conjunctivitis, and scleritis, etc.

In one embodiment, a topical application of low molecular weight heparin or pegylated heparin nanoparticles, such as Lovenox, or heparin mimetics, such as PG500, PG 545, etc., with or without antivirals, with ivermectin or niclosamide at picogram to microgram concentrations with or without antivirals, work synergistically to treat conjunctivitis caused by bacteria and viruses.

In one embodiment, a topical application of low molecular weight heparin, such as Lovenox or catechins of pegylated heparin or antibody-coated pluralities of nanoparticles or other non-anticoagulative heparins, where antibody, aptamer or mRNA conjugated with nanoparticles prevents the virus from entering the cells from 0.1 mg to 10 mg and Ebselen which also has an antiviral, antibacterial, anti-inflammatory, anti-prostaglandin and neuroprotective effect at a 0.00000001%-5% concentration with or without antivirals such as Favipiravir or an antibiotic, work synergistic to treat conjunctivitis caused by bacteria and viruses.

In one embodiment, a topical application of low molecular weight heparin, such as Lovenox, etc., from 0.01 mg to 10 mg with apilimod or vacuolin-1, or Wnt inhibitor or Rock inhibitor or probenecid at microgram to nanogram concentrations, work synergistically for neuronal growth of the cornea after refractive surgery, such as LASIK, Smile, or cataract surgery, etc.

In one embodiment, the conjunctivitis is treated initially with non-specific artificial tear drops and cold compress while more severe cases of bacterial infections are managed with antibiotic drops or ointments, such as Sulfacetamide, or ofloxacin or Polytrim, or Ciloxan (ciprofloxacin), combined or sequentially as anti-inflammatory agents, are useful except for steroid which requires exclusion of viral infection, anti-integrins or GSK-inhibitors, etc. Preference is given if viral infections, such as COVID-19 is suspected, to Wnt inhibitors, ivermectin, and an antiviral, such as acyclovir or valcyclovir or ebselen and to low molecular weight heparin or antibody-coated heparin nanoparticles if other viruses are involved.

In one embodiment of bacterial or viral conjunctivitis, Lovenox or low molecular weight heparin or non-anticoagulant heparin can be used combined or sequentially as, from 0.1 mg to 10 mg or more daily alone because of its antiviral effect or in addition to other antivirals to treat diseases, such as the SARS-CoV-2, COVID-19, or their mutations virus or herpes virus and other viruses, with antivirals such as Baricitinib, a Janus kinases inhibitor as an anti-TNF, Glidesivir, Favipiravir, Xofluza Remdesivir that blocks virus replication, nanoviricides, Oya1, interferon, umifenovir, tamivir ribavirin, baloxavir, histone deacetylases (HDACs), such as Sodium Phenylbutyrate (PB) and Valproic Acid (VPA), melatonin, can be used orally, as pills or gummy or liposomes or with semifluorinated alkanes or as a spray, intranasally, topically, by inhalation, or systemically with or without IL-6 inhibitors, etc. or Ebselen and or Ivermectin or other antivirals such as saquinavir, indinavir, ritonavir, nelfinavir, amprenavir, fosamprenavir, lopinavir, atazanavir, tipranavir, darunavir, etc.

In one embodiment of bacterial or viral conjunctivitis, Lovenox alone or in combination or sequentially as with ivermectin, or Ebselen and/or glutathione peroxidase and superoxide dismutase (SOD)—metabolize oxidative toxic intermediates requiring zinc, selenium, manganese iron, copper, and for ideal catalytic activity applied to the eye with mycophenolic acid, an immunomodulator, potent antiviral activity or an antibiotic, doxycycline or a capsid inhibitor GS-6207 (Lenacapavir), can be used in bacterial conjunctivitis or blepharoconjunctivitis because of their antibacterial effect, anti-viral effect, and its anti-inflammatory action or can be used in combination with an antibiotic or a disinfectant solution, such as hypochlorous acid or sodium hypochlorite or N-chlorotaurine (NTC), dimethylated derivatives of NCT (N-chloro-2,2-dimethyltaurine [DM-NCT] and N,N-dichloro-2,2-dimethyltaurine or their nanoparticles, which has also synergistic effect with low molecular weight heparin which as soothing effect in addition to antiviral or bacterial, and anti-inflammatory action in the nose, lung, or brain.

Hypochlorous acid (HCLO) and its anion hypochlorite (OCl$^-$) is naturally produced compound by the white blood cells by the enzyme myeloperoxidase to eliminate invading bacteria, viruses, or fungi in the body. It penetrates the cell wall of the bacteria, protein, and nucleic acids to denature and deactivate them.

In one embodiment, stable Hypochlorous acid can be produced by either adding chlorine to the water to form hypochlorite, and ClO$^-$ (HClO and ClO$^-$ are oxidizers). Hypochlorous acid can also be made by electrolysis of salt (Na Cl) in water (H$_2$O) producing hypochlorous acid and sodium hydroxide (NAOH). Stable hypochlorous acid has a pH of 5-6. At pH 11-13, the chlorine is mostly in the form of hypochlorite solution, whereas at pH 5, most of the chlorine is present as hypochlorous acid (HOCl). The hypochlorous acid with a long shelf life can be produced.

In one embodiment, Hypochlorous acid at concentrations of <500-50 or less, parts per million is not toxic and can be used as topical drops or spray for conjunctivitis blepharitis keratitis, or intranasally as inhalation at a concentration of <50 parts per million.

In one embodiment, the viral conjunctivitis is treated combined or sequentially with topical administration of liquid or ointment of Baricitinib, a Janus kinase inhibitor as an anti-TNF, Glidesivir, Favipiravir, Xofluza Remdesivir, nitazoxanide, Artemisinin, nanoviricides, Oya1, interferon, umifenovir, tamivir ribavirin, baloxavir can be used topically, orally, systemically, or with or without IL-6 inhibitors, etc. and Lovenox and/or Ivermectin, and Ebselen nanoparticles with or without or N-chlorotaurine (NTC), dimethylated derivatives of NCT (N-chloro-2,2-dimethyltaurine [DM-NCT] and N,N-dichloro-2,2-dimethyltaurine nanoparticles.

In one embodiment, the viruses causing conjunctivitis can also be drained in the nose through the nasolacrimal duct and infect the nose, through and pharynx. In one embodiment, the conjunctival and the nasal cavities are treated combined or sequentially by drops using the described antivirals with antibody-coated pluralities of nanoparticles of low molecular with heparin as spray drops or inhalation simultaneous with the treatment of the conjunctiva with or without dimethylated derivatives of NCT (N-chloro-2,2-dimethyltaurine [DM-NCT] and N,N-dichloro-2,2-dimethyltaurine nanoparticles.

In one embodiment, all forms of Heparins, such as high molecular weight heparin or heparin nanoparticles, low molecular weight heparin, unfractionated heparin, heparin analogues, heparin mimics containing glucosamine saccharides and acrylamide, and sulfated polysaccharides containing heparin activity heparin fragments, recombinant heparin or pegylated heparin nanoparticles or heparin mimetics have similar blocking effect on the viruses, such as SARS-CoV-2, COVID-19, or their mutations, etc., bacteria and inflammation.

In one embodiment of bacterial or viral conjunctivitis, Lovenox can be used in bacterial conjunctivitis or blepharoconjunctivitis, because of its antibacterial effect, anti-viral effect, and its anti-inflammatory action or in combination or sequentially with NSAIDs such as Ketorolac 0.4% in allergic conjunctivitis as topical medication ointment or spray.

In one embodiment of bacterial or viral conjunctivitis, Lovenox can be used in bacterial conjunctivitis or blepharoconjunctivitis because of its antibacterial effect, anti-viral effect, and its anti-inflammatory action or dimethyl fumarate (DMF), or a Janus kinase inhibitor as an anti-TNF alpha with Ebselen and tetracyclines and its derivatives, or glutathione peroxidase and superoxide dismutase (SOD)—requiring additional zinc, or manganese, for ideal catalytic activity applied to the conjunctiva, nasal passages or used orally or by injection or as inhalation in severe inflammatory conditions, such as multiple sclerosis, psoriasis, to inhibit protein Gasdermin D pore formation, and uncontrolled cellular damage or pyroptosis, in combination or sequentially with one or more antivirals, Favipiravir, nitazoxanide, Remdesivir, and/or molnupiravir or MK-4482/EIDD-2801 and/or a protease inhibitor, such as ritonavir, saquinavir, and indinavir administered in a physiological solution or semifluorinated alkane or a physiological liquid for inhalation with or without an inhaler in a COVID-19 upper or lower respiratory infection of its vasculitis in brain vasculitis, or multisystemic inflammatory disease or orally or intravenously or subcutaneously, etc., where the low molecular heparin attaches to the SARS-CoV-2, COVID-19, or their mutations, ACE-2 receptor and prevents or treats the infection.

In one embodiment of bacterial or viral conjunctivitis, Lovenox or Dalteparin can be used in bacterial conjunctivitis or blepharoconjunctivitis because of its antibacterial effect, anti-viral effect, and its anti-inflammatory action or in combination or sequentially with one or more antivirals Remdesivir, Favipiravir, or a protease inhibitor, such as ritonavir, saquinavir, and indinavir, molnupiravir or MK-4482/EIDD-2801 or nitazoxanide administered in a physiological solution or semifluorinated alkane with an additional solvent, such as polyethylene glycol (PEG) or ethanol, or a physiological liquid applied topically in the conjunctiva to treat a viral blepharoconjunctivitis or a viral keratitis, where the low molecular heparin or heparin mimetics attaches to the SARS-CoV-2, COVID-19, or their mutations, ACE-2 receptor and prevents or treats the infection applied topically or using an inhaler.

In one embodiment, Lovenox or enoxaparin sodium solution is prepared at 10-100 mg/ml at pH of 5.5-7.5 administered in a physiological solution or semifluorinated alkane or a physiological liquid intra-nasally with a Rock inhibitor and or TGF beta inhibitors as slow release polymeric nanoparticles alone or in combination or sequentially with 1-2 antivirals and a decongestant administered in a physiological solution or semifluorinated alkane or a physiological liquid intra-nasally or by an inhaler to treat SARS-CoV-2, COVID-19 or their mutations as prophylaxis or therapy.

In one embodiment, Lovenox or enoxaparin sodium solution or heparin nanoparticles or pegylated heparin nanoparticles, or heparin mimetics is prepared at 1-100 mg/ml at pH of 5.5-7.5 alone as powder, inhalation dose from 0.1 mg to 20 mg or more daily solution or polymeric nanoparticles for slow release poly (lactic glycolic) acid or in combination or sequentially with 1-2 antivirals and a decongestant administered in a physiological solution or semifluorinated alkane or a physiological liquid intra-nasally or by an inhaler to treat COVID-19 as prophylaxis or therapy.

In one embodiment, Lovenox or enoxaparin sodium solution or pegylated emoxaparin nanoparticles, or heparin mimetics, such as PG-500 or PG-545, are prepared at 1-100 mg/ml at pH of 5.5-7.5 alone as powder, or spray for Inhalation dose from 0.1 mg to 20 mg or more daily solution or polymeric nanoparticles for slow release or in combination or sequentially with 1-2 or more antivirals, Wnt inhibitor ivermectin or niclosamide, GSK inhibitor or anti-integrins and a decongestant administered in a physiological solution or semifluorinated alkane with an additional solvent, such as polyethylene glycol (PEG) or ethanol or a physiological liquid intra-nasally or by an inhaler, such as a delivery device selected from the group consisting of a nebulizer, an inhaler, or an aerolizer, ultrasonic nebulizer, jet nebulizer, to treat SARS-CoV-2, COVID-19, or their mutations and other viral respiratory diseases as prophylaxis or therapy.

In one embodiment, Lovenox or enoxaparin sodium or pegylated enoxaparin nanoparticles or heparin mimetics solution is prepared at 1-100 mg/ml at pH of 5.5-7.5 alone as powder, inhalation dose from 0.1 mg to 20 mg or more daily solution or polymeric antibody-coated pluralities of nanoparticles for slow release or in combination or sequentially with 1-2 or more antivirals, Wnt inhibitor ivermectin or niclosamide, GSK inhibitor or anti-integrins or TNF alpha inhibitors Baricitinib, a Janus kinases inhibitor, and/or IL-1β inhibitors, such as canakinumab or DMF, and a decongestant with or without stabilized hypochlorous acid solution at pH 5-7 or sodium hypochlorite solution or administered in a physiological solution or semifluorinated alkane with an additional solvent such as polyethylene glycol (PEG) or alcohol or a physiological liquid intra-nasally with or without an antibiotic ointment applied to the nasal passages or by an inhaler, ultrasonic nebulizer, jet nebulizer to treat SARS-CoV-2, COVID-19, or their mutations or other viruses as prophylaxis or therapy of respiratory viral infection or viral encephalitis or severe vasculitis.

In one embodiment, Lovenox or enoxaparin sodium solution or anther Anticoagulants heparin is prepared at 1-100 mg/ml at a pH of 5.5-7.5 alone or in combination or sequentially with 1-2 antivirals such as remdesivir and one protease inhibitor or other anti-virals, such as ganciclovir or acyclovir or valacyclovir, Cidofovir, Vidarabine, Penciclovir, Foscarnet Fomivirsen Famciclovir or Oseltamivir phosphate, Rimantadine, Amantadine, Zanamivir, Telbivudine, Lamivudine, Entecavir, Emtricitabine, capsid inhibitor GS-6207 (Lenacapavir), Adefovir, IL6 inhibitor, administered in a physiological solution or semifluorinated alkane or a physiological liquid intranasally as slow release polymeric nanoparticles for topical application in viral keratitis as topical drops, spray or inhalation in inflammatory vasculitis of the brain or the lung or topical application in the eye.

In one embodiment, Lovenox or enoxaparin sodium solution or another anticoagulant, heparin or heparin nanoparticles is prepared at 10-100 mg/ml at a pH of 5.5-7.5 as powder, solution or polymeric nanoparticles for slow release, alone or in combination or sequentially with 1-2 antivirals and remdesivir that blocks virus replication and one protease inhibitor or other anti-virals with or without stabilized hypochlorous acid, NCT of up to 0.5 mM concentration or sodium hypochlorite for inhalation or topic intranasal application, in treatment of viral diseases of the eye, nose, upper and lower respiratory disease and viral cerebral vasculitis or orally with or without DMF for intestinal complication of COVID-19.

In one embodiment, Lovenox or enoxaparin sodium solution or another anticoagulant, heparin or heparin or heparin mimics containing glucosamine saccharides and acrylamide antibody-coated nanoparticles is prepared at 10-100 mg/ml at a pH of 5.5-7.5 as powder, solution or in combination or sequentially with 1-2 or more antivirals and remdesivir that blocks virus replication and one protease inhibitor or other anti-virals with or without stabilized hypochlorous acid (NaCLO), N-chlorotaurine (NTC), dimethylated derivatives of NCT (N-chloro-2,2-dimethyltaurine [DM-NCT] and N,N-dichloro-2,2-dimethyltaurine [DM-NDCT] nanoparticles or sodium hypochlorite at 0.05-1.5 wt %; or more or hypochlorous acid (HCLO) in combination with water or semifluorinated alkanes at similar concentrations or stabilized hypochlorous acid 0.10% for inhalation or for topic intranasal application along with an antibiotic ointment applied with or without Ebselen and or glutathione peroxidase and superoxide dismutase (SOD)—requiring additional zinc, or manganese, for ideal catalytic activity applied to the nasal passages, in treatment of viral. bacterial diseases of the eye, nose, upper and lower respiratory disease and viral cerebral vasculitis where endothelial cell of the vessels are damaged by the released cytokine, or orally for intestinal complication of SARS-CoV-2, COVID-19, or their mutations in Multisystem Inflammatory Syndrome in Children (MIS-C).

In one embodiment, low molecular weight heparin or pegylated heparin nanoparticles at 0.01 mg to 300 mg·ml solution, preferably 0.05-0.1 wt % or 1-10 mg/ml is used alone or in combination with DMF at microgram to milligram concentrations, doxycycline at concentrations of 0.5%-10% doxycycline alone or in combination with sodium hypochlorite of 0.001-2 wt % or hypochlorous acid, N-chlorotaurine (NTC), dimethylated derivatives of NCT (N-chloro-2,2-dimethyltaurine [DM-NCT] and N,N-dichloro-2,2-dimethyltaurine [DM-NDCT] nanoparticles, or with or without probenecid in water or semifluorinated alkanes with additional solvents, such as polyethylene glycol (PEG) or ethanol as topical, mucosal, oral, intranasal, inhalation, etc. an antibiotic ointment, such as doxycycline, applied to the nasal passages to treat bacterial or viral conjunctivitis or nasal and respiratory tract, influenza, COVID-19, etc., viral, RNA or DNA viruses including prions or bacterial respiratory infection or cerebral vasculitis, necrotizing scleritis, encephalitis, intestinal multisystem disease in SARS-CoV-2, COVID-19, or their mutations.

In one embodiment, low molecular weight heparin or heparin antibody-coated pluralities of nanoparticles at 0.01 mg to 300 mg·ml solution, preferably 0.05-0.1 wt % or 1-10 mg/ml is used alone or in combination with doxycycline at concentrations of 0.5%-10% doxycycline alone or with dexamethasone 400-2000 mg/ml in combination or sequentially in water of semifluorinated alkanes with or without probenecid as topical, mucosal, oral, intranasal, tetracycline derivatives, an antibiotic ointment etc. applied to the nasal passages by inhalation, etc. act simultaneously as an antiviral, antibacterial, and an anti-inflammatory in respiratory viral infections, anti-inflammatory or as topical drops in the eye for ocular and adnexal inflammation or uveitis or scleritis.

In one embodiment, low molecular weight heparin or heparin mimics containing glucosamine saccharides and acrylamide to bind to 13-Secretase (BACE-1) involved in Alzheimer's disease (AD) or pegylated heparin nanoparticles at 0.01 mg to 300 mg·ml solution, preferably 0.05-0.1 wt % or 1-10 mg/ml is used as spray or aerosolized for inhalation alone or in combination with doxycycline at concentrations of 0.5%-10% doxycycline alone or rifampin 0.1 mg to 5 mg/ml and Rock inhibitors with dexamethasone 400-2000 mg/ml in water or semifluorinated alkanes with an additional solvent, such as polyethylene glycol (PEG) or alcohol as topical, mucosal, oral, intranasal, inhalation, or the use of inhalator to treat vascular endothelial cell damage in the lung or in the brain, etc. by preventing COVID-19 or other viruses to attach to the endothelial cell wall, prevent complement factors activation, and causing damage and subsequent attachment of the platelets and blood clot formation.

In one embodiment, one administers subcutaneously or intravenously, etc. low molecular weight heparin or heparin mimetics combined with LY6E, a naturally occurring protein in the body, to prevent the virus attachment to the ACE-2 receptors and inhibition of virus to enter the endothelial cells and damage them in respiratory viral infection or viral brain encephalitis through an inhalation preparation or intravenously or subcutaneously.

In one embodiment of a case of conjunctivitis or viral or bacterial respiratory or brain infection, one can administer topically or spray for inhalation a combination or sequentially with mycophenolic acid an IL-17 inhibitor or cyclosporine as antiviral and anti-inflammatory and an antiviral agent in a 0.5-1 mg/ml physiological solution or semifluorinated alkanes, as emulsion or micelles or nanomicelles, liposomes, or oil in water, with 0.001-20 or more mg/ml of low molecular weight heparin or heparin mimetics, or heparin antibody-coated pluralities of nanoparticles and at least one or more antivirals, in combination or sequentially topically or for inhalation or with Lifitegrast at concentration of 1 mg/ml or dexamethasone, at 10 microgram/ml to 4 mg/ml one-three times to five times a day or more or 1-2 drops a day, with doxycycline and minocycline to reduce bacterial spread, and act as anti-inflammatory agents, etc.

In one embodiment, all accessible body cavities involved with a viral or bacterial infection, such as the bladder, uterus, abdominal cavity, eye, or CNS cavities or in the joint or subcutaneously can be treated with non-toxic doses of the above described preparations in a non-toxic dose along with TNF alpha inhibitor Baricitinib, a Janus kinase inhibitor or IL-beta inhibitors or DMF in a physiological solution or semifluorinated alkane or a physiological liquid by intracavity administration or injection or intravenously or intraarterial as is needed and prevent post encephalitis induced dementia.

In one embodiment using intranasal delivery to the brain takes a shorter and faster route than the systemic administration. Since the blood vessel are separated from the brain by the presence of the blood brain barrier. In addition, the nasal delivery bypasses the general circulation that brings polymeric slow release nanoparticles to the liver where they are taken up from circulation and never reach the brain.

In one embodiment, at least two antivirals used in an appropriate medium at a lower concentration that is administered alone to increase effectiveness of the preparation against the viral infection while reducing their toxicity and treat a viral infection.

In one embodiment, at least two antivirals PEGylated or non-PEGylated are combined with one or more protease inhibitors or polymerase inhibitors with LMWH, or mycophenolic acid to increase effectiveness of the preparation against the viral infection while reducing their toxicity and treat a viral infection.

In one embodiment, at least two antivirals are combined with anti-inflammatory agents such as Baricitinib, DMF, complement inhibitors (C1, C3, C5) and one pathway inhibitor sequentially or as a cocktail at reduced concentrations to increase their efficacy and reduced their side effects.

In one embodiment, the vaccine is created to act simultaneously therapeutically and as vaccine by killing the viruses or bacteria or fungi after they have grown in the cell culture media or other culture media, using at least one antiviral or one antibiotic, a tetracycline or antifungals and methylene blue at concentrations of <5 μg/ml or more, this remaining mixture will have an antiviral, methylene blue and/or an antibiotic, such as tetracycline or antifungal that can be administered to a person as a therapeutic medication/vaccine while after its absorption in the body through inhalation, nose or orally in the intestinal tract or administration intramuscularly or intravenously or intraperitoneally acts as vaccine because, it is made of a composite of medications, such as methylene blue and at least one antiviral and/or antibacterial or antifungal plus antigenic material from the viruses such as antigenic membrane protein or bacterial protein, etc. Stimulating the body's immune response to produce neutralizing antibodies against viruses or bacteria or fungi, etc. This vaccination cocktail is made of a non-toxic dose of methylene blue that penetrates the membrane wall of the bacteria and virus, etc. to attach itself to the RNA and DNA of the organism and corrupts their genetic material, or in conjunction with one or more antivirals or one more antibiotics, etc., such as tetracycline derivative, etc., or antifungals, such as vorcanazol, etc. that enter now with ease the viral and bacterial membranes or fungi to enter the cytoplasm of the viruses or bacteria or fungi and attach to their RNA and DNA, thus damaging it and killing these organisms, while the remaining membranes of the virus and/or bacteria still remains antigenic producing an immune response to the organism.

In one embodiment, this above-mentioned mixture can be made in a large quantities to act also now therapeutic, i.e., they can kill the organism locally. However, when they are absorbed inside the body, the dead membranes of these organisms maintain their antigenic characteristic and induce a humoral or cellular immune response as a vaccine does by enhancing the immune response. Therefore, the vaccine acts now both therapeutically by killing the viruses or bacterias or fungi, etc. and simultaneously acts as vaccine since it contains also the antigenic material of the organism, plus antivirals and or antibiotics or antifungals or antiparasites that it carries.

In another embodiment, the antigen of the viruses or bacteria, etc., obtained as above, is added to one or more antivirals or one or more antibiotics to build this mixture that acts both therapeutically or as vaccine after administration, nasally, orally, intramuscularly or intravenously killing the viruses or bacteria, etc. and simultaneously acting as a vaccine enhancing the immune response to the specific virus or bacteria or fungi.

In another embodiment, the antigen of the viruses or bacteria, etc. is added to one or more antivirals or one or more antibiotics with or without methylene blue at less than 4 microgram/ml concentration to build this mixture that acts both therapeutically to which a pathway inhibitor and/or LMWH is added in order to act as anti-inflammatory reducing the inflammatory response to the mixture while acting as a vaccine simultaneously because it carries the antigen of the specific virus and bacteria or fungi along with the appropriate medications.

In one embodiment, the antigen/medication of the viruses or bacteria, etc. obtained as above is added to one or more antivirals or one or more antibiotics to build this mixture that acts both therapeutically to which other compound are added, such as LMWH or heparin mimetic, to prevent side effects of blood coagulation, or in addition to catechins or linoleic acid etc.

In one embodiment, the approach to therapy of moderate to severe viral inflammatory disease or persistent viruses after therapy, etc. is to use messenger RNA coated CRISPR (crRNA) directed to a specific region of the virus where Cas-9 or Cas-13, etc. conjugated via thiol, not a modified virus, with antibody-coated very small 1-20 nm in size or preferably 1-10 nm nanoparticles of gold, silver or zinc which penetrate the membranes of the viruses with ease and have an antiviral activity combined with an mRNA inhibitor, such as plitidepsin or Aplidin, along with one or more antivirals, such as Remdesivir, Favipiravir or nitazoxanide or Lopinavir or methylene blue, etc. or with or without pathway inhibitors and with LMWH or heparin mimetic in a solution or in a semifluorinated alkane or with or without linoleic acid, and administered as intranasal spray or by inhalation, orally, etc. to damage the mRNA viruses, such as SARS-CoV-2 or COVID-19 or other respiratory viruses or HIV virus, etc.

In one embodiment, the approach to therapy of moderate to severe viral inflammatory disease or persistent viruses after therapy, is to use messenger RNA conjugated CRISPR interference (CRISPRi) or using a catalytically dead (dCas9 protein), which does not have endonuclease activity for genes regulation (i.e. cutting or replacing it) while directed to specific region of the virus where dCas 9 or dCas 13, etc. conjugated with an antibody coating, not with a modified virus, but with very small 1-20 nm in size or preferably 1-10 nm antiviral nanoparticles of gold, silver or zinc with an mRNA inhibitor, such as remdesivir or plitidepsin or Aplidin, via thiol in a cationic milieu.

In one embodiment of therapeutic vaccination, a combination of methylene blue with dead or without dead viruses or an mRNA virus vaccine, etc. plus antivirals, e.g. polymerase inhibitor such as remdesivir, or plitidepsin or Aplidin, or lopinavir, a protease inhibitor, and pathway inhibitors and LMWH and/or heparin mimetic are prepared for inhalation using a mixed micelle system where two or more medications can be mixed for multiple inhalation using an inhaler or with a mucomyst by inhalation, which contains acetylcysteine, n-acethylsystein or its derivatives, which act as an anti-inflammatory and antithrombotic when combined with antivirals and cell pathway inhibitors for therapeutic vaccines, etc., or by spraying through the nose or mouth all at non-toxic concentrations the micelles can be administered with or without PEG for ease of penetration through the mucosa covering the nasal mucosa, reaching the brain through the olfactory or trigeminal nerves or through the throat, trachea, bronchi and lung alveoli to reach the alveoli of the lung capillaries with ease.

In one embodiment, the antigens of multiple viruses or mRNAs, or mutations the same virus, bacteria, etc. is added to one or more antivirals or one or more antibiotics, such as tetracycline derivatives with or without methylene blue at about a 4 microgram/ml concentration with antibody-conjugated gold, silver, or zinc, etc. small nanoparticles of less than 20 nm preferably 1-10 nm in diameter to build this mixture that acts both therapeutically to many viruses, the so-called universal therapeutic vaccine against viruses or bacteria or fungi, etc. to which a pathway inhibitor is added in order to act as anti-inflammatory reducing the inflammatory response to the mixture, while acting as a vaccine simultaneously because it carries the antigen of the specific virus and bacteria or fungi along with the appropriate medications, forming a cocktail for vaccination against, e.g., numerous strains of viruses or bacteria or fungi etc.

In another embodiment, the antigen of the viruses or bacteria, etc. is added to one or more antivirals or one or more antibiotics with or without methylene blue at less than a 4 microgram/ml concentration to build this mixture that acts both therapeutically to which a pathway inhibitor is added in order to act as anti-inflammatory reducing the inflammatory response to the mixture while acting as a vaccine simultaneously because it carries the antigen of the specific virus and bacteria or fungi along with the appropriate medications forming a cocktail for vaccination against, e.g., numerous viruses to bacteria for immunization of children or adults.

In one embodiment this above-mentioned mixture, can be made in a large quantities to act also now therapeutic, i.e., they can kill the organism locally, however when they are absorbed inside the body the dead membranes of these organism maintain their antigenic characteristic and induce a humoral or cellular immune response as a vaccine does enhancing the immune response. Therefore, the vaccine acts now both therapeutically by killing the viruses or bacteria or fungi etc. and simultaneously acts as vaccine since it contains also the antigenic material of the organism, plus antivirals and/or antibiotics, anti-fungals, or antiparasites that it carries.

In one embodiment to reduce an inflammatory response, one can deliver the therapeutic combination of an antiviral incrementally or encapsulated in wax, gelatin, polycaprolactone, or as a capsule, pill, or dry powder for inhalation by combining one antiviral such as protease inhibitor, such as Ebselen and/or a polymerase inhibitor, such as remdesivir, faviravir, and/or with a transcription inhibitor, such as abacavir combined with Mpro or Ganovo to block the entry of the virus in the cell and/or antibody coated nanoparticles or LNP or gold nanoparticles etc. with one or more cell pathway inhibitors, such as Rock inhibitor Fasudil or ROCK2, Fasudil1-(5-Isoquinolinesulfonyl)-2 Methylpiperazine Calcium Channel Blockers, and/or Molnupiravir a polymerase inhibitor polymerase inhibitor, AT-527. orally or with RBD inhibitor, heparin mimetic, LMWH, lenolic acid, or with one anticoagulant, such as rivaroxaban (Xarelto), dabigatran (Pradaxa), apixaban (Eliquis) or edoxaban (Lixiana), etc. or orally or intramuscularly, subcutaneously, etc., by injection, or by inhalation, or with a mucomyst by inhalation or intravenously which contains acetylcysteine, n-acethylsystein, or its derivatives, where they act as an anti-inflammatory and antithrombotic, or by inhalation at very low doses that can be increased incrementally by the doctor/patient until neutralizing antibodies are measured in the serum of the patient and prevent a severe immune response that can produce blood clots in the main vessels or dissolving blood clot if they have formed.

In one embodiment, in cell culture of viruses including SARS-CoV-2 or 19 or Omicron etc. or their mutations or any other viruses, the methylene blue can be combined with one or more DNA or RNA damaging agents without damaging or crosslinking the viral proteins, such as an antiviral, an antimetabolite, such as Floxuridine, 5-Fluorouracil, 6 Mercaptopurine, cytarabine, flurabine, or para-aminobenzoic acid (PABA), or sulfonamide, the antimetabolite antibiotics preventing replication of DNA or RNA or actinomycine-D, etc., ribavirin, a nucleoside reverse transcriptase inhibitor (NRTI) targets enzymes, including inosinate dehydrogenase, thymidylate synthase, cytidine-5'-triphosphate synthetase, etc. that block RNA and DNA of viruses or other antivirals, such as a chemotherapeutic agent, salvianolic acid A & B, an antiviral agent, or an antineoplastic agent, or an antitumorgenic agent, or an immunotherapeutic agent such as mycophenolic acid or antimitotic agent or their analogues or a prodrug that are activated by viral proteases, such as paclitaxel, combretastatin, bryostatin, colchicine, or discodermolide at low non-toxic concentrations to kill the organism in the cell culture or to be administered after preparation as a vaccine subsequently locally, nasally, orally, intravenously, or intramuscularly, etc. or administered to the patient combined with one or more inflammatory pathway inhibitors and/or LMWH or another anticoagulant absorbed inside the body through various routes of administrations, such as the nose, orally, intravenously, intra-arterially, locally, etc. where the dead membrane of these organisms are sieved out and they maintain their antigenic characteristics and induce both a humoral and/or cellular immune response as a vaccine, thereby enhancing the immune response while the medications kill the viruses, therefore this vaccine acts now both therapeutically and prophylactically, while the pathway inhibitors, etc. prevent severe inflammatory processes, or radiotherapeutic agents and/or chemotherapeutic agents are provided.

In one embodiment, lipid nanoparticles combined with one or more antivirals or a vaccine, such as an mRNA vaccine, etc., is delivered through inhalation to avoid systemic absorption of the nanoparticles through the reticuloendothelial cells, or in the liver or spleen, while reducing the amount of medication that is given alone or in combination with one or more pathway inhibitors to prevent post vaccination inflammatory processes, and the therapeutic vaccine can be self-administered by the patient at any frequency or concentration as prescribed by the physician with or without LMWH or another anticoagulant, such as a mucomyst by inhalation, which contains acetylcysteine, n-acethylsystein, or its derivatives that act as an anti-inflammatory, Entyvio (vedolizumab), ustekinumab and IL-12/23 Xeljanz and antithrombotic when combined with antivirals and cell pathway inhibitors for therapeutic vaccines, etc. with or without lineolic acid.

In another embodiment, the therapeutic vaccine uses lipid nanoparticles combined with antivirals or an existing vaccine, and is delivered through inhalation to avoid systemic absorption of the nanoparticles through the reticuloendothelial cells, or in the liver or spleen, while reducing the amount of medication when it is given alone or in combination with one or more pathway inhibitors to prevent post vaccination excessive inflammatory processes, and the therapeutic vaccine can be self-administered by the patient at any frequency or concentration as prescribed by the physician with or without LMWH or another anticoagulant or with a mucomyst by inhalation, which contains acetylcysteine, n-acethylsystein, or its derivatives that act as an anti-inflammatory and antithrombotic when combined with antivirals and cell pathway inhibitors for therapeutic vaccines, etc., or lineolic acid, or catechins, etc. self-administered by inhalation to treat viral encephalitis with or without methylene blue boosting other vaccines when administered together as adjuvant.

In one embodiment, the gold, silver, zinc, or other metallic or non-metallic antibody-coated nanoparticles combined with antivirals, antibacterials, or antitumorals as a vaccine is delivered through inhalation to avoid systemic absorption of the nanoparticles through the reticuloendothelial cells, or in the liver or spleen, while reducing the amount of medication given alone or in combination with one or more pathway inhibitors to prevent post vaccination inflammatory processes and the therapeutic vaccine can be self-administered by the patient at any frequency or concentration as prescribed by the physician with or without LMWH or another anticoagulant or lineolic acid. The same combination can be given through other routes to the body as needed.

In one embodiment, metallic or non-metallic antibody-coated nanoparticles, such as gold, silver, or zinc oxide with or without PEG, etc. are conjugated with an mRNA in which the nucleoside is modified to carry the vaccine inside the cell eliminating the use of polymer hydrid nanoparticles (LPNs) or can carry any other gene to the organ as needed, by either local injection, inhalation, intra-arterially, intravenously, orally, in the eye, inside other body cavities, or in the circulation etc. as needed.

In one embodiment, the antibody-coated polyethylene glycol coated metallic nanoparticles, such as gold, silver, or zinc oxide at 1-10 nm diameter or more can be conjugated with a Dcr, a catalytically dead (dCas9 protein), CRISPR, or CRISPRi via thiol in a cationic milieu to temporarily or permanently cut or modify the desired gene(s) in the body or selectively in the desired organs, etc.

In one embodiment, involving the in vitro culture of bacteria, fungi or parasites, or a malignant or benign tumor, the methylene blue can be combined with one or more DNA or RNA damaging agents without damaging or crosslinking the bacteria, fungi, or parasites, or a tumor's proteins, such as an antiviral, an antimetabolite, such as Floxuridine, 5-Fluorouracil, 6-Mercaptopurine, cytarabine, flurabine, tacrolimus, para-aminobenzoic acid (PABA), or sulfonamide, the antimetabolite antibiotics preventing replication of DNA or RNA or actinomycine-D, etc., ribavirin, a nucleoside reverse transcriptase inhibitor (NRTI) target enzymes, including inosinate dehydrogenase, thymidylate synthase, cytidine-5'-triphosphate synthetase, etc. that block RNA and DNA viruses or bacteria, fungi, or the tumor cells, a chemotherapeutic agent, salvianolic acid A & B, an antiviral agent, an antineoplastic agent, an antitumorgenic agent, or an immunotherapeutic agent, such as mycophenolic acid or an antimitotic agent or their analogues or prodrug that are activated by viral proteases, such as paclitaxel, combretastatin, bryostatin, colchicine, or discodermolide at low non-toxic concentrations to kill the organism in the cell culture or the tumor cells and to be used as a vaccine locally, intravenously, nasally, by inhalation, or administered to the patient combined with one or more inflammatory pathway inhibitors and/or LMWH absorbed inside the body through various routes of administration, where the dead membranes or cytoplasmic proteins of these dead organisms, viral, bacteria, fungi, or a patient's tumor cell maintain their antigenic characteristics without being crosslinked and induce a humoral and/or cellular immune response as a vaccine, thereby enhancing the immune response with or without natural killer cells, while the medications kills the bacteria, fungi, parasites, or a patient's tumor cells. As such, the vaccine acts both in a therapeutical and prophylactical manner by eliminating the causative agents, while the pathway inhibitors, etc. prevent severe inflammatory processes or provided with a combination of radiotherapeutic agents or chemotherapeutic agents at a low non-toxic level with or without other medications, such as LMWH, or another anticoagulant, etc.

In one embodiment, the patients, after recovery from the respiratory viral infection, such as the SARS-CoV-2 infection, COVID-19, or other viral diseases, such as EBV, etc., have prolonged symptoms of the disease, these include severe fatigue, neuropathy, shortness of breath and dizziness, weakness and hypoxemia, headaches or confusion, increased depression and anxiety, gastrointestinal symptoms, coronary plaque rupture, a heart attack, chronic inflammation, myocarditis, simmering encephalitis, or bronchitis, etc. that translates into hundreds or thousands of patients, considering the millions or people affected just from the COVID-19 virus.

In one embodiment, the cause of the chronic disease is due to still living viruses in the respiratory tract or elsewhere that create chronic infections, and are treated with repeat full doses or ½, ⅓, ¼, or a lower percentage dose of an existing vaccine alone or combined with one or more pathway inhibitors, such as Wnt, GSK, Rock inhibitors, or anti-integrins injected intramuscularly, or preferably, by inhalation or orally.

In one embodiment, the cause of the chronic disease is due to still living viruses in the respiratory tract or elsewhere or persistence of viral antigens in the tissue, e.g., in the lung, heart, or brain, etc. that create chronic infections, are treated with repeat full doses or ½, ⅓, ¼, or a lower percentage dose of a therapeutic vaccine which has an antiviral effect and a vaccine effect to activate the immune system alone, or preferably combined with one or more pathway inhibitors, such as Wnt, GSK, Rock inhibitors, or anti-integrins injected intramuscularly, or preferably, by inhalation or orally, and/or combined for a period of time with anticoagulants to prevent blood clotting such as an LMWH, or heparin mimetics, or another anticoagulant, complement C3 or C5 inhibitors, or steroids or DMF or Tocilizumab, intravenously, intramuscularly, or by inhalation, etc.

In one embodiment, the therapeutic vaccine can be made in a viral cell culture for the growth of the virus prior to preparation as a vaccine, as described above, or the virus is grown in egg as is known in the art, where the eggs produce numerous copies of the viruses, the virus is extracted and killed or weakened with a combination of methylene blue at doses of <4 μg/ml or more, and one or more antiviral medications, antineoplastics, and/or anticytotoxic medications, etc. are used to damage the RNA or DNA without crosslinking the membrane proteins, such as the S-protein of the virus or affecting the cytoplasmic proteins that induce antigenic response, and with or without pathway inhibitors or other agents for reducing the inflammatory response of the host, and are prepared as known in the art prior to filtration and conjugation of lipid nanoparticles, nano-emulsions, micelles, solid lipid nanoparticles, or gold, zinc, or silver antibody coated nanoparticles with thiol binding for the vaccination without using a viral vector that has the potential of an immune response to the viral antigen, such as seen with Adenovirus 5, or AAD virus or Adenovirus 26 or the use of other viruses from chimpanzees, birds, etc. In one embodiment, to reduce the immune response to egg proteins, one can deliver the vaccine encapsulated in vax or gelatin, by measuring the viral physical titer, thermal and colloidal stability, molar mass and size, and nucleic acid content aggregation, etc. combined with pathway inhibitors such as ivermectin or niclosamide etc. orally that are released in the intestine, in low doses that can be increased incrementally until neutralizing antibodies are measured in the serum of the patient and prevent a severe immune response that can produce blood clots in the main vessels.

In one embodiment, where the patient has an egg allergy, mRNA vaccines are made as known in the art and/or combined with therapeutic vaccines having one or more antivirals, but delivered by inhalation or orally along with pathway inhibitors that the patient can administer to himself or herself by inhalation or orally incrementally as prescribed by a doctor or administered intramuscularly by a health professional. The combination of pathway inhibitors with a vaccine with or without LMWH or another anticoagulant reduces or eliminates the side effects of vaccinations.

In one embodiment, recombinant virus-like particles are used to elicit an immune response to viral proteins with or without polysaccharides or proteins, with combined or separate administration of pathway inhibitors, such as Wnt inhibitors (e.g., ivermectin or niclosamide) by inhalation or orally, and/or combined with 4-phenylchalcone oxide at concentrations of <400 mg/kg, an inhibitor of soluble epoxide hydrolase that produces leucotoxine and leucotoxinediol given by inhalation or orally, etc. to combat post vaccination side effects of fluid leakage in the lung, brain, intestine, or kidney.

In one embodiment with children, the immune response to the invading viruses or SAR-CoV-2 and its mutations, such as COVID-19, etc. or in bacterial infections, such as tuberculosis (TB), is not strong enough to kill viruses or bacteria by antivirals and antibiotics, etc. or monoclonal antibodies, thereby it may not be recognized while the children can carry the virus to others. In these situations, management of the disease should be different than adults by administering a combination of immune stimulation (i.e., a vaccine), adjuvants and treatment medication(s) as described above to eradicate the disease process, rather than just one medication.

In one embodiment, the therapeutic vaccine (i.e., vaccine plus medications) can be used as a booster to stimulate the immune response with other vaccines and subsequent to the vaccination using any other vaccine.

In one embodiment, the therapeutic vaccine (i.e., vaccine plus medications) can be used as a booster to stimulate immune response with other vaccines and subsequent to the vaccination using any other vaccine in combination with oral administration of microbiome to enhance the effect of gut microbiome and its anti-inflammatory effect on the diseases processes by producing short chain fatty acid in the gut that are absorbed by the gut blood vessels.

In one embodiment, the vaccine alone or with heparin, such as the Johnson & Johnson (J&J) COVID-19 vaccine, carrying an antigen such as an adenovirus protein or another viral protein used as a vector, etc. in addition to SAR-CoV-2 or Covid 19 or their mutations' protein, such as an s-protein can initiate a so-called generalized heparin induced thrombosis which is manifested by fatigue, headache, and simultaneous thrombosis and thrombocytopenia about 5 to 14 days after vaccination or a side effect of the use of heparin or LMWH immune response or viral antigen building an immunocomplex on the platelets and monocytes against platelet factor (4 PF4), where activation of monocyte and platelet produces blood clots. In one embodiment, the heparin is replaced with another anticoagulant, such as rivaroxaban (Xarelto), dabigatran (Pradaxa), apixaban (Eliquis) or edoxaban (Lixiana) administration in combination or sequential administration of a Wnt inhibitors, such as ivermectin or niclosamide, or with Rock inhibitors or integrin inhibitors or GSK inhibitors, and/or an immunosuppressant such as mycophenolic acid, cyclosporine, etc., Bariticinib, with or without plasmapheresis, or kidney dialysis to remove the antigens and cytokines from the blood and to stop the autoimmune response of the body, and the standard dose of vaccination is reduced to ½ or ¼th of the standard dose to avoid an excessive immune response.

In one embodiment, one can grow many different viruses in different the cell culture media or in egg and produce numerous copies of the viruses. The viruses are then extracted and killed or weakened with a combination of methylene blue at doses of <4 mg/liter or more and one or more antivirals medications and one or more antineoplastic or anticytotoxic medications, etc. to damage the RNA or DNA without crosslinking the membrane proteins, such the S-protein of the COVID-19 virus or the cytoplasmic and capsid membrane proteins or glycoprotein of any other viruses that have been grown without crosslinking them or affecting the cytoplasmic protein or their capsid membrane that induce an antigenic response with or without pathway inhibitors or other agents reducing the inflammatory response of the host and prepared as known in the art prior to filtration and conjugated with lipid nanoparticles, nanoemulsions, micelles, solid lipid nanoparticles and/or antibody coated nanoparticles of gold, zinc, silver, etc. with thiol binding, thereby producing a vaccine that simultaneously acts against many known or unknown viruses without using a viral vector that has the potential of an immune response to the viral antigen, such as seen with Adenovirus 5, AAD virus, or Adenovirus 26 or the use of other viruses, from chimpanzees, birds, etc. In one embodiment to reduce immune response, one can deliver the vaccine incrementally or encapsulated in vax or gelatin, by measuring the viral physical titer, thermal, and colloidal stability, molar mass and size, and nucleic acid content aggregation, etc. combined with pathway inhibitors, such as ivermectin or niclosamide with one anticoagulant, such as rivaroxaban (Xarelto), dabigatran (Pradaxa), apixaban (Eliquis) or edoxaban (Lixiana), etc. orally that are released in the intestine, or by intramuscular, subcutaneous, etc. injection, or by inhalation at very low doses that can be increased incrementally by the doctor/patient until neutralizing antibodies are measured in the serum of the patient and prevent severe immune response that can produce blood clot in the main vessels.

In one embodiment, the therapeutic vaccine has multiple antivirals and the viral envelope or capsid protein or glycoprotein is combined with a toll-like receptor 2 or TLR4 or VLP to stimulate simultaneously T-Cell response in addition to the humoral response produced by B-cells against viral antigens, conjugated with antibody coated metallic or nonmetallic nanoparticles where the combination therapy cannot only vaccinate a person, but simultaneously attack the viruses including various coronaviruses after its administration with pathway inhibitors with or without apixaban (Eliquis) anticoagulant, administered intramuscularly, orally, or by inhalation at a very low concentration dose that can be subsequently repeated in different intervals, using higher concentration or volume doses, until the neutralizing antibodies are discovered in the blood of the patient.

Figure 7A:
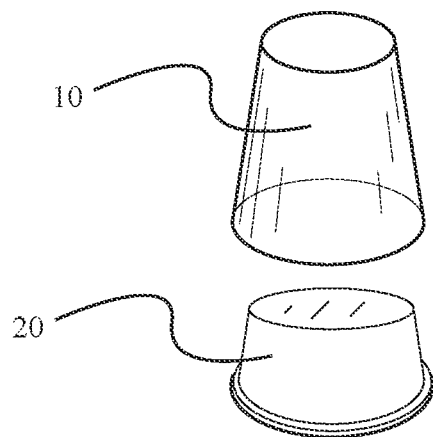
FIG. 7A illustrates a nasal implant with an outer shell and an inner filter shell that cooperates with the outer shell, according to another embodiment of the invention, wherein the inner filter shell is shown separated from the outer shell.
Figure 7B:
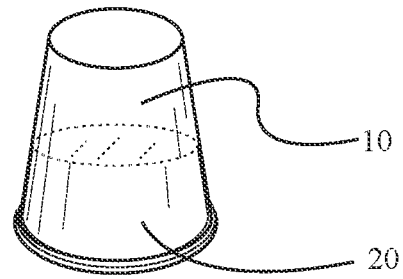
FIG. 7B illustrates the nasal implant of FIG. 7A with the outer shell and the inner filter shell, wherein the inner filter shell is shown disposed in the outer shell.

In one embodiment, to reduce immune response, one can deliver the therapeutic vaccine incrementally or encapsulated in wax, gelatin, or polycaprolactone, or the therapeutic vaccine can be freeze-dried to be thawed with a physiologic solution before administration combined with one or more antivirals such as a protease inhibitor, and/or a polymerase inhibitor, remdesivir and/or with a transcription inhibitor combined with cell pathway inhibitors, such as a Rock inhibitor, Fasudil or ROCK2, 1-(5-Isoquinolinesulfonyl)-2 Methylpiperazine Calcium Channel Blockers, with one anti-coagulant, such as rivaroxaban (Xarelto), dabigatran (Pradaxa), apixaban (Eliquis) or edoxaban (Lixiana), etc. or orally that are released in the intestine, or administered by intramuscular or subcutaneous injection, or by inhalation, or with a mucomyst, which contains acetylcysteine, n-acethylsystein, or its derivatives by inhalation or intravenously, where they act as an anti-inflammatory and antithrombotic or by inhalation at very low doses that can be increased incrementally by the doctor/patient until neutralizing antibodies are measured in the serum of the patient and prevent a severe immune response that can produce a blood clot in the main vessels.

In one embodiment, in patients with a severe coronavirus infection or its mutations, one can prevent the kidney damage by administering a low dose of metformin or Klotho that strengthens the heart muscle and skeletal muscles and enhances the recovery from the infection.

In another embodiment, in patients with a severe coronavirus infection or its mutations that affects the liver, there is an increase of insoluble bilirubin in the plasma that can affect among others the brain function, and in these situations, whole body radiation is administered using a strong light, e.g., ultraviolet A (UVA) radiation (460-490 nm) to convert the bilirubin to soluble bilirubin that now can be excreted through the gallbladder as bile. In addition, the UVA radiation may be applied as needed hourly that simultaneously kills the viruses on the surface area of the skin and just beneath the skin, contributing to faster recovery of the patients or the persons. The UVA radiation may be applied night for sterilization. To protect the eyes of the patient, UV blocking glasses may be worn by the patient.

In one embodiment, at least two antivirals are combined or applied sequentially with LMWH or a heparin mimetic with catechins to prevent attachment of the virus to the cell membrane receptors, the medication is administered intravenous or inside a body cavity or preferably as a spray, inhalation through an inhaler, through the nose such as nebulizer, a dry powder inhaler, liquid or suspension inhaler, breath actuated nebulizer, injector, topically, orally, intramuscularly, locally, or as described by Peyman U.S. Pat. Nos. 7,678,078 and 10,272,035, where the container is filled with a defined amount of semifluorinated alkane and nanoparticle emulsion and appropriate medication using compressed oxygen instead of air to spray the semifluorinated/medication as a fine spray or in nebulized form in the nasal cavity or mouth while the person inhales.

In one embodiment, if the patient cannot tolerate methylene blue, or is allergic to it, methylene blue can be replaced in the first step toward the vaccine production after the growth of the organism in cell culture or another suitable medium by administration of higher than normal doses of antimetabolite, such as Floxuridine, 5-Fluorouracil, 6 Mercaptopurine, cytarabine, flurabine, or para-aminobenzoic acid (PABA), or sulfonamide, the antimetabolite antibiotics preventing replication of DNA or RNA or actinomycine-D, etc., ribavirin, a nucleoside reverse transcriptase inhibitor (NRTI) targets enzymes, including inosinate dehydrogenase, thymidylate synthase, cytidine-5'-triphosphate synthetase, etc. that block RNA and DNA of viruses or an antiviral agent, an antineoplastic agent, an antitumorigenic agent, or an immunotherapeutic agent, such as mycophenolic acid or an antimitotic agent or their analogues or prodrug that are activated by viral proteases, such as paclitaxel, combretastatin, bryostatin, colchicine, or discodermolide at low non-toxic concentrations to kill the organism in the cell culture, or platinum anti-cancer medication and its derivatives or combination thereof, followed in combination with second step of administration of one or more non-toxic doses of antivirals or antibacterials or antiparasites anti-tumoral agents (in tumor therapeutic vaccine) to the dead organism or tumor cells prior to the administration to the patient and with one or more cell inflammatory pathway inhibitors, baricitinib, LMWH, heparin mimetics at a non-toxic concentration, etc. as second step of therapeutic vaccines formulation.

In one embodiment, the antiviral medication can be a polymerase inhibitor, such as remdesivir and an additional compound can be another antiviral or any other medication that modifies the side effects of viruses, such as inflammation or inhibition of cellular response to the virus, etc. with or without cell pathway inhibitors, etc.

In one embodiment, in the past, one has concentrated efforts to produce a vaccine that produces neutralizing antibody to the S-antigen which is the receptor protein on the SARS-CoV-2, and COVID-19 and their variants, such as the UK's B.1.1.7 variants, South Africa's B.1.351 variants, Brazil's P.1 variants and India's B.1.617. In contrast, the present therapeutic vaccine produces neutralizing antibodies against all antigenic proteins or glycoproteins of the viruses, and other related, future coronaviruses, covering other vulnerable areas of the viruses, etc., thus there is less chance for the virus to mutate and escape the therapeutic vaccine and the addition of medication in these cases with two antivirals, enhances the vaccination effect by the body's immune humoral and cellular response and covers practically all viruses, including those that have survived the initial vaccination using a standard vaccination processes, such as mRNA vaccine etc. to prevent new mutations. This methodology applies also to other coronaviruses alpha, beta, and gamma coronaviruses, though so far humans are affected only with beta coronaviruses, while the others have affected various animals.

In one embodiment, a nasal or sublingual implant is 3D-printed using known 3D printing technology controlled by software of a computer for multiple drug delivery in a slow release manner or nanoparticles, used for prophylactic, therapeutic, or therapeutic vaccination (see FIGS. 1-6). Creating one or two intranasal degradable implants containing nanoparticles or antibody-coated nanoparticles of gold nanoparticles or slow release medications as a therapeutic vaccine or therapeutic after vaccination having a cone structure with or without a centrally located filter that can block organisms smaller than viruses, etc. and can be removed after a period of time or replaced for repeated therapeutic vaccination and treatment.

In FIG. 1, an illustrative nasal delivery implant 10 is depicted. FIG. 2 depicts a pair of nasal delivery implants 10 connected to one another via a clip member 12 so that the implants 10 are able to be inserted into the nostrils of a person 18 (see FIG. 5). In FIG. 3, an illustrative nasal delivery implant 14 with a perforated wall is shown. In FIG. 4, an illustrative nasal delivery implant 16 with a spring-shaped wall is shown.

In one embodiment, the degradable nasal delivery implant may have or not have a filter. For example, in FIGS. 7A and 7B, a nasal implant with an outer shell 10 and an inner filter shell 20 that cooperates with the outer shell 10 is shown. The nasal implant of FIGS. 7A and 7B may be biodegradable or non-biodegradable. The outer shell 10 of the implant in FIGS. 7A and 7B may be formed from a flexible or semi-flexible material (e.g., a flexible or semi-flexible polymeric material, such as silicone). The inner filter shell 20 of the implant in FIGS. 7A and 7B may be formed from an N95 filter material or any filter material that blocks particles having a size larger than 0.06 microns. The filtering implant of FIGS. 7A and 7B can be formed as a single unit for each nostril or comprise two connected nostril portions that are attached to one another via a bridge, as previously described.

Figure 2:
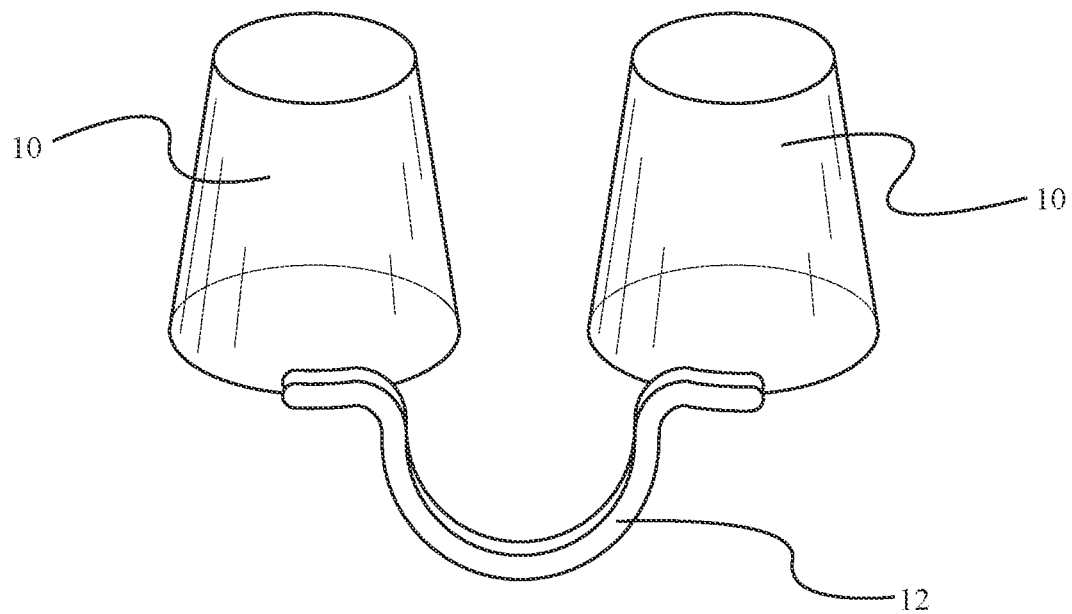
FIG. 2 illustrates a double nasal drug delivery implant, according to another embodiment of the invention, where the implant comprises a pair of conical portions connected to one another by a clip.
Figure 3:
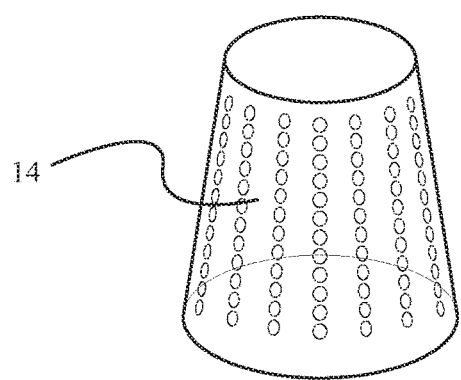
FIG. 3 illustrates a perforated nasal drug delivery implant, according to yet another embodiment of the invention, where the wall of the conical implant is perforated.
Figure 4:
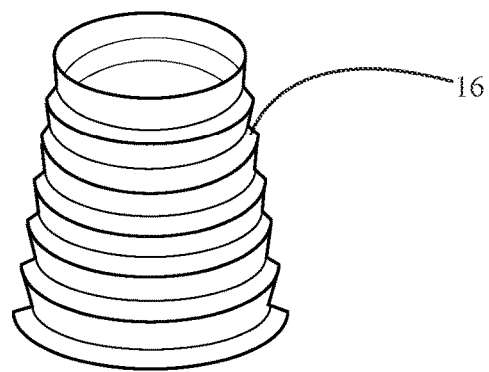
FIG. 4 illustrates a spring-loaded nasal drug delivery implant, according to still another embodiment of the invention.
Figure 5:
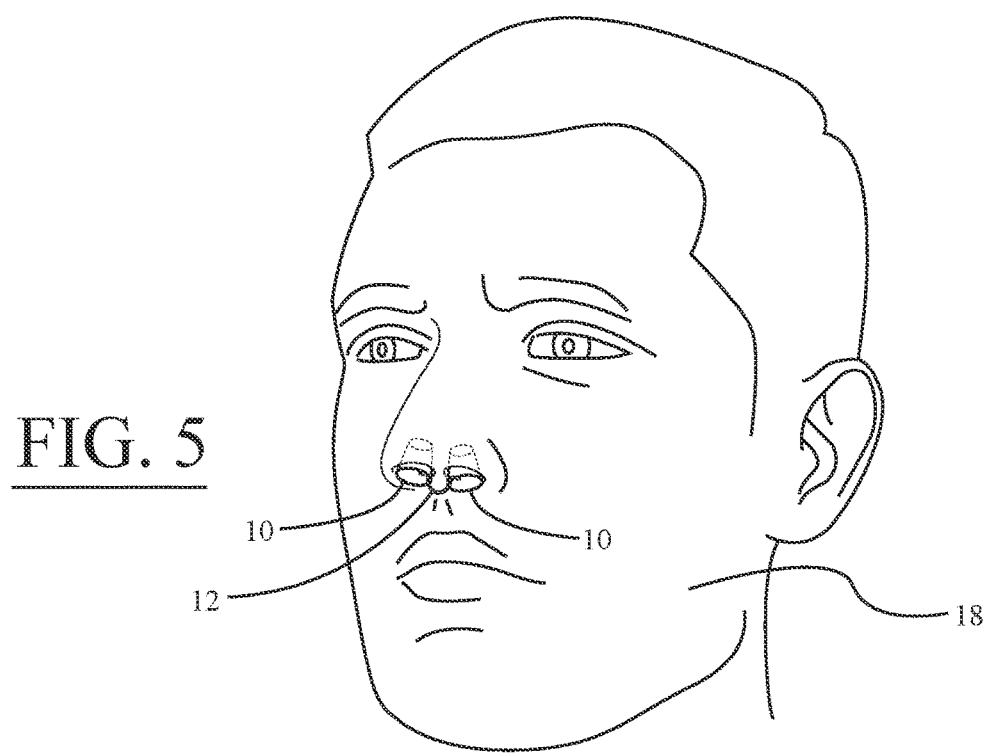
FIG. 5 illustrates the double nasal drug delivery implant of FIG. 2 disposed in the nose of a person.
Figure 6:
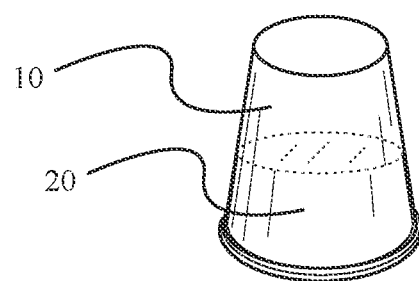
FIG. 6 illustrates a double cone nasal drug delivery implant containing an N95 filter, according to yet another embodiment of the invention, where the N95 filter is configured to block small organisms, such as viruses.

In one embodiment, the therapeutic vaccine delivery systems are 3-D printed to provide a nasal slow release, or sublingual release or as a capsule with medication(s) for oral delivery, or as an example, the nasal delivery device covers the medication to the nasal pathway, pharynx, larynx, trachea, bronchi, and lung alveoli, having a polymeric base such as a hydrogel or any polymer organic or synthetic compound such as beeswax, cellulose derivatives, poly (ethylene glycol) PEG, and poly(N-vinyl pyrrolidone), polylactic acid, polyglycolic acid, or PGLA, poly($\beta$-amino esters, or polymeric nanoparticles, PEI, dextran, dextrin, poly(glutamic acid), poly(aspartamides), chitosans, poly(l-lysine), etc. PNIPAAm, crosslinked gels, PNIPAAm copolymers, and various Pluronics or a mixture of two block copolymers, poly(l-histidine)-b-PEG (polyHis-b-PEG) and poly(l-lactic acid)-b-PEG-b-polyHis-ligand (pLLA-b-PEG-b-polyHisligand), antibody coated gold nanoparticles capable of endosomal disruption, escape, or beeswax are used in a drug capsule as a binding agent, or the use of porous silicon or other semiflexible polymers or plastics carrier of medications made in shape of cylinder or semi-cylinder, a flexible tube with a wider base leading to a narrower top, for insertion in the nostrils of any size that fits comfortably in the entrance of the nose or having a connected base that holds the dividing wall of nose tighter like a clip (see FIGS. 1-3), which releases medication/therapeutic vaccine over a day to a week or can be replaced as needed with a fresh one, having the same function, as delivering the medication or the therapeutic vaccines by other routes of administration having at least two antivirals, antibacterials, antiparasitics or antifungals medication, etc. or medication with one or more dead viruses, bacteria, parasites, including malaria, etc. where the organisms are killed in the process of producing a vaccine or weakened organisms with a high dose of methylene blue, i.e., >5 mg/L, and antiviral, antibacterial, antiparasites, antifungals, such as anti-malaria parasites, etc. depending on the infection, combined with at least one inflammatory cell inhibitor, such as Wnt, Rock, GSK or integrin inhibitors where the medication is slowly released when the polymer dissolves in nasal fluid and is inhaled or administered orally, intramuscularly, intravenously etc. or by inhalation to treat one or more respiratory viral/bacterial/fungal infection(s), parasitic infection or it works as a prophylaxis for the viral infection, bacterial infection, fungal infection or parasitic infection etc. or during the infection as a therapeutic vaccination stimulating simultaneously the humoral and cellular response to one or more viruses or bacteria, fungi or parasites affecting the lung, brain, heart, liver, kidney, or intestinal tract, etc.

In one embodiment, the therapeutic vaccine is administered with an inhaler.

In one embodiment, the therapeutic vaccine is injected with or without conjugation with gold nanoparticles via thiol for cellular absorption or penetration, subcutaneously, intramuscularly, intravenously for inhalation or orally, or intramuscularly etc. in a physiologic saline solution, or dissolved in semifluorinated alkanes.

In one embodiment, creating a therapeutic vaccine against malaria where the organism such as *Plasmodium falciparum* (P0 malaria parasites or *P. vivax, P. ovale*, and *P. malariae* genus with over hundred species are transmitted by *Anopheles* mosquitos. The malaria parasites have two different lifestyles: (1) initially ingested by the mosquitoes from an infected victim where they grow in the insect's stomach and produce sporozoites (sporogonic style) before (2) infecting another subject, where the sporocytes grow in the host liver cells before entering the red blood cells, then regrow and multiply as merozoites and burst the red blood cells. Circulating infected parasites in humans produce the symptoms of chill and fever. The parasites can again be picked up by mosquitos to undergo sporogonic cycle generating zygots, oocyst, and sporocytes.

In one embodiment, the malaria parasites are cultivated in various stages in vitro as known in the art (described by Frederick L. Schuster in *Clin Microbiol Rev.* 2002 July; 15(3): 355-364. Cultivation of *Plasmodium* spp.).

In one embodiment, the principle of therapeutic vaccine is by harvesting viruses, or bacteria, or fungi or parasites, or tumor cells, etc. form the cell culture or appropriate medium, then the viruses, bacteria, fungi, or parasites, etc. are killed with a high dose of methylene blue >4 mg/L with or without gold nanoparticles for cell penetration and damaging the RNA or the DNA of the organism along with methylene blue and kept for a period of time for penetration of the methylene blue in the viruses, bacteria, or fungi, or parasites, of tumor cells etc., other substances can be added to the medium, such as peptide nucleic acid or anti-neoplastics to enhance the effect of the methylene blue on the RNA or DNA, then the dead viruses, bacteria, fungi, or parasites, etc. are separated from the rest of the medium to which, depending on the organism, antivirals, antibacterials, or antifungals, or antiparasites, etc. at a non-toxic therapeutic concentration of the appropriate medication is added, depending on the volume or the medication needed, route of administration to create simultaneously an immune and a therapeutic response in the body without inducing the side effects of medication, in general at low doses so that the combination cocktail initiates an immune response (humoral and cellular) to viruses, bacteria, fungi, parasites, or tumor cells, etc. and to which one adds cell pathway inhibitors such as Wnt, Rock, GSK, or integrin inhibitors to prevent an excessive immune response, or additional medications, such as low molecular weight heparin, Mucomyst, or pluralities of antibody-coated nanoparticles, anti-TGFs or baricitinib, tocilizumab, steroid etc. is needed or metformin to protect the kidneys with GSK inhibitors or kidney dialysis or electrophoresis is done to remove excessive toxins, the treatment can be repeated as needed until the viruses, bacteria, fungi, or parasites are eliminated and verified by PCR, etc.

In one embodiment, the therapeutic vaccine with methylene blue can be replaced with another medication with a similar toxic effect on RNA or DNA of viruses, or bacteria, or fungi or parasites and the rest of the medications described above are added to enhance the therapeutic vaccine effect for a needed period of time in the post-operative period or in therapy resistant organisms.

In one embodiment, an intravenous administration of a therapeutic vaccine is done to maintain a non-toxic amount of the medication in the circulation, this volume is significantly reduced if therapeutic vaccine is injected subcutaneously or intramuscularly or by inhalation so it does not cause a localized toxicity to the tissue exposed while still the immune response is maintained, in fact might be used therapeutically when there is a localized response to the originally administered vaccine.

In one embodiment of providing an antimalarial vaccine, adding the *Plasmodium*-specific kinase PfCRK4 inhibitor such as citric acid or a quinine derivative to the medium enhances the killing effect of methylene blue (MB) with or without gold nanoparticles, etc.

In one embodiment, one adds to the methylene blue at least two additional antimalarial medications at a non-toxic dose, such as one of chloroquine, amodiaquine, quinine, quinidine, mefloquine, primaquine, lumefantrine (see the table below) and halofantrine, etc., which are active against the erythrocytic stage of parasites and one of primaquine to kill intrahepatic forms of the parasites or gametocytes to which one adds one of gold or silver or zinc nanoparticles (with or without antibodies), preferably 1-10 nm in diameter in size that are capable of entering into live parasites damaging it RNA or DNA of the organism or with cell penetrating peptides providing an antigenic dead parasites/medication(s) the so called therapeutic vaccine which are capable of inducing an antigenic response from the host, e.g., a patient, or an animal etc. when administered to a patient/animal, and the patient/animal is immunized against the future infection by malaria species.

In one embodiment of a therapeutic vaccine, one adds an inflammatory cell pathway inhibitor, such as Wnt, Rock, integrin or GSK inhibitors or preferably Ivermectin at a non-toxic concentration which also acts as an antimalarial agent and anti-inflammatory compound to prevent over activation of a patient's immune response, the therapeutic vaccine can be administered orally to be absorbed by the intestinal tract to reach liver directly. In one embodiment, the compound, such as baricitinib or TGF beta inhibitors or compliment C3 or C5 inhibitors, or metformin at low doses as long as needed etc. are added.

In one embodiment, various components of the therapeutic vaccine can be administered in therapy resistant bacterial, viral, fungal or parasitic infections, to stimulate humoral or cellular immune response such as killer cells, in combination or separately to the patient by inhalation, intramuscular, subcutaneous, or intravenous injection or locally at non-toxic dose or preferably orally to be absorbed by the gut and its circulation reaching the liver more directly to damage the liver parasites that are growing in the liver, whereas intravenous administration reaches the erythrocytes phase of infection to treat it directly repeatedly as needed.

In one embodiment, after administration of an antimalarial therapeutic vaccine by nasal inhalation, orally as a capsule or hydrogel in beeswax, etc., an excessive immune response is treated by kidney dialysis, electrophoresis, hemodialysis to remove the dead parasites, cytokines, etc. and prevent a cytokine storm in cases of a multi-system inflammatory response (MIS-C) in children that may also treated with Wnt inhibitors, such as ivermectin or niclosamide orally or by inhalation, etc. in one embodiment with lung infection nasal inhalation of therapeutic vaccine is preferred.

In one embodiment of an already infected person, a therapeutic vaccination of the patient can be continued with repeated therapeutic vaccination administration to the patient for 3-4 times in an interval of 6 days to kill new parasites that can be released from the liver cells that are treated and simultaneously an immune response is created in the patient.

In one embodiment, after the treatment with a therapeutic vaccine, one continues the therapy with methylene blue at a lower concentration of 1-2 mg/L to inhibit selectively the glutathione reductase of *Plasmodium falciparum*, or in combination with a lower dose of an antimalarial agent, such as chloroquine, at lower nontoxic concentrations to maintain a medication level in the plasma of the patient that can damage the parasite, but not the patient and treat methemoglobinemia if it is present, the only contraindication for use of methylene blue is if it is given systemically to a patient lacking glucose-6-phosphate dehydrogenase (G6PD enzyme which can be evaluated rapidly in any laboratory with an on-site screening testing for G6PD enzyme deficiency using a finger prick to obtain blood samples.

In one embodiment, the therapeutic vaccine is produced, in the lab, with high toxic doses of >5 m/L, however, after its preparation one uses an antimalarial medication, and the dead parasites at a non-toxic dose of methylene blue at <4 mg/l in combination with a non-toxic concentration of antimalarial medication and a non-toxic dose of gold, silver, or zinc nanoparticles are used as desired repeatedly as needed in combined with cell pathway inhibitors or complement inhibitors until the parasites are eliminated.

In one embodiment, the therapeutic vaccine is combined with a non-toxic doses of methylene blue or other medications and an immunosuppressants, such as mycophenolic acid, Rapamycin, or an antiviral agent, an antibacterial or antifungal or an antineoplastic agent, an antitumorigenic agent, or an immunotherapeutic agent, TLR 4 or an antimitotic agent or their analogues or prodrugs or Monoclonal antibodies or polyclonal antibodies conjugated with or without nanoparticles for the treatment of each disease.

In one embodiment for treatment of malaria parasites, the patient is treated with a non-toxic dose of immunosuppressant(s), or after initial treatment with a therapeutic vaccine, the patient can be treated for a period of time with non-toxic doses of immunosuppressant agents, such as mycophenolic acid at 19 μmol/L of Rapamycin at 13.7 μmol/L.

In one embodiment, the therapeutic vaccine is administered simultaneously or sequentially by intravenous administration of culture grown killer cells, or engineered cytotoxic T-cells using gene editing technologies to change the DNA of the T-cells to overcome the tumor's barriers and to kill the parasites with or without adjuvants or a therapy resistant infection.

In one embodiment, a vaccine cocktail is prepared from viruses or bacteria, fungi, or parasites, etc. in a semifluorinated alkane, a physiological saline solution, the organism is killed with high doses of methylene blue (>5 mg/L) or another medication that damages RNA or DNA of the organism and filtered to obtain the dead viruses or bacteria, fungi, or parasites transferred in a solution containing methylene blue at a non-toxic concentrations of 2 mg/L MB having an adjuvant, such as the toll-like receptor 4, 7 and 8, with Alum or another adjuvant with or without viral like particles (VLPs), etc., with or without one or more inflammatory cell pathway inhibitors or another anti-inflammatory compound, such as Ivermectin, or one or two antivirals, antibiotics, antifungals, or antiparasites where the dead organisms or at least one or more parts of its proteins such as an S-antigen or glycoprotein or Bispecific antibodies, protein, glycoprotein saccharide etc. are conjugated with gold, silver, zinc, or organic nanoparticles and the cocktail, is collected, and prepared and stored in a refrigerator with or without a Benzalkonium chloride (BAk) solution of 0.01% or less concentration at a low temperature and can be used for repeated self-vaccination/administration as needed by nasal spray, inhalation, or oral pills or gummies or intraperitoneal, intramuscular, subcutaneous, or intravenous or local administration, or can be used as adjuvant to another vaccine prepared by other means, such as mRNA vaccines or monoclonal or polyclonal antibody-coated nanoparticles, or LNP, etc. or after administration of another vaccine for the same organism, but self-administered is preferred by inhalation or orally, weekly, or monthly as needed to eliminate the organism or self-administration intranasal as a spray or nebulization, or injected by professionals intravenously or intramuscularly, etc. to eliminate all potential pathogens, such as viruses that might remain in the nasal cavity, throat, pharynx, trachea, or in the alveoli and potentially reactivate and induce an epidemic or pandemic infection or therapy resistant bacteria and fungi or parasites that hide in the liver cells, etc.

In one embodiment, the therapeutic vaccine can be freeze dried for storage, then thawed with water prior to it being administered.

TABLE 1

List of antimalarial medications and their combinations.

High first dose quinine, Primaquine, halofantrine, Ivermectin, Primaquine in gametocyte development, Tafenoquine in preventing relapse, Cycloguanil and proguanil, Amodiaquine, Amodiaquine plus sulfadoxine-pyrimethamine, dihydroartemisinin-piperaquine, Doxycycline, Atovaquone proguanil (Malarone) in chemoprophylaxis, and Antimicrobial, Atovaquone-proguanil combination, Artesunate-Mefloquine combination, Artesunate Artemisinin, oral pyronaridine, Pyronaridine-artesunate, Dihydroartemisinin-piperaquine KAE609 (cipargamin; formerly NITD609, a new synthetic antimalarial spiroindolone analogue against asexual and sexual stages of Plasmodium falciparum, synthetic trioxolane drug. Arterolane Maleate-Piperaquine Phosphate, dispersible tablet of arterolane, maleate (AM) Piperaquine phosphate (PQP), Arterolane Maleate-Piperaquine Phosphate, Artemether-Lumefantrine, e 4-aminoquinoline drug hydroxychloroquine (HCQ), Halofantrine, Cysteine and aspartic protease inhibitors, Lead compounds at nanomolar concentrations, Ferroquine combination with Artesunate, Malaria antibodies coated nanoparticles or lipid nanoparticles (LNP).

TABLE 2

List of immunosuppressants and antimalarials.

Mycophenolic acid, Rapamycine, cyclosporine A, etc.
Plant toxins cytotoxic agents, etc. reactive oxygen species (ROS), radiation (UV, X-ray, gamma), cisplatin, oxaliplatin, and carboplatin), cyclophosphamide, chlorambucil, and temozolomide.
Imatinib has antimalarial activity by inhibition of the erythrocyte tyrosine kinase that causes parasite entrapment and termination of the infection or in addition to inflammatory pathway inhibitors, Lenzilumab and an antimalarial monoclonal antibody.

In one embodiment, one uses the therapeutic vaccine (i.e., medication and simultaneous or sequential vaccination) in respiratory viral diseases, drug resistant bacteria, drug resistant fungi, or drug resistant parasites, or a tumor where the initial steps are similar by: (1) growing the organism or tumor cells or fungi in appropriate culture; (2) then killing the organism by using one or two medications that affect DNA or RNA of the organism or tumor cells in an above non-toxic concentration (e.g., methylene blue at a concentration >4 mgL or any other cytotoxic or antineoplastic, etc. medication at a above non-toxic concentration/L, filtering out the organisms protein or antigens; (3) combining the proteins, glycoproteins, or antigens with at least one or two anti-organism drugs (i.e., drug resistant or not resistant) at a non-toxic concentration of the medication e.g., 2 mg/L methylene blue and/or other antivirals, antibacterials, antifungals, anti-neoplastics, or anti-parasites, (4) addition of an immune stimulator, such as one or more toll-like receptors 2, 4, saponin, or VLP, etc. or complement(s) after in vitro and in vivo animal experimentation to find out their effect at a tolerable volume locally, intramuscularly, intranasally by inhalation, or orally, etc. at known non-toxic doses, or intravenously at a non-toxic dose and volume combined with anti-inflammatory medications or cell pathway inhibitors, such as Wnt, Rock, GSK, or integrin inhibitors or in combination as needed with other medications, such as anticoagulants (e.g., LMWH, n-acethylsystein, etc.), DMF, Baricitinib, etc. or anti-VEGF agents, such as bevasizumab (Avastin, etc.) to revive an exhausted cellular immune response and the therapeutic vaccine can be administered repeatedly as needed to kill potential existing pathogens and induce simultaneously a humoral or cellular response by measuring the neutralizing serum antibodies and if the patient is immunosuppressed, one administers simultaneously or sequentially culture-grown natural killer cells, etc. with or without checkpoint inhibitors and TGF beta inhibitors, and if the immune response creates a cytokine storm response (LDH level above 300 value as an inflammatory signature in the body), the patient is treated with kidney dialysis plus metformin administration or serum electrophoresis to remove the cytokines, etc. The treatment is repeated for each organism until they are dead, or repeated treatment is performed using the therapeutic vaccine with another medication.

In one embodiment, one uses the therapeutic vaccine (i.e., medication and simultaneous or sequential vaccination) by utilizing any existing vaccine, such as those using mRNA, viral S-protein, or using another carrier instead of LPN, such as modified adeno-associated viral vector, etc. and combine it with appropriate antivirals, antibacterials, antifungals, antiparasites, antitumors, and/or antibody-coated nanoparticles, etc. collecting the polysaccharides, proteins, glycoproteins, glycan, or antigens, or part of the proteins or bispecific antibodies, with at least one anti-"organism" drug (i.e., regardless of being drug resistant or not resistant) at a non-toxic concentration or addition of an immune stimulator, such as one or more toll-like receptors 2, 4, etc. or VLPs or complement(s) after in vitro and in vivo animal experimentation to find out their effect at a tolerable volume locally, intramuscularly, intranasally, by inhalation, orally, subcutaneously, intramuscularly, intravenously, etc. at known non-toxic doses, or intravenously at a non-toxic dose and volume with anti-inflammatory medications or cell pathway inhibitors, such as Wnt, Rock, GSK, or integrin inhibitors added alone or in combination as needed with other medications, such as anticoagulants (e.g., LMWH, mucomyst, DMF, Baricitinib, etc.) or anti-VEGF agents, such as bevacizumab (Avastin, etc.) and the therapeutic vaccine can be administered repeatedly as needed to induce simultaneously a humoral or cellular response by measuring the neutralizing serum antibodies, and if the patient is immunosuppressed, one administers simultaneously or sequentially culture-grown natural killer cells, etc. with or without checkpoint inhibitors and TGF beta inhibitors, and if the immune response creates a cytokine response, the patient is treated with kidney dialysis plus metformin administration or serum electrophoresis to remove the cytokines, etc. The treatment is repeated for each organism until they are dead, or the treatment is repeated using the therapeutic vaccine with other medications.

In Table 3 below, most of the drug resistance organisms that can be treated with the described therapeutic vaccine are listed. It should be understood that medications or method can be modified but the basic methodology remains the same (i.e., the multipronged attack on the organism and strengthening simultaneously the immune response of the patient).

It is estimated that >2.4 million of therapy resistance infections occur, not counting the malignant or benign tumors and about 3,000 cases of Clostridioides *difficile* occurs each year as a result of therapy resistant bacteria etc.

In one embodiment, chemotherapeutic agents are used instead of methylene blue, or with a combination of methylene blue with or without gold zinc nanoparticles etc. to damage the RNA or DNA of the organism.

Anti-tumor chemotherapeutic agents can be used in the process of therapeutic vaccine formation (e.g., if the patient is allergic to methylene blue), usually initially at least two drugs at higher than non-toxic concentrations and subsequently when the protein antigens (or proteoglycans) is separated from the organism, and co-administered with the same medications at below the toxic concentration, e.g. the chemotherapeutic agents, that are approved by the FDA as described below. The therapeutic vaccine is combined with one of the cell inflammatory pathway inhibitors, such as Wnt inhibitors, Rock, GSK, integrin inhibitors, or one of the TGF beta inhibitors, or other anti-inflammatory agents.

Anticancer chemotherapy agents mostly affect RNA or DNA of the cells for treatment of certain types of cancer, and can have their side effects. Therefore, when used in combination with a vaccine as therapeutic vaccines, their concentrations are reduced below the approved therapeutic levels, and at least two or more chemotherapeutic agents are used in combination to create a 1-2 punch, and are more effective since they affect the organisms in different way. In one embodiment, not all medicines and drugs used to treat cancer work the same way, such as targeted therapy, hormone therapy, and immunotherapy.

In one embodiment, chemotherapy affects the cell cycle. Interestingly, most normal cells will recover from the therapy, but cancer cells are mutated cells and usually do not recover after therapy.

In one embodiment, two drugs act in a different way on the cells or the organisms, such as alkylating agents act by damaging its DNA, such as Altretamine, Dacarbazine, Cyclophosphamide. Ifosfamide, Lomustine, Mechlorethamine Bendamustine, Busulfan, Carboplatin, Carmustine Chlorambucil, Cisplatin, Melphalan, Oxaliplatin, Temozo-

TABLE 3

| List of drug resistant organisms. |
| --- |
| Carbapenem-resistant *Acinetobacter*, *Clostridioides difficile*, *Candida auris*, *Enterobacterales*, *Neisseria gonorrhoeae*, and drug-resistant *Campylobacter*. *Candida*, ESBL-producing *Enterobacterales*, Vancomycin-resistant *Enterococci* (VRE) ontyphoidal *Salmonella*, multidrug-resistant *Pseudomonas aeruginosa*, *Shigella*, *Salmonella serotype Typhi*, Methicillin-resistant *Staphylococcus aureus* (MRSA), Drug-resistant *Tuberculosis*, *Streptococcus pneumoniae*, Erythromycin-Resistant Group A *Streptococcus*, Clindamycin-resistant Group B *Streptococcus*, Drug-resistant *Mycoplasma genitalium*, Azole-resistant *Aspergillus fumigatus*, Drug-resistant *Bordetella pertussis*, Carbapenem-resistant *Acinetobacter*, Drug-resistant *Candida auris* (*C. auris*). Drug-resistant *C. auris*, *Clostridioides difficile* (*C. difficile*), *C. difficile* or *C. diff*, previously *Clostridium difficile*, Carbapenem-resistant *Enterobacterales* (CRE), Drug-resistant *Neisseria gonorrhoeae*, Drug-resistant *gonorrhea*, Drug-resistant *N. gonorrhoeae*, Drug-resistant *Campylobacter*, Drug-resistant *Campylobacter*, Drug-resistant *Candida* Species, Dozens of *Candida* species-a group of *fungi*-: Drug-resistant *Candida* species Pathogen. ESBL-producing *Enterobacterales*, Extended-spectrum β-lactamase, ESBL-producing *Enterobacterales* Pathogen, Vancomycin-resistant *Enterococcus* (VRE), Multidrug-resistant *Pseudomonas aeruginosa*, Multidrug-resistant *P. aeruginosa*, Drug-resistant nontyphoidal *Salmonella*, Drug-resistant *Salmonella serotype Typhi*, Typhoid fever, Drug-resistant *Salmonella serotype Typhi* Pathogen, Drug-resistant Shigella, Methicillin-resistant *Staphylococcus aureus* (*S. aureus*) (MRSA), Resistant staph (short for *Staphylococcus*), Drug-resistant *Streptococcus pneumoniae* (*S. pneumoniae*) Bacteria Pneumococcus, Drug-resistant *S. pneumoniae*. Drug-resistant Tuberculosis (TB), multidrug-resistant TB (MDR TB), or extensively drug-resistant TB (XDR TB), *Mycobacterium tuberculosis* (*M. tuberculosis*), Erythromycin-resistant Group A *Streptococcus*, Clindamycin-resistant Group B *Streptococcus*.: Resistant group B strep, GBS, Azole-resistant *Aspergillus fumigatu*, Drug-resistant *Mycoplasma genitalium*, Drug-resistant *Bordetella pertussis*, lyme disease caused by bacterium *Borrelia burgdorfei*or parasite Babesia, Bacteria Ehrlichiosis, Anaplasmosis, Bacteria *Borrelia miyamotoi*, Powassan virus, Bacteria Tularemia and *Borrelia lonestari*, or single cell organism protozoa, *mycobacterum* leprae causing Leprosis, etc. | lomide, Thiotepa, Trabectedin. Nitrosoureas are alkylating agents that pass the blood-brain barrier to reach brain tumors, such as Carmustine Streptozocin, and Lomustine.

TABLE 4

List of chemotherapeutic drugs.

Antimetabolites: interfere with DNA and RNA by acting as a substitute to the DNA, but cannot reproduce itself for the building blocks of RNA and DNA. These are: 5-fluorouracil (5-FU), 6-mercaptopurine (6-MP), Capecitabine (Xeloda), Cladribine, Clofarabine, Cytarabine (Ara-C)Floxuridine, Decitabine, Fludarabine, Gemcitabine (Gemzar), Hydroxyurea, Methotrexate, Thioguanine, Nelarabine, Trifluridine/tipiracil combination, Pentostatin, Pralatrexate,, Pemetrexed (Alimta), Anti-tumor antibiotics: these work by changing the DNA inside cancer cells prevent them to grow and multiply, Anthracyclines: interfere with enzymes involved in copying DNA and the cell cannot reproduce. Daunorubicin, Doxorubicin liposomal, Epirubicin, Doxorubicin (Adriamycin), Idarubicin, Valrubicin can permanently damage the heart at high doses, Bleomycin Mitoxantrone, Mitomycin-C, Dactinomycin, Topoisomerase inhibitors: are plant alkaloids which interfere with enzymes called topoisomerases that separate the strands of DNA. Topoisomerase inhibitors block different enzymes and prevent the production of their copies such as Topoisomerase I inhibitors: Topotecan Irinotecan liposoma, Irinotecan, Topoisomerase II inhibitors include: Teniposide, Etoposide (VP-16), Mitoxantrone (also acts as an anti-tumor antibiotic), mitotic inhibitors; such as plant alkaloids work by stopping cells from dividing, mitotic inhibitors include the taxanes and vinca alkaloids, Taxanes include: Nab-paclitaxel, Paclitaxel, Cabazitaxel, Docetaxel; Vinca alkaloids include: Vincristine Vinorelbine, Vincristine liposomal, Vinblastine, other chemotherapy drugs Eribulin, Hydroxyurea, Ixabepilone, Mitotane, All-trans-retinoic acid, Arsenic trioxide, Asparaginase, Omacetaxine, Procarbazine, Pegaspargase, Romidepsin, Vorinostat.

In one embodiment, one utilizes targeted therapies of proteins, glycoproteins or receptors (e.g., on the cancer cells, etc.) with immunotherapy drugs to boost or alter the patient's immune system, by either blocking the activity of the enzyme acyl-CoA:cholesterol acyltransferase (ACAT) or administering toll-like receptor 4 boosting T-cells that can fight cancer cells or the viruses etc.

In one embodiment, a therapeutic vaccine can be prepared by obtaining a tumor cell biopsy as known in the art, growing the cell in a culture medium damaging the DNA of the tumor, by administering to the cell culture at least one of methylene blue at a toxic concentration with one or more chemotherapeutic agents at a toxic level obtaining antigenic proteins, glycoproteins, or proteoglycans as known in the art, administering the antigens with at least two chemotherapeutic agents or methylene blue at or below the non-toxic concentration to damage the tumor cells' DNA and its metastatic cells and combining the cocktail with one or more cell pathway inhibitors to a prevent cytokine storm and an Anti-VEGF, and/or a checkpoint inhibitor and or an antico-agulant, such as LMWH, or mucomyst, or immunoglobin is delivered to prevent blood clotting, either by inhalation or intravenously or orally which contains acetylcysteine, n-ac-ethylsystein, etc. and/or resveratrol and culture grown killer cells intravenously, intra-arterially, in the desired place, or by inhalation, or orally, as capsule etc.

TABLE 5

List of most frequent cancers for which therapeutic vaccine can be used.

Bladder cancer, colon and rectal cancer, breast cancer, kidney cancer, leukemia, lung cancer, liver cancer, melanoma, endometria cancer, non-Hodgkin's lymphoma, pancreatic cancer, thyroid cancer prostate cancer, retinoblastoma, Adrenocortical carcinoma, anal cancer, astrocytoma, Kaposi's Sarcoma, Basal Cell Carcinoma of the Skin, other skin cancers, bone cancer, Brain tumors Bronchial tumors, Carinoid tumors, Meduloblastoma, cervical cancer, hairy cell lumphoma, Esophageal cancer Ewing Sarcoma, eye cancers, Gallbladder cancer, gastric cancer, gastrointestinal cancer, ovarian cancer, testicular cancer, metastatic cancer, hypopharyngeal cancer, head and neck cancer, lip and oral cavity cancer, throat cancer, lung cancer. Mesothelioma, squamatous cancer, Meyeloproliferative neoplasm, nasal cavity cancer, neuroblastoma, Non-small cell lung cancer, parathyroid cancer, pharyngeal cancer, pheochromocytoma, pituitatry tumors, Multiple Myeloma, Primary CNS lymphoma, peritoneal cancer, vaginal cancer, penile cancer, vulvar cancer, osteosarcoma, soft tissue sarcoma, uterine sarcoma, wilms' tumor, etc.

In one or more embodiment, the steps of therapeutic vaccines are similar, namely: (1) growing the organism, (2) killing the organism with a high dose of at least two medications, (3) retrieving the antigenic protein/proteoglycans from the dead organism, (4) combining the antigen (proteoglycans) with or without gold nanoparticles at low non-toxic dose of at least two appropriate medications depending on the organism (e.g., for viruses one uses two antiviral polymerase inhibitor and a protease inhibitor, etc. and adds immune stimulators such as toll-like receptor 4 to the cocktail and/or monoamine oxidase inhibitors, and spermidine), (5) add one of anti-inflammatory cell pathway inhibitors to prevent immune over reaction, (6) if needed, use culture-grown killer cells to enhance the killing of the organisms, (7) add anticoagulant to prevent blood clotting, etc., and (8) use kidney dialysis or hemodialysis or electrophoresis to remove toxins in case of a cytokine storm combined with Bariticinib or DMF metformin at low dose etc. to reduce inflammatory response. The steps can be administered simultaneously or sequentially.

In one or more embodiments, the steps of the therapeutic vaccines are similar, namely: (1) growing the organism, and (2) killing the organism with a high dose of at least two medications that damage RNA and DNA.

In one embodiment, the medications used to kill the organism are conjugated with cell penetrating peptides (CPPs) or ACPPs or cyclodextrin etc. and the nucleoside transporter ENT2 enabling targeted cell-penetrating anti-DNA autoantibody which penetrates the organism's membrane and localizes itself in the nuclei or the DNA or RNA and damages them, in addition to ENT2 which is a bispecific antibody, such as Deoxymab-1 (DX1) prevents repair of damaged DNA or RNA with or without Ceapin-A7 and KIRA8 to remove the damaged cells, bacteria, viruses, fungi, or parasites.

In one embodiment, one retrieves the antigenic protein/glycoproteins from the organisms with damaged RNA/DNA, and includes proteins, glycoproteins, or saccharides to be used for vaccination alone or collectively.

In one embodiment, one combines the antigen (proteoglycans, etc.) with or without gold nanoparticles at a low non-toxic dose of at least two appropriate medications depending on the organism, e.g., for viruses one uses of one an antiviral polymerase inhibitor and a protease inhibitor, etc. to which one adds immune stimulators such as toll-like receptor 4 and spermidine to the cocktail or anti-depressant agents, such as monoamine oxidase inhibitors, or use with an mRNA vaccine, or diamidobenzimidazole (diABZI-4), to trigger the stimulator of interferon genes (STING), thereby enhancing the immune response, and with or without Ceapin-A7 and KIRA8 to eliminate the damaged cells, bacteria, viruses, fungi, or parasites.

In one embodiment, an mRNA vaccine is prepared for vaccination of human or animal against viral, bacterial, fungal, or parasitic infections and it is combined with one or more medications against the organism, at or below the toxic levels of the medication and combine them with inflammatory cell pathway inhibitors or the anti-inflammatory agents, such as steroids or non-steroidal anti-inflammatory drugs (NSAIDs) with or without anticoagulants n-acetylcysteine to create a therapeutic vaccine and administer it during the infection to kill the organism (e.g., viruses, bacteria, fungi, or parasites) and enhance immune humoral and cellular response.

In one embodiment, one administers a therapeutic vaccine with at least two types of antibody-coated nanoparticles, and anti-inflammatory cell pathway inhibitors or mycophenolate mofetil or other macrolides and abatacept, combined with methotrexate, with an TGF beta inhibitor given orally or intranasally, as a spray or powder, intramuscularly, etc. to prevent immune over reaction, to prevent fibrosis and scar formation of the affected organ and to treat the disease.

In one embodiment, the therapeutic vaccine stimulates the person's or animal's immune system, which is not limited to B cells activation, but also T-cells that destroy the infected cells and the organisms (e.g. viruses, bacteria, fungi, parasites, or tumor cells) since the protein that induces the antigenic response in the host is not limited to just few proteins or glycoproteins of the organism, but therapeutic vaccine has a mixture of hundreds of proteins glycoproteins, saccharides, etc., thereby creating a killer cell response of the immune system to eliminate the organism and create the immune memory to hundreds of antigens present in an organism, thus the immune response is broad and the immune memory covers the present and potentially future mutation of organisms. In addition, the therapeutic vaccine is administered with antivirals, antifungals, antiparasitics, antibacterials, or anti-tumor medications depending on the organism and contain anti-inflammatory compounds, or in immune suppressed individuals is given along with culture grown killer cells and an anticoagulant, such as mucomyst, n-acetylcysteine, immunoglobulin, or in combination with other medications that reduce the van willebrand factor in the patient to reduce blood clot formation, with or without metalloproteinase inhibitors such as doxycycline or tetracycline, etc. to prevent excessive tissue damage or scarring after an infection in the lung or brain, etc.

In one embodiment, the medications and adjuvants can be administered simultaneously or sequentially by oral, intramuscular, intravenous, transdermal, inhalation or by nasal spray as needed, or potentially administered in low doses, but more frequently while judging the immune response of the person or animal by measuring the neutralizing antibodies in the blood, etc.

In one embodiment, a therapeutic vaccine is formed from one or more known antivirals, such as methylene blue, etc. or an mRNA vaccine or one or more antiviral nucleotide analogues or mimetics, such as sofosbuvir (tenofovir) that are synthetic, chemically modified nucleoside and inhibit the viral metabolism and also damage the RNA or DNA of the virus (see below), etc., such as in HIV, herpes virus, hepatitis B lamivudine/entecavir or hepatitis C virus, etc. or herpes infections (acyclovir) or arthropod-borne viruses or flavivirus, producing hemorrhagic fevers, encephalitis/myelitis, neuropathic or teratogenic manifestations (ZIKV), where a nucleoside can inhibit RNA dependent polymerases, helicase, NTPase, methyltransferase to produce a therapeutic vaccine that is then added to non-toxic doses of another medication (antiviral, antibacterial, antifungal, antiparasitic, etc.) with Deoxymab-1 (DX1) preventing repair of damaged DNA or RNA, or combined with anti-inflammatory pathway inhibitors and medications that inhibit blood coagulation such as mucomyst or n-acetylcysteine, or immunoglobulin, etc.

In one embodiment, at least one or more nuclease analogue or mimetics are used with or without methylene blue with or without beta-propiolactone to damage the DNA or RNA of the virus in preparation for a therapeutic vaccine in vitro in which the nuclease mimetic enters the cells to inhibit viral enzyme such as DNA or RNA polymerases or one uses anti-flavivirus nucleosides, or an antimetabolite, etc. to damage the RNA or DNA of the organism in combination with inhibitors of flavivirus RdRp, such as GS-441524, GS-5734, 2'-C-methyladenosine, 2'-C-methylguanosine, 2'-C-methylcytidine, Sofosbuvir, 2'-C-ethynyladenosine, NITD449, TD008, NITD20, NITD203, 4'-C-azidocytidine, 4'-C-azidocytidine, RO-9187, T-1106, 6-Methyl-7-deazaadenosine, N6-(9-antranylmethyl) adenosine, N6-benzyl-5'-O-triisopropylsilyl, N6-benzyl-5'-O-triisopropylsilyl adenosine, N6-benzyl-5'-O-trityladenosine N6-benzyl-5'-O-tert-butyldimethylsilyl-adenosine, N6-benzyl-5'-O-tert-butyldimethylsilyl-adenosine, 2',5'Di-O-trityluridine, 3',5'Di-O-trityluridine with or without the inhibitors of flaviviral methyltransferase, such as Ribavirin and other nucleoside synthesis inhibitors, ETAR, IM18, 6-Azauridine, or in combination with rigid amphipathic nucleosides, 5-(Perylen-3-yl)ethynyl-arabino-uridine, 5-(Perylen-3-yl) ethynyl-2'-deoxy-uridine, or 5-(Pyren-1-yl)ethynyl-2'-deoxy-uridine in a concentration that damages the RNA or DNA of the organism, but does not crosslink the proteins, or glycoproteins of the virus to be used at a non-toxic level and volume when administered in animals or humans with cellular inflammatory pathway inhibitors, such as Wnt inhibitors, Rock inhibitors, GSK inhibitors, or integrin inhibitors, etc. to control the immune response and a non-toxic concentration of nuclease analogue or mimetics as a therapeutic vaccine with or without Ceapin-A7 and KIRA8 and spermidine to enhance removal of the damaged cells and organisms with or without immunoglobulin to prevent potential chronic inflammation and Alzheimer's disease or pulmonary fibrosis, when administered by nasal inhalation for brain/lung involvement in viral pneumonia or encephalitis, or by intramuscular administration, etc.

In one embodiment, the therapeutic vaccine is used as prophylaxis or therapy of ongoing infection, etc.

In one embodiment, one or more nucleoside analogue are used for in vitro and in vivo antiflaviviral activities, e.g., to damage the RNA/DNA of the organism or to kill the viruses (organism) in vitro with a toxic concentration, but administer them at below the non-toxic concentrations, and with anti-inflammatory cell pathway inhibitors to be used as a therapeutic vaccine, in vivo in combination with one or more antivirals and Ceapin A7 or KIRA-8 to remove damaged cells or dead organisms, with or without spermidine or toll like receptor 4 to enhance an immune response by nasal application or combined with immunoglobulin to prevent blood clot formation after vaccination of a patient.

In one embodiment, other viral inhibitors of flaviviral nucleoside analogue can be used alone or with one or more nucleoside analogue additions, such as NS5 RdRp, or other antivirals, such as 7-Deza-2'-methyladenosine, Sofosbuvir, NITD008, T-1106, BCX4430, or inhibitors of flaviviral NS5 RdRp and/or heterobase substitutions and ribose modifications flaviviral RdRp nucleoside inhibitors or 1'-Cyano substituted nucleosides, or GS-441524, a 1'-cyano substituted C-nucleoside derived from 4-aza-7,9-dideazaadenosine, in combination with a phosphoramidate prodrug of GS-441524, referred to as GS-5734, or 2'-C-methyl substituted nucleosides or 2'-Fluoro-2'-C-methyl substituted nucleosides, or 2'-C-Methyl-nucleoside, C7 carbamoyl moiety to NITD008 molecule or another 2'-ethynyl modified derivative, referred to as NITD449, and 3'-C- and 3'-O-substituted nucleosides, or 4'-Azido substituted nucleosides, 4'-azido modified nucleoside analogue, 4'-azidocytidine (R-1479) and 4'-azido-aracytidine, or prodrug of 4'-azido-cytidine, called balapiravir, or imino-C-nucleoside analogue BCX4430, or heterocyclic base-modified nucleosides, including T-1106, 93-95 6-methyl-7-deazaadenosine, and numerous N6-alkyl or aryl substituted nucleosides, or in combination with T-1106 or ribavirin or 6-Methyl-7-deazaadenosine or N6-Alkyl or aryl substituted nucleosides, or tritylated nucleosides, or alkylated, silylated, or acylated pyrimidine nucleosides, or 2',5'di-O-trityluridine and 3',5'di-O-trytiluridine or tritylated nucleosides, or nucleoside inhibitors of flaviviral MTase, methylation reactions by S-adenosyl-1-methionine is the nucleoside analogue S-adenosyl-1-homocysteine (SAH) or flexible nucleoside analogues known as "fleximers", or nucleoside inhibitors of flaviviral NTPase/helicase, or nucleoside inhibitors of flaviviral NTPase/helicaseRibavirin or its derivatives or other nucleoside synthesis inhibitors or 6-azauridine and 5-aza-7-deaz-aguanosine, 6-Azauridine and its derivatives are inhibitors of orotidine monophosphate decarboxylase, blocking cellular de novo pyrimidine biosynthesis, or 6-azauridine and 5-aza-7-deazaguanosine, or 6-Azauridine and its derivatives.

In one embodiment, the therapeutic vaccine is produced with nucleoside analogue in combination with another antiviral, such as favipiravir, to be used as booster shots with the existing vaccines such as mRNA vaccine with or without nanobodies obtained from llamas and alpacas to attach to the RBD-ACE2, or multiple antibodies to spike proteins or the use of ACE2 decoys or administered together with a known antiviral such as remdesivir, etc. and anti-inflammatory pathway inhibitors and Ceapin-A7 and KIRA8 or spermidine to strengthen the immune response.

In one embodiment of a therapeutic vaccine (TVac), the antibody includes viral, bacterial, or fungal nuclear components/proteins or with or without lipids/proteins or with polysaccharides/protein, or an mRNA vaccine (where a single stranded RNA carries the gene's genetic sequence that is read by the ribosome) for synthesis of an antigenic protein, stimulating the antibody production by the immune cells, the antibody is produced after exposure of a person by contact with an antigen through the skin, mucosa, by inhalation, digestion, or if it is injected in the person in combination with or without gold nanoparticles conjugated with thiol along with a low non-toxic dose of at least two appropriate medications against the organism, e.g., for viruses one uses one of an antiviral polymerase inhibitor and a protease inhibitor, etc. with or without immune stimulators, such as toll-like receptor 4 and spermidine and one of the anti-inflammatory pathway inhibitors, e.g., a Wnt inhibitor, Rock inhibitor, GSK-3 inhibitor, or integrin inhibitor.

In one embodiment, the nuclear components DNA or RNA is obtained and isolated with standard methodology using kits with TRIzol, magnetic beads, centrifugation, then combined with the proteins of the organism to enhance the immune response with or without gold nanoparticles of 1-5 nanometers in diameter at a low non-toxic dose of at least two appropriate medications depending on the organism, e.g., for viruses one uses of one antiviral polymerase inhibitor and a protease inhibitor nucleoside analogues, etc. to which one adds immune stimulators, such as toll-like receptor 4 and spermidine and a pathway inhibitor.

In one embodiment, the therapeutic vaccine (TVac) is administered as needed repeatedly by measuring the neutralizing antibodies in serum as a booster vaccine alone or in combination with other vaccines such as an mRNA vaccine or DNA/protein vaccine, or polysaccharide/protein vaccine or glycoprotein vaccine, or anti-tumor vaccine or anti-venom vaccine, etc. with one of cell inflammatory pathway inhibitor and n-acetylcysteine for treatment or prophylaxis of a disease.

In one embodiment, the cell pathway inhibitors or complement inhibitors, or caspases inhibitors, are used in a therapeutic vaccine to reduce the initiation of apoptosis and severe inflammatory response in the tissue, when administered with a therapeutic vaccine as a prophylaxis or therapeutic with appropriate antivirals, antiparasitics, or antineoplastics with a pathway inhibitor and an immune stimulator combined or separately as prescribed intervals by the physician.

In one embodiment, the therapeutic vaccine (TVac) is administered as needed repeatedly by measuring the neutralizing antibodies in a serum or used as a booster vaccine alone or in combination with other vaccines, such as an mRNA vaccine or DNA/protein/vaccine or polysaccharide/protein vaccine or glycoprotein/vaccine, or anti-tumor vaccine or anti-venom vaccine, with antivirals, antibacterials, antiparasitics, or antineoplastic medication, etc. with one of cell inflammatory pathway inhibitor and or caspases inhibitors, such as VX-765 a novel Caspase-1 inhibitor, which is an enzyme regulating the generation of IL-1b and IL-18 or Ivachtin or Caspase-6 inhibitor Z-VEID-FMK or Caspase-3 inhibitor Z-DQMD-FMK or caspase inhibitor Boc-D-FMK or Z-VEID-FMK etc. or a pan-caspase inhibitor and or toll-like receptor 4, etc. or VLP to enhance an immune response and complement inhibitors and n-acetylcysteine to prevent blood clot formation for treatment or prophylaxis of a disease, whereas the antivirals, antifungals, antineoplastic medication, or antiparasitics are given as a cocktail or separately as needed daily or as ordered by a physician.

In one embodiment, using therapeutic vaccines which is a cocktail of antigens obtained from the viruses or fungi, or bacteria or parasites or a tumor plus appropriate non-toxic doses of antifungal, antivirals, antiparasitics, or antineoplastic medication with non-toxic doses of anti-inflammatory cell pathway inhibitors, such as Wnt, Rock, or GSK-3 inhibitors or antiparasitics, and/or complement inhibitors, and or pan caspase inhibitors, or Toll-like receptor 4, etc. to enhance immune response or antibody-coated nanoparticles or slow release antibody-coated nanoparticles administered by inhalation, digestion, injection, or intravenous intramuscular or nasal inhalation or through the skin and mucosa, etc. as a cocktail or cocktails or separately during the vaccination which can be given initially by at least twice in an interval of two weeks or more or as needed prophylactically or therapeutically at intervals of 2 weeks as needed, whereas the antivirals, antifungals, or antineoplastic medication are administered as needed daily, or as ordered by a physician.

In one embodiment, using therapeutic vaccines which is a cocktail of antigens obtained from the viruses or fungi, or parasites or a tumor conjugated with polymeric nanoparticles or microparticles with or without antibody-coated nanoparticles that can be an organic material such as hydrogel, silicon, or porous hydrogel or porous silicon or slow release polymeric nanoparticles of polylactic acid, polyglycolic acid or in combinations of nanoparticles of hydrogel and alginate, etc. or are metallic nanoparticles, such as gold, silver, zinc, etc. or non-metallic nanoparticles, etc. where the pluralities of nanoparticles can carry one type of antigen, e.g., viral protein or carry many viral proteins plus viral glycoproteins or viral polysaccharides, or DNA or mRNA of an organism, etc. in different nanoparticles or different nanoparticles can carry the antigen of one virus or more viruses and some nanoparticles carry the antigen of a mutated virus etc., plus appropriate non-toxic doses of antivirals, antifungals, antiparasitics, or antineoplastic medications with non-toxic doses of anti-inflammatory cell pathway inhibitors, such as Wnt or Rock, or GSK-3 or anti-TGF beta, and/or complement inhibitors 3, 6 etc., and or a pan caspase inhibitors, such as MX1013 that inhibits caspase-1, 3, 6, 7, 8, and 9, or Toll-like receptor 4, etc. to enhance an immune response or the various nanoparticles can be administered sequentially alone or in combinations, where the antibody-coated pluralities of nanoparticles or slow release antibody nanoparticles are administered by inhalation, digestion, or intravenous injection or nasal inhalation, etc., or through the skin and mucosa, intramuscular injection, or orally etc., depending on the organ involved or given in many forms of combinations sequentially etc. or as a cocktail or cocktails which can be give initially at least twice in an interval of two weeks or more or as needed prophylactically as needed thereafter or therapeutically at intervals of two weeks or more, as needed whereas and the antivirals, antifungals, antineoplastic medications, etc. can be administered as needed daily or as ordered by a physician.

In one embodiment, the therapeutic vaccine is given with pluralities of nanoparticles with, e.g., antivirals etc. administered to an immunosuppressed person to cover multiple organisms simultaneously, such as viruses and bacteria or parasites and fungi, or a tumor, etc. in combination with at least one or more antivirals and/or one or more antibacterials or one or more antiparasitics and one or more antifungals or one or more antineoplastic medications, in a non-toxic dose with cell pathway inhibitors, and immune stimulators or caspase inhibitor, etc. or an anticoagulant as a cocktail of pluralities of nanoparticles.

In one embodiment, the patient has a therapy-resistant virus, for which he or she had received antiviral medication without success, the patient is administered a therapeutic vaccine (a vaccine and antiviral), and if the virus does not respond to the therapy, a combination of antiviral therapeutic vaccine and an antibacterial vaccine (or therapeutic antibacterial vaccine) is given, by nasal inhalation, orally, intramuscularly, or intravenously, to enhance the stimulation of the cellular and humoral response that now acts strongly against the original therapy-resistant virus and eliminates it, the combination of the antiviral and antibacterial therapeutic vaccine is given simultaneously or sequentially with one of the cell inflammatory pathway inhibitors, one of the complement inhibitors and Ceapin-A7 and KIRA8 or one of the caspase inhibitors to reduce over reaction of the immune response and an antiviral for a longer time until the infection is eliminated.

In one embodiment, the patient has a therapy-resistant bacteria, for which he or she had received antibacterial medication without success, the patient is administered a therapeutic vaccine (a vaccine and antibiotic), and if the bacteria does not respond to the therapy, a combination of an antibacterial therapeutic vaccine and an antiviral vaccine (or therapeutic antiviral vaccine) is given, by nasal inhalation, orally, intramuscularly, or intravenously, to enhance the stimulation of the cellular and humoral immune response that now acts strongly against the original therapy-resistant bacteria and eliminates it, the combination of the antibacterial and antiviral therapeutic vaccine is given simultaneously or sequentially with one of the cell inflammatory pathway inhibitors, one of the complement inhibitors and Ceapin-A7 and KIRA8 or one of the caspase inhibitors to reduce overreaction of the immune response and an antibacterial for a longer time as needed until the infection is eliminated.

In one embodiment, the patient has a therapy-resistant tumor, for which he or she had received antineoplastic medication without success, the patient is administered a therapeutic vaccine (a vaccine and antineoplastic), and if the tumor does not respond to the therapy, a combination of an antineoplastic therapeutic vaccine and an antibacterial vaccine (or antibacterial therapeutic vaccine) is given, by nasal inhalation, orally, intramuscularly, or intravenously, to enhance the stimulation of the cellular and humoral immune response that now acts strongly against the original therapy-resistant tumor and eliminates it, the combination of the antineoplastic and antibacterial therapeutic vaccine is given simultaneously or sequentially with one of the cell inflammatory pathway inhibitors, one of the complement inhibitors and Ceapin-A7 and KIRA8 or one of the caspase inhibitors to reduce overreaction of the immune response and an antiviral for a longer time until the infection is eliminated.

In one embodiment, the patient has a therapy-resistant fungi, for which he or she had received antifungal medication without success, the patient is administered a therapeutic vaccine (a vaccine and antifungal), and if the fungi does not respond to the therapy, a combination of an antifungal therapeutic vaccine and an antibacterial vaccine (or therapeutic antibacterial vaccine) is given, by nasal inhalation, orally, intramuscularly or intravenously, or locally to enhance the stimulation of the cellular and humoral immune response that now acts strongly against the original therapy-resistant fungi and eliminates it, the combination of the antibacterial and antifungal therapeutic vaccine is given simultaneously or sequentially with one of the cell inflammatory pathway inhibitors, one of the complement inhibitors and Ceapin-A7 and KIRA8 or one of the caspase inhibitors to reduce overreaction of the immune response and an antiviral for a longer time until the infection is eliminated.

In one embodiment, the patient has a therapy-resistant parasite, for which he or she had received anti-parasitic medication without success, the patient is administered a therapeutic vaccine (a vaccine and anti-parasitic medication), an if the parasite does not respond to the therapy, a combination of antiviral (or antibacterial) vaccine (or therapeutic vaccine) and an anti-parasitic therapeutic vaccine is given, by nasal inhalation, orally, intramuscularly, intravenously, or locally to enhance the stimulation of the cellular and humoral response that now acts strongly against the original therapy-resistant parasite and eliminates it, the combination of anti-parasitic and antibacterial therapeutic vaccine is given simultaneously or sequentially with one of the cell inflammatory pathway inhibitors, one of the complement inhibitors and Ceapin-A7 and KIRA8 or one of the caspase inhibitors to reduce overreaction of the immune response and an anti-parasitic medication for a longer time as needed until the infection is eliminated.

In the embodiments described above, the therapeutic vaccination can be used for vaccination and therapy of humans, wild animals, farm animals, pets, birds, fish or any other living being that can be infected with any organism or in a neoplastic disease, such as cancer of any organs.

In one embodiment, two or more antivirals are combined at non-toxic doses, and are administered intranasally, intravenously or subcutaneously, intramuscularly, orally, etc. for preventing viral attachment to the cells, entry into cells, and viral assembly, etc.

In one embodiment, the TMPRSS2 inhibitor, camostat and/or heparin, LMWH, or heparin mimetics, etc. inhibit entry of the virus into the cells. In this embodiment, one, two, or more antivirals are used in a nasal application to: (1) prevent virus attachment to the cells; (2) uncoat the virus inside the cell using, e.g., the antiviral Amantadine, etc. to prevent the virus from using the cell mechanism to replicate; (3) these are combined with prevention of the proteins for assembly by the virus, using a protease inhibitors, such as Darunavir, ebselon, or ritonavir, saquinavir, and indinavir, etc.; (4) addition of transcription inhibitors, such as nucleoside reverse transcriptase inhibitor (NRTI), etc.; (5) prevention of assembly of the viral protein with a polymerase inhibitor, such as remdesivir, Acyclovir, or valcyclovir, etc.; (6) blocking the RNA or DNA with methylene blue or the use of nucleoside analogues, such as Foscarnet, Fomivirsen, Famciclovir or Oseltamivir, etc.; and (7) prevention of release of viral particles from the infected cells with antiviral Zanamivir.

In one embodiment, temporary nasal implants are used for drug delivery in combination with slow release nanoparticles, or the addition of antibody-coated pluralities of polymeric nanoparticles with or without low molecular weight heparin, and linoleic acid with or without anti-inflammatory pathway inhibitors to prevent reinfection and to reduce an inflammatory response in the nose and respiratory pathway or brain inflammation and reduce viral loads in vaccinated, reinfected, and/or unvaccinated patients or the temporary nasal implant can be used after its nostril implantation for analysis through the mail sent to a laboratory, etc. after one or more days or nights to measure the viral load in the nose.

In one embodiment, the temporary nasal implant is used to deliver therapeutic vaccines for respiratory inflammation or infection or central nervous system infection, etc.

In one embodiment, the nasal swab or implant is used for measurement of the viral load in the nose alone, or in a patient with chronic or "long-covid", the persistence of the virus is proven, also by obtaining aqueous fluid from the eye by taking a small volume liquid biopsy from the anterior chamber of the eye as described in U.S. Pat. No. 10,278,920, the entire disclosure of which is incorporated herein by reference, for lab analysis or administration of antivirals, etc.

In one or more embodiments, the steps of the therapeutic vaccines are similar, namely: (1) growing the organism in the cell culture, etc.; (2) killing the organism with a high dose of at least two medications that damage RNA and DNA; (3) obtaining the antigens from the dead RNA and/or DNA of the damaged viruses and adding medications at a low non-toxic dose to the patient, but still toxic enough to the viruses, with or without inflammatory pathway inhibitors and a PARP inhibitor that blocks the RNA and/or DNA repair; and (4) with or without toll-like receptor 4, etc. to enhance an immune response, the therapeutic vaccine that can be used both prophylactically, or for treatment if the patient or animal is infected since it still kills the viruses while stimulating body's immune response to the virus as often as needed by administration nasally, orally, intramuscularly, intravenously, locally, or inside an organ, e.g., inside an eye or the brain where the blood brain barrier prevents medications, etc. from penetrating the brain or the eye.

In one embodiment, the initial steps of growing viruses, bacteria, fungi, parasites or tumor cells are performed, then the second step of damaging the RNA and/or DNA is done either with a toxic dose of methylene blue >4 mg/liter alone or combined with peptide nucleic acids (PNAs) that damage specific RNA by attaching tightly to the organism's DNA/RNA, thus inhibiting, e.g., bacterial, viral, fungal, parasitic, or tumor cell's protein production for the organism's survival, either methylene blue or PNA can be used in vitro with or without toxic doses of antivirals, antibacterials, antifungals, antiparasitics, or anti-neoplastic medications as needed to kill the organisms, then after filtering the medications, the dead viruses, bacteria, fungi, parasites, or tumor cells are used as vaccine antigens including their proteins, glycoproteins, saccharides, etc. combined with nontoxic doses of antivirals, antibacterials, antifungals, antiparasitics, or anti-neoplastic medications alone depending on the organism with or without a PARP inhibitor to prevent RNA and/or DNA from regenerating and preventing future mutations, and other anti-inflammatory pathway inhibitors, such as Wnt, Rock, GSK, and/or integrin inhibitors are administered at non-toxic concentrations and volumes to prevent excessive an immune response, or with toll-like receptors or other adjuvants, etc., to enhance immune response administered intramuscularly, or by nasal inhalation, spray, etc., or orally as a capsule or injected subcutaneously or injected inside a body cavity to damage the viruses, bacteria, fungi, parasites, or tumors and inducing a cellular and humoral immune response, with or without an anticoagulant, such as low molecular weight heparin, a heparin mimetic, n-acetylsystein, Abelacimab, etc., to prevent blood clotting and the therapeutic vaccine can be repeatedly administered as needed to adults and children or at a low dose or an increasing dose, until a sufficient neutralizing antibody response is achieved in the serum of the patient, which can be human adults or children or animals, etc.

In one embodiment, the therapeutic vaccine is combined with natural killer cells prepared from a patient, and grown in the lab in a large quantity, and administered for treatment of a parasitic infection, therapy of viruses, resistant bacteria, e.g., tuberculosis, leprosy, syphilis, aids, COVID-19 and its mutations, a severe viral infection, Ebola, Zika, etc., malaria, malignant or benign tumors, a pancreatic neoplasm, brain, breast, prostate, lung, cervical, uteural, or ovary tumors, intestinal, colon, neoplastic lesions or melanoma, and other skin tumors, breast, prostate bladder cancer, kidney, brain, sarcomas, lung cancers, and spinal cord tumors, genital tumors, etc. where the treatment is personalized by obtaining natural killer cells from the same patient and grow them in the culture with the organisms.

In one embodiment, a tumor becomes resistant to checkpoint inhibitors, and creates a milieu in which the newly grown tumor cells become resistant to the standard immune therapies which include check point inhibitors. In order to treat these conditions, one administers a combination of two different therapeutic vaccines, one directed toward the existing tumor cells plus one or two antineoplastic medications in combination with another vaccine that is directed toward another antigen, e.g., against a bacteria, to restimulate the cellular immune response (killer cells) and humoral immune response of the body against the therapy-resistant tumor cells that kills and removes them when simultaneously one administers a cell pathway inhibitor with immune stimulators, such as toll-like receptor 4 and anti-VEGFs, such as Bevacizumab, Cilengitide, etc. as a cocktail and/or with monoamine oxidase inhibitors, melatonin and spermidine and to prevent exhaustion of the cellular immune response.

In one embodiment, a large tumor can receive surgical excision and a combination of thermotherapy with one or more immune therapy medications and/or PARP inhibitor to prevent mutation of the tumor and an antitumor medication at a non-toxic dose in combination with administration of therapeutic vaccines that can be repeatedly administered with different antigens and natural killer cells to remove the dead cells or destroy the remaining tumor cells, thus stimulating the immune cellular response with natural killer cells over a period of time while adding toll-like receptor 4 or an adjuvant, or pegylated interferon to the cocktail and/or a monoamine oxidase inhibitor and spermidine and an anti-VEGF to prevent exhaustion of the cellular immune response.

In one embodiment for cancer therapy, additional thermotherapy with or without anti-VEGFs that weakens the tumor's ability to resist immune therapy which is administered with or without PARP inhibitors to prevent mutation of the tumor while improving the tumor microenvironment which mitigates tumor's resistance and when checkpoint inhibitors may not be working.

In one embodiment, some tumors develop resistance to checkpoint inhibitors and continue to grow, to prevent additional growth, intravenous, intra-arterial, or local administration, etc. of killer cells, antineoplastic medication, such as PARP inhibitors, and natural killer cells and/or a pan-caspase inhibitor and/or toll-like receptor 4, etc. enhance the immune response to kill and remove the dead tumor cells.

In one or more embodiments, the steps of the therapeutic vaccines are similar, for all viruses, bacteria, fungi, parasites or tumor cells, collectively called "pathogens" namely:
(1) growing the organism; (2) killing the organism with a high dose of at least two medications that damage RNA and DNA of the viruses, bacteria, fungi, parasites or tumor cells; (3) filtering out the free toxic components, obtaining the antigens and adding medications at a non-toxic level with or without a PARP inhibitor or peptide nucleic acid or beta-propiolactone, etc.; (4) adding one more anti-inflammatory pathway inhibitors and anti-pathogenic medications; and (5) adding one or more adjuvants, such as toll-like receptor 4, or saponin, etc. to enhance an immune response, as a therapeutic vaccine that can be used prophylactically, or for treatment as needed.

In one embodiment, the first step of growing viruses, bacteria, fungi, parasites or tumor cells is performed, then the second step of damaging the RNA and/or DNA is done either with a toxic dose of methylene blue >4 mg/liter alone or with the use of peptide-like molecules called "peptoids" or other biomimetic molecules that can inactivate viruses, etc. by damaging the organism's DNA/RNA and inhibiting, e.g., bacterial, viral, fungal, parasitic, or tumor repair or mutation, or the production needed for the organism's survival. The medication may further include PARP inhibitors.

In one embodiment, methylene blue, peptoids or proteases can be combined to damage the viral membranes and can be used in vitro with or without toxic doses of antivirals, antibacterials, antifungals, antiparasitics or anti-neoplastic medications, such as mycophenolic acid or iododeoxyuridine and methisazone or Masitinib a proteinase inhibitor or with or without monoclonal antibody-coated nanoparticles or polyclonal antibody-coated nanoparticles to kill the organisms, then after filtering the medications, the dead viruses, bacteria, fungi, parasites or tumor cell antigens are used as a vaccine antigen including their proteins, glycoproteins, saccharides, etc. which are now combined with non-toxic doses of antiviral, antibacterial, antifungal, antiparasitics, or antineoplastic medications alone depending on the organism with or without PARP inhibitors or anti-inflammatory pathway inhibitors, such as Wnt, Rock, GSK, integrin inhibitors, and mycophenolic acid administered at non-toxic concentrations and volumes to prevent an excessive immune response, with toll-like receptors or other adjuvants, etc., to enhance an immune response administered intramuscularly, or by nasal inhalation, spray, etc. or orally as a capsule or injected subcutaneously or injected inside a body cavity or subcutaneously to damage the viruses, bacteria, fungi, parasites, or tumors and inducing a cellular and enhancing a humoral and cellular immune response, with or without an anticoagulant, such as low molecular weight heparin, heparin mimetics, n-acethylsystein, Abelacimab, etc., to prevent blood clotting and the therapeutic vaccine can be repeatedly administered as needed, or at low dose or increasing dose until a sufficient neutralizing antibody response is achieved in the serum of the patient, which may be human adults or children or animals.

In one embodiment, the therapeutic vaccine can be delivered with a temporary nasal implant for prophylaxis or therapeutic indications, the therapeutic vaccine uses antigenic material from the bacteria, viruses, fungi, parasites, or tumor cells in which the DNA and/or RNA is damaged in vitro by numerous medications such as gold nanoparticles, methylene blue, antineoplastic medications, peptoids, etc., where the peptides, protein glycoproteins, saccharides, or PNA, etc. and antigenic molecules of the organism are used to induce a humoral or cellular immune response with or without PARP inhibitors to prevent live organisms from mutating with or without toll-like receptors while other adjunct medications are antivirals, antibacterials, antiparasitics, antifungals, or anti-neoplastic medications depending on the organism, with or without culture-grown killer cells as needed or immunosuppressive drugs, such as mycophenolic acid, etc., and inflammatory cell pathway inhibitor(s)

are added, with anticoagulants or mono or polyclonal antibody-coated nanoparticles as a cocktail or one or more combinations of these medications are administered preferentially through the nasal inhalation or as an implant with or without a slow release antibody-coated temporary porous implant as prophylaxis or therapeutic when the patient is already infected or alternatively administered orally, intramuscularly, locally, or subcutaneously to a human patient and/or to an animal.

In one embodiment, the temporary nasal implant is sprayed with a therapeutic vaccine prior to implantation to release the medication/vaccine slowly in the nose, etc.

In one embodiment, in order to vaccinate against future mutations in viruses, bacteria, fungi, parasites, tumor cells, etc., the following steps are performed:

A) A variety of viruses, such as Rhinoviruses, Coxsackie viruses, Adenoviruses and coronaviruses SAR-Cov-2 and its mutations (Covid-19), alpha, beta, and delta, Omicron etc. mutations, respiratory syncytial virus (RSV), Epstein Barr Virus (EBV), *H. influenzae* type b (Hib) influenza, Human parainfluenza viruses (HPIVs) viruses and RSV Middle East respiratory virus, pandemic H1N1, and H7N9 and their mutations, influenza viruses, Epstein-Barr viruses, measles virus, enteroviruses, varicella-zoster virus and arboviruses, Japanese encephalitis virus, West Nile virus, and Murray Valley encephalitis virus, AIDS, ebola, etc. are grown on yeast to multiply and simultaneously mutate, then as with the method of producing a therapeutic vaccine, the DNA and/or RNA of the virus and yeast is damaged by medications, such as gold nanoparticles (GNP), methylene blue at high concentrations >5 mg/liter or antineoplastic medications, peptoids, etc., or PNA, or PARP inhibitors, etc.

B) Then, the peptides, protein glycoproteins or saccharides, molecules of the filtered organism plus yeast wall, etc. is separated from the culture media for examination of potentially mutated viruses, etc.

C) After which, the antigenic material is used to induce a humoral or cellular immune response combined with or without a PARP inhibitor to prevent mutation in the organism if any of the organisms are alive, plus toll-like receptors while other adjunct medications may be administered.

D) Non-toxic doses of antivirals, antibacterials, antiparasitics, antifungals, or anti-neoplastic medications, depending on the organism, are added as a therapeutic vaccine and administered to the patient to enhance an immune response with or without culture-grown killer cells sequentially as needed or in addition to immunosuppressive drugs, such as mycophenolic acid, etc., and inflammatory cell pathway inhibitor(s) are added, with anticoagulants or mono or polyclonal antibody-coated nanoparticles as a cocktail or with non-toxic doses or a PARP inhibitor to effectively prevent viral, bacterial, fungal, and tumor cell mutations.

E) One or more combinations of these therapeutic vaccines are administered to the patient preferentially through the nasal inhalation, orally, intraperitoneally, intramuscularly, locally, intravenously, subcutaneously, etc. or as a nasal temporary implant with or without slow release antibody-coated nanoparticles with a temporary porous nasal implant as a therapeutic vaccine prophylaxis or when the human or animal patient is already infected.

In one embodiment, the use of yeast as a cell culture permits the viruses not only to grow on them, but also potentially the viruses mutate rapidly, or their mutation is promoted with light, electrical pulse, etc. so that even when the mutation has not occurred in the animal or human, this new vaccine's antigenic components contain antigenic material from the mutated and unmutated viruses, thereby inducing a humoral and cellular immune response against the past, present and future mutations of the organism and when administered with or without an PARP inhibitor, etc. (such as olaparib niraparib, rucaparib, talazoparib) to effectively prevent viral, bacteria, fungal and tumor cell mutation to the animal or human.

In one embodiment, this therapeutic vaccine technology can also be used for treating therapy-resistant bacterial, fungal, and parasitic organisms or against therapy-resistant tumor cells using the complementary components as needed, such as two or more antivirals, two or more antibiotics, two or more antiparasitics, two or more antifungals, and/or two or more antineoplastic medications at non-toxic concentrations plus anti-inflammatory pathway inhibitors and anticoagulants as a cocktail or sequentially administered to the animal or human.

In one embodiment, a variety of viruses, bacteria, fungi, parasites, or tumor cells are grown on appropriate culture with or without mutation stimulating means, such as reactive oxygen species or UV light, or light combined with quantum dot administration to the cell culture that generates an electric pulse after slow-pulsed light exposure, or focused ultrasound at temperature of 43° C. or electrical or chemical pulse stimulus leading to depolarization and repolarization cycles at a rate of 1-20 per second or more and relaxation in or focused ultrasound with or without microbubbles and imaging simultaneously the temperature and controlling it at 40-43° C. as described in U.S. Pat. No. 11,090,385, the entire disclosure of which is incorporated herein by reference, to change the molecule structure of the cell or viruses or bacteria of parasites or tumor cells, stimulating heat shock protein production, upregulating expression of the nucleic acid, and encouraging mutation in the organism in presence of nutritious media, enhancing multiplication of these organisms that ultimately induces viruses, the bacteria, fungi, or tumor cells not only to grow, but also divide and mutate after multiple generations, then as with the method of producing a therapeutic vaccine, the DNA and/or RNA of the bacteria, fungi, parasites, or tumor cells are damaged by medications, such as gold nanoparticles (GNPs), zinc NPs, or silver NPs of 1-10 nm in size, or zinc NPs with or without laser or ultrasound radiation that heats up the GNPs that preferably absorbs the radiation which is attached to DNA or RNA of the virus, bacteria, fungi, parasites, or tumor cells and damages them with or without a high concentration of methylene blue >4 mg/liter that attaches to the RNA and/or DNA with or without low light radiation with or without GNPs that damages the DNA or RNA, or with or without toxic doses of anti-neoplastic medications, and/or peptoids or peptide nucleic acid (PNA), etc. where the peptides, proteins, glycoproteins, or saccharides, molecules of the organism are separated from the culture media by a filter, etc. is now used to produce a therapeutic vaccine with a non-toxic dose of antivirals, antibacterials, antifungals, antiparasitics, or anti-neoplastic medication with or without PARP inhibitors to prevent mutation and are administered to a human or animal with or without toll-like receptors to induce a humoral or cellular immune response while other adjunct medications are administered as a cocktail or separately, such as culture grown killer cells, etc. as needed or immunosuppressive drugs, such as mycophenolic acid, etc. and anti-inflammatory cell pathway inhibitor(s), with anticoagulants or mono or polyclonal antibody-coated nanoparticles as a cocktail and/or with a PARP inhibitor (called poly (ADP-ribose) polymerase inhibitor) to effectively prevent viral, bacteria, fungal and tumor cell mutation, one or more combinations of these medications are administered preferentially through nasal inhalation, orally, intramuscularly, locally, intravenously, subcutaneously, etc. or as a nasal implant with or without slow release antibody-coated nanoparticles as prophylaxis or therapeutic when the patient human or animal is already infected.

In one embodiment, the use of culture media and repeated generation of the organism can induce mutation with or without medications, such as reactive oxygen species or UV light or electrical stimulus, depolarization and repolarization cycles and/or focused ultrasound that enhances multiplication of these organisms that ultimately induces the virus, bacteria, fungi, or tumor cells not only to grow, but also potentially mutate after multiple generations of growth, which occurs faster in viruses than bacteria or tumor cells in vitro thus even when the mutation has not occurred in animal or human, the induction or growth by electrical stimulus, electrophoresis, or light creates faster next generation variant and mutations than otherwise would happen, therefore, the new vaccine produced from these culture grown organisms which have antigenic components from the organism and its mutations induces a humoral and cellular immune response against the past, present, and future mutations of the organism, thus, this accelerated vaccine technology, has a predictive value for recognizing future mutations if analyzed for its genetic component and useful for treatment of therapy-resistant viruses, bacterial, fungal, and parasitic organisms or against therapy-resistant tumor cells since it can be administered prophylactically/therapeutically and acts against future mutations of these organisms when used with the complementary components, such as two or more antivirals, two or more antibiotics, two or more antiparasitics, two or more antifungals and two or more anti-neoplastic medications at non-toxic concentrations plus anti-inflammatory cell pathway inhibitors and anticoagulants and PARP inhibitors to effectively prevent viral, bacteria, fungal and tumor cell mutation as a cocktail or when administered sequentially, for intravenous, intraarterial, intramuscular, by nasal inhalation, or orally in inside a body cavity, etc.

In one embodiment, methylene blue (MB) at concentrations of >4 microgram/ml in cell or tissue culture is used to damage the DNA and RNA of the viruses, bacteria, fungi, parasites, or tumor cells, with or without addition of peptide nucleic acid (PNA), and/or a protease inhibitor, and/or poly (ADP-ribose) polymerase inhibitor (PARP) inhibitors fixate the DNA or RNA, preventing them from becoming active or mutating, similarly beta-propiolactone (BPL) can be used to damage DNA or RNA, however, beta-propiolactone is an alkylating agent designated by the FDA as a carcinogenic compound and preferably should be used at very low concentrations. After killing the "pathogens", the vaccine is washed and filtered to eliminate all unbound MB and BPL, then one or more antivirals, antibacterials, antifungals, antiparasitics, and/or anti-neoplastics are added at a nontoxic concentration with or without adjuvants such as viral-like particles (VLP), TLR, FICA Saponin-based adjuvants (SBAs) etc. and their combinations, with anti-inflammatory cell pathway inhibitors added to the vaccine cocktail to build a therapeutic vaccine against various pathogens.

In one embodiment, combination of BPL above 1:1000 and at low concentrations and MB<0.26 microgram/ml reduces the toxicity and reduces the aggregation in the culture media and increases the antiviral efficacy.

In one embodiment, the therapeutic vaccine is made of many viruses including sarbecoviruses, or herpes viruses, merbecoviruses and or numerous others. In one embodiment, the therapeutic vaccine made from one virus can be mixed with another or multiple related vaccines for viruses, etc. prior to their administration.

In one embodiment, the therapeutic vaccine made for viruses can be mixed with a therapeutic vaccine made for bacteria, fungi, parasites, or against tumor cells so that all collectively stimulate cellular and humoral response of the body, particularly in immune suppressed patients.

In one embodiment, methylene blue at concentrations of >1 microgram/ml in a cell or tissue culture at media temperature of 24-43° C. controlled with a proportional integral derivative system that controls the temperature of the media at an exact desired level to enhance damage to the viruses, bacteria, fungi, and/or tumor cells without denaturing the proteins, glycoproteins, saccharides, etc. (that occurs at temperatures of 45-50 degrees Celsius or more) to damage selectively the DNA and RNA of the viral, bacterial, and fungal particles, or parasites or tumor cells, with or without addition of peptide nucleic acid (PNA), and/or a protease inhibitor (Ebselen) and/or poly (ADP-ribose) polymerase inhibitor (PARP) inhibitors fixate the DNA or RNA, preventing them from becoming active or mutating, similarly beta-propiolactone can be used to damage DNA or RNA, however, beta-propiolactone is an alkylating agent designated by the FDA as a carcinogenic compound and preferably should be used at very low concentrations. After killing the pathogens, the vaccine is washed and filtered to eliminate all unbound MB and BPL, then one adds one or more antivirals, antibacterials, antifungals, anti parasitics, and/or anti-neoplastics at a nontoxic concentration with or without adjuvants, such as viral-like particles (VLP), TLR, etc. is added to the vaccine cocktail to build a therapeutic vaccine against various pathogens or stored at room temperature or below freezing at zero degrees C. for transport as needed.

In one embodiment, a combination of BPL above 1:1000 and at low concentrations and MB<0.26 microgram/ml at a temperature of 37-40 degrees C. reduces the toxicity of MB and BPL, and reduces the aggregation in the culture media and increases the antiviral efficacy for use in tissue culture, cell culture, or for administration to a patient.

In one embodiment, combination of BPL at low concentrations 1:1000 V/V and MB of <0.25% microgram/ml at temperatures of 25-43 degrees C. in tissue culture, or for administration reduces the toxicity of MB and increases the antivirals, antibiotics, antifungals, anti parasitics and antineoplastics efficacy of vaccine stalk to which non-toxic concentrations of antiviral, antibiotic, anti-fungal, antiparasitic, and/or anti neoplastic medications are added to build a therapeutic vaccine cocktail for administration intranasally, intramuscularly, orally, nasally subcutaneously, intraarterially, or using a therapeutic implant with or without adjuvants, such as viral-like particles (VLP), TLR, etc. for delivery of the vaccine cocktail as needed.

Although the body's immune system produces peptoids to kill many pathogens, such as viral, bacterial, parasitic, fungal, or neoplastic cells, these peptoids do not discriminate between the pathogen and the normal tissue. This means that the peptoids or the synthetically produced mimetic counter parts, can also damage normal tissue. The peptide can be produced synthetically that works the same way, i.e., penetrating the membrane of viruses, bacteria, fungi, parasites or tumor cells and latch to DNA or RNA preventing their function or replication of the pathogen while maintaining the protein, glycoprotein and saccharides antigenicity of the organism with or without adjuvants, such as viral-like particles (VLP), TLRs, Specol, Titermax adjuvants, Ribi adjuvant, aluminum salt adjuvants, etc.

In one embodiment, peptoids are easy to make, such as LL-37, and are a part of cathelicidins host defense peptides when added to the tissue culture or cell culture in preparation of therapeutic vaccine penetrates the viral or the pathogen's envelope and attach to RNA and DNA preventing them from being activated. Initially the LL-37 binds to the surface membrane of the pathogen at low concentrations of 8 µM, then translocates in the preplasmic space within <30 minutes and stops the growth of the pathogen leading to lysis of the pathogen, one also can add antiviral, anti-bacterial, antifungal, antiparasitic, or antineoplastic medication to the tissue culture or cell culture which now penetrates the pathogen damaged membrane by LL-37 killing these organisms, then the culture media is washed and filtered to obtain the antigenic proteins, saccharides, glycoproteins from the organism, subsequently one adds non-toxic doses of antivirals, antibiotics, antifungals, anti-parasitics, and/or anti-neoplastics to create a therapeutic vaccine which can be stored with or without BAC, adjuvants, or anti-inflammatory agents and kept at a low temperature without the need to freeze it, though freezing the vaccine will not affect its efficacy and can be melted before its application, to be administered as needed by inhalation, orally, subcutaneously or intramuscularly or injected inside a tumor or in nasal implant.

In one embodiment, methylene blue and beta-propiolactone (BPL) at >1/2000 V/V can be used both at low concentrations, combinations to prevent the side effects of viral aggregation, e.g., methylene blue at doses of <0.5 microgram/ml and BPL at <0.5 mg/ml with or without anti-virals, etc. used for vaccine production in tissue or cell culture with or without LL-37 peptoids that are subsequently washed and filtered to remove free methylene blue and or beta-propiolactone or LL37 away from the culture medium while adding an anti-inflammatory agent, such as steroids or inflammatory cell pathway inhibitors to it, with or without toll-like receptors which is stimulated in presence of other adjuvants to enhance the immune response after administration to a patient and one or more antivirals, antibacterials, antifungals, antiparasitics, or anti-neoplastics with or without PARP inhibitors, etc. medication at non-toxic doses or low concentrations as a therapeutic vaccine, or for treatment, or prophylaxis, in viral, bacterial, fungal, parasitic, and/or neoplastic pathogens, to be administered as needed by inhalation, orally, subcutaneously, intramuscularly, or injected inside a tumor or inside a cavity, such as a nasal implant.

In one embodiment, for production of the therapeutic vaccine LL-37, a peptoid at low concentrations enhances the effect of antiviral, antibacterial, antifungal, or antineoplastic medication used in the tissue culture or cell culture for production of vaccines.

In one embodiment, for production of therapeutic vaccine Nsp13 inhibitors, MB or BPL, such as bananin, and chromone-4c at low concentrations enhances the effect of antiviral, antibacterial, antifungal, and/or anti-neoplastic medication used in tissue culture or cell culture vaccination that can be washed and filtered and used with antiviral, antibacterial, antifungal, or antineoplastic medication at non-toxic concentrations as a cocktail with adjuvants in therapeutic vaccine production.

In one embodiment, for production of a therapeutic vaccine with PARP inhibitors and a protease inhibitor Ebselen or a combination with rifampin and inflammatory cell pathway inhibitors enhances the effect of an antiviral, antibacterial, antifungal, or anti-neoplastic medication used in vaccination specifically for nasal application to enhance recovery from diseases of the brain and lung by the above-described pathogens and preventing future Alzheimer diseases after viral infections.

In one embodiment, peptoids and beta-propiolactone or methylene blue at low concentrations and peptide nucleic acid (PNA) can be combined to block DNA and RNA and can be used for vaccine production in tissue or cell culture of viruses, bacteria, fungi, parasites or cancer cells where the DNA and RNA of the organism is damaged by PNA, leaving the protein glycoproteins and saccharides intact to act immunogenic, then the dead organism in the tissue culture is washed to remove free methylene blue or beta-propiolactone, to which now depending on the organism, antiviral, antibacterial, antiparasitic, antifungal, and/or antineoplastic medication is added at a non-toxic concentrations, then one adds adjuvants for enhancing the immune response, and steroids or anti-inflammatory cell pathway inhibitors, to reduce an overactive immune response. The therapeutic vaccine cocktail is now stored in refrigerator to be administered to the person as needed by inhalation, orally, subcutaneously, intramuscularly, or injected inside a tumor.

In one embodiment, in a tissue culture, the peptoid LL-37 and peptide nucleic acid can be used to make a therapeutic vaccine with an antineoplastic medication, etc. to damage the RNA or DNA in the viral, bacterial, fungal, parasitic, or tumor cell in the culture media to create a peptoid therapeutic vaccine, though if needed, methylene blue or beta-propiolactone at a very low concentration or peptide nucleic acid (PNA) or PARP inhibitors can be added, without the use of heat, light, or the potentially carcinogenic medications, the vaccine/in culture medium is then washed and filtered to remove free methylene blue and/or beta-propiolactone and use the remaining proteins, glycoproteins, saccharides, etc. to make a therapeutic vaccine, with additional antivirals, antibacterials, anti parasitics, antifungals, and/or anti-neoplastic medications, plus anti-inflammatory pathway inhibitors to reduce the inflammatory response or add VLP, toll-like receptors, or oval albumin or aluminum-based compound called adjuvant or recombinant spider silk protein or Saponin-based adjuvants (SBAs), etc. to the vaccine to stimulate an immune response against the pathogens in the body. In this embodiment, peptoids and/or synthetic peptoids are being used for the production of a new vaccine.

In one embodiment, the therapeutic vaccine can be administered at low concentrations in young children or elderly or immune suppressed, etc. to gradually initiate the immune response and increase the dose at different intervals of one month and more until satisfactory neutralizing antibodies (NA) are present in the blood without causing as side effects to the patient.

In one embodiment, the therapeutic vaccine (i.e., the vaccine and antivirals) is administered to patients with previous viral diseases, such as herpes, or viruses with CNS affinity to prevent reactivation of the hidden or latent herpes viruses or other viruses such as EBV in the patient after vaccination against the same or another virus, e.g., coronaviruses and their mutations, etc. or antivirals are added against another viral infection to prevent reactivation of the second latent virus residing in the body (e.g., in the eye, brain, or nasal or oral cavity etc.).

In one embodiment, the nasal inhalation or nasal implantation of the therapeutic vaccine provides not only general immunity to the person or animal, but simultaneously creates a mucosal immunity in the nasal mucosa, the bronchi, lung mucosa and in the brain, through the olfactory nerves, which is important in treatment of viruses that are transmitted mostly through air, etc.

In one embodiment, the therapeutic vaccine is administered with an antibiotic such as rifampin or rifampicin with or without pathway inhibitors by inhalation to prevent simultaneous co-existence of the bacteria specially in immunosuppressed patients.

In one embodiment, in a population affected with a virus after vaccination, the measurement of a neutralizing antibody (NA) in the circulation of a patient indicates the duration of the effect of the vaccine in a patient, repeated examination of a small sample of the population can provide not only the information on the duration of the immunity, but also the effect of NA on the mutations, thereby eliminating the need for a large scale evaluation of the entire population.

In one embodiment, the nasal therapeutic implants for both nostrils are administered repeatedly after 3-6 months or more, may serve as a prophylaxis, vaccination, and/or therapeutic for the patient and prolong the duration of immunity in the patients and the general population, and is economical compared to systemic administration of larger doses, thereby preventing spread of the disease.

In one embodiment, one can produce a combination vaccine made of numerous viruses or mutations so that the therapeutic vaccine described with the methodology in this application can used against numerous viruses, RNA or DNA viruses (see the lists above, etc.) or administered at low concentrations with other viral therapeutic vaccines such as mRNA vaccines, administration of low doses at low concentrations orally, through the nose, as an implant, by mouth, or intramuscularly, the vaccination can be repeated once a month or every three months or longer while examining the serum antibodies against the viruses.

In one embodiment, the described methodology can be used against chronic bacterial infections, or viral infections which are therapy-resistant, such as the use of rifampin in therapy resistant tuberculosis, leprosy, herpes, zoster virus, Epstein Bar infection, etc.

In one embodiment, the above-described methodology can be used against all fungi, to be administered as needed by inhalation, topically, orally, subcutaneously, intramuscularly, injected inside the lesion or tumors, injected in a body cavity, or via a nasal implant, etc.

In one embodiment, the methodology of creating a therapeutic vaccine can be used for treatment of neoplastic diseases, benign or malignant, tumors, to be administered as needed by inhalation, topically, orally, subcutaneously, intramuscularly, or injected inside a tumor or a body cavity, such as bladder, etc.

In one embodiment, this therapeutic vaccine can be used against parasitic infections regardless of their location along with specific medication described to be administered as needed, topically, orally, subcutaneously, intramuscularly, or injected intravenously, etc.

In one embodiment, the therapeutic vaccine can be applied topically, on the mucosal, or skin surface, can be inhaled or delivered through a nasal implant, or taken orally as pills, or injected locally, subcutaneously, inside a body cavity, subcutaneously or intramuscularly, or administered as a nasal implant, etc.

In one embodiment, after COVID infection, in unvaccinated patients, the symptoms of COVID last long and may not disappear soon, in these cases there is an elevated level of interferon in the body as if the infection has never left the patient, the symptoms could be related to chronic inflammation in the brain leading potentially to Alzheimer or lung (pulmonary fibrosis) or kidney or other organs, heart disease, and chronic fatigue syndrome.

In one embodiment, these patients can be treated with a therapeutic vaccine by nasal administration in addition to the use of Ebselen, a protease inhibitor, which is attached to Mpro in combination with rifampicin and the inflammatory pathway inhibitors, such as rho kinase inhibitors and for the kidney involvement, the systemic, oral or low dose intraperitoneal or intravenous administration might be desirable after initial inhalation therapy with the therapeutic vaccine to reactivate immune response to remove the antigenic material from the body and reduce inflammatory process, a combination with baricitinib can also be a desirable therapy.

In one embodiment, the therapeutic vaccine with or without adjuvants saponin or TLR agonist can be used without exception for all viruses, bacteria, fungi, parasites, benign or malignant lesions, and might have a role in management of autoimmune diseases or chronic inflammatory processes, such as Alzheimer's disease, Parkinson's disease, rheumatoid disease, etc. though the general principles are described, specific variations or additions such as diphenhydramine, lactoferrin, lenzilumab (an anti-granulocyte-macrophage colony-stimulating factor (GM-CSF) monoclonal antibody), and inflammatory cell pathway inhibitors, etc. are applied for each therapy.

In one embodiment, methylene blue at concentrations or >4 microg/ml in cell or tissue culture is used to damage the DNA and RNA of the viruses, bacteriae, and fungi or parasites or tumor cells, with or without addition of peptide nucleic acid (PNA), and/or a protease inhibitor and or poly (ADP-ribose) polymerase inhibitor (PARP) inhibitors to fixate the DNA or RNA, preventing them from becoming active or mutating, similarly beta-propiolactone can be used to damage DNA or RNA, however, beta-propiolactone is an alkylating agent designated by the FDA as a carcinogenic compound and preferably should be used at very low concentrations. After killing the pathogens, the vaccine is washed and filtered to eliminate all unbound MB and BPL, then one adds one or more antivirals, antibacterials, antifungi, anti parasitics, anti-neoplastics at a nontoxic concentration with or without adjuvants, such as viral-like particles (VLP), TLR, FICA and Saponin-based adjuvants (SBAs), etc. or their combinations is added to the vaccine cocktail to build a therapeutic vaccine against various pathogens.

In one embodiment, combination of BPL above 1:1000 and at low concentrations and MB<0.26 Microgam/ml reduces the toxicity and reduces the aggregation in the cuture media and increases the antiviral efficacy In one embodiment, the therapeutic vaccine is made of many viruses including sarbecoviruses and merbecoviruses and/or numerous others. In one embodiment, the therapeutic vaccine made from one virus can be mixed with another or multiple related viruses prior to their administration.

In one embodiment, the therapeutic vaccine made for viruses can be mixed with therapeutic vaccine made for bacteria, fungi, parasites, or against tumor cells so that all collectively stimulate cellular and humoral response of the body particularly in immune suppressed patients.

In one embodiment, methylene blue blue and its derivatives at concentrations or >2 microg/ml in cell or tissue or cell culture at a media temperature of 24-43C is controlled with a proportional integral derivative (PID) system that controls the temperature of the media at an exact desired level to enhance damage to the viruses, bacteria, fungi, or tumor cells without denaturing the proteins, glycoproteins, saccharides, etc. (that occurs at temperatures of 47-50 or more Celsius) to damage selectively the DNA and RNA of the viral, bacterial, and fungi or parasites or tumor cells, with or without addition of peptide nucleic acid (PNA), and/or a protease inhibitor (Ebselen) and/or poly (ADP-ribose) polymerase inhibitor (PARP) inhibitors fixate the DNA or RNA, preventing them from becoming active or mutating, similarly beta-propiolactone can be used to damage the DNA or RNA, however, beta-propiolactone is an alkylating agent designated by the FDA as a carcinogenic compound and preferably should be used at very low concentrations. After killing the pathogens, the vaccine is washed and filtered to eliminate all unbound MB blue and its derivatives and BPL, then one adds one or more antivirals, antibacterials, antifungi, anti-parasitics, and/or anti-neoplastics at a nontoxic concentration or in combination with Monocolonal Antibodies (MABs) with or without adjuvants, such as viral-like particles (VLP), TLR, etc. is added to the vaccine cocktail to build a therapeutic vaccine against various pathogens or stored at room temperature or below or frozen at zero degree C. for transport as needed.

In one embodiment, a combination of BPL above 1:1000 and at low concentrations and MB blue and its derivatives <0.26 Microgam/ml at a temperature of 37-40 degrees C. reduces the toxicity of MB and BPL and reduces the aggregation in the cuture media and increases the antiviral efficacy for use in tissue culture, cell culture, or for administration to a patient.

In one embodiment, combination of BPL and at low concentrations of 1:1000 V/V and MB of <0.25% microgral/ml at tempretures of 25-43 C in tissue culture or for administration reduces the toxicity of methylene blue and its derivatives and increases the antivirals, antibiotics, antifungals, anti parasitics and anti-neoplastic's efficacy of vaccine stalk to which non-toxic concentrations of antivirals, antibiotics, anti-fungals, antiparasitic, or anti-neoplastic medications are added to build a therapeutic vaccine cocktail for administration intranasally, intramuscularly, orally, subcutaneously, or intraarterially or using a therapeutic implant with or without adjuvants, such as viral like particles (VLP), TLR, etc. for delivery of the vaccine cocktail as needed.

Although the body's immune system produces peptoids to kill many pathogens, such as viral, bacteria, parasitic, fungal, or neoplastic cells, these peptoids do not discriminate between the pathogen and the normal tissue. This means that the peptoids or the synthetically produced mimetic counterparts, can also damage normal tissue. The peptide can be produced synthetically that works the same way, i.e., penetrating the membrate of viruses, bacteria, fungi, parasites, or tumor cells and latches to NAD or ARN preventing their function or replication of the pathogen, while maintaining the protein, glycoprotein, and saccharides antigenicity of the organism with or without adjuvants such as viral-like particles (VLP), TLRs, etc.

In one embodiment, peptoids are easy to make, such as LL-37, and are a part of Cathelicidins host defense peptides when added to the tissue culture or cell culture in preparation of therapeutic vaccine penetrates the viral or other pathogen's envelope and attaches to RNA and DNA preventing them from being activated. Initially, the LL-37 binds to the surface membrane of the pathogen at low concentrations of 8 µM, then translocates in the preplasmic space within <30 minutes and stops the growth of the pathogen leading to lysis of the pathogen, one also can add antiviral, or anti-bacterials, antifungals or antiparasites or antineoplastic medication to the tissue culture which now penetrates the pathogen damaged membrane by LL-37 killing these organisms, then the culture media is washed and filtered to obtain the antigenic proteins, saccharides, glycoproteins from the organism, subsequently one adds non-toxic doses of antivirals, antibiotics, antifungals, antiparsites, or antineoplastics to create a therapeutic vaccine which can be stored with or without BAC, or adjuvants or anti-inflammatory agents and kept at a low temperature without the need to freeze it, though freezing the vaccine will not affect its efficacy and can be melted before its application, to be administered as needed by inhalation, orally, subcutaneously or intramuscularly or injected inside a tumor or in a nasal implant.

In one embodiment, MB and beta-Propiolactone (at >1/2000 V/V) can be used both at low concentrations to prevent the side effects of viral aggregation, e.g., methylene blue derivatives at doses of <0.5 microgram/ml and BPL at <0.5 mg/ml with or without anti-virals, etc. used for vaccine production in tissue or cell culture with or without the LL-37 peptoid that are subsequently washed and filtered to remove free methylene blue and or beta-propiolactone away from the culture medium while adding an anti-inflammarory agent, such as a steroid or inflammatory cell pathway inhibitors to it, with or without Toll-like Receptors which is stimulated in presence of LL-37 or other adjuvants to enhance the immune response after administration to a patient and one or more antivirals or antibacterials, antifungi, antiparasites, and/or antineoplastic medications at a non-toxic doses or low concentrations as a therapeutic vaccine or for treatment or prophylaxis, in viral, bacterial, fungal, parasitic and neoplastic pathogens, to be administered as needed by inhalation, orally, subcutaneously or intramuscularly or injected inside a tumor or as a nasal implant.

In one embodiment, for production of a therapeutic vaccine, the LL-37 peptoid enhances the effect of antivirals, antibacterials, antifungals, or anti-neoplastic medication used in vaccination.

In one embodiment, for production of therapeutic vaccine Nsp13 inhibitors, MB blue and its derivatives or BPL, such as bananin, and chromone-4c at low concentrations enhances the effect of antivirals, antibacterials, antifungals, or anti-neoplastic medication used in tissue culture or cell culture vaccination that can be washed and filtered and used with antivirals, antibacterials, antifungals, or anti-neoplastic medication at non-toxic concentrations as a cocktail with adjuvants in therapeutic vaccine production.

In one embodiment, for production of a therapeutic vaccine with a protease inhibitor, Ebselen or a combination with rifampin and inflammatory cell pathway inhibitors enhances the effect of antivirals, antibacterials, antifungals, or antineoplastic medications used in vaccination specifically for nasal application to cover disease of the brain and lung by the above-described pathogens and preventing future Alzheimer diseases after viral infections.

In one embodiment, peptoids and betapropiolactone or methylene blue and its derivatives at low concentrations and a peptide nucleic acid (PNA) can be combined to block DNA and RNA and can be used for vaccine prediction in tissue or cell culture of viruses, bacteria, fungi, parasites or cancer cells where the DNA and RNA of the organism is damaged by PNA leaving the protein glycoproteins and saccharide intact to act immunogenic, then the dead organism in tissue culture is washed to remove free methylene blue blue and its derivatives or beta propiolactone, to which now depending on the organism antiviral, antibacterial, antiparasitic, antifungal, or anti-neoplastic medication is added at a non-toxic concentrations, then one adds adjuvants for enhancing immune response, and steroids or anti-inflammatory cell pathway inhibitors, to reduce overactive immune response. The therapeutic vaccine is now stored in refrigerator to be administered to the person as needed by inhalation, orally, subcutaneously, or intramuscularly or injected inside a tumor.

In one embodiment, in tissue culture, the peptoid LL-37 and peptide nucleic acid can be used to make a therapeutic vaccine with an antineoplastic medication, etc. to damage the RNA or DNA in the viral, bacterial, fungi, parasitic, or tumor cell in the culture media to create a peptoid therapeutic vaccine, though if needed methylene blue blue and its derivatives or beta-propiolacone at a very low concentration or peptide nucleic acid (PNA) can be added, without the use of heat or light or the potentially carcinogenic medications, the vaccine in culture medium is then washed and filtered to remove free methylene blue blue and its derivatives and/or beta-propiolactone and use the remaining proteins, glucoproteins, saccharides, etc. to make a therapeutic vaccine, with additional antivirals or antibacterials or anti-parasites or antifungals, or anti-neoplastics plus pathway inhibitors to reduce inflammatory response or add VLP, Toll Like Receptors, or oval albumin or aluminum-based compound called adjuvants or recombinant spider silk proteins or Saponin-based adjuvants (SBAs), etc. to the vaccine to stimulate an immune response against the pathogens in the body.

In one embodiment, the therapeutic vaccine (i.e., vaccine and antivirals) when administered to a patient with a previous viral disease, such as Herpes, prevents reactivation of the Herpes viruses in the patient after vaccination against another virus, e.g., coronaviruses and their mutations, etc.

In one embodiment, the nasal inhalation or nasal implant with the therapeutic vaccine provides not only general immunity to the person or animal, but simultaneously create a mucosal immunity in the nasal mucosa, the bronchi, lung mucosa and in the brain through the olfactory nerves which is important in treatment of viruses that are transmitted mostly through air, etc.

In one embodiment, the therapeutic vaccine is administered with an antibiotic, such as rifampin or Rifampicin, with or without pathway inhibitors by inhalation to prevent simultaneous co-existence of the bacteria, especially in immunosuppressed patients.

In one embodiment, in a population affected with a virus after vaccination, the measurement of neutralizing antibody (NA) in the circulation of a patient indicates the duration of the effect of the vaccine in a patient, repeated examination of a small sample of the population can provide not only the information on the duration of the immunity, but also the effect of the NA on the mutations thereby, eliminating the need for a large scale evaluation of the entire population.

In one embodiment, the nasal therapeutic implants for both nostrils are administered repeatedly after 3-6 months or more, may serve as a prophylaxis, or vaccination or therapeutic for the patient and prolong the duration of immunity in the patients and the general population, and is economical compared to systemic administration of larger doses, preventing spread of the disease.

In one embodiment, one can produce a universal vaccine if the therapeutic vaccine described in this application is used against one virus is used with numerous viruses, RNA or DNA viruses (see the table above) or administered at a low concentration of viral therapeutic vaccine, such as mRNA vaccine adminstrated at a low dose (e.g., mRNA therapeutic vaccine at low concentration) orally, through the nose or as an implant, by mouth, or intramuscularly of the vaccine which can be repeated once a month or every three months or longer while examining the serum antibodies against the virus.

In one embodiment, the described therapeutic vaccine can be used against chronic bacterial infections, therapy resistant infections with rifampin, such as in tuberculosis, leprosy, herpes, *zoster* infection, etc.

In one embodiment, the above-described therapeutic vaccine can be used against all fungi, to be administered as needed by inhalation, topically, orally, subcutaneously, intramuscularly, or injected inside a tumor of a body cavity or nasal implant, etc.

In one embodiment, the therapeutic vaccine of creating a therapeutic vaccine can be used for treatment of neoplastic diseases, benign or malignant tumors, to be administered as needed by inhalation, topically, orally, subcutaneously, intramuscularly, or injected inside a tumor, or a body cavity, such as bladder, etc.

In one embodiment, this therapeutic vaccine can be used against the parasitic infections regardless of their location along with specific medication described to be administered as needed by topically, orally, subcutaneously, intramuscularly, or injected intravenously, etc.

In one embodiment, the therapeutic vaccine can be applied topically, on the mucosal or skin surface, can be inhaled or delivered through a nasal implant, or taken orally as pills, or injected locally, subcutaneously, inside a body cavity, subcutaneously or intramuscularly or nasal implant, etc.

In one embodiment, after COVID infection in unvaccinated patients, the symptoms of COVID last long and may not disappear soon, in these cases there is an elevated level of interferon in the body as if the infection has never left the patient, the symptoms could be related to chronic inflammation in the brain leading potentially to Alzheimer's disease or lung disease (pulmonary fibrosis) or kidney disease or disease associated with other organs, heart disease and chronic fatigue syndrome.

In one embodiment, these patients can be treated with a therapeutic vaccine by nasal administration in addition to the use of Ebselen a protease inhibitor which is attached to Mpro in combination with rifampicin and the inflammatory pathway inhibitors, such as rho kinase inhibitors, and for the kidney involvement the systemic, oral, or at low dose intraperitoneal or intravenous administration might be desirable after initial inhalation therapy with therapeutic vaccine to reactivate immune response to remove the antigenic material from the body and reduce the inflammatory process, a combination with baricitinib can also be a desirable therapy.

In one embodiment, the therapeutic vaccine with or without adjuvants saponinor TLR agonist can be used without exception on all viruses, bacteria, fungi, parasites, benign or malignant lesions and might have a role in management of autoimmune diseases or chronic inflammatory processes such as Alzheimer's, Parkinson's, and rheumatois disease, etc. though the general principles are described specific variations or additions such as diphenhydramine, lactoferrin, lenzilumab (an anti-granulocyte-macrophage colony-stimulating factor (GM-CSF) monoclonal antibody) and inflammatory cell pathway inhibitors, etc. applied for each therapy.

In one embodiment, one grows a virus in the yeast, then adds methylene blue and its derivatives and/or antivirals or antibacterials or antifungals or a antineoplastic medication to kill the virus, bacteria, fungi, parasites, or tumor cells, separates the dead virus, bacteria, fungi, parasites, or tumor cells by a purification technique, and administers the collected vaccine and adds non-toxic doses of antivirals, antibacterials, anti-fungals, anti-neoplastic medications for administration in humans and one or more adjuvants, by nasal inhalation, subcutaneous injection, intramuscular injection, or oral ingestion, etc.

In one embodiment, the therapeutic vaccine can be combined with fluoxetine selective serotonin reuptake inhibitors (SSRI) increasing the melatonin levels and simultaneously reducing platelet aggregation in viral infections, such as COVID-19, EBV, etc. that can be administered orally or by inhalation.

In one embodiment, the adjuvants are added to the therapeutic vaccine combined with immunizing peptides, such as Freund's (FCA) a water in oil emulsion, or heat-killed mucobacterium tuberculosis which is released slowly but should be preferably by killing the bacteria using higher doses of methylene blue and its derivatives combined with with peptide nucleic acid since mineral oil produces granulomatous response, Ribi, and Titermax or Aluminum salt adjuvants or TLR s to stimulate the immune response increasing the the activity of antibodies after one or more times of administration.

In one embodiment, the adjuvants are added to the therapeutic vaccine combined with immunizing peptides, such as Freund's Incomplete Adjuant (FIA) a water in oil emusion, or heat-killed mucobacterium tuberculosis.

In one embodiment, the therapeutic vaccine against viruses, bacteria, parasites, or tumor cells induces an immune response against the proteins, glycoproteins, and saccharides of the pathogen and not only one specific protein, such as a spike protein or mRNA therefore produces a more robust humoral and cellular response, therefore a combination of a therapeutic vaccine with an mRNA vaccine enhances the immune response in patients which are treated with anticancer medications that reduces their normal immune response or in elderly patients, etc.

In one embodiment, some respiratory viruses, such as smallpox, rubella, measles varicella-*zoster* virus infection, cause systemic disease and some non-systemic respiratory viruses, such as influenza viruses, SARS-CoV-2, coronaviruses, human metapneumovirus (hMPV), HSV-1 or HSV-2 parainfluenza viruses, RSV primarily infect the mucosal surfaces and/or epithelial cells, and are best treated by nasal application of the therapeutic vaccine or multiple antiviral medications or as a nasal slow release implant to prevent mutation of viruses and recurrent positive viral tests that lead to propagation of the infection.

In one embodiment of growing the organism in the yeast culture, the steps include first adding methylene blue and its derivatives and/or PNA and or antivirals, antibacterials, antifungals, or antineoplatic medications to kill the virus, separating the dead virus, bacteria, fungi, parasites, and/or tumor cells by a purification technique, administering the collected vaccine with added non-toxic doses of antivirals, antibacterials, and anti fungals, and/or anti-neoplastic medications along with adjuvant(s) for administration in a human by nasal inhalation, subcutaneous injection, intramuscular injection, or oral injestion one or more times to induce an immune response.

In one embodiment, the therapeutic vaccine can be added to an mRNA vaccine or another vaccine, such as Corbevax, sinovax, Corona vac, COH04S1 spike and nucleocapsid proteins, etc. to strengthen the response to the combination vaccine that can be administered to the patient as a single dose or separately, one or more times.

Any of the features, attributes, or steps of the above-described embodiments and variations can be used in combination with any of the other features, attributes, and steps and routes of administration of the above-described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method for producing an immunogenic coronavirus composition, the method comprising:
    growing coronaviruses on a cell culture or other appropriate medium;
    harvesting the coronaviruses from the cell culture or other appropriate medium;
    killing the coronaviruses in the cell culture or other appropriate medium with a dose of methylene blue that is greater than 2.0 micrograms per milliliter so as to damage the RNA and/or the DNA of the coronaviruses, wherein the coronaviruses remain in contact with the methylene blue for a period of time that is sufficient for the methylene blue to penetrate the coronaviruses and attach to RNA or DNA of the coronaviruses and prevent multiplication of the coronaviruses;
    separating the dead coronaviruses from a remainder of the cell culture or other appropriate medium using a filter and/or centrifuge;
    adding antivirals at non-toxic concentrations to the dead coronaviruses so as to form an immunogenic composition; and
    administering the immunogenic composition to a patient in need thereof.

2. The method according to claim 1, wherein the method further comprises the steps of:
    administering metformin with a glycogen synthase kinase (GSK) 269962 inhibitor to protect the kidneys of the patient; and
    performing kidney dialysis or electrophoresis to remove excess toxins from the body of the patient.

3. The method according to claim 1, wherein the method further comprises the step of:
    repeatedly administering the immunogenic composition to the patient as needed until the coronaviruses are eliminated and verified by polymerase chain reaction and/or imaging.

4. The method according to claim 1, wherein the step of killing the coronaviruses in the cell culture or other appropriate medium further comprises conjugating the methylene blue with gold nanoparticles so as to enhance a penetration of the methylene blue into the coronaviruses and attach to the RNA or DNA of the coronaviruses and prevent multiplication of the coronaviruses.

5. The method according to claim 1, wherein the method further comprises the step of:
    administering one or more inflammatory cell pathway inhibitors to the patient to block an inflammatory tissue response together with the antivirals and/or one or more adjuvants so that the immunogenic composition is able to induce an immune response of the patient, the one or more inflammatory cell pathway inhibitors being selected from the group consisting of Rock inhibitors, Wnt inhibitors, glycogen synthase kinase-3 (GSK-3) inhibitors, integrin inhibitors, IL-1 inhibitors, IL-6 inhibitors, and combinations thereof.

6. The method according to claim 1, wherein the step of killing the coronaviruses in the cell culture or other appropriate medium further comprises killing the coronaviruses with at least two medications that damage the RNA and/or DNA of the coronaviruses; and the method further comprises the steps of:
filtering the dead coronaviruses from the remainder of the cell culture or other appropriate medium;
extracting the antigens from the damaged coronavirus; and
adding one or more additional medications to the extracted antigens, the one or more additional medications being selected from the group consisting of a poly (ADP-ribose) polymerase (PARP) inhibitor, a peptide nucleic acid, beta-propiolactone, an inflammatory cell pathway inhibitor, and an adjuvant, wherein the inflammatory cell pathway inhibitor is selected from the group consisting of a Rock inhibitor, a Wnt inhibitor, a glycogen synthase kinase-3 (GSK-3) inhibitor, an integrin inhibitor, an IL-1 inhibitor, an IL-6 inhibitor, and combinations thereof.

7. The method according to claim 1, wherein the step of administering the immunogenic composition further comprises repeatedly administering the immunogenic composition as needed to the patient at a low dose or a gradually increasing dose until an immunogenic response is achieved.

8. The method according to claim 1, wherein the cell culture on which the coronaviruses are grown and harvested comprises yeast culture media to produce variants.

9. The method according to claim 8, wherein the method further comprises the step of:
administering light or electrical pulses to the coronaviruses grown in the yeast culture media so as to encourage the mutation of the coronaviruses to be harvested and killed for administration.

10. The method according to claim 1, wherein the method further comprises the step of:
administering the immunogenic composition to the patient as topical drops, an ointment, spray for inhalation, in an inhaler, nasally by spraying powder, intravenously, by intramuscular injection, systemically, or orally as a capsule.

11. The method according to claim 1, wherein the method further comprises the step of:
administering the immunogenic composition to the patient using a conical nasal drug delivery implant, the immunogenic composition being delivered to one or more nasal passageways of a patient.

12. The method according to claim 11, wherein the conical nasal drug delivery implant is formed from a semi-flexible polymeric material by 3D printing the conical nasal drug delivery implant.

13. The method according to claim 11, wherein the conical nasal drug delivery implant is attached to a pair of glasses, an outer nose cover, an elastic headband configured to be worn on the head of the patient, or is held in place by elastic components on the conical nasal drug delivery implant itself.

14. The method according to claim 1, wherein the immunogenic composition is mixed with another immunogenic composition.

15. The method according to claim 1, wherein the method further comprises the step of:
adding synthetically produced peptoids to the tissue culture or other appropriate medium, the synthetically produced peptoids penetrating the envelope of the coronaviruses, and attaching to RNA and DNA of the coronaviruses so as to prevent the RNA and DNA from being activated.

16. The method according to claim 1, wherein the method further comprises the step of:
adding one or more adjuvants to induce an immune response of the patient.

17. A method for producing an immunogenic composition, the method comprising:
growing viruses on a cell culture or other appropriate medium;
harvesting the viruses from the cell culture or other appropriate medium;
killing the viruses in the cell culture or other appropriate medium with a dose of methylene blue that is greater than 2.0 micrograms per milliliter so as to damage the RNA and/or the DNA of the viruses, wherein the viruses remain in contact with the methylene blue for a period of time that is sufficient for the methylene blue to penetrate the viruses and attach to RNA or DNA of the viruses and prevent multiplication of the viruses;
separating the dead viruses from a remainder of the cell culture or other appropriate medium using a filter and/or centrifuge;
adding antivirals at non-toxic concentrations to the dead viruses so as to form an immunogenic composition; and
administering the immunogenic composition to a patient in need thereof.

* * * * *